US006495576B2

(12) United States Patent
Kort et al.

(10) Patent No.: US 6,495,576 B2
(45) Date of Patent: Dec. 17, 2002

(54) AMINAL DIONES AS POTASSIUM CHANNEL OPENERS

(75) Inventors: Michael E. Kort, Lake Bluff, IL (US); Robert J. Gregg, Libertyville, IL (US); William A. Carroll, Evanston, IL (US); Arturo Perez Medrano, Grayslake, IL (US); Jürgen Dinges, Grayslake, IL (US); Fatima Z. Basha, Lake Forest, IL (US)

(73) Assignee: Abbott Laboratories, Abbott Park, IL (US)

(*) Notice: Subject to any disclaimer, the term of this patent is extended or adjusted under 35 U.S.C. 154(b) by 0 days.

(21) Appl. No.: 10/046,465

(22) Filed: Jan. 14, 2002

(65) Prior Publication Data
US 2002/0165264 A1 Nov. 7, 2002

Related U.S. Application Data

(60) Provisional application No. 60/267,024, filed on Feb. 7, 2001.

(51) Int. Cl.$^7$ ...................... A61K 31/44; C07D 213/02
(52) U.S. Cl. .................. 514/352; 514/255.06; 514/332; 514/336; 514/342; 514/617; 544/336; 546/263; 546/280.1; 546/283.4; 546/309; 564/185
(58) Field of Search ............................ 514/255.06, 332, 514/336, 342, 352, 617; 544/336; 546/263, 280.1, 283.4, 309; 564/185

(56) References Cited

U.S. PATENT DOCUMENTS

| | | |
|---|---|---|
| 3,636,105 A | 1/1972 | Fest et al. ...................... 564/48 |
| 4,146,646 A | 3/1979 | Percival et al. .............. 424/324 |
| 5,397,790 A | 3/1995 | Butera et al. ................ 514/310 |
| 5,401,753 A | 3/1995 | Butera et al. ................ 514/310 |
| 5,403,853 A | 4/1995 | Butera et al. ................ 514/399 |
| 5,403,854 A | 4/1995 | Butera et al. ................ 514/415 |
| 5,464,867 A | 11/1995 | Antane et al. .............. 514/524 |
| 5,466,712 A | 11/1995 | Butera et al. ................ 514/524 |
| 5,506,252 A | 4/1996 | Butera et al. ................ 514/399 |
| 5,512,585 A | 4/1996 | Antane et al. ................ 514/352 |
| 5,750,574 A | 5/1998 | Gilbert ........................ 514/604 |
| 5,763,474 A | 6/1998 | Herbst et al. ................ 514/399 |
| 5,780,505 A | 7/1998 | Antane et al. ................. 54/522 |
| 5,846,999 A | 12/1998 | Antane et al. ................ 514/524 |
| 5,872,139 A | 2/1999 | Herbst et al. ................ 514/357 |
| 6,166,050 A | 12/2000 | Lombardo et al. ..... 514/255.03 |

FOREIGN PATENT DOCUMENTS

| | | |
|---|---|---|
| WO | 94/29277 | 12/1994 |
| WO | 96/15103 | 5/1996 |
| WO | 97/48682 | 12/1997 |
| WO | 98/02413 | 1/1998 |
| WO | 98/33763 | 8/1998 |
| WO | 99/32495 | 7/1999 |
| WO | 00/51973 | 9/2000 |
| WO | 00/63160 | 10/2000 |
| ZA | 695324 | 7/1969 |

OTHER PUBLICATIONS

Andersson, Pharmacological Reviews 45:253 (1993).
Andersson, Prostate 30:202–215 (1997).
Andersson, Urology, 50(Suppl 6A): 74–84 (1997).
Asano, Anesth. Analg. 90(5):1146–51 (2000).
Augustin, Tetrahedron 36:1801 (1980).
Bosch, BJU International 83(suppl 2): 7–9 (1999).
Bruger, J. Fluorine Chem. 20:813 (1982).
Buchheit, Pulmonary Pharmacology & Therapeutics 12:103 (1999).
Butera, J. Med. Chem. 43:1187 (2000).
DeLean et al., Am. J. Physiol., 235:E97 (1980).
Farina and Baker, J. Org. Chem. 55:5833 (1990).
Freedman, et al., The Neuroscientist, 2:145–152 (1996).
Garlid, Circ. Res. 81(6):1072–82 (1997).
Gehlert, et al., Prog. Neuro–Psychopharmacol & Bio. Psychiat., v18:1093–1102 (1994).
Gilbert, J. Med. Chem. 43:1203 (2000).
Goldstein and Berman., Int. J. Impotence Res., 10:S84–S90 (1998).
Gopalakrishnan et al., Drug Development Research, 28:95–127 (1993).
Grover, J Mol Cell Cardio. 32:677 (2000).
Hampel, Urology 50(Suppl 6A):4–14 (1997).
Hanaineh–Abdelnour, Tetrahedron 55:11859 (1999).
Howe et al., J. Pharmacol. Exp. Ther., 274:884–890 (1995).
IUPAC 1974 Recommendations for Section E, Fundamental Stereochemistry, Pure Appl. Chem. 45:13–30 (1976).
K.S. Schroeder et al., J. Biomed. Screen, 1:75–81 (1996).
Katritzky, Belyakov, Tymoshenko, J. Comb. Chem. 1:173 (1999).
Katritzky, Chem Rev. 98:409 (1998).
Katritzky, J. Heterocyclic Chem. 33:1935 (1996).
Katritzky, Urogdi, Mayence, J. Org. Chem. 55:2206 (1990).
Klockner and Isenberg, Pflugers Arch 405:329–339 (1985).
Kostrzewska, Acta Obstet. Gynecol. Scand. 75(10), 886–91 (1996).
Lawson, Pharmacol. Ther. 70:39–63 (1996).

(List continued on next page.)

Primary Examiner—Zinna Northington Davis
(74) Attorney, Agent, or Firm—Michael J. Ward

(57) ABSTRACT

Compounds of formula (I)

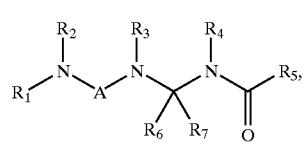

may be useful in treating diseases prevented by or ameliorated with potassium channel openers. Also disclosed are potassium channel opening compositions and a method of opening potassium channels in a mammal

71 Claims, No Drawings

OTHER PUBLICATIONS

Lee, Int. J. Impot. Res. 11(4):179–188 (1999).
Loudon and Boutin, J. Org. Chem. 49:4277 (1984).
Loudon et al., Org. Chem. 49:4272 (1984).
Morrison, Am. J. obstet. Gynecol, 169(5):1277–85 (1993).
Nurse et al., Br. J. Urol., 68:27–31 (1991).
Paio, Zaramella, J. Comb. Chem. 1:317 (1999).
Pandita, The J. of Urology 162:943 (1999).
Prescott, Ed., Methods in Cell Biology, Academic Press, New York, NY, 14:33 et seq. (1976).
Quast et al., Mol. Pharmacol., 43:474–481 (1993).
Resnick, The Lancet 346:94–99 (1995).
Rodrigues, Br. J. Pharmacol 129(1):110–4 (2000).
Sanborn, Semin. Perinatol. 19:31–40 (1995).
Spanswick et al., Nature 390:521–25 (Dec. 4, 1997).
Steglich, Chem. Ber. 107:1488 (1974).
Vergoni, Life Sci. 50(16):PL135–8 (1992).
Wallis and Lane, Org. React. 3:267–306 (1946).
Yamamoto et al., JACS 117:9653 (1995).

AMINAL DIONES AS POTASSIUM CHANNEL OPENERS

This application claims priority from U.S. Provisional Application Serial No. 60/267,024, filed Feb. 7, 2001, incorporated herein by reference.

TECHNICAL FIELD

Novel aminal dione compounds and their derivatives can open potassium channels and are useful for treating a variety of medical conditions.

BACKGROUND OF INVENTION

Potassium channels play an important role in regulating cell membrane excitability. When the potassium channels open, changes in the electrical potential across the cell membrane occur and result in a more polarized state. A number of diseases or conditions may be treated with therapeutic agents that open potassium channels; see for example (Lawson, Pharmacol. Ther., v. 70, pp. 39–63 (1996)); (Gehlert et al., Prog. Neuro-Psychopharmacol & Biol. Psychiat., v. 18, pp. 1093–1102 (1994)); (Gopalakrishnan et al., Drug Development Research, v. 28, pp. 95–127 (1993)); (Freedman et al., The Neuroscientist, v. 2, pp. 145–152 (1996)); (Nurse et al., Br. J. Urol., v. 68 pp. 27–31 (1991)), (Howe et al., J. Pharmacol. Exp. Ther., v. 274 pp. 884–890 (1995)); (Spanswick et al.; Nature, v. 390 pp. 521–25 (Dec. 4, 1997)); (Dompeling Vasa. Supplementum (1992) 3434); (WO9932495); (Grover, J Mol Cell Cardiol. (2000) 32, 677), and (Buchheit, Pulmonary Pharmacology & Therapeutics (1999) 12, 103). Such diseases or conditions include asthma, epilepsy, male sexual dysfunction, female sexual dysfunction, pain, bladder overactivity, stroke, diseases associated with decreased skeletal blood flow such as Raynaud's phenomenon and intermittent claudication, eating disorders, functional bowel disorders, neurodegeneration, benign prostatic hyperplasia (BPH), dysmenorrhea, premature labor, alopecia, cardioprotection, coronary artery disease, angina and ischemia.

Bladder overactivity is a condition associated with the spontaneous, uncontrolled contractions of the bladder smooth muscle. Bladder overactivity thus is associated with sensations of urgency, urinary incontinence, pollakiuria, bladder instability, nocturia, bladder hyerreflexia, and enuresis (Resnick, The Lancet (1995) 346, 94–99; Hampel, Urology (1997) 50 (Suppl 6A), 4–14; Bosch, BJU International (1999) 83 (Suppl 2), 7–9 Potassium channel openers (KCOs) act as smooth muscle relaxants. Because bladder overactivity and urinary incontinence can result from the spontaneous, uncontrolled contractions of the smooth muscle of the bladder, the ability of potassium channel openers to hyperpolarize bladder cells and relax bladder smooth muscle may provide a method to ameliorate or prevent bladder overactivity, pollakiuria, bladder instability, nocturia, bladder hyperreflexia, urinary incontinence, and enuresis (Andersson, Urology (1997) 50 (Suppl 6A), 74–84; Lawson, Pharmacol. Ther., (1996) 70, 3963; Nurse., Br. J. Urol., (1991) 68, 27–31; Howe, J. Pharmacol. Exp. Ther., (1995)274, 884–890; Gopalakishnan, Drug Development Research, (1993) 28, 95–127).

The irritative symptoms of BPH (urgency, frequency, nocturia and urge incontinence) have been shown to be correlated to bladder instability (Pandita, The J. of Urology (1999) 162, 943). Therefore the ability of potassium channel openers to hyperpolarize bladder cells and relax bladder smooth muscle may provide a method to ameliorate or prevent the symptoms associated with BPH. (Andersson, Prostate (1997) 30: 202–215).

The excitability of corpus cavernosum smooth muscle cells is important in the male erectile process. The relaxation of corporal smooth muscle cells allows arterial blood to build up under pressure in the erectile tissue of the penis leading to erection (Andersson, Pharmacological Reviews (1993) 45, 253). Potassium channels play a significant role in modulating human corporal smooth muscle tone, and thus, erectile capacity. By patch clamp technique, potassium channels have been characterized in human corporal smooth muscle cells (Lee, Int. J. Impot. Res. (1999) 11(4),179–188). Potassium channel openers are smooth muscle relaxants and have been shown to relax corpus cavernosal smooth muscle and induce erections (Andersson, Pharmacological Reviews (1993) 45, 253; Lawson, Pharmacol. Ther., (1996) 70, 39–63, Vick, J. Urol. (2000) 163: 202). Potassium channel openers therefore may have utility in the treatment of male sexual dysfunctions such as male erectile dysfunction, impotence and premature ejaculation.

The sexual response in women is classified into four stages: excitement, plateau, orgasm and resolution. Sexual arousal and excitement increase blood flow to the genital area, and lubrication of the vagina as a result of plasma transudation. Topical application of KCOs like minoxidil and nicorandil have been shown to increase clitoral blood flow (Kim, et al., J. Urol. (2000) 163 (4): 240). KCOs may be effective for the treatment of female sexual dysfunction including clitoral erectile insufficiency, vaginismus and vaginal engorgement (Goldstein and Berman., Int. J. Impotence Res. (1998) 10:S84–S90), as KCOs can increase blood flow to female sexual organs.

Potassium channel openers may have utility as tocolytic agents to inhibit uterine Contractions to delay or prevent premature parturition in individuals or to slow or arrest delivery for brief periods to undertake other therapeutic measures (Sanborn, Semin. Perinatol. (1995) 19, 31–40, Morrison, Am. J. Obstet. Gynecol. (1993) 169(5), 1277–85). Potassium channel openers also inhibit contractile responses of human uterus and intrauterine vasculature. This combined effect would suggest the potential use of KCOs for dysmenhorrea (Kostrzewska, Acta Obstet. Gynecol. Scand. (1996) 75(10), 886–91). Potassium channel openers relax uterine smooth muscle and intrauterine vasculature and therefore may have utility in the treatment of premature labor and dysmenorrhoea (Lawson, Pharmacol. Ther., (1996) 70, 39–63).

Potassium channel openers relax gastrointestinal smooth tissues and therefore may be useful in the treatment of functional bowel disorders such as irritable bowel syndrome (Lawson, Pharmacol. Ther., (1996) 70, 39–63).

Potassium channel openers relax airway smooth muscle and induce bronchodilation. Therefore potassium channel openers may be useful in the treatment of asthma and airways hyperreactivity (Lawson, Pharmacol. Ther., (1996) 70, 39–63; Buchheit, Pulmonary Pharmacology & Therapeutics (1999) 12, 103; Gopalakrishnan, Drug Development Research, (1993) 28, 95–127).

Neuronal hyperpolarization can produce analgesic effects. The opening of potassium channels by potassium channel openers and resultant hyperpolarization in the membrane of target neurons is a key mechanism in the effect of opioids. The peripheral antinociceptive effect of morphine results from activation of ATP-sensitive potassium channels, which causes hyperpolarization of peripheral terminals of primary afferents, leading to a decrease in action potential generation (Rodrigues, Br. J. Pharmacol. (2000) 129(1), 11–04). Opening of $K_{ATP}$ channels by potassium channel openers plays an important role in the antinociception mediated by alpha-2 adrenoceptors and mu opioid receptors. KCOs can potentiate the analgesic action of both morphine and dexmedetomidine via an activation of $K_{ATP}$ channels at the spinal cord level (Vergoni, Life Sci. (1992) 50(16), PL135–8; Asano, Anesth. Analg. (2000) 90(5), 1146–51). Thus, potassium channel openers can hyperpolarize neuronal cells and have shown analgesic effects. Potassium channel openers therefore may be usefull as analgesics in the treatment of various pain states including but not limited to migraine and dyspareunia (Lawson, Pharmacol. Ther., (1996) 70, 39–63; Gopalakrishnan, Drug Development Research, (1993) 28, 95–127; Gehlert, Prog. Neuro-Psychopharmacol. & Biol. Psychiat., (1994) 18, 1093–1102).

Epilepsy results from the propagation of nonphysiologic electrical impulses. Potassium channel openers hyperpolanize neuronal cells and lead to a decrease in cellular excitability and have demonstrated antiepileptic effects. Therefore potassium channel openers may be useful in the treatment of epilepsy (Lawson, Pharmacol. Ther., (1996) 70, 39–63; Gopalakrishnan, Drug Development Research, (1993) 28, 95–127, Gehlert, Prog. Neuro-Psychopharmacol. & Biol. Psychiat, (1994) 18, 1093–1102).

Neuronal cell depolarization can lead to excitotoxicity and neuronal cell death. When this occurs as a result of acute ischemic conditions, it can lead to stroke. Long-term neurodegeneration can bring about conditions such as Alzheimer's and Parkinson's diseases. Potassium channel openers can hyperpolarize neuronal cells and lead to a decrease in cellular excitability. Activation of potassium channels has been shown to enhance neuronal survival. Therefore potassium channel openers may have utility as neuroprotectants in the treatment of neurodegenerative conditions and diseases such as cerebral ischemia, stroke, Alzheimer's disease and Parkinson's disease (Lawson, Pharmacol. Ther., (1996) 70, 39–63; Gopalakrishnan, Drug Development Research, (1993) 28, 95–127; Gehlert, Prog. Neuro-Psychopharmacol & Biol. Psychiat., (1994) 18, 1093–1102; Freedman, The Neuroscientist (1996) 2, 145).

Potassium channel openers may have utility in the treatment of diseases or conditions associated with decreased skeletal muscle blood flow such as Raynaud's syndrome and intermittent claudication (Lawson, Pharmacol. Ther., (1996) 70, 39–63, Gopalakiishnan, Drug Development Research, (1993) 28, 95–127; Dompeling Vasa. Supplementum (1992) 3434; and WO9932495).

Potassium channel openers may be useful in the treatment of eating disorders such as obesity (Spanswick, Nature, (1997) 390, 521–25; Freedman, The Neuroscientist (1996) 2, 145).

Potassium channel openers have been shown to promote hair growth therefore potassium channel openers have utility in the treatment of hair loss and baldness also known as alopecia (Lawson, Pharmacol. Ther., (1996) 70, 39–63; Gopalakrishnan, Drug Development Research, (1993) 28, 95–127).

Potassium channel openers possess cardioprotective effects against myocardial injury during ischemia and reperfusion. (Garlid, Circ. Res. (1997) 81(6), 1072–82). Therefore, potassium channel openers may be useful in the treatment of heart diseases (Lawson, Pharmacol. Ther., (1996) 70,39–63; Grover, J. Mol. Cell Cardiol. (2000) 32, 677).

Potassium channel openers, by hyperpolarization of smooth muscle membranes, can exert vasodilation of the collateral circulation of the coronary vasculature leading to increase blood flow to ischemic areas and could be useful for the coronary artery disease (Lawson, Pharmacol. Ther:, (1996) 70,39–63; Gopalakrishnan, Drug Development Research, (1993) 28,.95–127).

U.S. Pat. No. 3,636,105 discloses a group of 1-fluoroacetylamino-2,2,2-trichloroethyl urea rodenticide agents. U.S. Pat. No. 4,146,646 discloses a group of bisamides as fungicide agents. ZA 695324 discloses a group of thioureas useful as insecticide, acaricidal, and rodenticide agents. U.S. Pat. No. 5,397,790 discloses a group of substituted isoquinolinyl-1,2-diaminocyclobutene-3,4-diones as smooth muscle relaxants. U.S. Pat. No. 5,401,753 and U.S. Pat. No. 5,403,854 disclose groups of substituted N-heteroaryl-1,2-diaminocyclobutene-3,4-diones as smooth muscle relaxants. U.S. Pat. No. 5,403,853, U.S. Pat. No. 5,466,712, and WO 98/33763 disclose groups of substituted N-aryl-1,2-diaminocyclobutene-3,4-diones. U.S. Pat. No. 5,464,867 and U.S. Pat. No. 5,512,585 disclose groups of substituted N-heteroaryl-N'-alkyl-1,2-diaminocyclobutene-3,4-diones as smooth muscle relaxants. U.S. Pat. No. 5,506,252 and WO 96/15103 disclose groups of substituted N-aryl- and N-heteroaryl-1,2-diaminocyclobutene-3,4-diones as smooth muscle relaxants. U.S. Pat. No. 5,750,574 discloses a group of substituted fluorinated N-arylmethylamino derivatives of cyclobutene-3,4-dione as agents for reducing the adverse effects of smooth muscle contractions. U.S. Pat. No. 5,763,474, U.S. Pat. No. 5,780,505, U.S. Pat. No. 5,846,999, and WO 98/02413 disclose groups of substituted N-arylmethylamino derivatives of cyclobutene-3,4-diones as smooth muscle relaxants U.S. Pat. No. 5,872,139 and WO 97/48682 disclose groups of N-heterocyclylmethylamino derivatives of cyclobutene-3,4-dione as agents for reducing the adverse effects of smooth muscle contractions. U.S. Pat. No. 6,166,050 discloses a group of amino(heterocyclylanilino)-3-cyclobutene-1,2-diones as inhibitors of leukocyte adhesion mediated by VLA-4. WO 94/29277 discloses a group of 3,4-diaminocyclobutene-1,2-diones as inhibitors of cGMP phosphodiesterase. WO 00/51973 and WO 00/63160 discloses groups of substituted N-(cyclohexylmethyl)amino-3 -cyclobutene-1,2-diones as inhibitors phosphodiesterase V. WO 00/73260 discloses a group of 3,4-diamino-3-cyclobutene-1,2-diones as inhibitors of leukocyte adhesion mediated by VLA-4.

Compounds of the present invention are novel, hyperpolarize cell membranes, open potassium channels, relax smooth muscle cells, inhibit bladder contractions and may be useful for treating diseases that can be ameliorated by opening potassium channels.

SUMMARY OF THE INVENTION

In its principle embodiment, the present invention discloses compounds having formula (I)

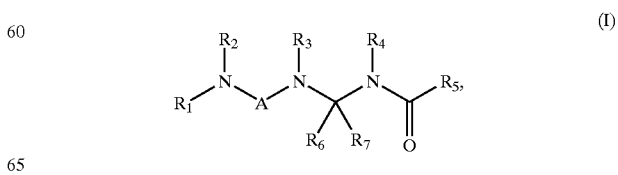

or a pharmaceutically acceptable salt thereof, wherein

A is selected from the group consisting of

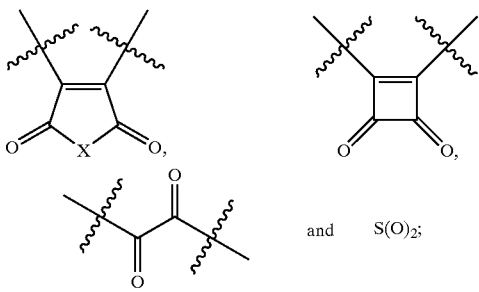

and S(O)$_2$;

X is selected from the group consisting of CH$_2$, O and N(Z);

Z is selected from the group consisting of hydrogen and alkyl;

R$_1$ is selected from aryl, arylalkyl, heterocycle and heterocyclealkyl;

R$_2$, R$_3$ and R$_4$ are independently selected from hydrogen and alkyl;

R$_5$ is selected from aryl, arylalkenyl, arylalkyl, aryloxyalkyl, heterocycle and heterocyclealkyl, R$_6$ is selected from hydrogen, alkenyl, alkenyloxyalkyl, alkenyloxy(alkenyloxy)alkyl, alkoxyalkyl, alkoxycarbonyl, alkoxycarbonylalkyl, alkoxycarbonyl(halo)alkyl, alkoxy(halo)alkyl, alkyl, alkylcarbonyl, alkylcarbonylalkyl, alkylcarbonyl(halo)alkyl, alkylcarbonyloxyalkyl, alkylsulfinylalkyl, alkylsulfonylalkyl, alkylthioalkyl, alkynyl, aryl, arylalkoxyalkyl, arylalkoxycarbonyl, arylalkoxycarbonylalkyl, arylalkyl, arylcarbonyl, arylcarbonylalkyl, arylcarbonyloxyalkyl, aryl(halo)alkyl, aryloxyalkyl, aryloxycarbonyl, aryloxycarbonylalkyl, arylalkylthioalkyl, arylsulfonylalkyl, carboxy, carboxyalkyl, carboxy(halo)alkyl, cyanoalkyl, cyano(halo)alkyl, cycloalkenyl, cycloalkenylalkyl, cycloalkyl, cycloalkylalkoxyalkyl, cycloalkylalkyl, cycloalkylcarbonyl, cycloalkyloxyalkyl, cycloalkylalkylthioalkyl, formyl, haloalkenyl, haloalkyl, haloalkylcarbonyl, haloalkynyl, heterocycle, heterocyclealkoxyalkyl, heterocyclealkyl, heterocyclecarbonyl, heterocycleoxyalkyl, heterocyclealkylthioalkyl, hydroxyalkyl, mercaptoalkyl, sulfamylalkyl, sulfamyl(halo)alkyl, (NR$_9$R$_{10}$)alkyl, (NR$_9$R$_{10}$)carbonyl, and (NR$_9$R$_{10}$)carbonylalkyl;

R$_7$ is selected from hydrogen, haloalkyl, and lower alkyl; or

R$_6$ and R$_7$ taken together with the carbon atom to which they are attached, together form a 5 or 6 membered carbocyclic ring wherein the 5 or 6 membered carbocyclic ring is optionally substituted with 1 or 2 substituents independently selected from alkenyl, alkoxy, alkyl, alkynyl, halogen, haloalkoxy, and haloalkyl;

R$_9$ and R$_{10}$ are independently selected from hydrogen, alkoxysulfonyl, alkyl, alkylcarbonyl, alkylsulfonyl, aryl, arylalkyl, arylcarbonyl, arylsulfonyl and formyl.

DETAILED DESCRIPTION OF THE INVENTION

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof All patents, patent applications, and literature references cited in the specification are herein incorporated by reference in their entirety.

In its principle embodiment, the present invention discloses compounds having formula (I)

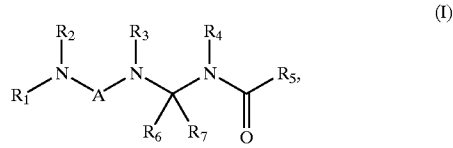

(I)

or a pharmaceutically acceptable salt thereof, wherein

A is selected from the group consisting of

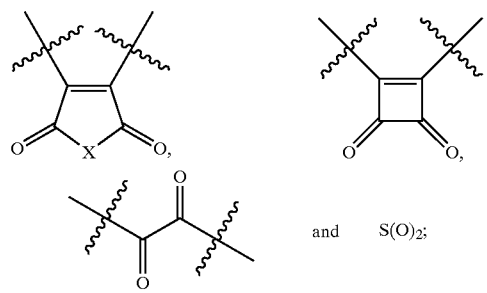

and S(O)$_2$;

X is selected from the group consisting of CH$_2$, O and N(Z);

Z is selected from the group consisting of hydrogen and alkyl;

R$_1$ is selected from aryl, arylalkyl, heterocycle and heterocyclealkyl;

R$_2$, R$_3$ and R$_4$ are independently selected from hydrogen and alkyl;

R$_5$ is selected from aryl, arylalkyl, aryloxyalkyl, heterocycle and heterocyclealkyl;

R$_6$ is selected from hydrogen, alkenyl, alkenyloxyalkyl, alkenyloxy(alkenyloxy)alkyl, alkoxyalkyl, alkoxycarbonyl, alkoxycarbonylalkyl, alkoxycarbonyl(halo)alkyl, alkoxy(halo)alkyl, alkyl, alkylcarbonyl, alkylcarbonylalkyl, alkylcarbonyl(halo)alkyl, alkylcarbonyloxyalkyl, alkylsulfinylalkyl, alkylsulfonylalkyl, alkylthioalkyl, alkynyl, aryl, arylalkoxyalkyl, arylalkoxycarbonyl, arylalkoxycarbonylalkyl, arylalkyl, arylcarbonyl, arylcarbonylalkyl, arylcarbonyloxyalkyl, aryl(halo)alkyl, aryloxyalkyl, aryloxycarbonyl, aryloxycarbonylalkyl, arylalkylthioalkyl, arylsulfonylalkyl, carboxy, carboxyalkyl, carboxy(halo)alkyl, cyanoalkyl, cyano(halo)alkyl, cycloalkenyl, cycloalkenylalkyl, cycloalkyl, cycloalkylalkoxyalkyl, cycloalkylalkyl, cycloalkylcarbonyl, cycloalkyloxyalkyl, cycloalkylalkylthioalkyl, formyl, haloalkenyl, haloalkyl, haloalkylcarbonyl, haloalkynyl, heterocycle, heterocyclealkoxyalkyl, heterocyclealkyl, heterocyclecarbonyl, heterocycleoxyalkyl, heterocyclealkylthioalkyl, hydroxyalkyl, mercaptoalkyl, sulfamylalkyl, sulfamyl(halo)alkyl, $(NR_9R_{10})$alkyl, $(NR_9R_{10})$carbonyl and $(NR_9R_{10})$carbonylalkyl;

$R_7$ is selected from hydrogen, haloalkyl, and lower alkyl; or $R_6$ and $R_7$ taken together with the carbon atom to which they are attached, together form a 5 or 6 membered carbocyclic ring wherein the 5 or 6 membered carbocyclic ring is optionally substituted with 1 or 2 substituents independently selected from alkenyl, alkoxy, alkyl, alkynyl, halogen, haloalkoxy, and haloalkyl;

$R_9$ and $R_{10}$ are independently selected from hydrogen, alkoxysulfonyl, alkyl, alkylcarbonyl, alkylsulfonyl, aryl, arylalkyl, arylcarbonyl, arylsulfonyl and formyl.

In another embodiment of the present invention, compounds have formula (I) wherein A is selected from

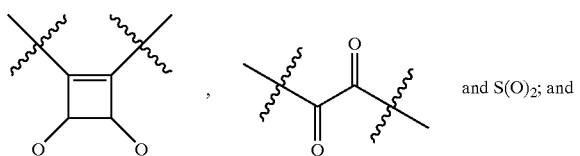

and $S(O)_2$; and $R_1$, $R_2$, $R_3$, $R_4$, $R_5$, $R_6$ and $R_7$ are as defined in formula (I).

In another embodiment of the present invention, compounds have formula (II)

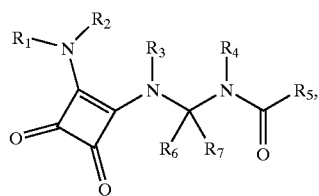

(II)

or a pharmaceutically acceptable salt thereof, wherein $R_1$, $R_2$, $R_3$, $R_4$, $R_5$, $R_6$ and $R_7$ are as defined in formula (I).

In another embodiment of the present invention, compounds have formula (II) wherein $R_1$ is heterocycle; $R_5$ is aryl; and $R_2$, $R_3$, $R_4$, $R_6$ and $R_7$ are as defined in formula (I).

In another embodiment of the present invention, compounds have formula (II) wherein $R_1$ is heterocycle wherein said heterocycle is selected from optionally substituted pyridinyl and optionally substituted pyrazinyl; $R_5$ is aryl wherein said aryl is optionally substituted phenyl; and $R_2$, $R_3$, $R_4$, $R_6$ and $R_7$ are as defined in formula (I).

In another embodiment of the present invention, compounds have formula (II) wherein $R_1$ is heterocycle wherein said heterocycle is selected from optionally substituted pyridinyl and optionally substituted pyrazinyl; $R_2$ is hydrogen; $R_3$ is hydrogen; $R_4$ is hydrogen; $R_5$ is aryl wherein said aryl is optionally substituted phenyl; $R_6$ is selected from hydrogen and alkyl; and $R_7$ is hydrogen.

In another embodiment of the present invention, compounds have formula (II) wherein $R_1$ is heterocycle wherein said heterocycle is optionally substituted pyridinyl; $R_2$ is hydrogen; $R_3$ is hydrogen; $R_4$ is hydrogen; $R_5$ is aryl wherein said aryl is optionally substituted phenyl; $R_6$ is selected from arylalkyl and heterocyclealkyl wherein the aryl portion of said arylalkyl is optionally substituted phenyl and the heterocycle portion of said heterocyclealkyl is optionally substituted pyridinyl; and $R_7$ is hydrogen.

In another embodiment of the present invention, compounds have formula (II) wherein $R_1$ is heterocycle wherein said heterocycle is optionally substituted pyridinyl; $R_2$ is hydrogen; $R_3$ is hydrogen; $R_4$ is hydrogen; $R_5$ is aryl wherein said aryl is optionally substituted phenyl; $R_6$ is haloalkyl; and $R_7$ is hydrogen.

In another embodiment of the present invention, compounds have formula (II) wherein $R_1$ is heterocycle wherein said heterocycle is optionally substituted pyridinyl; $R_2$ is hydrogen; $R_3$ is hydrogen; $R_4$ is hydrogen; $R_5$ is aryl wherein said aryl is optionally substituted phenyl;, $R_6$ is selected from alkenyl, alkenyloxy(alkenyloxy)alkyl, cyanoalkyl and cycloalkylalkyl; and $R_7$ is hydrogen.

In another embodiment of the present invention, compounds have formula (II) wherein $R_1$ is heterocycle wherein heterocycle is optionally substituted pyridinyl; $R_5$ is aryl wherein aryl is selected from optionally substituted naphthyl and optionally substituted fluorenyl; and $R_2$, $R_3$, $R_4$, $R_6$ and $R_7$ are as defined in formula (I).

In another embodiment of the present invention, compounds have formula (II) wherein $R_1$ is heterocycle wherein heterocycle is optionally substituted pyridinyl; $R_2$ is hydrogen; $R_3$ is hydrogen; $R_4$ is hydrogen; $R_5$ is aryl wherein aryl is selected from optionally substituted naphthyl and optionally substituted fluorenyl; $R_6$ is selected from alkenyl, alkenyloxy(alkenyloxy)alkyl, arylalkyl wherein the aryl portion of said arylalkyl is optionally substituted phenyl, cyanoalkyl, cycloalkylalkyl and haloalkyl and $R_7$ is hydrogen.

In another embodiment of the present invention, compounds have formula (II) wherein $R_1$ is heterocycle wherein said heterocycle is optionally substituted pyridinyl; $R_2$ is hydrogen, $R_3$ is hydrogen; $R_4$ is hydrogen; $R_5$ is aryl wherein aryl is selected from optionally substituted naphthyl and optionally substituted fluorenyl 1; $R_6$ is alkyl; and $R_7$ is hydrogen.

In another embodiment of the present invention, compounds have formula (II) wherein $R_1$ is aryl; $R_5$ is aryl; and $R_2$, $R_3$, $R_4$, $R_6$ and $R_7$ are as defined in formula (I).

In another embodiment of the present invention, compounds have formula (II) wherein $R_1$ is aryl wherein said aryl is optionally substituted phenyl; $R_5$ is aryl wherein said aryl is optionally substituted phenyl; and $R_2$; $R_3$, $R_4$, $R_6$ and $R_7$ are as defined in formula (I).

In another embodiment of the present invention, compounds have formula (II) wherein $R_1$ is aryl wherein said aryl is optionally substituted phenyl $R_2$ is hydrogen; $R_3$ is hydrogen; $R_4$ is hydrogen; $R_5$ is aryl wherein said aryl is optionally substituted phenyl; $R_6$ is selected from alkenyl, alkenyloxy(alkenyloxy)alkyl, alkyl, arylalkyl wherein the aryl portion of said arylalkyl is optionally substituted phenyl, cyanoalkyl, cycloalkylalkyl and haloalkyl; and $R_7$ is hydrogen.

In another embodiment of the present invention, compounds have formula (II) wherein $R_1$ is aryl wherein said aryl is optionally substituted phenyl; $R_2$ is hydrogen, $R_3$ is hydrogen; $R_4$ is hydrogen; $R_5$ is aryl wherein said aryl is optionally substituted phenyl; $R_6$ is alkyl; and $R_7$ is hydrogen In another embodiment of the present invention, compounds have formula (II) wherein $R_1$ is heterocycle; $R_5$ is arylalkyl; and $R_2$, $R_3$, $R_4$, $R_6$ and $R_7$ are as defined in formula (I).

In another embodiment of the present invention, compounds have formula (II) wherein $R_1$ is heterocycle wherein said heterocycle is optionally substituted pyridinyl; $R_5$ is selected from arylalkyl, arylalkenyl and aryloxyalkyl wherein the aryl portion of said arylalkyl, arylalkenyl, and aryloxyalkyl is optionally substituted phenyl; and $R_2$, $R_3$, $R_4$, $R_6$ and $R_7$ are as defined in formula (I).

In another embodiment of the present invention, compounds have formula (II) wherein $R_1$ is heterocycle wherein said heterocycle is optionally substituted pyridinyl; $R_2$ is hydrogen; $R_3$ is hydrogen; $R_4$ is hydrogen, $R_5$ is selected from arylalkyl, arylalkenyl and aryloxyalkyl wherein the aryl portion of said arylalkyl is optionally substituted phenyl, the aryl portion of said arylalkenyl is optionally substituted phenyl and the aryl portion of said aryloxyalkyl is optionally substituted phenyl; $R_6$ is selected from alkenyl, alkenyloxy(alkenyloxy)alkyl, arylalkyl wherein the aryl portion of said arylalkyl is optionally substituted phenyl, cyanoalkyl, cycloalkylalkyl and haloalkyl; and $R_7$ is hydrogen.

In another embodiment of the present invention, compounds have formula (II) wherein $R_1$ is heterocycle wherein said heterocycle is optionally substituted pyridinyl, $R_2$ is hydrogen; $R_3$ is hydrogen; $R_4$ is hydrogen, $R_5$ is selected from arylalkyl, arylalkenyl and aryloxyalkyl wherein the aryl portion of said arylalkyl is optionally substituted phenyl, the aryl portion of said arylalkenyl is optionally substituted phenyl and the aryl portion of said aryloxyalkyl is optionally substituted phenyl; $R_6$ is selected from alkyl and arylalkyl wherein the aryl portion of said arylalkyl is optionally substituted phenyl; and $R_7$ is hydrogen.

In another embodiment of the present invention, compounds have formula (II) wherein $R_1$ is heterocycle, $R_5$ is heterocyclealkyl; and $R_2$, $R_3$, $R_4$, $R_6$ and $R_7$ are as defined in formula (I).

In another embodiment of the present invention, compounds have formula (II) wherein $R_1$ is heterocycle wherein said heterocycle is optionally substituted pyridinyl; $R_5$ is heterocyclealkyl wherein the heterocycle portion of said heterocyclealkyl is optionally substituted pyridinyl; and $R_2$, $R_3$, $R_4$, $R_6$ and $R_7$ are as defined in formula (I).

In another embodiment of the present invention, compounds have formula (II) wherein $R_1$ is heterocycle wherein said heterocycle is optionally substituted pyridinyl; $R_2$ is hydrogen; $R_3$ is hydrogen; $R_4$ is hydrogen; $R_5$ is heterocyclealkyl wherein the heterocycle portion of said heterocyclealkyl is optionally substituted pyridinyl; $R_6$ is selected from alkenyl, alkenyloxy(alkenyloxy)alkyl, arylalkyl wherein the aryl portion of said arylalkyl is optionally substituted phenyl, cyanoalkyl, cycloalkylalkyl and haloalkyl, and $R_7$ is hydrogen.

In another embodiment of the present invention, compounds have formula (II) wherein $R_1$ is heterocycle wherein said heterocycle is optionally substituted pyridinyl, $R_2$ is hydrogen; $R_3$ is hydrogen, $R_4$ is hydrogen, $R_5$ is heterocyclealkyl wherein the heterocycle portion of said heterocyclealkyl is optionally substituted pyridinyl; $R_6$ is alkyl; and $R_7$ is hydrogen.

In another embodiment of the present invention, compounds have formula (II) wherein $R_1$ is heterocycle; $R_5$ is heterocycle; and $R_2$, $R_3$, $R_4$, $R_6$ and $R_7$ are as defined in formula (I).

In another embodiment of the present invention, compounds have formula (II) wherein $R_1$ is heterocycle wherein said heterocycle is optionally substituted pyridinyl; $R_5$ is heterocycle wherein said heterocycle is selected from optionally substituted pyridinyl, optionally substituted thienyl and optionally substituted furyl; and $R_2$, $R_3$, $R_4$, $R_6$ and $R_7$ are as defined in formula (I).

In another embodiment of the present invention, compounds have formula (II) wherein $R_1$ is heterocycle wherein said heterocycle is optionally substituted pyridinyl; $R_2$ is hydrogen; $R_3$ is hydrogen; $R_4$ is hydrogen; $R_5$ is heterocycle wherein said heterocycle is selected from optionally substituted pyridinyl, optionally substituted thienyl and optionally substituted furyl; $R_6$ is selected from alkenyl, alkenyloxy (alkenyloxy)alkyl, arylalkyl wherein the aryl portion of said arylalkyl is optionally substituted phenyl, cyanoalkyl, cycloalkylalkyl and haloalkyl; and $R_7$ is hydrogen.

In another embodiment of the present invention, compounds have formula (II) wherein $R_1$ is heterocycle wherein said heterocycle is optionally substituted pyridinyl; $R_2$ is hydrogen; $R_3$ is hydrogen; $R_4$ is hydrogen; $R_5$ is heterocycle wherein said heterocycle is selected from optionally substituted pyridinyl, optionally substituted thienyl and optionally substituted furyl; $R_6$ is alkyl; and $R_7$ is hydrogen.

In another embodiment of the present invention, compounds have formula (III)

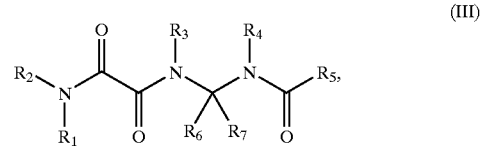

or a pharmaceutically acceptable salt therof, wherein $R_1$, $R_2$, $R_3$, $R_4$, $R_5$, $R_6$ and $R_7$ are as defined in formula (I).

In another embodiment of the present invention, compounds have formula (III) wherein $R_1$ is heterocycle; $R_5$ is aryl; and $R_2$, $R_3$, $R_4$, $R_6$ and $R_7$ are as defined in formula In another embodiment of the present invention, compounds have formula (III) wherein $R_1$ is heterocycle wherein said heterocycle is optionally substituted pyridinyl; $R_5$ is aryl wherein said aryl is optionally substituted phenyl; and $R_2$, $R_3$, $R_4$, $R_6$ and $R_7$ are as defined in formula (I).

In another embodiment of the present invention, compounds have formula (III) wherein $R_1$ is heterocycle wherein said heterocycle is optionally substituted pyridinyl; $R_2$ is hydrogen; $R_3$ is hydrogen; $R_4$ is hydrogen; $R_5$ is aryl wherein said aryl is optionally substituted phenyl; $R_6$ is selected from alkenyl, alkenyloxy(alkenyloxy)alkyl, arylalkyl wherein the aryl portion of said arylalkyl is optionally substituted phenyl, cyanoalkyl, cycloalkylalkyl and haloalkyl; and $R_7$ is hydrogen.

In another embodiment of the present invention, compounds have formula (III) wherein $R_1$ is heterocycle wherein said heterocycle is optionally substituted pyridinyl; $R_2$ is hydrogen; $R_3$ is hydrogen; $R_4$ is hydrogen; $R_5$ is aryl wherein said aryl is optionally substituted phenyl; $R_6$ is alkyl; and $R_7$ is hydrogen.

In another embodiment of the present invention, compounds have formula (IV)

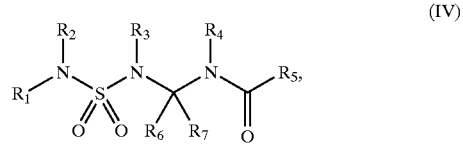

or a pharmaceutically acceptable salt therof, wherein $R_1$, $R_2$, $R_3$, $R_4$, $R_5$, $R_6$ and $R_7$ are as defined in formula (I).

In another embodiment of the present invention, compounds have formula (IV) wherein $R_1$ is heterocycle; $R_5$ is aryl; and $R_2$, $R_3$, $R_4$, $R_6$ and $R_7$ are as defined in formula (I).

In another embodiment of the present invention, compounds have formula (IV) wherein $R_1$ is heterocycle wherein said heterocycle is optionally substituted pyridinyl; $R_5$ is aryl wherein said aryl is optionally substituted phenyl; and $R_2$, $R_3$, $R_4$, $R_6$ and $R_7$ are as defined in formula (I).

In another embodiment of the present invention, compounds have formula (IV) wherein $R_1$ is heterocycle wherein said heterocycle is optionally substituted pyridinyl; $R_2$ is hydrogen; $R_3$ is hydrogen $R_4$ is hydrogen; $R_5$ is aryl wherein said aryl is optionally substituted phenyl; $R_6$ is selected from alkenyl, alkenyloxy(alkenyloxy)alkyl, arylalkyl wherein the aryl portion of said arylalkyl is optionally substituted phenyl, cyanoalkyl, cycloalkylalkyl and haloalkyl; and $R_7$ is hydrogen.

In another embodiment of the present invention, compounds have formula (IV) wherein $R_1$ is heterocycle wherein said heterocycle is optionally substituted pyridinyl; $R_2$ is hydrogen; $R_3$ is hydrogen; $R_4$ is hydrogen; $R_5$ is aryl wherein said aryl is optionally substituted phenyl; $R_6$ is alkyl; and $R_7$ is hydrogen.

Another embodiment of the present invention relates to pharmaceutical compositions comprising a therapeutically effective amount of a compound of formula I–IV or a pharmaceutically acceptable salt, ester, amide, or prodrug thereof in combination with a pharmaceutically acceptable carrier.

Another embodiment of the present invention relates to a method of treating male sexual dysfunction including, but not limited to, male erectile dysfunction and premature ejaculation, comprising administering a therapeutically effective amount of a compound of formula I–IV or a pharmaceutically acceptable salt, ester, amide, or prodrug thereof.

Another embodiment of the present invention relates to a method of treating female sexual dysfunction including, but not limited to, female anorgasmia, clitoral erectile insufficiency, vaginal engorgement, dyspareunia, and vaginismus comprising administering a therapeutically effective amount of a compound of formula I–IV or a pharmaceutically acceptable salt, ester, amide, or prodrug thereof.

Another embodiment of the present invention relates to a method of treating asthma, epilepsy, Raynaud's syndrome, intermittent claudication, migraine, pain, bladder overactivity, pollakiuria, bladder instability, nocturia, bladder hyperreflexia, eating disorders, urinary incontinence, enuresis, functional bowel disorders, neurodegeneration, benign prostatic byperplasia (BPH), dysmenorrhea, premature labor, alopecia, cardioprotection, and ischemia comprising administering a therapeutically effective amount of a compound of formula I–IV or a pharmaceutically acceptable salt, ester, amide, or prodrug thereof Another embodiment of the present invention relates to a process of preparing a compound of formula (V)

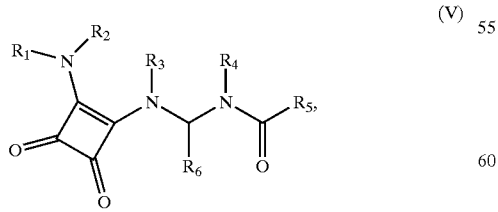

(V)

wherein $R_1$ is selected from aryl, arylalkyl, heterocycle and heterocyclealkyl;

$R_2$, $R_3$ and $R_4$ are independently selected from hydrogen and alkyl;

$R_5$ is selected from aryl, arylalkyl, heterocycle and heterocyclealkyl;

$R_6$ is selected from hydrogen, alkenyl, alkenyloxyalkyl, alkenyloxy(alkenyloxy)alkyl, alkoxyalkyl, alkoxycarbonyl, alkoxycarbonylalkyl, alkoxycarbonyl(halo)alkyl, alkoxy(halo)alkyl, alkyl, alkylcarbonyl, alkylcarbonylalkyl, alkylcarbonyl(halo)alkyl, alkylcarbonyloxyalkyl, alkylsulfinylalkyl, alkylsulfonylalkyl, alkylthioalkyl, alkynyl, aryl, arylalkoxyalkyl, arylalkoxycarbonyl, arylalkoxycarbonylalkyl, arylalkyl, arylcarbonyl, arylcarbonylalkyl, arylcarbonyloxyalkyl, aryl(halo)alkyl, aryloxyalkyl, aryloxycarbonyl, aryloxycarbonylalkyl, arylalkylthioalkyl, arylsulfonylalkyl, carboxy, carboxyalkyl, carboxy(halo)alkyl, cyanoalkyl, cyano(halo)alkyl, cycloalkenyl, cycloalkenylalkyl, cycloalkyl, cycloalkylalkoxyalkyl, cycloalkylalkyl, cycloalkylcarbonyl, cycloalkyloxyalkyl, cycloalkylalkylthioalkyl, formyl, haloalkenyl, haloalkyl, haloalkylcarbonyl, haloalkynyl, heterocycle, heterocyclealkoxyalkyl, heterocyclealkyl, heterocyclecarbonyl, heterocycleoxyalkyl, heterocyclealkylthioalkyl, hydroxyalkyl, mercaptoalkyl, sulfamylalkyl, sulfamyl(halo)alkyl, $(NR_9R_{10})$alkyl, $(NR_9R_{10})$carbonyl and $(NR_9R_{10})$carbonylalkyl; and $R_9$ and $R_{10}$ are independently selected from hydrogen, alkoxysulfonyl, alky, alkylcarbonyl, alkylsulfonyl, aryl, arylalkyl, arylcarbonyl, arylsulfonyl and formyl;

the process comprising:
(a) reacting an aldehyde of formula (VI)

(VI)

with three components, an amide of formula (VII)

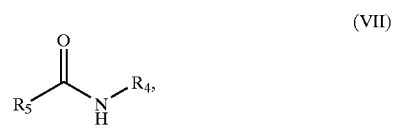

(VII)

1H-benzotriazole-polystyrene resin and an acid in a first solvent at about 50° C. to about 80° C., wherein $R_4$, $R_5$ and $R_6$ are as defined above;

(b) reacting the product of step (a) with a base and a compound of formula (VI)

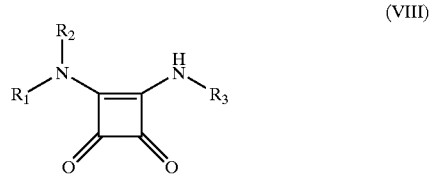

(VIII)

in a second solvent wherein $R_1$, $R_2$ and $R_3$ are as defined above to provide a compound of formula (V).

In another embodiment of the present invention is disclosed a process for preparing a compound of formula (V) using an acid selected from para-toluenesulfonic acid monohydrate and acetic acid.

In another embodiment of the present invention is disclosed a process for preparing a compound of formula (V) using a first solvent selected from 1,4-dioxane, 2-methoxyethanol, tetrahydrofuran, trimethyl orthoformate and mixtures thereof In another embodiment of the present invention is disclosed a process for preparing a compound of formula (V) using a first solvent selected from tetrahydrofuran:2-methoxyethanol in about a (1:1) ratio, tetrahydrofuran:trimethyl orthoformate in about a (1:1) ratio and 1,4-dioxane:trimethyl orthoformate in about a (1:0.3) to (1:3) ratio.

In another embodiment of the present invention is disclosed a process for preparing a compound of formula (V) wherein step (a) is conducted for a period of about 12 hours to about 48 hours.

In another embodiment of the present invention is disclosed a process for preparing a compound of formula (V) using a base selected from cesium carbonate, potassium carbonate and sodium carbonate.

In another embodiment of the present invention is disclosed a process for preparing a compound of formula (V) using a second solvent selected from dimethylacetamide, N,N-dimethylformamide, dimethylsulfoxide and mixtures thereof In another embodiment of the present invention is disclosed a process for preparing a compound of formula (V) wherein step (b) is conducted at about 15° C. to about 50° C.

In another embodiment of the present invention is disclosed a process for preparing a compound of formula (V) wherein step (b) is conducted for a period of about 24 hours to about 168 hours.

In another embodiment of the present invention is disclosed a process for preparing a compound of formula (V) wherein the acid is para-toluenesulfonic acid monohydrate; the first solvent is tetrahydrofuran:2-methoxyethanol in about a (1:1) ratio; step (a) is conducted at about 50° C. to about 80° C. and step (a) is conducted for a period of about 12 hours to about 48 hours.

In another embodiment of the present invention is disclosed a process for preparing a compound of formula (V) wherein the acid is para-toluenesulfonic acid monohydrate; the first solvent is tetrahydrofuran:2-methoxyethanol in about a (1:1) ratio; step (a) is conducted at about 50° C. to about 80° C., step (a) is conducted for a period of about 12 hours to about 48 hours; the base is cesium carbonate; the second solvent is dimethylacetamide; step (b) is conducted at about 18° C. to about 23° C.; and step (b) is conducted for a period of about 48 hours to about 168 hours.

Definition of Terms

As used throughout this specification and the appended claims, the following terms have the following meanings.

The term "alkenyl," as used herein, refers to a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 1,1-dimethyl-3-butenyl, 4-pentenyl, 5-hexenyl, 2-heptenyl, 2-methyl-1-heptenyl and 3-decenyl.

The term "alkenyloxy," as used herein, refers to an alkenyl group, as defined herein, appended to the parent molecular moiety through an oxy moiety, as defined herein. Representative examples of alkenyloxy include, but are not limited to, allyloxy, 2-butenyloxy and 3-butenyloxy.

The term "alkenyloxyalkyl," as used herein, refers to a alkenyloxy group, as defined herein, appended to the parent molecular moiety through an alkyl group, as defined herein. Representative examples of alkenyloxyalkyl include, but are not limited to, (allyloxy)methyl, (2-butenyloxy)methyl and (3-butenyloxy)methyl.

The term "alkenyloxy(alkenyloxy)alkyl," as used herein, refers to 2 independent alkenyloxy groups, as defined herein, appended to the parent molecular moiety through an alkyl group, as defined herein. Representative examples of alkenyloxy(alkenyloxy)alkyl include, but are not limited to, 1,2-bis(allyloxy)ethyl and 1,1-bis[(allyloxy)methyl]propyl.

The term "alkoxy," as used herein, refers to an alkyl group, as defined herein, appended to the parent molecular moiety through an oxy moiety, as defined herein. Representative examples of alkoxy include, but are not limited to, methoxy, ethoxy, propoxy, 2-propoxy, butoxy and tert-butoxy.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, methoxymethyl and 1,1-dimethyl-3-(methoxy)propyl.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl and tert-butoxycarbonyl.

The term "alkoxycarbonylalkyl," as used herein, refers to an alkoxycarbonyl group, as defined herein, appended to the parent molecular moiety through an alkyl group, as defined herein. Representative examples of alkoxycarbonylalkyl include, but are not limited to, methoxycarbonylmethyl, ethoxycarbonylmethyl, tert-butoxycarbonylmethyl and 1,1-dimethyl-2-(methoxycarbonyl)ethyl.

The term "alkoxycarbonyl(halo)alkyl," as used herein, refers to an alkoxycarbonyl group and at least one halogen, as defined herein, appended to the parent molecular moiety through an alkyl group, as defined herein. Representative examples of alkoxycarbonyl(halo)alkyl include, but are not limited to, 1,1-dichloro-2-methoxy-2-oxoethyl, 1,1-difluoro-2-methoxy-2-oxoethyl, 1,1-dichloro-3-methoxy-3-oxopropyl and 1,1-difluoro-3-methoxy-3-oxopropyl.

The term "alkoxy(halo)alkyl," as used herein, refers to an alkoxy group and at least one halogen, as defined herein, appended to the parent molecular moiety through an alkyl group, as defined herein. Representative examples of alkoxy (halo)alkyl include, but are not limited to, dichloro (methoxy)methyl, dichloro(ethoxy)methyl, dichloro(tert-butoxy)methyl, 1,1-dichloro-2-ethoxyethyl, 1,1-dichloro-2-methoxyethyl, 1,1-dichloro-3-methoxypropyl and 1,2-dichloro-3-methoxypropyl.

The term "alkoxysulfonyl," as used herein, refers to an alkoxy group, as defined herein, appended to the parent molecular moiety through a sulfonyl group, as defined herein. Representative examples of alkoxysulfonyl include, but are not limited to, methoxysulfonyl and ethoxysulfonyl.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 1-ethylpropyl, 2,2-dimethylpentyl, 2,3-dimethylpentyl, n-heptyl, n-octyl, n-nonyl and n-decyl.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl and 1-oxopentyl.

The term "alkylcarbonylalkyl," as used herein, refers to an alkylcarbonyl group, as defined herein, appended to the parent molecular moiety through an alkyl group, as defined herein. Representative examples of alkylcarbonylalkyl include, but are not limited to, 2-oxopropyl, 1,1-dimethyl-3-oxobutyl, 3-oxobutyl and 3-oxopentyl.

The term "alkylcarbonyl(halo)alkyl," as used herein, refers to an alkylcarbonyl group and at least one halogen, as defined herein, appended to the parent molecular moiety through an alkyl group, as defined herein. Representative examples of alkylcarbonyl(halo)alkyl include, but are not limited to, 1,1-dichloro-2-oxopropyl, 1,1-dichloro-3-oxobutyl, 1,1-difluoro-3-oxobutyl and 1,1-dichloro-3-oxopentyl.

The term "alkylcarbonyloxy," as used herein, refers to an alkylcarbonyl group, as defined herein, appended to the parent molecular moiety through an oxy moiety, as defined herein. Representative examples of alkylcarbonyloxy include, but are not limited to, acetyloxy and ethylcarbonyloxy.

The term "alkylcarbonyloxyalkyl," as used herein, refers to an alkylcarbonyloxy group, as defined herein, appended to the parent molecular moiety through an alkyl group, as defined herein. Representative examples of alkylcarbonyloxyalkyl include, but are not limited to, acetyloxymethyl and 2-(ethylcarbonyloxy)ethyl.

The term "alkylene" or "alkylene bridge" refers to a divalent group derived from a straight chain hydrocarbon of from 1 to 3 carbon atoms. Representative examples of alkylene or alkylene bridge include, —$CH_2$—, —$CH_2CH_2$—, and —$CH_2CH_2CH_2$—.

The term "alkylsulfinyl," as used herein, refers to an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfinylalkyl," as used herein, refers to an alkylsulfinyl group, as defined herein, appended to the parent molecular moiety through an alkyl group, as defined herein. Representative examples of alkylsulfinylalkyl include, but are not limited to, methylsulfinylmethyl and ethylsulfinylmethyl.

The term "alkylsulfonyl," as used herein, refers to an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylalkyl," as used herein, refers to an alkylsulfonyl group, as defined herein, appended to the parent molecular moiety through an alkyl group, as defined herein. Representative examples of alkylsulfonylalkyl include, but are not limited to, methylsulfonylmethyl and ethylsulfonylmethyl.

The term "alkylthio," as used herein, refers to an alkyl group, as defined herein, appended to the parent molecular moiety through a thio moiety, as defined herein. Representative examples of alkylthio include, but are not limited to, methylsulfanyl, ethylsulfanyl, propylsulfanyl, 2-propylsulfanyl and tert-butylsulfanyl.

The term "alkylthioalkyl," as used herein, refers to an alkylthio group, as defined herein, appended to the parent molecular moiety through an alkyl group, as defined herein. Representative examples of alkylthioalkyl include, but are not limited to, tert-butylsulfanylmethyl, 2-ethylsulfanylethyl, 2-methylsulfanylethyl and methylsulfanylmethyl.

The term "alkynyl," as used herein, refers to a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl and 1-butynyl.

The term "aryl," as used herein, refers to a monocyclic carbocyclic ring system or a bicyclic carbocyclic fused ring system having one or more aromatic rings.

Representative examples of aryl include, azulenyl, indanyl, indenyl, naphthyl, phenyl, tetrahydronaphthyl and fluorenyl.

The aryl groups of this invention may be substituted with 1, 2, 3, 4, or 5 substituents independently selected from alkenyl, alkoxy, alkoxycarbonyl, alkoxycarbonylalkyl, alkyl, alkylcarbonyl, alkylcarbonyloxy, alkylcarbonyloxyalkyl, alkylsulfinyl, alkoxysulfonyl, alkylsulfonyl, alkynyl, arylalkoxycarbonyl, arylalkoxycarbonylalkyl, arylcarbonyloxy, arylcarbonyloxyalkyl, aryloxycarbonyl, aryloxycarbonylalkyl, arylsulfonyl, carboxy, cyano, halo, haloalkyl, haloalkoxy, nitro, oxo, sulfamyl, sulfamylalkyl, —$NR_AR_B$, ($NR_AR_B$)alkyl, ($NR_AR_B$)carbonyl, ($NR_AR_B$)carbonylalkyl, furyl, imidazolyl, isothiazolyl, isoxazolyl, naphthyl, oxadiazolyl, oxazolyl, phenyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothiadiazolyl, benzothienyl, benzoxadiazolyl, benzoxazolyl, benzofuranyl, cinnolinyl, indolyl, naphthyridinyl, isobenzofuranyl, isobenzothienyl, isoindolyl, isoquinolinyl and quinolinyl wherein said furyl, imidazolyl, isothiazolyl, isoxazolyl, naphthyl, oxadiazolyl, oxazolyl, phenyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl benzimidazolyl, benzothiazolyl, benzothiadiazolyl, benzothienyl, benzoxadiazolyl, benzoxazolyl, benzofuranyl, benzopyranyl, benzothiopyranyl, cinnolinyl, indolyl, naphthyridinyl, isobenzofuranyl, isobenzothienyl, isoindolyl, isoquinolinyl, and quinolinyl may be substituted with 1, 2 or 3 substituents independently selected from alkenyl, alkoxy, alkoxycarbonyl, alkoxycarbonylalkyl, alkyl, alkylcarbonyl, alkylcarbonyloxy, alkylcarbonyloxyalkyl, alkylsulfinyl, alkoxysulfonyl, alkylsulfonyl, alkynyl, arylalkoxycarbonyl, arylalkoxycarbonylalkyl, arylcarbonyloxy, arylcarbonyloxyalkyl, aryloxycarbonyl, aryloxycarbonylalkyl, arylsulfonyl, cyano, halo, haloalkyl, haloalkoxy, nitro, sulfamyl, sulfamylalkyl, —$NR_AR_B$, ($NR_AR_B$)alkyl, ($NR_AR_B$)carbonyl and ($NR_AR_B$)carbonylalkyl as defined herein.

The term "arylalkoxy," as used herein, refers to an aryl group, as defined herein, appended to the parent molecular moiety through an alkoxy group, as defined herein. Representative examples of arylalkoxy include, but are not limited to, 2-phenylethoxy, 3-naphth-2-ylpropoxy and 5-phenylpentyloxy.

The term "arylalkoxyalkyl," as used herein, refers to an arylalkoxy group, as defined herein, appended to the parent molecular moiety through an alkyl group, as defined herein. Representative examples of arylalkoxyalkyl include, but are not limited to, 2-phenylethoxymethyl, 2-(3-naphth-2-ylpropoxy)ethyl and 5-phenylpentyloxymethyl.

The term "arylalkoxycarbonyl," as used herein, refers to an arylalkoxy group, as defined herein, appended to the parent molecular moiety through a carbonyl group, as defined herein. Representative examples of arylalkoxycarbonyl include, but are not limited to, benzyloxycarbonyl and naphth-2-ylmethyloxycarbonyl.

The term "arylalkoxycarbonylalkyl," as used herein, refers to an arylalkoxycarbonyl group, as defined herein, appended to the parent molecular moiety through an alkyl group, as defined herein. Representative examples of arylalkoxycarbonylalkyl include, but are not limited to, benzyloxycarbonylmethyl, 2-(benzyloxycarbonyl)ethyl and 2-(naphth-2-ylmethyloxycarbonyl)ethyl.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 1,1-dimethyl-2-phenylethyl, 3-phenylpropyl and 2-naphth-2-ylethyl.

The term "arylalkylthio," as used herein, refers to an arylalkyl group, as defined herein, appended to the parent molecular moiety through a thio moiety, as defined herein. Representative examples of arylalkylthio include, but are not limited to, 2-phenylethylthio, 3-naphth-2-ylpropylthio and 5-phenylpentylthio.

The term "arylalkylthioalkyl," as used herein, refers to an arylalkylthio group, as defined herein, appended to the parent molecular moiety through an alkyl group, as defined herein. Representative examples of arylalkylthioalkyl include, but are not limited to, 2-phenylethylsulfanylmethyl, 3-naphth-2-ylpropylsulfanylmethyl and 2-(5-phenylpentylsulfanyl)ethyl.

The term "arylcarbonyl," as used herein, refers to an aryl group, as defined herein, appended to the parent molecular moiety through a carbonyl group, as defined herein. Representative examples of arylcarbonyl include, but are not limited to, benzoyl and naphthoyl.

The term "arylcarbonylalkyl," as used herein, refers to an arylcarbonyl group, as defined herein, appended to the parent molecular moiety through an alkyl group, as defined herein. Representative examples of arylcarbonylalkyl include, but are not limited to, 2-oxo-3-phenylpropyl and 1,1-dimethyl-3-oxo-4-phenylbutyl.

The term "arylcarbonyloxy," as used herein, refers to an arylcarbonyl group, as defined herein, appended to the parent molecular moiety through an oxy moiety, as defined herein. Representative examples of arylcarbonyloxy include, but are not limited to, benzoyloxy and naphthoyloxy.

The term "arylcarbonyloxyalkyl," as used herein, refers to an arylcarbonyloxy group, as defined herein, appended to the parent molecular moiety through an alkyl group, as defined herein. Representative examples of arylcarbonyloxyalkyl include, but are not limited to, benzoyloxymethyl, 2-(benzoyloxy)ethyl and 2-(naphthoyloxy)ethyl.

The term "aryl(halo)alkyl," as used herein, refers to an aryl group and at least one halogen, as defined herein, appended to the parent molecular moiety through an alkyl group, as defined herein. Representative examples of aryl (halo)alkyl include, but are not limited to, dichloro(phenyl) methyl, 1,1-dichloro-2-phenylethyl, 1,1-difluoro-2-phenylethyl, 1,1-dichloro-3-phenylpropyl and 1,1-difluoro-3-phenylpropyl.

The term "aryloxy," as used herein, refers to an aryl group, as defined herein, appended to the parent molecular moiety through an oxy moiety, as defined herein. Representative examples of aryloxy include, but are not limited to, phenoxy, naphthyloxy, 3-bromophenoxy, 4-chlorophenoxy, 4-methylphenoxy and 3,5-dimethoxyphenoxy.

The term "aryloxyalkyl," as used herein, refers to an aryloxy group, as defined herein, appended to the parent molecular moiety through an alkyl group, as defined herein. Representative examples of aryloxyalkyl include, but are not limited to, phenoxymethyl, 2-phenoxyethyl, 3-naphth-2-yloxypropyl and 3-bromophenoxymethyl.

The term "aryloxycarbonyl," as. used herein, refers to an aryloxy group, as defined herein, appended to the parent molecular moiety through an oxy moiety, as defined herein. Representative examples of aryloxycarbonyl include, but are not limited to, phenoxycarbonyl and naphthyloxycarbonyl.

The term "aryloxycarbonylalkyl," as used herein, refers to an aryloxycarbonyl group, as defined herein, appended to the parent molecular moiety through an alkyl group, as defined herein. Representative examples of aryloxycarbonylalkyl include, but are not limited to, phenoxycarbonylmethyl, 2-(phenoxycarbonyl)ethyl and naphthyloxycarbonyl.

The term "arylsulfonyl," as used herein, refers to an aryl group, as defined herein, appended to the parent molecular moiety through a sulfonyl group, as defined herein. Representative examples of arylsulfonyl include, but are not limited to, naphthylsulfonyl, phenylsulfonyl and 4-fluorophenylsulfonyl.

The term "arylsulfonylalkyl," as used herein, refers to an arylsulfonyl group, as defined herein, appended to the parent molecular moiety through an alkyl group, as defined herein. Representative examples of arylsulfonylalkyl include, but are not limited to, 1,1-dimethyl-3-(phenylsulfonyl)propyl, naphthylsulfonylmethyl, 2-(phenylsulfonyl)ethyl, phenylsulfonylmethyl and 4-fluorophenylsulfonylmethyl.

The term "arylthio," as used herein, refers to an aryl group, as defined herein, appended to the parent molecular moiety through a thio moiety, as defined herein. Representative examples of arylthio include, but are not limited to, phenylsulfanyl, naphth-2-ylsulfanyl and 5-phenylhexylsulfanyl.

The term "arylthioalkyl," as used herein, refers to an arylthio group, as defined herein, appended to the parent molecular moiety through an alkyl group, as defined herein. Representative examples of arylthioalkyl include, but are not limited to, phenylsulfanylmethyl, 2-naphth-2-ylsulfanylethyl and 5-phenylhexylsulfanylmethyl.

The term "carbonyl," as used herein, refers to a —C(O)— group.

The term "carboxy," as used herein, refers to a —CO$_2$H group.

The term "carboxyalkyl," as used herein, refers to a carboxy group, as defined herenin appended to the parent molecular moiety through an alkyl group, as defined herein. Representative examples of carboxyalkyl include, but are not limited to, carboxymethyl, 2-carboxyethyl, 3-carboxypropyl and 3-carboxy-1,1-dimethylpropyl.

The term "carboxy(halo)alkyl," as used herein, refers to a carboxy group and at least one halogen, as defined herein, appended to the parent molecular moiety through an alkyl group, as defined herein. Representative examples of carboxy(halo)alkyl include, but are not limited to, carboxy (dichloro)methyl, carboxy(difluoro)methyl, 2-carboxy-1,1-dichloroethyl and 2-carboxy-1,1-difluoroethyl.

The term "cyano," as used herein, refers to a —CN group.

The term "cyanoalkyl," as used herein, refers to a cyano group, as defined herein, appended to the parent molecular moiety through an alkyl group, as defined herein. Representative examples of cyanoalkyl include, but are not limited to, cyanomethyl, 2-cyanoethyl, 3-cyanopropyl, 3-cyano-1,1-dimethylpropyl and 3-cyano-1,1-diethylpropyl.

The term "cyano(halo)alkyl," as used herein, refers to a cyano group and at least one halogen, as defined herein, appended to the parent molecular moiety through an alkyl group, as defined herein. Representative examples of cyano(halo)alkyl include, but are not limited to, 3-cyano-1,1-difluoropropyl, 1,1-dichloro-3-cyanopropyl and 3-cyano-1,1-bis(trifluoromethyl)propyl.

The term "cycloalkenyl," as used herein, refers to a cyclic hydrocarbon containing from 3 to 8 carbons and containing at least one carbon-carbon double bond formed by the removal of two hydrogens. Representative examples of cycloalkenyl include, but are not limited to, cyclohexene, 1-cyclohexen-2-yl, 3,3-dimethyl-1-cyclohexene, cyclopentene and cycloheptene.

The cycloalkenyl groups of this invention can be substituted with 1, 2, 3, 4, or 5 substituents independently selected from alkenyl, alkoxy, alkoxycarbonyl, alkoxycarbonylalkyl, alkyl, alkylcarbonyloxy, alkylcarbonyloxyalkyl, alkynyl, arylalkoxycarbonyl, arylalkoxycarbonylalkyl, arylcarbonyloxy, arylcarbonyloxyalkyl, aryloxycarbonyl, aryloxycarbonylalkyl, halo, haloalkoxy, haloalkyl, hydroxy, hydroxyalkyl, sulfamylalkyl, —$NR_AR_B$, ($NR_AR_B$)alkyl, ($NR_AR_B$)carbonyl and ($NR_AR_B$)carbonylalkyl.

The term "cycloalkenylalkyl," as used herein, refers to a cycloalkenyl group, as defined herein, appended to the parent molecular moiety through an alkyl group, as defined herein. Representative examples of cycloalkenylalkyl include, but are not limited to, (2,6,6-trimethyl-1-cyclohexen-1-yl)methyl, 1-cyclohexen-1-ylmethyl and 2-(2-cyclohepten-1-yl)ethyl.

The term "cycloalkyl," as used herein, refers to a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane and bicyclo[4.2.1]nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonane and tricyclo[3.3.1.1$^{3,7}$]decane (adamantane).

The cycloalkyl groups of this invention can be substituted with 1, 2, 3, 4, or 5 substituents independently selected from alkenyl, alkoxy, alkoxycarbonyl, alkoxycarbonylalkyl, alkyl, alkylcarbonylalkyl, alkylcarbonyloxy, alkylcarbonyloxyalkyl, alkylsulfonylalkyl, alkynyl, alkylcarbonyloxy, arylalkoxycarbonyl, arylalkoxycarbonylalkyl, arylalkyl, arylcarbonyloxy, arylcarbonyloxyalkyl, aryloxycarbonyl, aryloxycarbonylalkyl, arylsulfonylalkyl, cyanoalkyl, cycloalkylalkyl, halo, haloalkoxy, haloalkyl, heterocyclealkyl, hydroxy, hydroxyalkyl, sulfamylalkyl, —$NR_AR_B$, ($NR_AR_B$)alkyl, ($NR_AR_B$)carbonyl and ($NR_AR_B$)carbonylalkyl.

The term "cycloalkylalkoxy," as used herein, refers to a cycloalkyl group, as defined herein, appended to the parent molecular moiety through an alkoxy group, as defined herein. Representative examples of cycloalkylalkoxy include, but are not limited to, cyclopropylmethoxy, 2-cyclobutylethoxy, cyclopentylmethoxy, cyclohexylmethoxy and 4-cycloheptylbutoxy.

The term "cycloalkylalkoxyalkyl," as used herein, refers to a cycloalkylalkoxy group, as defined herein, appended to the parent molecular moiety through an alkyl group, as defined herein. Representative examples of cycloalkylalkoxyalkyl include, but are not limited to, cyclopropylmethoxymethyl, 2-cyclobutylethoxymethyl, cyclopentylmethoxymethyl, 2-cyclohexylethoxymethyl and 2-(4-cycloheptylbutoxy)ethyl.

The term "cycloalkylalkyl," as used herein, refers to a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl and 4-cycloheptylbutyl.

The term "cycloalkylcarbonyl," as used herein, refers to a cycloalkyl group, as defined herein, appended to the parent molecular moiety through a carbonyl group, as defined herein. Representative examples of cycloalkylcarbonyl include, but are not limited to, cyclopropylcarbonyl, 2-cyclobutylcarbonyl and cyclohexylcarbonyl.

The term "cycloalkyloxy," as used herein, refers to a cycloalkyl group, as defined herein, appended to the parent molecular moiety through an oxy moiety, as defined herein. Representative examples of cycloalkyloxy include, but are not limited to, cyclohexyloxy and cyclopentyloxy.

The term "cycloalkyloxyalkyl," as used herein, refers to a cycloalkyloxy group, as defined herein, appended to the parent molecular moiety through an alkyl group, as defined herein. Representative examples of cycloalkyloxyalkyl include, but are not limited to, 4-(cyclohexyloxy)butyl and cyclohexyloxymethyl.

The term "cycloalkylalkylthio," as used herein, refers to a cycloalkylalkyl group, as defined herein, appended to the parent molecular moiety through a thio moiety, as defined herein. Representative examples of cycloalkylalkylthio include, but are not limited to, (2-cyclohexylethyl)sulfanyl and cyclohexylmethylsulfanyl.

The term "cycloalkylalkylthioalkyl," as used herein, refers to a cycloalkylalkylthio group, as defined herein, appended to the parent molecular moiety through an alkyl group, as defined herein. Representative examples of cycloalkylalkylthioalkyl include, but are not limited to, 2-[(2-cyclohexylethyl)sulfanyl]ethyl and (2-cyclohexylethyl)sulfanylmethyl.

The term "cycloalkylthio," as used herein, refers to a cycloalkyl group, as defined herein, appended to the parent molecular moiety through a thio moiety, as defined herein. Representative examples of cycloalkylthio include, but are not limited to, cyclohexylsulfanyl and cyclopentylsulfanyl.

The term "cycloalkylthioalkyl," as used herein, refers to a cycloalkylthio group, as defined herein, appended to the parent molecular moiety through an alkyl group, as defined herein. Representative examples of cycloalkylthioalkyl include, but are not limited to, 4-(cyclohexylsulfanyl)butyl and cyclohexylsulfanylmethyl.

The term "formyl," as used herein, refers to a —C(O)H group.

The term "halo" or "halogen," as used herein, refers to —Cl, —Br, —I or —F.

The term "haloalkoxy," as used herein, refers to at least one halogen, as defined herein, appended to the parent molecular moiety through an alkoxy group, as defined herein. Representative examples of haloalkoxy include, but are not limited to, chloromethoxy, 2-fluoroethoxy, 1,2-difluoroethoxy, trifluoromethoxy and pentafluoroethoxy.

The term "haloalkenyl," as used herein, refers to at least one halogen, as defined herein, appended to the parent molecular moiety through an alkenyl group, as defined herein. Representative examples of haloalkenyl include, but are not limited to, 2,2-dichloroethenyl, 2,2-difluoroethenyl and 5-chloropenten-2-yl.

The term "haloalkyl," as used herein, refers to at least one halogen, as defined herein, appended to the parent molecular moiety through an alkyl group, as defined herein. Representative examples of haloalkyl include, but are not limited to, chloromethyl, trichloromethyl, 1,1-dichloroethyl, 2-fluoroethyl, trifluoromethyl, 2,2,2-trifluoroethyl, 2,2,2-trifluoro-1-(trifluoromethyl)-1-(methyl)ethyl, pentafluoroethyl and 2-chloro-3-fluoropentyl.

The term "haloalkylcarbonyl," as used herein, refers to a haloalkyl group, as defined herein, appended to the parent molecular moiety through a carbonyl group, as defined herein. Representative examples of haloalkylcarbonyl include, but are not limited to, chloromethylcarbonyl, trichloromethylcarbonyl and trifluoromethylcarbonyl.

The term "haloalkylsulfonyl," as used herein, refers to a haloalkyl group, as defined herein, appended to the parent molecular moiety through a sulfonyl group, as defined herein. Representative examples of haloalkylsulfonyl include, but are not limited to, chloromethylsulfonyl, trichloromethylsulfonyl and trifluoromethylsulfonyl.

The term "haloalkynyl," as used herein, refers to at least one halogen, as defined herein, appended to the parent molecular moiety through an alkynyl group, as defined herein. Representative examples of haloalkynyl include, but are not limited to and 4,4,4-trichlorobutyn-2-yl.

The term "heterocycle," as used herein, refers to a monocyclic or a bicyclic ring system. Monocyclic ring systems are exemplified by any 5 or 6 membered ring containing 1, 2, 3, or 4 heteroatoms independently selected from oxygen, nitrogen and sulfur. The 5-membered ring has from 0–2 double bonds and the 6-membered ring has from 0–3 double bonds. Representative examples of monocyclic ring systems include, but are not limited to, azetidinyl, azepinyl, aziridinyl, diazepinyl, 1,3-dioxolanyl, dioxanyl, 1,3-dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, thiomorpholine sulfone, thiopyranyl, triazinyl, triazolyl and trithianyl. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazolyl, benzothiazolyl, benzothiadiazolyl, benzothienyl, benzoxadiazolyl, benzoxazolyl, benzofuranyl, benzopyranyl, benzothiopyranyl, benzotriazolyl, benzodioxinyl, 1,3-benzodioxolyl, cinnolinyl, indazolyl, indolyl, indolinyl, indolizinyl, naphthyl, isobenzofuranyl, isobenzothienyl, isoindolyl, isoindolinyl, 1-isoindolinonyl, isoquinolinyl, 1-isoquinolinonyl, phthalazinyl, pyranopyridinyl, quinolinyl, quinolizinyl, quinoxalinyl, quinazolinyl, tetrahydroisoquinolinyl, tetrahydroquinolinyl and thiopyranopyridinyl.

The heterocycle groups of this invention can be substituted with 1, 2, or 3 substituents independently selected from alkenyl, alkoxy, alkoxycarbonyl, alkoxycarbonylalkyl, alkyl, alkylcarbonyl, alkylcarbonyloxy, alkylcarbonyloxyalkyl, alkylsulfinyl, alkoxysulfonyl, alkylsulfonyl, alkynyl, arylalkoxycarbonyl, arylalkoxycarbonylalkyl, arylcarbonyloxy, arylcarbonyloxyalkyl, aryloxycarbonyl, aryloxycarbonylalkyl, arylsulfonyl, carboxy, cyano, halo, haloalkyl, haloalkoxy, nitro, oxo, sulfamyl, sulfamylalkyl, —$NR_AR_B$, ($NR_AR_B$)alkyl, ($NR_AR_B$)carbonyl, ($NR_AR_B$) carbonylalkyl, furyl, imidazolyl, isothiazolyl, isoxazolyl, naphthyl, oxadiazolyl, oxazolyl, phenyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothiazolyl, benzothiadiazolyl, benzothiophenyl, benzoxadiazolyl, benzoxazolyl, benzofuranyl, cinnolinyl, indolyl, naphthyridinyl, isobenzofuranyl, isobenzothienyl, isoindolyl, isoquinolinyl, and quinolinyl wherein said furyl, imidazolyl, isothiazolyl, isoxazolyl, naphthyl, oxadiazolyl, oxazolyl, phenyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl, triazolyl, benzimidazolyl, benzothilazolyl, benzothiadiazolyl, benzothiophenyl, benzoxadiazolyl, benzoxazolyl, benzofuranyl, cinnolinyl, indolyl, naphthyridinyl, isobenzofuranyl, isobenzothienyl, isoindolyl, isoquinolinyl and quinolinyl may be substituted with 1 or 2 substituents independently selected from alkenyl, alkoxy, alkoxycarbonyl, alkoxycarbonylalkyl, alkyl, alkylcarbonyl, alkylcarbonyloxy, alkylcarbonyloxyalkyl, alkylsulfinyl, alkoxysulfonyl, alkylsulfonyl, alkynyl, arylalkoxycarbonyl, arylalkoxycarbonylalkyl, arylcarbonyloxy, arylcarbonyloxyalkyl, aryloxycarbonyl, aryloxycarbonylalkyl, arylsulfonyl, carboxy, cyano, halo, haloalkyl, haloalkoxy, nitro, sulfamyl, sulfamylalkyl, —$NR_AR_B$, ($NR_AR_B$)alkyl, ($NR_AR_B$)carbonyl and ($NR_AR_B$) carbonylalkyl.

The term "heterocyclealkoxy," as used herein, refers to a heterocycle group, as defined herein, appended to the parent molecular moiety through an alkoxy group, as defined herein. Representative examples of heterocyclealkoxy include, but are not limited to, 2-pyrid-3-ylethoxy, 3-quinolin-3-ylpropoxy and 5-pyrid-4-ylpentyloxy.

The term "heterocyclealkoxyalkyl," as used herein, refers to a heterocyclealkoxy group, as defined herein, appended to the parent molecular moiety through an alkyl group, as defined herein. Representative examples of heterocyclealkoxyalkyl include, but are not limited to, 2-pyrid-3-ylethoxymethyl, 2-(3-quinolin-3-ylpropoxy)ethyl and 5-pyrid-4-ylpentyloxymethyl.

The term "heterocyclealkyl," as used herein, refers to a heterocycle, as defined herein, appended to the parent molecular moiety through an alkyl group, as defined herein. Representative examples of heterocyclealkyl include, but are not limited to, pyrid-3-ylmethyl and pyrimidin-5-ylmethyl.

The term "heterocyclealkylthio," as used herein, refers to a heterocyclealkyl group, as defined herein, appended to the parent molecular moiety through a thio moiety, as defined herein. Representative examples of heterocyclealkylthio include, but are not limited to, 2-pyrid-3-ylethysulfanyl, 3-quinolin-3-ylpropysulfanyl and 5-pyrid-4-ylpentylsulfanyl.

The term "heterocyclealkylthioalkyl," as used herein, refers to a heterocyclealkylthio group, as defined herein, appended to the parent molecular moiety through an alkyl group, as defined herein. Representative examples of heterocyclealkylthioalkyl include, but are not limited to, 2-pyrid-3-ylethysulfanylmethyl, 2-(3-quinolin-3-ylpropysulfanyl)ethyl and 5-pyrid4-ylpentylsulfanylmethyl.

The term "heterocyclecarbonyl," as used herein, refers to a heterocycle, as defined herein, appended to the parent molecular moiety through a carbonyl group, as defined herein. Representative examples of heterocyclecarbonyl include, but are not limited to, pyrid-3-ylcarbonyl, quinolin-3-ylcarbonyl and thiophen-2-ylcarbonyl.

The term "heterocycleoxy," as used herein, refers to a heterocycle group, as defined herein, appended to the parent molecular moiety through an oxy moiety, as defined herein. Representative examples of heterocycleoxy include, but are not limited to, pyrid-3-yloxy and quinolin-3-yloxy.

The term "heterocycleoxyalkyl," as used herein, refers to a heterocycleoxy group, as defined herein, appended to the parent molecular moiety through an alkyl group, as defined herein. Representative examples of heterocycleoxyalkyl include, but are not limited to, pyrid-3-yloxymethyl and 2quinolin-3-yloxyethyl.

The term "heterocyclethio," as used herein, refers to a heterocycle group, as defined herein, appended to the parent molecular moiety through a thio moiety, as defined herein. Representative examples of heterocyclethio include, but are not limited to, pyrid-3-ylsulfanyl and quinolin-3-ylsulfanyl.

The term "heterocyclethioalkyl," as used herein, refers to a heterocyclethio group, as defined herein, appended to the parent molecular moiety through an alkyl group, as defined herein. Representative examples of heterocyclethioalkyl include, but are not limited to, pyrid-3-ylsulfanylmethyl and 2-quinolin-3-ylsulfanylethyl.

The term "hydroxy," as used herein, refers to an —OH group.

The term "hydroxyalkyl," as used herein, refers to 1 or 2 hydroxy groups, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypropyl, 2-ethyl-4-hydroxyheptyl, 2-hydroxy-1, -dimethylethyl and 3-hydroxy-1,1-dimethylpropyl.

The term "lower alkyl," as used herein, is a subset of alkyl as defined herein and refers to a straight or branched chain hydrocarbon group containing from 1 to 6 carbon atoms. Representative examples of lower alkyl include, but are not limited to, methyl, ethyl, n-propyl, iso-propyl, n-butyl, iso-butyl and tert-butyl.

The term "mercapto," as used herein, refers to a —SH group.

The term "mercaptoalkyl," as used herein, refers to a mercapto group, as defined herein, appended to the parent molecular moiety through an alkyl group, as defined herein. Representative examples of mercaptoalkyl include, but are not limited to, 2-sulfanylethyl and 3-sulfanylpropyl.

The term "—$NR_9R_{10}$," as used herein, refers to two groups, $R_9$ and $R_{10}$, which are appended to the parent molecular moiety through a nitrogen atom. $R_9$ and $R_{10}$ are independently selected from hydrogen, alkoxysulfonyl, alkyl, alkylcarbonyl, alkylsulfonyl, aryl, arylalkyl, arylcarbonyl, arylsulfonyl and formyl, as defined herein. Representative examples of —$NR_9R_{10}$ include, but are not limited to, acetylamino, amino, methylamino, (ethylcarbonyl)methylamino, ethylmethylamino, formylamino, methylsulfonylamino and phenylsulfonylamino.

The term "($NR_9R_{10}$)alkyl," as used herein, refers to a —$NR_9R_{10}$ group, as defined herein, appended to the parent molecular moiety through an alkyl group, as defined herein. Representative examples of ($NR_9R_{10}$)alkyl include, but are not limited to, acetylaminomethyl, aminomethyl, 2-aminoethyl, 2-(methylamino)ethyl, (ethylcarbonyl)methylaminomethyl, 3-(ethylmethylamino)propyl, 1,1-dimethyl-3-(dimethylamino)propyl, 2-(formylamino)ethyl, methylsulfonylaminomethyl, 2-(phenylsulfonylamino)ethyl and benzylsulfonylaminomethyl.

The term "($NR_9R_{10}$)carbonyl," as used herein, refers to a —$NR_9R_{10}$ group, as defined herein, appended to the parent molecular moiety through a carbonyl group, as defined herein. Representative examples of ($NR_9R_{10}$)carbonyl include, but are not limited to, aminocarbonyl, dimethylaminocarbonyl, ethylaminocarbonyl and benzylaminocarbonyl.

The term "($NR_9R_{10}$)carbonylalkyl," as used herein, refers to a ($NR_9R_{10}$)carbonyl group, as defined herein, appended to the parent molecular moiety through an alkyl group, as defined herein. Representative examples of ($NR_9R_{10}$)carbonylatkyl include, but are not limited to, aminocarbonylmethyl, dimethylaminocarbonylmethyl, 2-(ethylaminocarbonyl)ethyl and 3-(benzylaminocarbonyl)propyl.

The term "—$NR_AR_B$," as used herein, refers to two groups, $R_A$ and $R_B$, which are appended to the parent molecular moiety through a nitrogen atom. $R_A$ and $R_B$ are independently selected from hydrogen, alkyl, alkylcarbonyl and formyl, as defined herein. Representative examples of—$NR_AR_B$ include, but are not limited to, acetylamino, amino, methylamino, (ethylcarbonyl)methylamino, dimethylamino, ethylmethylamino and formylamino.

The term "($NR_AR_B$)alkyl," as used herein, refers to a —$NR_AR_B$ group, as defined herein, appended to the parent molecular moiety through an alkyl group, as defined herein. Representative examples of ($NR_AR_B$)alkyl include, but are not limited to, acetylaminomethyl, aminomethyl, 2-aminoethyl, 2-(methylamino)ethyl, (ethylcarbonyl)methylaminomethyl, 3-(ethylmethylamino)propyl, 1,1-dimethyl-3-(dimethylamino)propyl and 2-(formylamino)ethyl.

The term "($NR_AR_B$)carbonyl," as used herein, refers to a —$NR_AR_B$ group, as defined herein, appended to the parent molecular moiety through a carbonyl group, as defined herein. Representative examples of ($NR_AR_B$)carbonyl include, but are not limited to, aminocarbonyl, dimethylaminocarbonyl, methylaminocarbonyl, ethylaminocarbonyl and diethylaminocarbonyl.

The term "($NR_AR_B$)carbonylalkyl," as used herein, refers to a ($NR_AR_B$)carbonyl group, as defined herein, appended to the parent molecular moiety through an alkyl group, as defined herein. Representative examples of (NR$_A$R$_B$)carbonylalkyl include, but are not limited to, aminocarbonylmethyl, dimethylaminocarbonylmethyl, 2-(ethylaminocarbonyl)ethyl and 3-(diethylaminocarbonyl)propyl.

The term "nitro," as used herein, refers to a —NO$_2$ group.

The term "oxo," as used herein, refers to a (=O) moiety.

The term "oxy," as used herein, refers to a (—O—) moiety.

The term "sulfamyl," as used herein, refers to a —SO$_2$NR$_{94}$R$_{95}$ group, wherein R$_{94}$ and R$_{95}$ are independently selected from hydrogen, alkyl, aryl, and arylalkyl, as defined herein. Representative examples of sulfamyl include, but are not limited to, aminosulfonyl, methylaminosulfonyl, dimethylaminosulfonyl, phenylaminosulfonyl and benzylaminosulfonyl.

The term "sulfamylalkyl," as used herein, refers to a sulfamyl group, as defined herein, appended to the parent molecular moiety through an alkyl group, as defined herein. Representative examples of sulfamylalkyl include, but are not limited to, (aminosulfonyl)methyl, (dimethylaminosulfonyl)methyl, 2-(aminosulfonyl)ethyl, 3-(aminosulfonyl)propyl and 3-aminosulfonyl-1,1-dimethylpropyl.

The term "sulfamyl(halo)alkyl," as used herein, refers to a sulfamyl group and at least one halogen, as defined herein, appended to the parent molecular moiety through an alkyl group, as defined herein. Representative examples of sulfamyl(halo)alkyl include, but are not limited to, (aminosulfonyl)dichloromethyl, (aminosulfonyl)difluoromethyl, (dimethylaminosulfonyl)difluoromethyl, 2-(aminosulfonyl)-1,1-dichloroethyl, 3-(aminosulfonyl)-1,1-difluoropropyl, 3-aminosulfonyl-1,1-dichloropropyl and 3-(aminosulfonyl)-1,2-difluoropropyl.

The term "sulfinyl," as used herein, refers to a —S(O)— group.

The term "sulfonyl," as used herein, refers to a —SO$_2$— group.

The term "thio," as used herein, refers to a (—S—) moiety.

Compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976,45: 13–30. The present invention contemplates various stereoisomers and mixtures thereof and are specifically included within the scope of this invention. Stereoisomers include enantiomers and diastereomers, and mixtures of enantiomers or diastereomers. In particular, the carbon atom attached to R$_6$ and R$_7$ of formula (I–IV), may be individually the (R) enantiomer or individually the (S) enantiomer or a mixture thereof Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Preferred compounds of the present invention include 3-chloro-N-(1-{[3,4-dioxo-2-(5-pyrimidinylamino)-1-cyclobuten-1-yl]amino}-2,2-dimethylpropyl)benzamide;

N-(1-{[3,4-dioxo-2-(5-pyrimidinylamino)-1-cyclobuten-1-yl]amino}-2,2-dimethylpropyl)-3,5-difluorobenzamide;

N-(1-{[3,4-dioxo-2-(2-pyrazinylamino)-1-cyclobuten-1-yl]amino}-2,2-dimethylpropyl)-3,5-difluorobenzamide;

3-chloro-N-(1-{[3,4-dioxo-2-(2-pyrazinylamino)-1-cyclobuten-1-yl]amino}-2,2-dimethylpropyl)benzamide;

3-chloro-N-{1-[(3,4-dioxo-2-{[2-(trifluoromethyl)-3-pyridinyl]amino}-1-cyclobuten-1-yl)amino]-2,2-dimethylpropyl}benzamide;

3-chloro-N-[1-({2-[(2-methoxy-3-pyridinyl)amino]-3,4-dioxo-1-cyclobuten-1-yl}amino)-2,2-dimethylpropyl]benzamide;

3,5-difluoro-N-[1-({2-[(2-methoxy-3-pyridinyl)amino]-3,4-dioxo-1-cyclobuten-1-yl}amino)-2,2-dimethylpropyl]benzamide;

N-[2,2-dimethyl-1-({2-[(2-methyl-3-pyridinyl)amino]-3,4-dioxo-1-cyclobuten-1-yl}amino)propyl]-3,5-difluorobenzamide;

3-chloro-N-{1-[(3,4-dioxo-2-{[4-(trifluoromethyl)-3-pyridinyl]amino}-1-cyclobuten-1-yl)amino]-2,2-dimethylpropyl}benzamide;

3-chloro-N-{1-[(3,4-dioxo-2-{[4-(trifluoromethyl)-3-pyridinyl]amino}-1-cyclobuten-1-yl)amino]-2,2-dimethyl-3-phenylpropyl}benzamide;

3-chloro-N-[1-({2-[(2-methoxy-3-pyridinyl)amino]-3,4-dioxo-1-cyclobuten-1-yl}amino)-2,2-dimethyl-3-phenylpropyl]benzamide;

3-chloro-N-{1-[(3,4-dioxo-2-{[2-(trifluoromethyl)-3-pyridinyl]amino}-1-cyclobuten-1-yl)amino]-2,2-dimethyl-3-phenylpropyl}benzamide;

N-[2,2-dimethyl-1-({2-[(4-methyl-3-pyridinyl)amino]-3,4-dioxo-1-cyclobuten-1-yl}amino)propyl]-3,5-difluorobenzamide, 3,5-difluoro-N-[1-({2-[(4-methoxy-3-pyridinyl)amino]-3,4-dioxo-1-cyclobuten-1-yl}amino)-2,2-dimethylpropyl]benzamide;

N-(1-{[3,4-dioxo-2-(3-pyridinylamino)-1-cyclobuten-1-yl]amino}-2,2-dimethylpropyl)-3-(3-pyridinyl)propanamide;

3-chloro-N-[1-{[3,4-dioxo-2-(3-pyridinylamino)-1-cyclobuten-1-yl]amino}-2,2-dimethyl-3-(4-pyridinyl)propyl]benzamide;

4-(3-[(3-chlorobenzoyl)amino]-3-{[3,4-dioxo-2-(3-pyridinylamino)-1-cyclobuten-1-yl]amino}-2,2-dimethylpropyl)benzoic acid, N-(1-{[3,4-dioxo-2-(3-pyridinylamino)-1-cyclobuten-1-yl]amino}-2,2-dimethylpropyl)nicotinamide;

5-bromo-N-(1-{[3,4-dioxo-2-(3-pyridinylamino)-1-cyclobuten-1-yl]amino}-2,2-dimethylpropyl)nicotinamide;

3-{[(1-{[3,4-dioxo-2-(3-pyridinylamino)-1-cyclobuten-1-yl]amino}-2,2-dimethylpropyl)amino]carbonyl}benzoic acid;

N-(1-{[3,4-dioxo-2-(3-pyridinylamino)-1-cyclobuten-1-yl]amino}-2,2-dimethylpropyl)-3-(1H-tetraazol-5-yl)benzamide;

N-(1-{[3,4-dioxo-2-(3-pyridinylamino)-1-cyclobuten-1-yl]amino}-2,2-dimethylpropyl)-3-(3-pyridinyl)benzamide and pharmaceutically acceptable salts thereof The foregoing compounds, representative of formula (II), may be prepared by one skilled in the art using known synthetic methodology or by using synthetic methodology described in the Schemes and Examples contained herein.

Most preferred compounds of formula (I) include

N-(1-{[3,4-dioxo-2-(3-pyridinylamino)-1-cyclobuten-1-yl]amino}-2,2-dimethylpropyl)4-methylbenzamide;

4-chloro-N-(1-{[3,4-dioxo-2-(3-pyridinylamino)-1-cyclobuten-1-yl]amino}-2,2-dimethylpropyl)benzamide;

N-(1-{[3,4-dioxo-2-(3-pyridinylamino)-1-cyclobuten-1-yl]amino}-2,2-dimethylpropyl)-4-iodobenzamide;

N-(1-{[3,4-dioxo-2-(3-pyridinylamino)-1-cyclobuten-1-yl]amino}-2,2-dimethylpropyl)-4-(2-furyl)benzamide;

3-chloro-N-(1-{[3,4-dioxo-2-(3-pyridinylamino)-1-cyclobuten-1-yl]amino}-2,2-dimethylpropyl)benzamide, N-(1-{[3,4-dioxo-2-(3-pyridinylamino)-1-cyclobuten-1-yl]amino}-2,2-dimethylpropyl)-3-methylbenzamide;

N-(1-{[3,4-dioxo-2-(3-pyridinylamino)-1-cyclobuten-1-yl]amino}-2,2-dimethylpropyl)-3-fluorobenzamide;

N-(1-{[3,4-dioxo-2-(3-pyridinylamino)-1-cyclobuten-1-yl]amino}-2,2-dimethylpropyl)-3-iodobenzamide;

N-(1-{[3,4-dioxo-2-(3-pyridinylamino)-1-cyclobuten-1-yl]amino}-2,2-dimethylpropyl)-3,4-dimethylbenzamide;

N-(1-{[3,4-dioxo-2(3-pyridinylamino)-1-cyclobuten-1-yl]amino}-2,2-dimethylpropyl)-3,4-dimethoxybenzamide;

N-(1-{[3,4-dioxo-2-(3-pyridinylamino)-1-cyclobuten-1-yl]amino}-2,2-dimethylpropyl)-1-naphthamide;

3,5-dichloro-N-(1-{[3,4-dioxo-2-(3-pyridinylamino)-1-cyclobuten-1-yl]amino}-2,2-dimethylpropyl)benzamide;

N-(1-{[3,4-dioxo-2-(3-pyridinylamino)-1-cyclobuten-1-yl]amino}-2,2-dimethylpropyl)-3,5-dimethoxybenzamide;

(−)N-(1-{[3,4-dioxo-2-(3-pyridinylamino)-1-cyclobuten-1-yl]amino}-2,2-dimethylpropyl)-3,5-dimethoxybenzamide;

(+)N-(1-{[3,4-dioxo-2-(3-pyridinylamino)-1-cyclobuten-1-yl]amino}-2,2-dimethylpropyl)-3,5-dimethoxybenzamide;

N-(1-{[3,4-dioxo-2-(3-pyridinylamino)-1-cyclobuten-1-yl]amino}-2,2-dimethylpropyl)-3,5-difluorobenzamide;

4-chloro-N-(1-{[3,4-dioxo-2-(3-pyridinylamino)-1-cyclobuten-1-yl]amino{-2,2-dimethyl-4-pentenyl)benzamide, 4-chloro-N-(1-{[3,4-dioxo-2-(3-pyridinylamino)-1-cyclobuten-1-yl]amino}-2,2-dimethyl-3-phenylpropyl)benzamide;

4-chloro-N-(4-cyano-1-{[3,4-dioxo-2-(3-pyridinylamino)-1-cyclobuten-1-yl]amino}-2,2-diethylbutyl)benzamide;

N-(2,2-bis[(allyloxy)methyl]-1-{[3,4-dioxo-2-(3-pyridinylamino)-1-cyclobuten-1-yl]amino}butyl)-4-chlorobenzamide;

4-chloro-N-(1-{[3,4-dioxo-2-(3-pyridinylamino)-1-cyclobuten-1-yl]amino}-2-ethylbutyl)benzamide;

4-chloro-N-(2-cyclohexyl-1-{[3,4-dioxo-2-(3-pyridinylamino)-1-cyclobuten-1-yl]amino}-2-methylpropyl)benzamide;

N-(2-(1-adamantyl)-1-{[3,4-dioxo-2-(3-pyridinylamino)-1-cyclobuten-1-yl]amino}ethyl)-4-chlorobenzamide;

4-chloro-N-(2,2-dichloro-1-{[3,4-dioxo-2-(3-pyridinylamino)-1-cyclobuten-1-yl]amino}propyl)benzamide;

3-chloro-N-(2,2-dichloro-1-{[3,4-dioxo-2-(3-pyridinylamino)-1-cyclobuten-1-yl]amino}propyl)benzamide;

3-chloro-N-(1-{[3,4-dioxo-2-(3-pyridinylamino)-1-cyclobuten-1-yl]amino}-2,2,3,3,3-pentafluoropropyl)benzamide;

4-chloro-N-(1-{[2-(3-fluoroanilino)-3,4-dioxo-1-cyclobuten-1-yl]amino}-2,2-dimethylpropyl)benzamide;

4-chloro-N-(1-{[2-(4-fluoroanilino)-3,4-dioxo-1-cyclobuten-1-yl]amino}-2,2-dimethylpropyl)benzamide;

4-chloro-N-[1-({2-[(2-chloro-3-pyridinyl)amino]-3,4-dioxo-1-cyclobuten-1-yl}amino)-2,2-dimethylpropyl]benzamide;

N-[1-({2-[(5-bromo-6-fluoro-3-pyridinyl)amino]-3,4-dioxo-1-cyclobuten-1-yl}amino)-2,2-dimethylpropyl] 4-chlorobenzamide;

4-chloro-N-[1-({2-[(2-chloro-3-pyridinyl)amino]-3,4-dioxo-1-cyclobuten-1-yl}amino)2,2-dimethyl-3-phenylpropyl]benzamide;

N-[1-({2-[(2-chloro-3-pyrdinyl)amino]-3,4-dioxo-1-cyclobuten-1-yl}amino)-2,2-dimethylpropyl]-3-methylbenzamide;

4-chloro-N-(2,2-dimethyl-1-{[(3-pyridinylamino)sulfonyl]amino}propyl)benzamide;

N-(2,2-dimethyl-1-{[(3-pyridinylamino)sulfonyl]amino}propyl)4-iodobenzamide;

$N^1$-{1-[(4-chlorobenzoyl)amino]-2,2-dimethylpropyl}-$N^2$-(3-pyridinyl)ethanediamide;

N-(1-{[3,4-dioxo-2-(3-pyridinylamino)-1-cyclobuten-1-yl]amino}-2,2-dimethylpropyl)-3-phenylpropanamide;

N-[1-({2-[(2-chloro-3-pyridinyl)amino]-3,4-dioxo-1-cyclobuten-1-yl}amino)-2,2-dimethylpropyl]-3-(3-pyridinyl)propanamide;

N-(1-{[3,4-dioxo-2-(3-pyridinylamino)-1-cyclobuten-1-yl]amino}-2,2-dimethylpropyl)-3-vinylbenzamide;

N-(1-{[3,4-dioxo-2-(3-pyridinylamino)-1-cyclobuten-1-yl]amino}-2,2-dimethylpropyl)[1,1'-biphenyl]-3-carboxamide;

3-acetyl-N-(1-{[3,4-dioxo-2-(3-pyridinylamino)-1-cyclobuten-1-yl]amino}-2,2-dimethylpropyl)benzamide;

N-(1-{[3,4-dioxo-2-(3-pyridinylamino)-1-cyclobuten-1-yl]amino}-2,2-dimethylpropyl)-2-pyridinecarboxamide;

N-(1-{[3,4-dioxo-2-(3-pyridinylamino)-1-cyclobuten-1-yl]amino}-2,2-dimethylpropyl)-4-fluoro-3-(trifluoromethyl)benzamide;

N-(1-{[3,4-dioxo-2-(3-pyridinylamino)-1-cyclobuten-1-yl]amino}-2,2-dimethylpropyl)-2-phenylacetamide;

N-(1-{[3,4-dioxo-2-(3-pyridinylamino)-1-cyclobuten-1-yl]amino}-2,2-dimethylpropyl)-3-phenylprop-2-enamide;

4-chloro-N-(2,2-dichloro-1-{[3,4-dioxo-2-(3-pyridinylamino)-1-cyclobuten-1-yl]amino}pentyl)benzamide;

4-chloro-N-(1-{[3,4-dioxo-2-(4-pyridinylamino)-1-cyclobuten-1-yl]amino}-2,2-dimethylpropyl)benzamide;

4-chloro-N-(1-{[3,4-dioxo-2-(2-pyridinylamino)-1-cyclobuten-1-yl]amino}-2,2-dimethylpropyl)benzamide;

N-(1-{[3,4-dioxo-2-(3-pyridinylamino)-1-cyclobuten-1-yl]amino}-2,2-dimethylpropyl)benzamide;

(+)N-(1-[3,4-dioxo-2-(3-pyridinylamino)-1-cyclobuten-1-yl]amino}-2,2-dimethylpropyl)-3,5-difluorobenzamide;

(−)N-(1-{[3,4-dioxo-2-(3-pyridinylamino)-1-cyclobuten-1-yl]amino}-2,2-dimethylpropyl)-3,5-difluorobenzamide;

N-(2,2-dichloro-1-{[3,4-dioxo-2-(3-pyridinylamino)-1-cyclobuten-1-yl]amino}propyl)-3,5-difluorobenzamide;

4-chloro-N-{1-[(3,4-dioxo-2-{[5-(trifluoromethyl)pyridin-3-yl]amino}-1-cyclobuten-1-yl)amino]-2,2-dimethylpropyl}benzamide;

3,5-dichloro-N-{1-[(3,4-dioxo-2-{[5-(trifluoromethyl)pyridin-3-yl]amino}-1-cyclobuten-1-yl)amino]-2,2-dimethylpropyl}benzamide;

4-chloro-N-{1-[(3,4-dioxo-2-{[5-(trifluoromethyl)pyridin-3-yl]amino}-1-cyclobuten-1-yl)amino]-2,2-dimethyl-3-penylpropyl}benzamide;

N-(1-{[3,4-dioxo-2-(3-pyridinylamino)-1-cyclobuten-1-yl]amino}-2,2-dimethyl-3-phenylpropyl)-3,5-difluorobenzamide;

(+)3-chloro-N-(1-{[3,4-dioxo-2-(3-pyridinylamino)-1-cyclobuten-1-yl]amino}-2,2-dimethylpropyl) benzamide;

(−) 3-chloro-N-(1-{[3,4dioxo-2-(3-pyridinylamino)-1-cyclobuten-1-yl]amino}-2,2-dimethylpropyl)benzamide;

3,5-dichloro-N-(1-{[3,4-dioxo-2-(3-pyridinylamino)-1-cyclobuten-1-yl]amino}-2,2-dimethyl-3-phenylpropyl)benzamide;

3-chloro-N-(1-{[3,4-dioxo-2-(3-pyridinylamino)-1-cyclobuten-1-yl]amino}-2,2-dimethyl-3-phenylpropyl)benzamide;

N-(1-{[3,4-dioxo-2-(3-pyridinylamino)-1-cyclobuten-1-yl]amino}-2,2-dimethyl-3-phenylpropyl)-3-methylbenzamide;

N-[1-({2-[(2-chloropyridin-3-yl)amino]-3,4-dioxo-1-cyclobuten-1-yl}amino)-2,2-dimethyl-3-phenylpropyl]-3-methylbenzamide;

4-chloro-N-[1-({2-[(6-chloropyridin-3-yl)amino]-3,4-dioxo-1-cyclobuten-1-yl}amino)-2,2-dimethylpropyl]benzamide;

4-chloro-N-[1-({2-[(2-fluoropyridin-3-yl)amino]-3,4-dioxo-1-cyclobuten-1-yl}amino)-2,2-dimethylpropyl]benzamide;

3-chloro-N-(1-[3,4-dioxo-2-(3-pyridinylamino)-1-cyclobuten-1-yl]amino}-3,3-dimethylbutyl)benzamide;

N-(1-{[3,4-dioxo-2-(3-pyridinylamino)-1-cyclobuten-1-yl]amino}-2,2-dimethylpropyl)thiophene-2-carboxamide;

3-bromo-N-(1-{[3,4-dioxo-2-(3-pyridinylamino)-1-cyclobuten-1-yl]amino}-2,2-dimethylpropyl)benzamide;

3-bromo-N-[1-({2-[(2-chloropyridin-3-yl)amino]-3,4-dioxo-1-cyclobuten-1-yl}amino)-2,2-dimethylpropyl]benzamide;

N-(1-{[3,4-dioxo-2-(3-pyridinylamino)-1-cyclobuten-1-yl]amino}-2,2-dimethylpropyl)-9-oxo-9H-fluorene-4-carboxamide;

methyl 3-{[(1-{[3,4-dioxo-2-(3-pyridinylamino)-1-cyclobuten-1-yl]amino}-2,2-dimethylpropyl)amino]carbonyl}benzoate;

(+)N-(1-{[3,4-dioxo-2-(3-pyridinylamino)-1-cyclobuten-1-yl]amino}-2,2-dimethylpropyl)-3-methylbenzamide;

(−)N-(1-{[3,4-dioxo-2-(3-pyridinylamino)-1-cyclobuten-1-yl]amino}-2,2-dimethylpropyl)-3-methylbenzamide;

(+)N-(1-[3,4-dioxo-2-(3-pyridinylamino)-1-cyclobuten-1-yl]amino}-2,2-dimethyl-3-phenylpropyl)-3-methylbenzamide;

(−)N-(1-{[3,4-dioxo-2-(3-pyridinylamino)-1-cyclobuten-1-yl]amino}-2,2-dimethyl-3-phenylpropyl)-3-methylbenzamide;

(+)N-[1-({2-[(2-chloropyridin-3-yl)amino]-3,4-dioxo-1-cyclobuten-1-yl}amino)-2,2-dimethylpropyl]-3-methylbenzamide;

(−)N-[1-({2-[(2-chloropyridin-3-yl)amino]-3,4-dioxo-1-cyclobuten-1-yl}amino)-2,2-dimethylpropyl]-3-methylbenzamide;

(+)N-(1-{[3,4-dioxo-2-(3-pyridinylamino)-1-cyclobuten-1-yl]amino}-2,2-dimethyl-3-phenylpropyl)-3,5-difluorobenzamide;

N-(1-{[3,4-dioxo-2-(3-pyridinylamino)-1-cyclobuten-1-yl]amino}-2,2-dimethylpropyl)-3-(2-furyl)benzamide;

N-[1-({2-[(2-chloropyridin-3-yl)amino]-3,4-dioxo-1-cyclobuten-1-yl}amino)-2,2-dimethylpropyl]-3-fluorobenzamide;

3,5-dichloro-N-[1-({2-[(2-chloropyridin-3-yl)amino]-3,4-dioxocyclobut-1-en-1-yl}amino)-2,2-dimethylpropyl]benzamide;

4-chloro-N-[1-({2-[(2-methoxypyridin-3-yl)amino]-3,4-dioxo-1-cyclobuten-1-yl}amino)-2,2-dimethylpropyl]benzamide;

N-[1-({2-[(2-methoxypyridin-3-yl)amino]-3,4-dioxo-1-cyclobuten-1-yl}amino)-2,2-dimethylpropyl]-3-methylbenzamide;

3,5-difluoro-N-[1-({2-[(2-methoxypyridin-3-yl)amino]-3,4-dioxo-1-cyclobuten-1-yl}amino)-2,2-dimethylpropyl]benzamide;

N-[1-({2-[(2-methoxypyridin-3-yl)amino]-3,4-dioxo-1-cyclobuten-1-yl}amino)-2,2-dimethyl-3-phenylpropyl]-3-methylbenzamide;

3-chloro-N-[1-({2-[(2-methoxypyridin-3-yl)amino]-3,4-dioxo-1-cyclobuten-1-yl}amino)-2,2-dimethylpropyl]benzamide;

N-[1-({2-[(2-chloropyridin-3-yl)amino]-3,4-dioxo-1-cyclobuten-1-yl}amino)-2,2-dimethyl-3-phenylpropyl]benzamide;

N-(1-{[3,4-dioxo-2-(3-pyridinylamino)-1-cyclobuten-1-yl]amino}-2,2-dimethyl-3-phenylpropyl)benzamide;

N-[1-({2-[(2-chloropyridin-3-yl)amino]-3,4-dioxo-1-cyclobuten-1-yl}amino)-2,2-dimethylpropyl]-3-phenylpropanamide;

N-(1-{[3,4-dioxo-2-(3-pyridinylamino)-1-cyclobuten-1-yl]amino}-2,2-dimethylpropyl)-2-phenoxyacetamide;

N-[1-({2-[(2-chloropyridin-3-yl)amino]-3,4-dioxo-1-cyclobuten-1-yl}amino)-2,2-dimethylpropyl]-2-phenoxyacetamide;

N-(1-{[3,4-dioxo-2-(3-pyridinylamino)-1-cyclobuten-1-yl]amino}-2,2-dimethylpropyl)-2-methyl-2-phenylpropanarnide;

3-chloro-N-(1-{[3,4-dioxo-2-(pyrazin-2-ylamino)-1-cyclobuten-1-yl]amino}-2,2-dimethylpropyl)benzamide;

N-[1-({2-[(2-chloropyridin-3-yl)amino]-3,4-dioxo-1-cyclobuten-1-yl}amino)-3,3-dimethylbutyl]benzamide;

3-chloro-N-[1-({2-[(6-chloropyridin-3-yl)amino]-3,4-dioxo-1-cyclobuten-1-yl}amino)-2,2-dimethylpropyl]benzamide;

3-chloro-N-{1-[(3,4-dioxo-2-{[6-(trifluoromethyl)pyridin-3-yl]amino}-1-cyclobuten-1-yl)amino]-2,2-dimethylpropyl}benzamide;

3-chloro-N-[1-({2-[(2-chloropyridin-3-yl)amino]-3,4-dioxo-1-cyclobuten-1-yl}amino)-2,2-dimethylpropyl]benzamide;

N-(1-{[3,4-dioxo-2-(3-pyridinylamino)-1-cyclobuten-1-yl]amino}-2,2-dimethyl-3-phenylpropyl)isonicotinamide;

N-(1-{[3,4-dioxo-2-(3-pyridinylamino)-1-cyclobuten-1-yl]amino}-2,2-dimethyl-3-phenylpropyl)-3-phenylpropanamide;

N-(1-{[3,4-dioxo-2-(3-pyridinylamino)-1-cyclobuten-1-yl]amino}-2,2-dimethyl-3-phenylpropyl)-2-methyl-2-phenylpropanamide;

N-(1-{[3,4-dioxo2-(3-pyridinylamino)-1-cyclobuten-1-yl]amino}-2,2-dimethyl-3-phenylpropyl)-2-phenoxyacetamide;

N-(1-{[3,4-dioxo-2-(3-pyridinylamino)-1-cyclobuten-1-yl]amino}-2,2-dimethyl-3-phenylpropyl)nicotinamide;

N-(1-{[3,4-dioxo-2-(3-pyridinylamino)-1-cyclobuten-1-yl]amino}-2,2-dimethylpropyl)nicotinamide;

N-(1-{[3,4-dioxo-2-(3-pyridinylamino)-1-cyclobuten-1-yl]amino}-2,2-dimethylpropyl)isonicotinamide;

N-(1-{[3,4-dioxo-2-(3-pyridinylamino)-1-cyclobuten-1-yl]amino}-2,2-dimethylpropyl)-2-furamide;

N-(1-{[3,4-dioxo-2-(3-pyridinylamino)-1-cyclobuten-1-yl]amino}-2,2-dimethyl-3-pyridin-4-ylpropyl)-3-methylbenzamide;

(−) 3-chloro-N-(1-{[3,4-dioxo-2-(3-pyridinylamino)-1-cyclobuten-1-yl]amino}-2,2-dimethyl-3-phenylpropyl)benzamide, (+) 3-chloro-N-(1-{[3,4-dioxo-2-(3-pyridinylamino)-1-cyclobuten-1-yl]amino}-2,2-dimethyl-3-phenylpropyl)benzamide;

4-chloro-N-({[3,4-dioxo-2-(3-pyridinylamino)-1-cyclobuten-1-yl]amino}methyl)benzamide;

(+) 3,5-dichloro-N-[(1S)-1-({2-[(2-chloropyridin-3-yl)amino]-3,4-dioxocyclobut-1-en-1-yl}amino)-2,2-dimethylpropyl]benzamide;

(−) 3,5-dichloro-N-[(1R)-1-({2-[(2-chloropyridin-3-yl)amino]-3,4-dioxocyclobut-1-en-1-yl}amino)-2,2-dimethylpropyl]benzamide;

(+) N-(1-{[3,4-dioxo-2-(2-chloro3-pyridinylamino)-1-cyclobuten-1-yl]amino}-2,2-dimethylpropyl)-3,5-difluorobenzamide;

(−) N-(1-{[3,4-dioxo-2-(2-chloro3-pyridinylamino)-1-cyclobuten-1-yl]amino}-2,2-dimethylpropyl)-3,5-difluorobenzamide and pharmaceutically acceptable salts thereof.

Abbreviations

Abbreviations which have been used in the descriptions of the schemes and the examples that follow are: Ac for acetyl, COD for 1,4-cyclooctadiene; DMA for N,N-dimethylacetamide; DMAP for 4-dimethylaminopyridine, DME for dimethoxyethane; DMF for N,N-dimethylformamide; DMSO for dimethylsulfoxide; dppf for 1,1'-bis(diphenylphosphino)ferrocene; Et$_3$N for triethylamine; Et$_2$O for diethyl ether, EtOAc for ethyl acetate; EtOH for ethanol; HPLC for high pressure liquid chromatography, MeOH for methanol; NMP for 1-methyl-2-pyrrolidinone; pyr for pyridine; t-BuOH for tert-butanol; Tf for triflate or —OS(O)$_2$CF$_3$; TFA for trifluoroacetic acid; THF for tetrahydrofuran; and p-TsOH or TsOH for para-toluenesulfonic acid monohydrate.

Preparation of Compounds of The Invention

The compounds and processes of the present invention will be better understood in connection with the following synthetic schemes and methods which illustrate a means by which the compounds of the invention can be prepared.

The compounds of this invention may be prepared by a variety of synthetic routes. Representative procedures are described in Schemes 1–16.

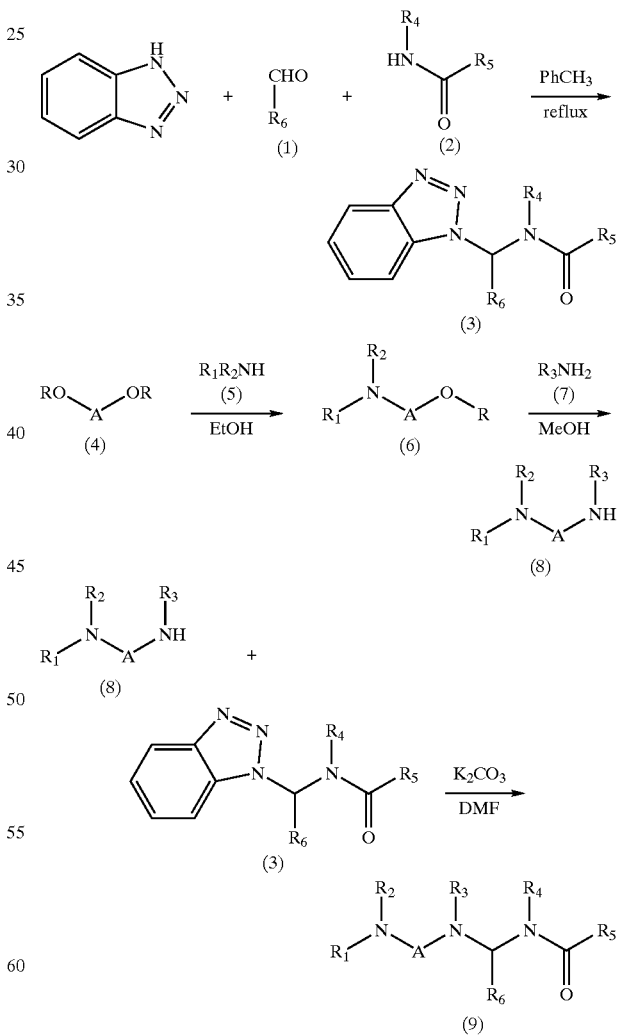

A preferred route for preparing aminals of general formula (9), wherein R$_1$, R$_2$, R$_3$, R$_4$, R$_5$ and R$_6$ are as defined in formula (I) is described in Scheme 1. A three-component condensation including benzotriazole, aldehydes of general formula (1), and amides of general formula (2) in the presence of an acid catalyst such as, but not limited to, p-toluenesulfonic acid monohydrate as described in Katritzky, Urogdi, Mayence, J. Org. Chem. (1990), 55, 2206); Katritzky, Chem. Rev. (1998), 98, 409; and Katritzky, J. Heterocyclic Chem. (1996), 33, 1935 provides benzotriazole adducts of general formula (3). Substitution of a bis (ether) precursor of general formula (4), wherein R is alkyl such as, but not limited to, ethyl, with a primary or secondary amine of general formula (5) provides adducts of general formula (6) which can undergo further substitution with ammonia or a primary amine of general formula (7) to provide amines of general formula (8). Benzotriazoles of general formula (3) can be treated with amines of general formula (8) as described in Katritzky, Urogdi, Mayence, J. Org. Chem. (1990), 55, 2206); Katritzky, Chem. Rev. (1998), 98, 409; and Katritzky, J. Heterocyclic Chem. (1996), 33, 1935 in a polar, aprotic solvent such as, but not limited to, DMF in the presence of a base such as, but not limited to, potassium carbonate or cesium carbonate to provide aminals of general formula (9).

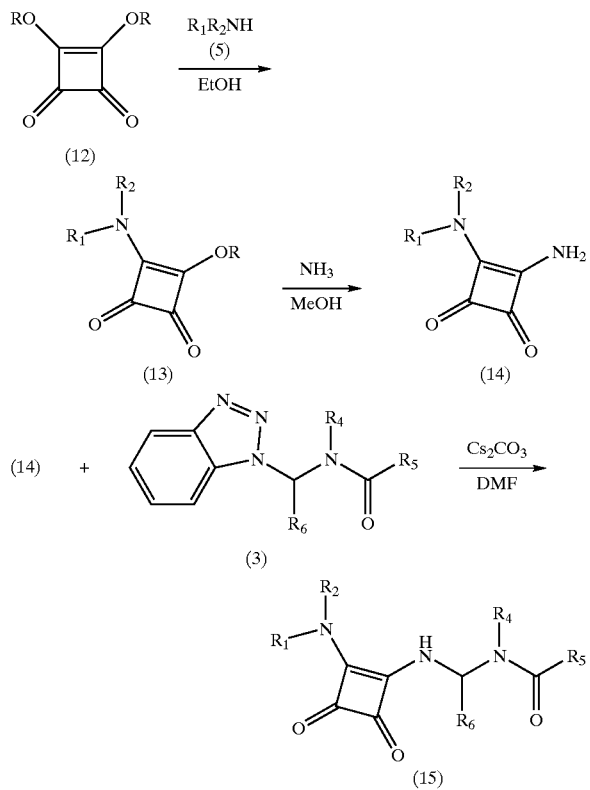

Squarate aminals of general formula (15), wherein $R_1$, $R_2$, $R_4$, and $R_5$ are as defined in formula (I), and $R_6$ is selected from alkyl such as, but not limited to, t-butyl, arylalkyl such as, but not limited to, phenethyl, or haloalkyl such as, but not limited to, —$CCl_2CH_3$ or —$CF_2CF_3$, can be prepared as described in Scheme 2. Dialkyl squarate esters of general formula (12), wherein R is alkyl, such as, but not limited to, diethyl squarate can be treated with amines of general formula (5) in an alcoholic solvent such as, but not limited to, ethanol as described in Butera, J. Med. Chem. (2000), 43, 1187; and Gilbert, J. Med. Chem. (2000), 43, 1203 to provide squarates of general formula (13). Squarates of general formula (13) can be treated with ammonia in an alcoholic solvent such as, but not limited to, methanol to provide squarates of general formula (14). Benzotriazoles of general formula (3) can be treated with squarates of general formula (14) in a polar, aprotic solvent such as, but not limited to, DMF in the presence of a base such as, but not limited to, cesium carbonate to provide squarate aminals of general formula (15).

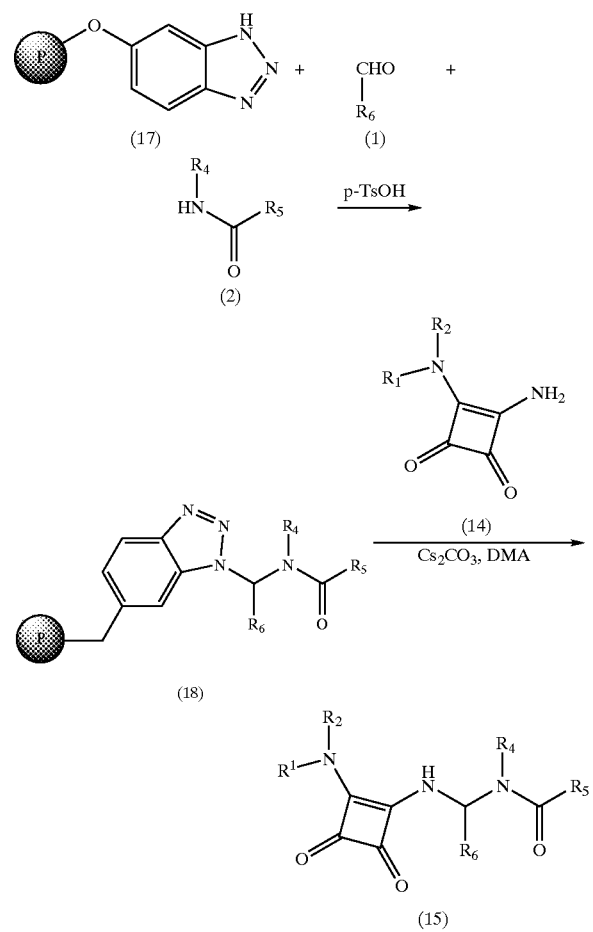

A process for the synthesis of squarate aminals of general formula (15), wherein $R_1$, $R_2$, and $R_5$ are as defined in formula (I), $R_4$ is hydrogen, and $R_6$ is selected from alkyl such as, but not limited to, t-butyl, arylalkyl such as, but not limited to, phenethyl, or haloalkyl such as, but not limited to, —$CCl_2CH_3$ or —$CF_2CF_3$, can be used as described in Scheme 3. Commercially available 1H-benzotriazole-polystyrene resin (Novabiochem) can be loaded in a three-component condensation including aldehydes of general formula (1), and amides of general formula (2) in the presence of an acid catalyst, but not limited to, p-toluenesulfonic acid monohydrate as described in Katritzky, Belyakov, Tymoshenko, J. Comb. Chem. (1999), 1, 173; and Paio, Zaramella, J. Comb. Chem. (1999), 1, 317 to provide benzotriazole adducts of general formula (18).

Benzotriazole adducts of general formula (18) can undergo nucleophilic displacement of the resin bound benzotriazole moiety with squarate amides of general formula (14) in a solvent such as, but not limited to, dimethylacetamide or a cosolvent such as, but not limited to, THF and dimethylacetamide in the presence of a base such as, but not limited to, cesium carbonate to provide aminals of general formula (15).

In the polymer-bound benzotriazole method as described in Scheme 3, the desired components are bound to the resin allowing for efficient purification. In the final product formation, an excess of a squarate of general formula (14) can be used to cleave only the desired products off the resin. The process described in Scheme 3 also offers the potential to create a combinatorial library (array synthesis) of squarate aminals of general formula (15) by enabling diversity at $R_1$, $R_2$, $R_5$, and $R_6$ to be explored.

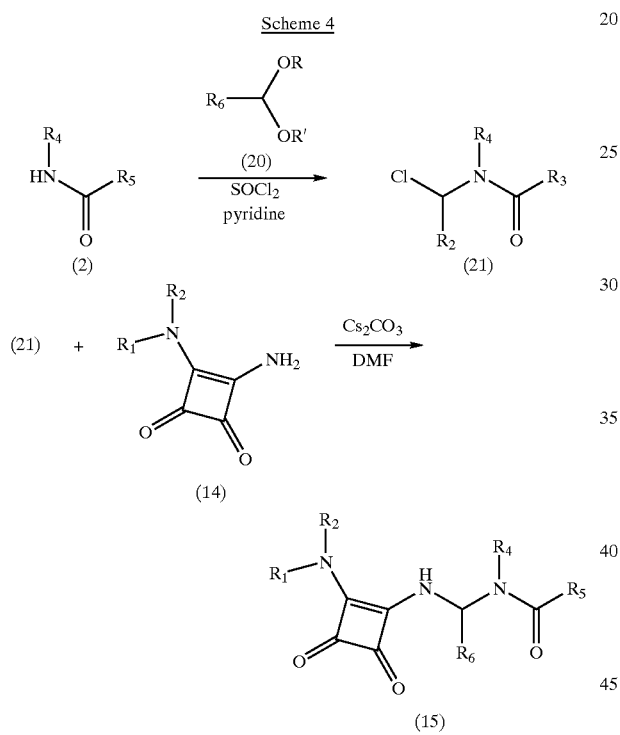

Squarate amnials of general formula (15), wherein $R_1$, $R_2$, $R_4$, and $R_5$ are as defined in formula (I) and $R_6$ is halo alkyl such as, but not limited to, —$CCl_3$ or —$CF_3$, can be prepared as described ill Scheme 4. Amides of general formula (2) can be treated with α-haloaldehyde hydrates or α-halohemiacetals of general formula (20), wherein R is hydrogen and R' is selected from hydrogen or alkyl, such as, but not limited to, 2,2,2-trichloro-1,1-ethanediol or 1-ethoxy-2,2,2-trifluoro-1-ethanol, followed by addition of a chlorinating agent such as, but not limited to, thionyl chloride and a base such as, but not limited to, pyridine to provide chloroamides of general formula (21). Chloroamides of general formula (21) can be treated with squarates of general formula (14) in a polar, aprotic solvent such as, but not limited to, DMF in the presence of a base such as, but not limited to, cesium carbonate to provide squarate aminals of general formula (15).

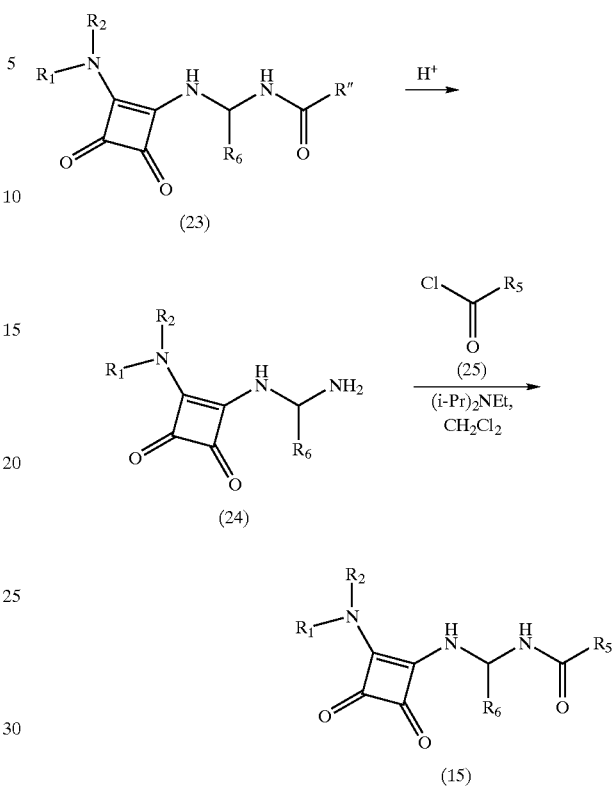

An alternate route for preparing squarate amnials of general formula (15), wherein $R_1$, $R_2$, $R_5$, and $R_6$ are as defined in formula (I) is described in Scheme 5. Squarate aminals of general formula (23), wherein R" is alkoxy, can be prepared following the strategy described in Scheme 2. Squarate aminals of general formula (23) can be treated with an acid such as, but not limited to, hydrobromic acid or trifluoroacetic acid to provide primary amines of general formula (24). Amines of general formula (24) can be treated with acid chlorides of general formula (25) in the presence of a base such as, but not limited to, diisopropylethylainine to provide squarate aminals of general formula (15).

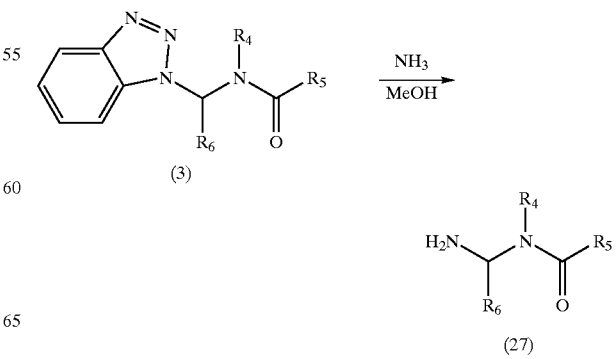

37

-continued

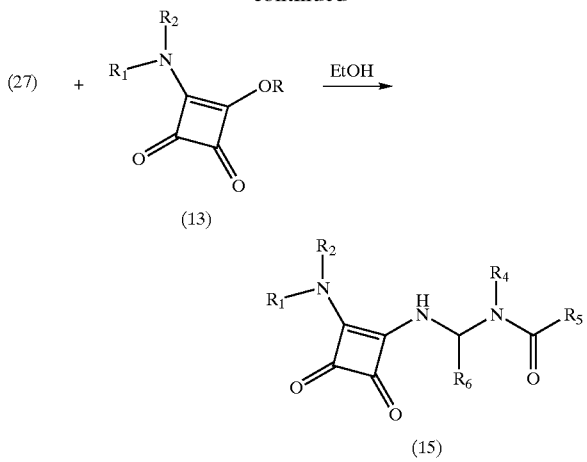

An alternate route for preparing squarate aminals of general formula (15), wherein $R_1$, $R_2$, $R_4$, $R_5$, and $R_6$ are as defined in formula (I) is described in Scheme 6. Compounds of general formula (3) can be treated with ammonia in an alcoholic solvent such as, but not limited to, methanol as described in Katritzky, Urogdi, Mayence, J. Org. Chem. (1990), 55, 2206; Katritzky, Chem. Rev. (1998), 98, 409; and Katritzky; J. Heterocyclic Chem. (1996), 33, 1935 to provide aminoamides of general formula (27). Aminoamides of general formula (27) can be treated with squarates of general formula (13) in alcoholic solvent such as, but not limited to, ethanol or a polar, aprotic solvent such as, but not limited to, acetonitrile to provide squarate aminals of general formula (15).

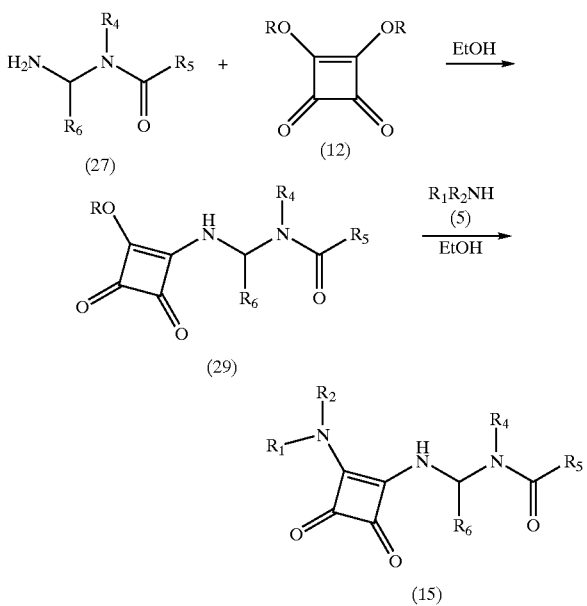

Squarate aminals of general formula (15), wherein $R_1$, $R_2$, $R_4$, $R_5$, and $R_6$ are as defined in formula (I), can be prepared as described in Scheme 7. Aminoamides of general formula (27) can be treated with dialkyl squarates of general formula (12), wherein R is alkyl, such as, but not limited to, diethyl squarate in an alcoholic solvent such as, but not limited to, ethanol or a polar, aprotic solvent such as, but not limited to,

38 acetonitrile to provide squarates of general formula (29). Squarates of general formula (29) can be treated with amines of general formula (5) in an alcoholic solvent such as, but not limited to, ethanol to provide squarate aminals of general formula (15).

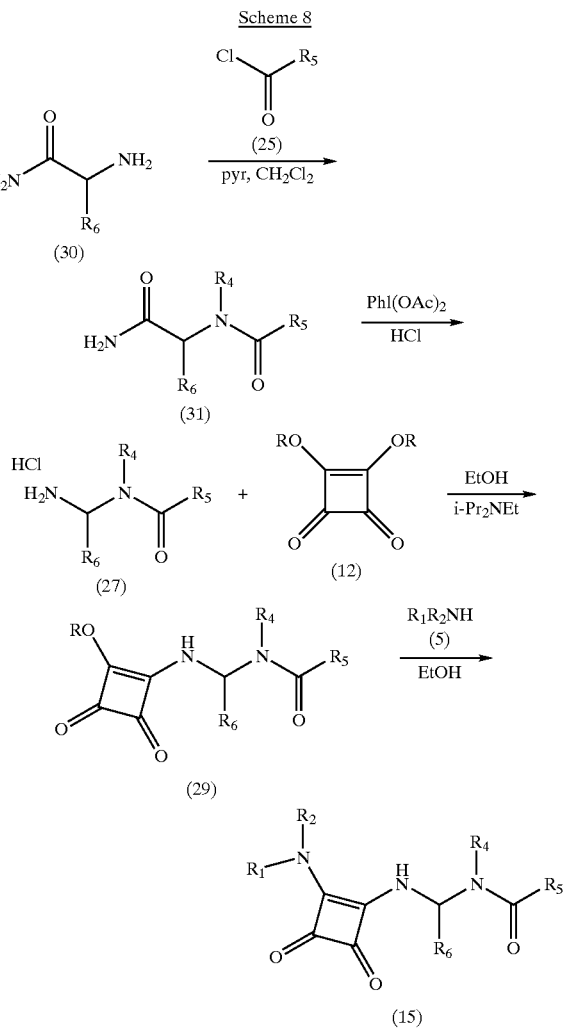

Squarate aminals of general formula (15), wherein $R_1$, $R_2$, $R_4$, $R_5$, and $R_6$ are as defined in formula (I), can be prepared as described in Scheme 8. Aminoacetamides of general formula (30) can be treated with acid chlorides of general formula (25) in the presence of a base such as, but not limited to, pyridine or triethylamine to provide the corresponding acylaminoamides of general formula (31). Acylaminoamides of general formula (31) can undergo a Hofmann rearrangement as described in Wallis and Lane, Org. React (1946), 3, 267–306, and references contained therein with reagents such as, but not limited to, iodosobenzene diacetate as described in Loudon et al., Org. Chem. (1984), 49, 4272; Loudon and Boutin, J. Org. Chem. (1984), 49, 4277, and Chan et al, Synth. Commun. (1988),53, 5158 to provide aminoamides of general formula (27), which can be typically isolated as their hydrochloride salts. Aminoamides of general formula (27) can be treated with squarates of general formula (12), wherein R is alkyl, such as, but not limited to, diethyl squarate in an alcoholic solvent such as, but not limited to, ethanol or a polar, aprotic solvent such as, but not limited to, acetonitrile to provide squarates of general formula (29). Squarates of general formula (29) can then be treated with amines of general formula (5) in an alcoholic solvent such as, but not limited to, ethanol to provide squarate aminals of general formula (15).

Scheme 9

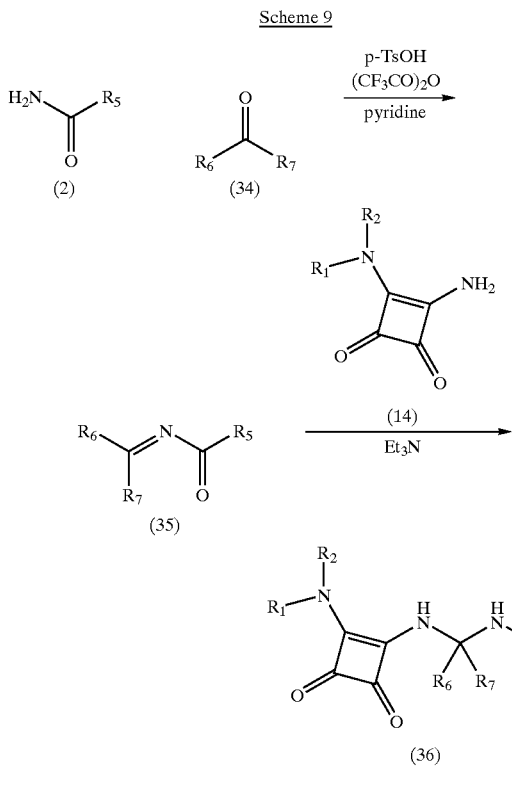

Geminally-substituted squarate aminals of general formula (36), wherein $R_1$, $R_2$, $R_5$, $R_6$, and $R_7$ are as defined in formula (I) and $R_6=R_7$ or $R_6$ and $R_7$ taken together with the carbon atom to which they are attached, together form a 5 or 6 membered carbocyclic ring, can be prepared as described in Scheme 9 or as described in Steglich, Chem. Ber. (1974), 107, 1488, and Burger, J. Fluorine Chem. (1982), 20, 813. Primary amides of general formula (2) can be treated with symmetrical ketones of general formula (34) in the presence of a dehydrating agent such as, but not limited to, trifluoroacetic anhydride and a base such as, but not limited to, pyridine to provide symmetrical imines of general formula (35). Symmetrical imines of general formula (35) can be treated with squarates of general formula (14) in the presence of a base such as, but not limited to, triethylamine to provide geminally-substituted squarate aminals of general formula (36).

Scheme 10

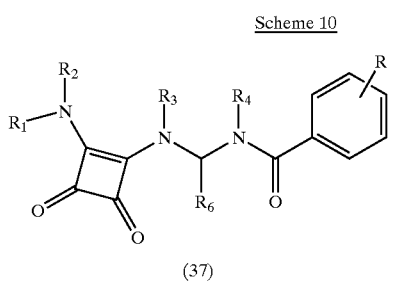

(37)
R = Br, I or OTf

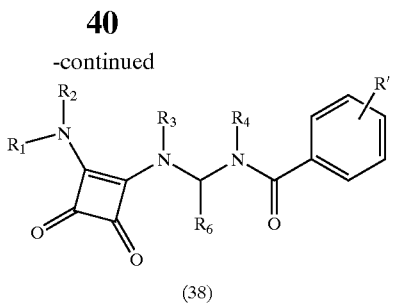

(38)

Squarate aminals of general formula (38), wherein $R_1$, $R_2$, $R_3$, $R_4$ and $R_6$ are as defined in formula (I) and R' is selected from alkoxycarbonyl, aryl, carboxy, heterocycle and —$NR_AR_B$ wherein $R_A$ and $R_B$ are as defined in formula (I), can be prepared as described in Scheme 10. Squarate aminals of general formula (37), wherein R is Br, I or —OS(O)$_2$CF$_3$, can be treated with a palladium catalyst, a trialkyltin reagent and triphenylarsine in a solvent such as, but not limited to, N-methylpyrrolidin-2-one as described in Farina and Baker, J. Org. Chem. (1990), 55, 5833 to provide aminals of general formula (38). Alternatively, cross-coupling reactions and carbonylations can be done on squarate aminals of general formula (37) using Buchwald, Stille, Suzuki or Heck coupling reaction conditions, all of which are well known to those skilled in the art of organic chemistry.

Scheme 11

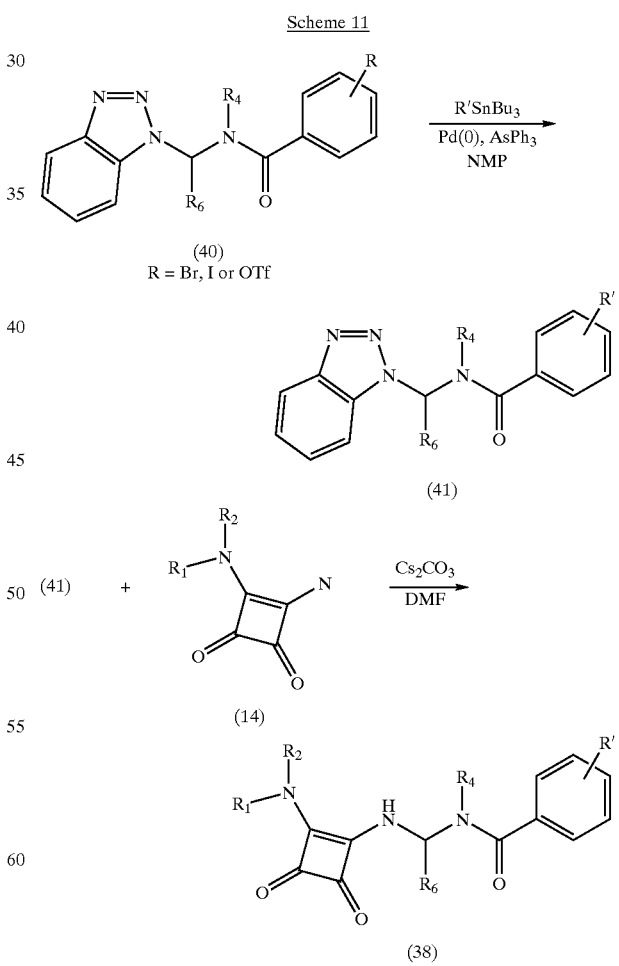

Scheme 11 describes a preferred method that provides squarate aminals of general formula (38), wherein $R_1$, $R_2$, $R_4$, and $R_6$ are as defined in formula (I) and R' is selected from alkoxycarbonyl, aryl, carboxy, heterocycle and —$NR_AR_B$ wherein $R_A$ and $R_B$ are as defined in formula (I). Benzotriazole compounds of general formula (40), wherein R is Br, I or —OS(O)$_2$CF$_3$, can be treated with a palladium catalyst, a trialkyltin reagent and triphenylarsine in a solvent such as, but not limited to, N-methylpyrrolidin-2-one as described in Farina and Baker, J. Org. Chem. (1990), 55, 5833 to provide elaborated benzotriazoles of general formula (41). Alternatively, cross-coupling reactions and carbonylations can be done on benzotriazoles of general formula (40) using Buchwald, Stille, Suzuki or Heck coupling reaction conditions all of which are well known to those skilled in the art of organic chemistry. Benzotriazoles of general formula (41) can be treated with squarates of general formula (14) in a polar, aprotic solvent such as, but not limited to, DMF in the presence of a base such as, but not limited to, cesium carbonate to provide squarate aminals of general formula (38).

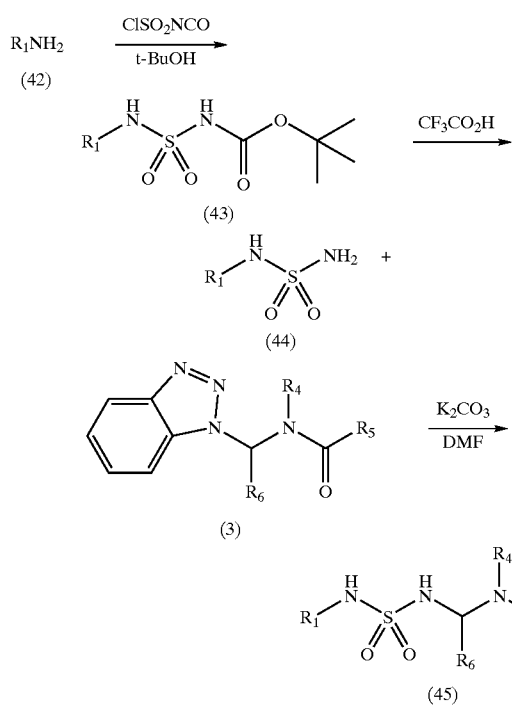

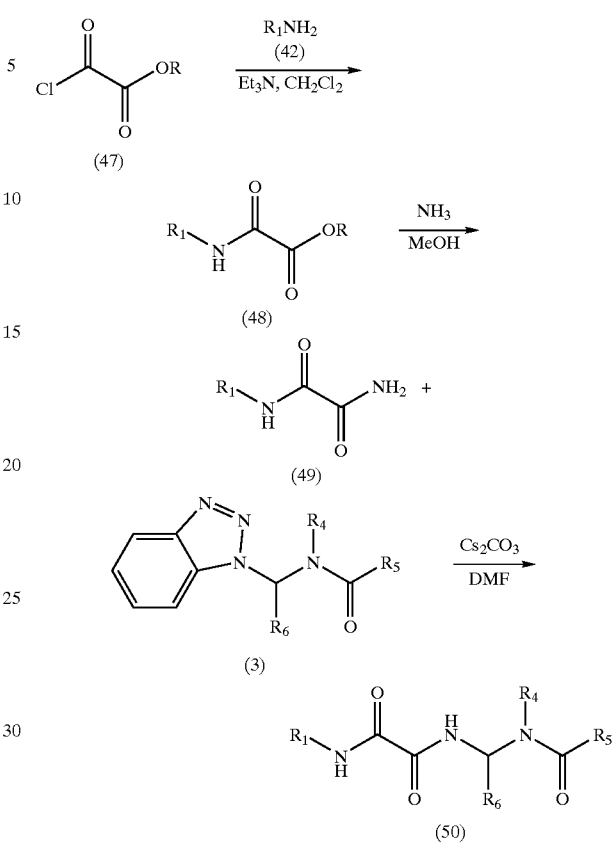

Sulfonylamino aminals of general formula (45), wherein $R_1$, $R_4$, $R_5$, and $R_6$ are as defined in formula (I), can be prepared as described in Scheme 12. Primary amines of general formula (42) can be treated with chlorosulfonyl isocyante in the presence of an alcoholic nucleophile such as, but not limited to, t-butanol as described in Abdaoui, Bioorg. Med. Chem. Lett. (1996), 4, 1227 to provide sulfonylamino carbamates of general formula (43). Sulfonylamino carbamates of general formula (43) can be treated with a protic acid such as, but not limited to, trifluoroacetic acid to provide amino sulfonamides of general formula (44). Amino sulfonamides of general formula (44) can be treated with benzotriazoles of general formula (3) in a polar, aprotic solvent such as, but not limited to, DMF in the presence of a base such as, but not limited to, potassium carbonate or cesium carbonate to provide sulfonylamino aminals of general formula (45)

Ethanediamide aminals of general formula (50), wherein $R_1$, $R_4$, $R_5$, and $R_6$ are as defined in formula (I) can be prepared as described in Scheme 13. Chloroalkyloxalates of general formula (47), wherein R is alkyl, such as, but not limited to, chloroethyloxalate can be treated with primary amines of general formula (42) in the presence of a base such as, but not limited to, triethylamine to provide amidoesters of general formula (48). Amidoesters of general formula (48) can be treated with ammonia in an alcoholic solvent such as, but not limited to, methanol to provide oxalamides of general formula (49). Oxalamides of general formula (49) can be treated with benzotriazoles of general formula (3) in a polar, aprotic solvent such as, but not limited to, DMF in the presence of a base such as, but not limited to, potassium carbonate or cesium carbonate to provide ethanediamide aminals of general formula (50).

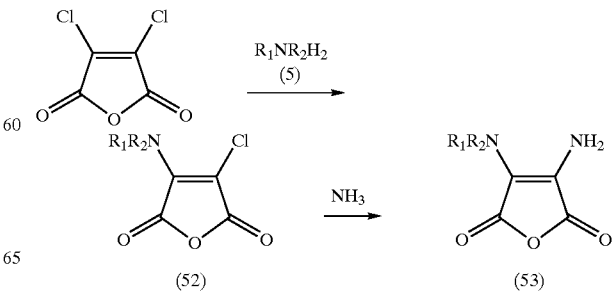

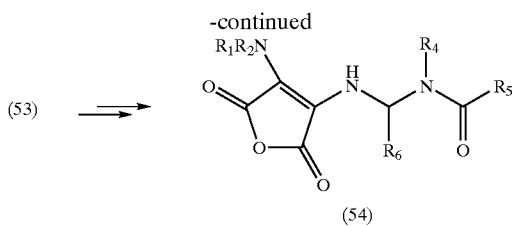

Aminals of general formula (54), wherein $R_1$, $R_2$, $R_4$, $R_5$ and $R_6$ are as defined in formula (I), can be prepared as described in Scheme 14. 3,4-Dichloro-2,5-furandione, purchased from Aldrich Chemical Company, can be treated with amines of general formula (5) as described in previous Schemes to provide furandiones of general formula (52). Furandiones of general formula (52) can be treated with ammonia as described in previous Schemes to provide compounds of general formula (53). Compounds of general formula (53) can be processed as described in Schemes 1–5 and Scheme 9 to provide aminals of general formula (54).

Alternatively, 3,4-dichloro-2,5-furandione can be processed as described in Schemes 6–8 to provide aminals of general formula (54).

Scheme 15

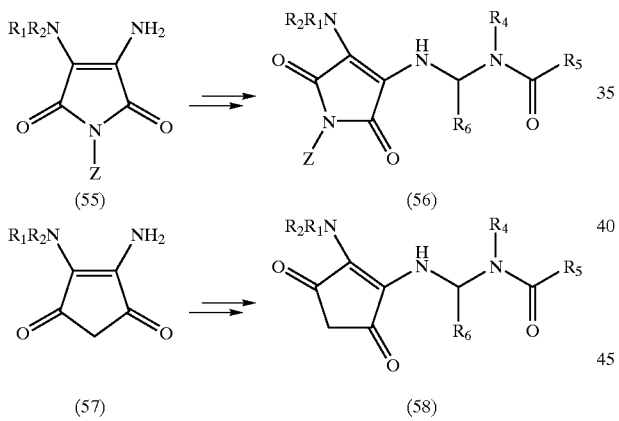

Aminals of general formula (56), wherein $R_1$, $R_2$, $R_4$, $R_5$ and $R_6$ are as defined in formula (I), can be prepared as described in Scheme 15. Pyrrole diones of general formula (55) can be prepared as described in Augustin, Tetrahedron (1980) 36, 1801; and Hanaineh-Abdelnour, Tetrahedron (1999) 55, 11859 and then processed as described in previous Schemes to provide aminals of general formula (56).

Aminals of general formula (5 8), wherein $R_1$, $R_2$, $R_4$, $R_5$ and $R_6$ are as defined in formula (I), can be prepared as described in Scheme 15. Cyclopentene diones of general formula (57) can be prepared as described in Lee et al., JOC (1995) 60, 735; and Yamamoto et al., JACS (1995) 117, 9653 and then processed as described in previous Schemes to provide aminals of general formula (58).

Scheme 16

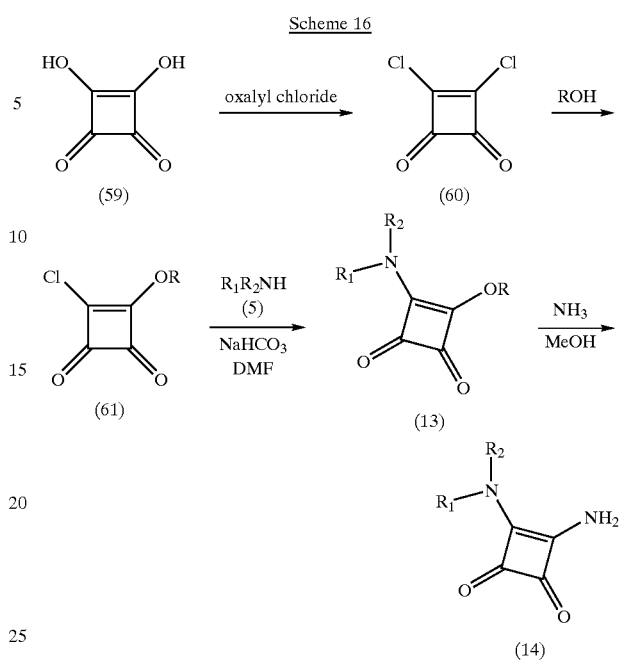

Squarate aminals of general formula (15), wherein $R_1$, $R_2$, $R_4$, and $R_5$ are as defined in formula (I) and $R_6$ is selected from alkyl such as, but not limited to, t-butyl, arylalkyl such as, but not limited to, phenethyl, or haloalkyl such as, but not limited to, —CCl$_2$CH$_3$ or —CF$_2$CF$_3$, can be prepared as described in Scheme 16. Squaric acid (59) can be treated with oxalyl chloride as described in Ohno et al., J. Chem. Soc., Perkin Trans. 1 (1993), 263; and Yamamoto et al., Tetrahedron (2000), 50, 7783, to provide 3,4-dichlorocyclobut-3-ene-1,2-dione (60) which can be treated with alcohols such as, but not limited to, methanol as described in Ohno et al., J. Chem. Soc., Perkin Trans. 1(1993), 263, to provide compounds of general formula (61) wherein R is alkyl. Compounds of general formula (61) can be treated with amines of general formula (5) in the presence of a base such as, but not limited to, sodium bicarbonate in a polar aprotic solvent such as, but not limited to, DMF, to provide squarates of general formula (13). Squarates of general formula (13) can be treated with ammonia in an alcoholic solvent such as, but not limited to, methanol to provide squarates of general formula (14). Benzotriazoles of general formula (3) can be treated with squarates of general formula (14) in a polar, aprotic solvent such as, but not limited to, DMF in the presence of a base such as, but not limited to, cesium carbonate to provide squarate aminals of general formula (15).

The compounds and processes of the present invention will be better understood by reference to the following examples, which are intended as an illustration of and not a limitation upon the scope of the invention.

EXAMPLE 1

N-(1-{[3,4-Dioxo-2-(3-pyridinylamino)-1-cyclobuten-1-yl]amino}-2,2-dimethylpropyl)-4-methylbenzamide

EXAMPLE 1A

3-Ethoxy-4-(3-pyridinylamino-3-cyclobutene-1,2-dione

3-Aminopyridine (2.77 g, 29.4 mmol) in ethanol (30 mL) was added to a refluxing solution of 3,4-diethoxy-3-cyclobutene-1,2-dione (5.00 g, 29.4 mmol) in ethanol (100 mL) over a period of 1hour. The mixture was heated at reflux for 24 hours, filtered, and the filtrate removed under reduced pressure. The residue was purified by flash chromatography on silica gel (elution with 5% EtOH/EtOAc) to provide 4.42 g of the title compound as a white powder. MS (DCI/NH$_3$) m/z 219 (M+H)$^+$.

EXAMPLE 1B

3-Amino-4-(3pyridinylamino)-3-cyclobutene-1,2-dione

The product from Example 1A (4.42 g, 20.2 mmol) in ethanol (80 mL) was treated with 2.0M NH$_3$ in methanol (30 mL) and stirred at ambient temperature for 16 hours. The solvent was removed under reduced pressure and the residue was triturated with diethyl ether to provide 3.80 g of the title compound as a pale yellow powder. MS (DCI/NH$_3$) m/z 190 (M+H)$^+$.

EXAMPLE 1C

N-(1-(1H-1,2,3-Benzotriazol-1-yl)-2,2-dimethylpropyl)-4-methylbenzamide

A suspension of p-toluamide (4.11 g, 30.4 mmol), pivaldehyde (2.62 g, 30.4 mmol), and benzotriazole (3.62 g, 30.4 mmol) in toluene (200 mL) was treated with p-toluenesulfonic acid (286 mg, 1.52 mmol). The solution was heated at reflux under Dean-Stark conditions for 10 hours, cooled gradually to ambient temperature, and further cooled to 5° C. The white precipitate which formed was collected by filtration and was washed with 50% diethyl ether/hexanes (100 mL) to provide 6.67 g of the title compound as a white solid.

MS (DCI/NH$_3$) m/z 323 (M+H)$^+$.

EXAMPLE 1D

N-(1-{[3,4-Dioxo-2-(3-pyridinylamino)-1-cyclobuten-1-yl]amino}-2,2-dimethylpropyl)-4-methylbenzamide The product from Example 1B (0.15 g, 0.79 mmol), and the product from Example 1C (0.26 g, 0.79 mmol) in DMF (3 mL) were treated with K$_2$CO$_3$ (0.55 g, 3.97 mmol). The reaction mixture was stirred at ambient temperature for 20 hours then diluted with 25 mL H$_2$O and extracted with EtOAc (2×50 mL). The combined extracts were dried over Na$_2$SO$_4$, and EtOH (5 mL) was added. The crude reaction mixture was filtered through a 0.5 inch silica gel plug and concentrated under reduced pressure to a volume of 20 mL. The title compound (0.13 g) was collected by filtration and dried under reduced pressure for 1 hour.

mp 258–259° C.; MS (DCI/NH$_3$) m/z 393 (M+H)$^+$; $^1$H NMR (DMSO-d$_6$) δ 9.89 (s, 1H), 8.58 (d, 1H, J=3Hz), 8.25 (d, 1H, J=5 Hz), 8.06 (br s, 1H) 7.94 (dd, 1H, J=8, 1 Hz), 7.77 (d, 2H, J=8 Hz), 7.38 (dd, 1H, J=8, 5 Hz), 7.29(d, 2H, J=8 Hz), 5.86 (t, 1H, J=8 Hz), 2.36(s, 3H), 1.06 (s, 9H); Anal. calcd for C$_{22}$H$_{24}$N$_4$O$_3$: C, 67.33; H, 6.16; N, 14.28. Found: C, 66.99, H, 5.94, N, 14.20.

EXAMPLE 2

4-Chloro-N-(1-{[3,4-dioxo-2-(3-pyridinylamino)-1-cyclobuten-1-yl]amino}-2.2-dimethylpropyl)benzamide

EXAMPLE 2A

N-(1-(1H-1,2,3-Benzotriazol-1-yl)-2,2-dimethylpropyl)-4-chlorobenzamide

A suspension of 4-chlorobenzamide, pivaldehyde, benzotriazole, and p-toluenesulfonic acid was processed as described in Example 1C to provide the title compound.

MS (DCI/NH$_3$) m/z 343 (M+H)$^+$.

EXAMPLE 2B

4-Chloro-N-(1-{[3,4-dioxo-2-(3-pyridinylamino)-1-cyclobuten-1-yl]amino}-2,2-dimethylpropyl)benzamide A suspension of the product from Example 1B, the product from Example 2A, and K$_2$CO$_3$ was processed as described in Example 1D to provide the title compound.

mp 257–258° C.; MS (DCI/NH$_3$) m/z 413 (M+H)$^+$; H NMR (DMSO-d$_6$) δ 9.90 (br s, 1H), 8.74 (d, 1H, J=7 Hz), 8.58 (d, 1H, J=2Hz), 8.25 (d, 1H, J=4 Hz), 8.06 (br s, 1H), 7.93 (d, 1H, J=8 Hz), 7.87 (d, 2H, J=8 Hz), 7.56 (d, 2H, J=8 Hz), 7.38 (dd, 1H, J=8, 5 Hz), 5.86 (s, 1H), 1.06 (s, 9H); Anal. calcd for C$_{21}$H$_{21}$ClN$_4$O$_3$: C, 61.09; H, 5.13; N, 13.57. Found: C, 60.86; H, 5.07; N 13.44.

EXAMPLE 3

N-(1-{[3,4-Dioxo-2-(3-pyridinylamino)-1-cyclobuten-1-yl]amino}-2,2-dimethylpropyl)-4-iodobenzamide

EXAMPLE 3A

N-(1-(1H-1,2,3-Benzotriazol-1-yl-2,2-dimethylpropyl)-4-iodobenzamide

A suspension of 4-iodobenzamide, pivaldehyde, benzotriazole, and p-toluenesulfonic acid was processed as described in Example IC to provide the title compound.

MS (DCI/NH$_3$) m/z 435 (M+H)$^+$.

EXAMPLE 3B

N-(1-{[3,4-Dioxo-2-(3-pyridinylamino)-1-cyclobuten-1-yl]amino}-2,2-dimethylpropyl)-4-iodobenzamide A suspension of the product from Example 1B , the product from Example 3A, and K$_2$CO$_3$ was processed as described in Example 1D to provide the title compound.

mp 256–257° C.; MS (ESI+) m/z 505 (M+H)+; 1H NMR (DMSO-d6) δ 9.90 (br s, 1H), 8.71 (d, 1H, J=8 Hz), 8.57 (d, 1H, J=3Hz), 8.25 (dd, 1H, J=5, 1 Hz), 8.05 (br s, 1H), 7.93 (dd, 1H, J=8, 1 Hz), 7.88 (d, 2H, J=8 Hz), 7.63 (d, 2H, J=8 Hz), 7.38 (dd, 1H, J=8, 5 Hz), 5.84 (br s, 1H), 1.05 (s, 9H); Anal. calcd for $C_{21}H_{21}IN_4O_3$: C, 50.01; H, 4.20; N, 11.11. Found: C, 50.37; H, 4.50; N, 10.80.

EXAMPLE 4

N-(1-{[3,4-Dioxo-2-(3-pyridinylamino)-1-cyclobuten-1-yl]amino}-2,2-dimethylpropyl)-4-(2-furyl)benzamide

EXAMPLE 4A

N-(1-(1H-1,2,3-Benzotriazol-1-yl)-2,2-dimethylpropyl)-4-(2-furyl)benzamide

A solution of Example 3A (51 mg, 0.12 mmol) in N-methylpyrrolidinone (2 mL) at 23° C. was treated with 2-(tributylstannyl)furan (41 μL, 0.13 mmol) followed by triphenylarsine (3.7 mg, 0.012 mmol) and then tris (dibenzylideneacetone)dipalladium(0) (5.4 mg, 0.006 mmol). The reaction mixture was stirred for 3.5 hours then partitioned between EtOAc (15 mL) and water (5 mL). The organic portion was washed with water (5 mL) then brine (5 mL) and dried ($Na_2SO_4$). Filtration and concentration afforded a oily residue which was purified by flash chromatography (elution with 5% EtOAc/1:1 hexanes:$CH_2Cl_2$) to provide 37 mg (84%) of the title compound as a white solid.

MS ($DCI/NH_3$) m/z 375 (M+H)+.

EXAMPLE 4B

N-(1-{[3,4-Dioxo-2-(3-pyridinylamino)-1-cyclobuten-1-yl]amino}-2,2-dimethylpropyl)-4-(2-furyl)benzamide A suspension of the product from Example 1B, the product from Example 4A, and $K_2CO_3$ was processed as described in Example 1D to provide the title compound.

mp 230–232° C.; MS ($DCI/NH_3$) m/z 445 (M+H)+; 1H NMR (DMSO-d6) δ 9.88 (br s, 1H), 8.67 (br s, 1H), 8.55 (d, 1H, J=2.7 Hz), 8.23 (dd, 1H, J=4.6, 1.0 Hz), 8.04 (br s, 1H), 7.96–7.87 (m, 3H), 7.83–7.77 (m, 3H), 7.37 (dd, 1H, J=8.5, 4.8 Hz), 7.10 (d, 1H, J=3.4 Hz), 6.62 (dd, 1H, J=3.4, 2.0 Hz), 5.86 (br t, 1H, J=6.8 Hz), 1.04 (s, 9H), Anal. calcd for $C_{25}H_{24}N_4O_4$: C, 67.55; H, 5.44; N, 12.60. Found: C, 66.92; H, 5.46; N, 12.69.

EXAMPLE 5

3-Chloro-N-(1-{[3,4-dioxo-2-(3-pyridinylamino)-1-cyclobuten-1-yl]amino}-2.2-dimethylpropyl) benzamide

EXAMPLE 5A

N-(1-(1H-1,2,3-Benzotriazol-1-yl)-2,2-dimethylpropyl)-3-chlorobenzamide

A suspension of 3-chlorobenzamide, pivaldehyde, benzotriazole, and p-toluenesulfonic acid was processed as described in Example 1C to provide the title compound.

MS ($DCI/NH_3$) m/z 343 (M+H)+.

EXAMPLE 5B 3-chloro-N-(1-{[3,4-Dioxo-2-(3-pyridinylamino)-1-cyclobuten-1-yl]amino}-2,2-dimethylpropyl) benzamide A suspension of the product from Example 1B, the product from Example 5A, and $K_2CO_3$ was processed as described in Example 1D to provide the title compound.

MS (ESI) m/z 413 (M+H)+; 1H NMR (DMSO-d6) δ 9.73 (br s, 1H), 9.40 (br d, 1H, J=8.4 Hz), 8.77 (d, 1H, J=2.5 Hz), 8.50 (d, 1H, J=8.4 Hz), 8.26 (dd, 1H, J=5.5, 1.1 Hz), 7.93 (br s, 1H), 7.79 (br s, 1H), 7.83 (d, 1H, J=7.9Hz),7.61 (br d, 1H, J=8.6 Hz),7.58 (t, 1H,J=8.2Hz), 7.41 (dd, 1H,J=8.7, 4.8 Hz), 5.47 (t, 1H, J=8.5 Hz), 0.90 (s, 9H); Anal. calcd for $C_{21}H_{51}ClN_4O_3$: C, 61.09; H, 5.13; N, 13.57. Found: C, 61.56; H, 5.02; N 13.79.

EXAMPLE 6

N-(1-{[3,4-Dioxo-2-(3-pyridinylamino)-1-cyclobuten-1-yl]amino}-2,2-dimethylpropyl)-3-methylbenzamide

EXAMPLE 6A

N-(1-(1H-1,2,3-benzotriazol-1-yl)-2,2-dimethylpropyl)-3-methylbenzamide

A suspension of m-toluamide, pivaldehyde, benzotriazole, and p-toluenesulfonic acid was processed as described in Example 1C to provide the title compound.

MS ($DCI/NH_3$) m/z 323 (M+H)+.

EXAMPLE 6B

N-(1-{[3,4-Dioxo-2-(3-pyridinylamino)-1-cyclobuten-1-yl]amino}-2,2-dimethylpropyl-3-methylbenzamide A suspension of the product from Example 1B, the product from Example 6A, and $K_2CO_3$ was processed as described in Example 1D to provide the title compound.

mp 236–237° C.; MS (ESI+) m/z 393 (M+H)+; 1H NMR (DMSO-d6) δ 9.93 (br s, 1H), 8.64 (br d, 1H, J=7.1 Hz), 8.57 (d, 1H, J=2.7 Hz) 8.25 (dd, 1H,J=4.7, 1.4 Hz),8.08 (br s, 1H), 7.93 (br d, 1H, J=7.9 Hz), 7.66–7.60 (m, 2H), 7.41–7.34 (m, 3H), 5.87 (br t, 1H, J=6.8 Hz), 2.37 (s, 3H), 1.05 (s, 9H); Anal. calcd for $C_{22}H_{24}N_4O_3$: C, 67.33; H, 6.16; N, 14.28. Found: C, 66.98; H, 6.17, N, 14.10.

EXAMPLE 7

N-(1-{[3,4-Dioxo-2-(3-pyridinylamino)-1-cyclobuten-1-yl]amino}-2,2-dimethylpropyl)-3-fluorobenzamide

EXAMPLE 7A

N-(1-(1H-1,2,3-Benzotriazol-1-yl)-2,2-dimethylpropyl)-3-fluorobenzamide

A suspension of 3-fluorobenzamide, pivaldehyde, benzotriazole, and p-toluenesulfonic acid was processed as described in Example 1C to provide the title compound.

MS ($DCI/NH_3$) m/z 327 (M+H)+.

EXAMPLE 7B

N-(1-{[3,4-Dioxo-2-(3-pyridinylamino)-1-cyclobuten-1-yl]amino}-2.2-dimethylpropyl)-3-fluorobenzamide A suspension of the product from Example 1B, the product from Example 7A, and $K_2CO_3$ was processed as described in Example 1D to provide the title compound.

mp 231–232° C.; MS ($DCI/NH_3$) m/z 397 (M+H)+; 1H NMR (DMSO-d6) δ 9.88 (s, 1H), 8.75 (d, 1H, J=8 Hz), 8.59

(d, 1H, J=2 Hz), 8.26 (dd, 1H, J=5, 1 Hz), 8.04 (br s, 1H), 7.94 (ddd, 1H, J=8, 3, 1 Hz), 7.71 (dt, 1H, J=8, 1 Hz), 7.66 (ddd, 1H, J=10, 3, 2 Hz), 7.55 (td, 1H, J=10, 6 Hz), 7.44–7.37 (m, 2H), 5.88 (t, 1H, J=8 Hz), 1.07 (s, 9H); Anal. calcd for $C_{21}H_{21}FN_4O_3$ $0.5H_2O$: C, 62.21 H, 5.47; N, 13.82. Found: C, 62.12; H, 5.52; N. 14.07.

EXAMPLE 8

N-(1-{[3,4-Dioxo-2-(3-pyridinylamino)-1-cyclobuten-1-yl]amino}-2.2-dimethylpropyl)-3-iodobenzamide

EXAMPLE 8A

N-(1-(1H-1,2,3-Benzotriazol-1-yl)-2,2-dimethylpropyl)-3-iodobenzamide

A suspension of 3-iodobenzamide, pivaldehyde, benzotriazole, and p-toluenesulfonic acid was processed as described in Example 1C to provide the title compound.

MS (DCI/NH$_3$) m/z 435 (M+H)$^+$.

EXAMPLE 8B

N-(1-{[3,4-Dioxo-2-(3-pyridinylamino)-1-cyclobuten-1-yl]amino}-2,2-dimethylpropyl)-3-iodobenzamide A suspension of the product from Example 1B, the product from Example 8A, and $K_2CO_3$ was processed as described in Example 1D to provide the title compound.

mp 234–236° C.; MS (DCI/NH$_3$) m/z 505 (M+H)$^+$; $^1$H NMR (DMSO-d$_6$) δ 10.03 (br s, 1H), 8.77 (br d, 1H, J=7.0 Hz), 8.69 (d, 1H, J=2.4 Hz), 8.33 (dd, 1H, J=4.8, 1.4 Hz), 8.15 (t, 1H, J=1.4 Hz), 8.10 (br s, 1H), 8.06 (ddd, 1H, J=8.5, 2.7, 1.4 Hz), 7.93 (br d, 1H, J=7.4 Hz), 7.83 (br d, 1H, J=7.9 Hz), 7.56 (dd, 1H, J=8.5, 5.2 Hz), 7.80 (t, 1H, J=7.8 Hz), 5.85 (br t, 1H, J=6.9 Hz), 1.09 (s, 9H); Anal. calcd for $C_{21}H_{21}IN_4O_3$: C, 50.01; H, 4.20; N, 11.11. Found: C, 49.56; H, 4.03; N, 10.86.

EXAMPLE 9

N-(1-{[3,4-Dioxo-2-(3-pyridinylamino)-1-cyclobuten-1-yl]amino}-2,2-dimethylpropyl)-3,4-dimethylbenzamide A mixture of 1H-benzotriazole polystyrene (purchased from Novabiochem, 1.33 mmol/g, 500 mg, 0.665 mmol), pivalaldehyde (580 mg, 6.70 mmol), 3,4-dimethylbenzamide (1.00 g, 6.70 mmol) and p-toluenesulfonic acid (50 mg, 0.30 mmol) in anhydrous THF (3 mL) and 2-methoxyethanol (3 mL) was heated at 65° C. for 24 hours. The resin was filtered to remove solvent and washed sequentially with DMF (3×0.5 mL), methanol (0.5 mL), DMF (3×0.5 mL), CH$_2$Cl$_2$ (3×0.5 mL), diethyl ether (2×0.5 mL) and dried.

The resin (126 mg, 0.133 mmol) was stirred with the product from Example 1B (30 mg, 0.66 mmol) and cesium carbonate (100 mg, 0.310 mmol) in anhydrous dimethylacetamide (2 mL) for 7 days at 23° C. The solution was filtered and the filtrate concentrated under reduced pressure. The residue was purified by preparative reverse-phase HPLC (elution with aqueous acetonitrile +0.5% TFA) to provide 7 mg (13%) of the title compound.

MS (DCI/NH$_3$) m/z 407 (M+H)$^+$; $^1$H NMR (DMSO-d$_6$) δ 13.19 (br s, 1H), 11.67 (s, 1H), 8.63 (br d, 1H, J=7.0 Hz), 8.55 (d, 1H, J=2.0 Hz), 8.13 (dd, 1H, J=8.8, 2.0 Hz), 7.98 (d, 1H, J=9.2 Hz), 7.87 (br d, 1H, J=0.8 Hz), 7.49–7.30 (m, 3H), 5.87 (br t, 1H, J=6.8 Hz), 2.34 (s, 6H), 1.06 (s, 9H).

EXAMPLE 10

N-(1-{[3,4-dioxo-2-(3-pyridinylamino)-1-cyclobuten-1-yl]amino}-2,2-dimethylpropyl)-2,3-dimethoxybenzamide A suspension of resin-bound benzotriazole was treated with 2,3-dimethoxybenzamide, pivaldehyde, and p-toluenesulfonic acid and was then processed with the product from Example 1B and $Cs_2CO_3$ as described in Example 9 to provide the title compound.

MS (ESI) m/z 439 (M+H)$^+$; $^1$H NMR (DMSO-d$_6$) δ 9.94 (s, 1H), 8.26 (d, 1H, J=8.5 Hz), 7.33–7.15 (m, 5H), 7.08–7.03 (m, 2H), 6.23 (s, 1H), 5.73 (t, 1H, J=8.2 Hz), 3.79 (s, 6H), 1.08 (s, 9H).

EXAMPLE 11

N-(1-{[3,4-Dioxo-2-(3-pyridinylamino)-1-cyclobuten-1-yl]amino}-2,2-dimethylpropyl)-1-naphthamide A suspension of resin-bound benzotriazole was treated with 1-naphthamide, pivaldehyde, and p-toluenesulfonic acid and was then processed with the product from Example 1B and $Cs_2CO_3$ as described in Example 9 to provide the title compound.

MS (ESI) m/z 429 (M+H)$^+$; $^1$H NMR (DMSO-d$_6$) δ 9.88 (s, 1H), 8.75 (d, 1H, J=8 Hz), 8.59 (d, 1H, J=2Hz), 8.31–8.17 (m, 3H), 8.26 (d, 1H, J=5 Hz), 8.06 (br s, 1H), 7.94 (dd, 1H, J=8, 1Hz), 7.74 (br d, 1H, J=8 Hz), 7.71 (dt, 1H, J=8, 1Hz), 7.66 (ddd, 1H, J=10, 3, 2 Hz), 7.42–7.34 (m, 1H), 7.35 (dd, 1H, J=8, 5 Hz), 5.88 (t, 1H, J=8 Hz), 1.07 (s, 9H).

EXAMPLE 12

3,5-Dichloro-N-(1-{[3,4-dioxo-2-(3-pyridinylamino)-1-cyclobuten-1-yl]amino}-2,2-dimethylpropyl)benzamide

EXAMPLE 12A

N-(1-(1H-1,2,3-Benzotriazol-1-yl)-2,2-dimethylpropyl)-3,5-dichlorobenzamide

A suspension of 3,5-dichlorobenzamide, pivaldehyde, benzotriazole, and p-toluenesulfonic acid was processed as described in Example 1C to provide the title compound.

MS (DCI/NH$_3$) m/z 377 (M+H)$^+$.

EXAMPLE 12B 3,5-Dichloro-N-(1-{[3,4-dioxo-2-(3-pyridinylamino)-1-cyclobuten-1-yl]amino}-2,2-dimethylpropyl)benzamide A suspension of the product from Example 1B, the product from Example 12A, and $K_2CO_3$ was processed as described in Example 1D to provide the title compound.

mp 260–262° C.; MS (ESI+) m/z 447 (M+H)$^+$; $^1$H NMR (DMSO-d$_6$) δ 9.88 (br s, 1H), 8.86 (d, 1H, J=7.8 Hz), 8.57 (d, 1H, J=2.7 Hz), 8.25 (dd, 1H, J=4.7, 1.3 Hz), 8.02 (br s, 1H), 7.86 (br d, 1H, J=8.4 Hz), 7.67 (s, 3H), 7.39 (dd, 1H, J=8.1, 4.4 Hz), 5.84 (t, 1H, J=8.3 Hz), 1.06 (s, 9H); Anal. calcd for $C_{21}H_{20}Cl_2N_4O_3$: C, 56.39; H, 4.51; N, 12.53. Found: C, 56.16; H, 4.49, N, 12.34.

EXAMPLE 13
N-(1-{[3,4-Dioxo-2-(3-pyridinylamino)-1-cyclobuten-1-yl]amino}-2 2-dimethylpropyl)-3,5-dimethoxybenzamide

EXAMPLE 13A
N-(1-(1H-1,2,3-Benzotriazol-1-yl)-2,2-dimethylpropyl)-3,5-dimethoxybenzamide A suspension of 3,5-dimethoxybenzamide, pivaldehyde, benzotriazole, and p-toluenesulfonic acid was processed as described in Example 1C to provide the title compound.
MS (ESI+) m/z 369 (M+H)$^+$.

EXAMPLE 13B
N-(1-{[3,4-dioxo-2-(3-pyridinylamino)-1-cyclobuten-1-yl]amino}-2,2-dimethylpropyl)-3,5-dimethoxybenzamide A suspension of the product from Example 1B, the product from Example 13A, and $K_2CO_3$ was processed as described in Example 1D to provide the title compound.
MS (ESI+) m/z 439 (M+H)$^+$; $^1$H NMR (DMSO-d$_6$) δ 10.82 (br s, 1H), 8.80 (d, 1H, J=2.4 Hz), 8.62 (d, 1H, J=7.8 Hz), 8.56 (d, 1H, J=7.9 Hz), 8.35 (d, 1H, J=5.1 Hz), 8.28 (br d, 1H, J=8.8 Hz), 7.66 (dd, 1H, J=8.5, 5.1 Hz), 6.92 (d, 2H, J=2.4 Hz), 6.67 (t, 1H, J=2.4 Hz), 5.82 (t, 1H, J=8.3 Hz), 3.82 (s, 6H), 1.07 (s, 9H); Anal. calcd for $C_{23}H_{26}N_4O_5$: C, 63.00; H, 5.98; N, 12.78. Found: C,62.76; H, 6.11; N, 12.98.

EXAMPLE 14
(−) N-(1-{[3,4-Dioxo-2-(3-pyridinylamino)-1-cyclobuten-1-yl]amino}-2,2-dimethylpronyl)-3,5-dimethoxybenzamide The product from Example 13B was chromatographed over a Daicel Chiral Technologies Chiralcel AS chiral column (2.0 cm×25 cm) eluting with 7% ethanol/hexanes (flow rate=10 mL/minute) to provide of the title compound as the levorotatory enantiomer.
$[α]_D^{23}$=−14° (c 0.10, DMSO); MS (ESI+) m/z 439 (M+H)$^+$; $^1$H NMR (DMSO-d$_6$) δ 10.82 (br s, 1H), 8.80 (d, 1H, J=2.4 Hz), 8.62 (d, 1H, J=7.8 Hz), 8.56 (d, 1H, J=7.9 Hz), 8.35 (d, 1H, J=5.1 Hz), 8.28 (br d, 1H, J=8.8 Hz), 7.66 (dd, 1H, J=8.5, 5.1 Hz), 6.92 (d, 2H, J=2.4 Hz), 6.67 (t, 1H, J=2.4 Hz), 5.82 (t, 1H, J=8.3 Hz), 3.82 (s, 6H), 1.07 (s, 9H);

EXAMPLE 15
(+) N-(1-{[3,4-Dioxo-2-(3-pyridinylamino)-1-cyclobuten-1-yl]amino}-2,2-dimethylpropyl)-3,5-dimethoxybenzamide The product from Example 13B was chromatographed over a Daicel Chiral Technologies Chiralcel AS chiral column (2.0 cm×25 cm) eluting with 7% ethanol/hexanes (flow rate=10 mL/minute) to provide of the title compound as the dextrorotatory enantiomer.
$[α]_D^{23}$+16° (c 0.11, DMSO); MS (ESI+) m/z 439 (M+H)$^+$; $^1$H NMR (DMSO-d$_6$) δ 10.82 (br s, 1H), 8.80 (d, 1H, J=2.4 Hz), 8.62 (d, 1H, J=7.8 Hz), 8.56 (d, 1H, J=7.9 Hz), 8.35 (d, 1H, J=5.1 Hz), 8.28 (br d, 1H, J=8.8 Hz), 7.66 (dd, 1H, J=8.5, 5.1 Hz), 6.92 (d, 2H, J=2.4 Hz), 6.67 (t, 1H, J=2.4 Hz), 5.82 (t, 1H, J=8.3 Hz), 3.82 (s, 6H), 1.07 (s, 9H);

EXAMPLE 16
N-(1-{[3,4-Dioxo-2-(3-pyridinylamino)-1-cyclobuten-1-yl]amino}-2,2-dimethylpropyl)-3,5-difluorobenzamide

EXAMPLE 16A
N-(1-(1H-1,2,3-benzotriazol-1-yl)-2,2-dimethylpropyl)-3,5-difluorobenzamide A suspension of 3,5-difluorobenzamide, pivaldehyde, benzotriazole, and p-toluenesulfonic acid was processed as described in Example 1C to provide the title compound.
MS (ESI+) m/z 345 (M+H)$^+$.

EXAMPLE 16B
N-(-1-{[3,4-Dioxo-2-(3-pyridinylamino)-1-cyclobuten-1-yl]amino}-2,2-dimethylpropyl)-3,5-difluorobenzamide A suspension of the product from Example 1B, the product from Example 16A, and $K_2CO_3$ was processed as described in Example 1D to provide the title compound.
MS (ESI+) m/z 415 (M+H)$^+$; $^1$H NMR(DMSO-d$_6$) δ 9.85 (br s, 1H), 8.76 (br d, 1H, J=8.2 Hz), 8.55 (d, 1H, J=2.7 Hz), 8.23 (d, 1H, J=4.5 Hz), 8.05–7.96 (m, 1H), 7.91 (dd, 1H, J=7.8, 1.0 Hz), 7.59–7.42 (m, 3H), 7.38 (dd, 1H, J=8.5, 4.7 Hz), 5.83 (t, 1H, J=8.3 Hz), 1.06 (s, 9H);

EXAMPLE 17
4-Chloro-N-(-1-{[3,4-dioxo-2-(3-pyridinylamino)-1-cyclobuten-1-yl]amino}-2,2-dimethyl-4-pentenyl)benzamide

Example 17A
N-[1-(1H-1,2,3-Benzotriazol-1-yl)-2,2-dimethyl-4-pentenyl]-4-chlorobenzamide A suspension of 4-chlorobenzamide, 2,2-dimethyl-4-pentenyl, benzotriazole, and p-toluenesulfonic acid was processed as in Example 1C to provide the desired compound.
MS (ESI+) m/z 369 (M+H)$^+$.

EXAMPLE 17B
4-Chloro-N-(-1-{[3,4-dioxo-2-(3-pyridinylamino)-1-cyclobuten-1-yl]amino}-2,2-dimethyl-4-pentenyl)benzamide A suspension of the product from Example 1B, the product from Example 17A, and $K_2CO_3$ was processed as described in Example 1D to provide the title compound.
mp 242–243° C.; MS (DCI/NH$_3$) m/z 439 (M+H)$^+$; $^1$H NMR (DMSO-d$_6$) δ 9.87 (s, 1H), 8.74 (d, 1H, J=6 Hz), 8.56 (d, 1H, J=3Hz), 8.25 (dd, 1H, J=5, 1 Hz), 8.03 (br s, 1H), 7.93 (dd, 1H, J=8, 1 Hz), 7.87 (d, 2H, J=8 Hz), 7.57 (d, 2H, J=8 Hz), 7.38 (dd, 1H, J=8, 5 Hz), 5.93–5.83 (m, 2H), 5.11-5.05 (m, 2H), 2.22 (dd, 1H, J=14, 8 Hz), 2.12 (dd, 1H, J=14, 8 Hz), 1.02 (s, 3H), 1.01 (s, 3H); Anal. calcd for $C_{23}H_{23}ClN_4O_3$: C, 62.94; H, 5.28, N, 12.77. Found: C, 62.85; H, 5.20; N, 12.87.

EXAMPLE 18
4-Chloro-N-(-1-{[3,4-dioxo-2,4,3-pyridinylamino)-1-cyclobuten-1-yl]amino}-2,2-dimethyl-3-phenylpropyl)benzamide

EXAMPLE 18A
2,2-Dimethyl-3-phenylpropanal

To a solution of oxalyl chloride (10.1 g, 79.4 mmol) in methylene chloride (70 mL) at −78° C. was added dimethylsulfoxide (10.0 mL, 139 mmol). The solution was stirred at −78° C. for 10 minutes then a solution of 2,2-dimethyl-3-phenylpropanol (6.52 g, 39.7 mmol) in methylene chloride (15 mL) was added. After stirring the reaction at −78° C. for 30 minutes, triethylamine (20.1 g, 198 mmol) was added and the reaction mixture was stirred for 10 minutes, then at 0° C.

for 5 minutes. The reaction mixture was quenched with saturated aqueous ammonium chloride (20 mL) and the aqueous layer was extracted with diethyl ether (2×50 mL). The organic portions were individually washed with brine (15 mL), dried over anhydrous sodium sulfate, and concentrated under reduced pressure. The residue was redissolved in diethyl ether and the resulting precipitate was filtered through a pad of Celite. The filtrate was concentrated under reduced pressure to provide the title compound (6.89 g) as an oil.

EXAMPLE 18B

N-[1-(1H-1,2,3-Benzotriazol-1-yl)-2,2-dimethyl-3-phenylpropyl]-4-chlorobenzamide A suspension of p-chlorobenzamide (3.02 g, 20.0 mmol), the product from Example 18A (3.24 g, 20.0 mmol), and benzotriazole (2.38 g, 20.0 mmol) in benzene (75 mL) was treated with p-toluenesulfonic acid (190 mg, 1.00 mmol). The solution was heated at reflux under Dean-Stark conditions for 10 hours, then cooled gradually to ambient temperature. The solvent was removed under vacuum and the residue was purified by flash chromatography (elution with 15% EtOAc/hexanes) to provide the title compound (3.63 g) as a white solid.

MS (ESI) m/z 419 (M+H)$^+$.

EXAMPLE 18C

4-Chloro-N-(-1-{[3,4-dioxo-2-(3-pyridinylamino)-1-cyclobuten-1-yl]amino}-2,2-dimethyl-3-phenylpropyl)benzamide A suspension of the product from Example 1B, the product from Example 18B, and $K_2CO_3$ was processed as described in Example 1D to provide the title compound.

mp 223–224° C.; MS (ESI+) m/z 489 (M+H)$^+$; $^1$H NMR (DMSO-d,) δ 9.90 (br s, 1H), 8.84 (br s, 1H), 8.59 (d, 1H, J=3 Hz), 8.26 (dd, 1H, J=5, 2 Hz), 8.14 (br s, 1H), 7.96–7.92 (m, 1H), 7.91 (d, 2H, J=8 Hz), 7.76 (d, 2H, J=8 Hz), 7.39 (dd, 1H, J=8, 5 Hz), 7.32–7.20 (m, 5H), 5.95 (br s, 1H), 2.74 (ABq, 2H, $J_{AB}$=13 Hz, $\Delta v_{AB}$=32 Hz), 0.97 (s, 3H), 0.95 (s, 3H); Anal. calcd for $C_{27}H_{25}ClN_4O_3$ 0.5 $H_2O$: C, 65.12; H, 5.26; N, 11.25. Found: C, 65.02; H, 5.39, N. 11.36.

EXAMPLE 19

4-Chloro-N-(4-cyano-1-{[3,4-dioxo-2-(3-pyridinylamino)-1-cyclobuten-1-yl]amino}-2,2-diethylbutyl)benzamide

EXAMPLE 19A

4-Ethyl-4-formylhexanenitrile 2,2-Diethyl-4-cyanobutanol, oxalyl chloride and dimethylsulfoxide were processed as described in Example 18A to provide the title compound.

EXAMPLE 19B

N-[1-(1H-1,2,3-benzotriazol-1-yl)-2,2-diethyl-4-cyanobutyl]-4-chlorobenzamide

The product from Example 19A, 4-chlorobenzamide, benzotriazole, and p-toluenesulfonic acid were processed as described in Example 1C to provide the title compound.

MS (ESI) m/z 410(M+H)$^+$.

EXAMPLE 19C

4-Chloro-N-(4-cyano-1-{[3,4-dioxo-2-(3-pyridinylamino)-1-cyclobuten-1-yl]amino}-2,2-diethylbutyl)benzamide A suspension of the product from Example 1B, the product from Example 19B, and $K_2CO_3$ was processed as described in Example 1D to provide the title compound.

mp 242–243° C.; MS (ESI+) m/z 480 (M+H)$^+$; $^1$H NMR (DMSO-d$_6$) δ 10.50 (br s, 1H), 9.04 (br s, 1H), 8.82–8.61 (m, 2H), 8.24 (d, 1H, J=4 Hz), 8.00–7.91 (m, 1H), 7.89 (d, 2H, J=8 Hz), 7.57 (d, 2H, J=8 Hz), 7.32 (dd, 1H, J=8,5 Hz), 5.47 (br s, 1H), 2.90–2.51 (m, 2H), 1.85 (br s, 1H), 1.60(br s, 1H), 1.48–1.25 (m, 4H), 0.85 (t, 3H, J=8 Hz), 0.78 (t, 3H, J=8 Hz); Anal. calcd for $C_{25}H_{26}ClN_5O_3$ ⅓$H_2O$: C, 61.79; H, 5.53; N, 14.41. Found: C, 61.90; H, 5.34; N, 14.16.

EXAMPLE 20

N-(2,2-Bis[(allyloxy)methyl]-1-{[3,4-dioxo-2-(3-pyridinylamino)-1-cyclobuten-1-yl]amino}butyl)-4-chlorobenzamide

EXAMPLE 20A 2,2-Bis[(allyloxy)methyl]butanal 2,2-Bis(allyloxymethyl)-1-butanol, oxalyl chloride and dimethylsulfoxide were processed as described in Example 18A to provide the title compound.

EXAMPLE 20B

N-[2,2-Bis[(allyloxy)methyl]-1-(1H-1,2,3-benzotriazol-1-yl)butyl]4-chlorobenzamide The product from Example 20A, 4-chlorobenzamide, benzotriazole, and p-toluenesulfonic acid were processed as described in Example 1C to provide the title compound.

MS (ESI) m/z 469 (M+H)$^+$.

EXAMPLE 20C

N-(2,2-Bis[(allyoxy)methyl]-1-{[3,4-dioxo-2-(3-pyridinylamino)-1-cyclobuten-1-yl]amino}butyl)-4-chlorobenzamide A suspension of the product from Example 1B, the product from Example 20B, and $K_2CO_3$ was processed as described in Example 1D to provide the title compound.

mp 176–177° C.; MS (ESI+) m/z 539 (M+H)$^+$; $^1$H NMR (DMSO-d$_6$) δ 9.79 (br s, 1H), 8.69 (br s, 1H), 8.56 (d, 1H, J=3 Hz), 8.25 (dd, 1H, J=5, 1 Hz), 8.03 (br s, 1H), 7.90 (ddd, 1H, J=8, 2, 1 Hz), 7.78 (d, 2H, J=8 Hz), 7.58 (d, 2H, J=8 Hz), 7.38 (dd, 1H, J=8, 5 Hz), 6.12 (br s, 1H), 5.95–5.84 (m, 2H), 5.31–5.23 (m, 2H), 5.19–5.14 (m, 2H), 4.00–3.94 (m, 4H), 3.56 ($_{AB}$q, 2H, $J_{AB}$=10 Hz, $\Delta v_{AB}$=53 Hz), 3.49–3.45 (m, 2H), 1.60–1.49 (m, 2H), 0.88 (t, 3H, J=8 Hz); Anal. calcd for $C_{28}H_{31}ClN_4O_5$: C, 62.39; H, 5.80; N, 10.39. Found: C, 62.33, H, 5.75; N, 10.39.

EXAMPLE 21

4-Chloro-N-(1-{[3,4-dioxo-2-(3-pyridinylamino)-1-cyclobuten-1-yl]amino}-2-ethylbutyl)benzamide

EXAMPLE 21A

N-[1-(1H-1,2,3-Benzotriazol-1-yl)-2-ethylbutyl]-4-chlorobenzamide

A suspension of 4-chlorobenzamide, 2-ethylbutanal, benzotriazole, and p-toluenesulfonic acid was processed as in Example 1C to provide the title compound.

MS (ESI+) m/z 357 (M+H)$^+$.

EXAMPLE 21B

4-Chloro-N-(1-{[3,4-dioxo-2-(3-pyridinylamino)-1-cyclobuten-1-yl]amino}-2-ethylbutyl)benzamide A suspension of the product from Example IB, the product from Example 21A, and $K_2CO_3$ was processed as described in Example 1D to provide the title compound.

mp 232–233° C.; MS (DCI/NH$_3$) m/z 427 (M+H)$^+$; $^1$H NMR (DMSO-d$_6$) δ 9.92 (br s, 1H), 9.11 (br s, 1H), 8.57 (d, 1H, J=2 Hz), 8.24 (dd, 1H, J=5, 2 Hz), 8.20 (br s, 1H), 7.95–7.93 (m, 1H) 7.90 (d, 2H, J=8 Hz), 7.58 (d, 2H, J=8 Hz), 7.37 (dd, 1H, J=8, 5 Hz), 5.74 (br s, 1H), 1.99 (br s, 1H), 1.58–1.35 (m, 4H), 0.89 (q, 6H, J=7 Hz); Anal. calcd for $C_{22}H_{23}ClN_4O_3$: C, 61.90; H, 5.43; N, 13.12. Found: C, 61.60; H, 5.30; N, 13.30.

EXAMPLE 22

4-Chloro-N-(2-cyclohexyl-1-{[3,4-dioxo-2-(3-pyridinylamino)-1-cyclobuten-1-yl]amino}-2-methylpropyl)benzamide

EXAMPLE 22A

2-Cyclohexyl-2-methylpropanal

2-Cyclohexyl-2-methyl-1-propanol, oxalyl chloride and dimethylsulfoxide were processed as described in Example 18A to provide the title compound.

EXAMPLE 22B

N-[1-(1H-1,2,3-Benzotriazol-1-yl)-2-cyclohexyl-2-methylpropyl]-4-chlorobenzamide The product from Example 22A, 4-chlorobenzamide, benzotriazole, and p-toluenesulfonic acid were processed as described in Example 1C to provide the title compound.

MS (ESI) m/z 383 (M+H)$^+$.

EXAMPLE 22C

4-Chloro-N-(2-cyclohexyl-1-{[3,4-dioxo-2-(3-pyridinylamino)-1-cyclobuten-1-yl]amino}-2-methylpropyl)benzamide A suspension of the product from Example 1B, the product from Example 22B, and $K_2CO_3$ was processed as described in Example 1D to provide the title compound.

mp 275–276° C.; MS (ESI+) m/z 326 (M-C$_8$H$_5$ClN (amide))$^+$; $^1$H NMR (DMSO-d$_6$) δ 9.82 (br s, 1H), 8.61 (br s, 1H), 8.57 (d, 1H, J=3 Hz), 8.24 (dd, 1H, J=5, 1 Hz), 7.95 (s, 1H), 7.94 (ddd, 1H, J=8, 3, 1 Hz), 7.85 (d, 2H, J=8 Hz), 7.57 (d, 2H, J=8 Hz), 7.38 (dd, 1H, J=8, 5 Hz), 6.13 (br s, 1H), 1.84–1.60 (m, 6H), 1.38 (t, 1H, J=12 Hz), 1.19–1.00 (m, 4H), 0.99 (s, 3H), 0.92 (s, 3H); Anal. calcd for $C_{26}H_{29}ClN_4O_3$: C, 64.92; H, 6.08; N, 11.65. Found: C, 64.56; H, 6.13; N, 11.54.

EXAMPLE 23

N-(2-(1-Adamantyl)-1-{[3,4-dioxo-2-(3-pyridinylamino)-1-cyclobuten-1-yl]amino}ethyl)-2-chlorobenzamide

EXAMPLE 23A

1-Adamantylacetaldehyde 2-(1-Adamantyl)ethanol, oxalyl chloride and dimethylsulfoxide were processed as described in Example 18A to provide the title compound.

MS (DCI/NH$_3$) m/z 179 (M+H)$^+$.

EXAMPLE 23B

N-[2-(1-Adamantyl)-1-(1H-1,2,3-benzotriazol-1-yl)ethyl]-4-chlorobenzamide

The product from Example 23A, 4-chlorobenzamide, benzotriazole, and p-toluenesulfonic acid were processed as described in Example 1C to provide the title compound.

MS (ESI) m/z 435 (M+H)$^+$.

EXAMPLE 23C

N-(2-(1-Adamantyl)-1-{[3,4-dioxo-2-(3-pyridinylamino)-1-cyclobuten-1-yl]amino}ethyl)-2-chlorobenzamide A suspension of the product from Example 1B, the product from Example 23B, and $K_2CO_3$ were processed as described in Example 1D to provide the title compound.

mp 224–225° C.; MS (ESI+) m/z 505 (M+H)$^+$; $^1$H NMR (DMSO-d$_6$) δ 9.91 (br s, 1H), 9.16 (br s, 1H), 8.57 (d, 1H, J=3 Hz), 8.34 (br s, 1H), 8.23 (dd, 1H, J=5, 1 Hz), 7.94–7.90 (m, 1H), 7.90 (d, 2H, J=8 Hz), 7.58 (d, 2H, J=8 Hz), 7.37 (dd, 1H, J=8, 5 Hz), 5.96 (m 1H), 1.92 (br s, 1H), 1.73–1.57 (m, 14H); Anal. calcd for $C_{28}H_{29}ClN_4O_3$ $\cdot$ ⅔H$_2$O: C, 65.05; H, 5.91, N, 10.84. Found: C, 64.94; H, 5.84; N, 11.08.

EXAMPLE 24

4-Chloro-N-(2,2-dichloro-1-{[3,4-dioxo-2-(3-pyridinylamino)-1-cyclobuten-1-yl]amino}-propyl)benzamide

EXAMPLE 24A 2,2-Dichloropropionaldehyde

Chlorine gas was bubbled through dimethylformamide (14.7 g, 0.202 mmol) for 5 minutes. The solution was heated to 45–55° C. and a solution of propionaldehyde (11.7, 0.202 mmol) in dimethylformamide (29.5 g, 0.404 mmol) was added slowly, maintaining the reaction temperature at 45–55° C. (a cooling bath was necessary to control the temperature). During the addition, Cl$_2$ was bubbled through the reaction to maintain a yellow color. After the addition, the reaction mixture was heated at 45–55° C. for 30 minutes. The solution was cooled to 0° C. and diethyl ether (100 mL) was added followed by cold water (100 mL). The organic portion was separated and washed with aqueous sodium bicarbonate (20 mL), brine (20 mL), dried (sodium sulfate), and concentrated under reduced pressure to provide 21.1 g of the title compound as an oil.

EXAMPLE 24B

N-[1-(1H-1,2,3-Benzotriazol-1-yl)-2,2-dichloropropyl]-4-chlorobenzamide

4-Chlorobenzamide, the product from Example 24A, benzotriazole, and p-toluenesulfonic acid were processed as described in Example 1C to provide the title compound.

MS (ESI) m/z 381 (M–H)$^-$.

EXAMPLE 24C

4-Chloro-N-(2,2-dichloro-1-{[3,4-dioxo-2-(3-pyridinylamino)-1-cyclobuten-1-yl]amino}-propyl)benzamide A suspension of the product from Example 1B, the product from Example 24B, and $K_2CO_3$ was processed as described in Example 1D to provide the title compound.

mp 201–202° C.; MS (ESI+) m/z 453 (M+H)+; 1H NMR (DMSO-d6) δ 10.24 (br s, 1H), 9.44 (br d, 1H, J=8.4 Hz); 8.59 (d, 1H, J=2.4 Hz), 8.48 (d, 1H, J=8.2 Hz), 8.28 (dd, 1H, J=5.8, 1.1 Hz), 7.90–7.78 (m, 1H), 7.81 (d, 2H, J=8.8 Hz), 7.61 (d, 2H, J=8.7 Hz), 7.41 (dd, 1H, J=8.6, 4.8 Hz), 6.66 (t, 1H, J=8.5 Hz), 2.22 (s, 3H); Anal. calcd for $C_{19}H_{15}Cl_3N_4O_3$: C, 50.30; H, 3.33; N, 12.35. Found: C, 50.55; H, 3.52; N, 12.29.

EXAMPLE 25

3-Chloro-N-(2,2-dichloro-1-{[3,4-dioxo-2-(3-pyridinylamino)-1-cyclobuten-1-yl]amino}-propyl)benzamide

EXAMPLE 25A

N-[1-(1H-1,2,3-Benzotriazol-1-yl)-2,2-dichloropropyl]-3-chlorobenzamide

3-Chlorobenzamide, the product from Example 24A, benzotriazole, and p-toluenesulfonic acid were processed as described in Example 1C to provide the title compound.
MS (ESI) m/z 381 (M−H)−.

EXAMPLE 25B

3-Chloro-N-(2,2-dichloro-1-{[3,4-dioxo-2-(3-pyridinylamino)-1-cyclobuten-1-yl]amino}-propyl)benzamide A suspension of the product from Example 1B, the product from Example 25A, and $K_2CO_3$ was processed as described in Example 1D to provide the title compound.
mp 202–204° C.; MS (ESI+) m/z 453 (M+H)+; 1H NMR (DMSO-d6) δ 10.23 (br s, 1H), 9.49 (br d, 1H, J=8.5 Hz); 8.59 (d, 1H, J=2.7 Hz), 8.47 (d, 1H, J=8.6 Hz), 8.29 (dd, 1H, J=5.7, 0.9 Hz), 7.94 (br s, 1H), 7.91 (br s, 1H), 7.83 (d, 1H, J=7.8 Hz), 7.69 (br d, 1H, J=8.5 Hz), 7.57 (t, 1H, J=8.1 Hz), 7.41 (dd, 1H, J=8.6, 4.8 Hz), 6.66 (t, 1H, J=8.5 Hz), 2.19 (s, 3H); Anal. calcd for $C_{19}H_{15}Cl_3N_4O_3$: C, 50.30; H, 3.33; N, 12.35; Found: C, 50.48; H, 3.40; N, 12.51.

EXAMPLE 26

3-Chloro-N-(1-{[3,4-dioxo-2-(3-pyridinylamino)-1-cyclobuten-1-yl]amino}-2,2,3,3,3-pentafluoropropyl)benzamide

EXAMPLE 26A

Pentafluoropropanal

Pentafluoropropanol, oxalyl chloride and dimethylsulfoxide were processed as described in Example 18A to provide the title compound.
MS (DCI/NH3) m/z 149 (M+H)+.

EXAMPLE 26B

N-[1-(1H-1,2,3-Benzotriazol-1-yl)-2,2,3,3,3-pentafluoropropyl]-4-chlorobenzamide 3-Chlorobenzamide, the product from Example 26A, benzotriazole, and p-toluenesulfonic acid were processed as described in Example 1C to provide the title compound.
MS (ESI−) m/z 403 (M−H)−.

EXAMPLE 26C

3-Chloro-N-(1-{[3,4-dioxo-2-(3-pyridinylamino)-1-cyclobuten-1-yl]amino}-2,2,3,3,3-pentafluoropropyl)benzamide A suspension of the product from Example 1C, the product from Example 26B, and $Cs_2CO_3$ was processed as described in Example 1D to provide the title compound.
mp 212–213° C.; MS (ESI+) m/z 475 (M+H)+; 1H NMR (DMSO-d6) δ 10.18 (br s, 1H), 9.93 (br d, 1H, J=8.4 Hz); 8.62 (d, 1H, J=8.7 Hz), 8.57 (d, 1H, J=2.7 Hz), 8.28 (dd, 1H, J=5.8, 0.9 Hz), 7.91 (br s, 1H), 7.87 (br s, 1H), 7.83 (br d, 1H, J=7.9 Hz), 7.70 (br d, 1H, J=8.6 Hz), 7.58 (t, 1H, J=8.1 Hz), 7.39 (dd, 1H, J=8.6, 4.8 Hz), 7.01–6.87 (m, 1H); Anal. calcd for $C_{19}H_{12}ClF_5N_4O_3$: C, 48.07; H, 2.55; N, 11.80. Found: C, 48.13; H, 2.61; N, 11.94.

EXAMPLE 27

4-Chloro-N-(1-{[3,4-dioxo-2-(3-fluoroanilino)-1-cyclobuten-1-yl]amino}-2,2-dimethylpropyl)benzamide

EXAMPLE 27A

3-Ethoxy-4-(3-fluoro-phenylamino)-cyclobut-3-ene-1,2-dione

A solution of 3-fluoroaniline and 3,4-diethoxy-3-cyclobutene-1,2-dione in ethanol was processed as described in Example IA to provide the title compound.
MS (DCI/NH3) m/z 236 (M+H)+.

EXAMPLE 27B

3-Amino-4-(3-fluoro-phenylamino)-cyclobut-3-ene-1,2-dione

A solution of the product from Example 27A and ammonia in methanol was processed as described in Example 1B to provide the title compound.
MS (DCI/NH3) m/z 207 (M+H)+.

EXAMPLE 27B 4-chloro-N-(1-{[3,4-dioxo-2-(3-fluoroanilino)-1-cyclobuten-1-yl]amino}-2,2-dimethylpropyl)benzamide A suspension of the product from Example 2A, the product from Example 27B, and $K_2CO_3$ was processed as described in Example 1D to provide the title compound.
mp 271–272° C.; MS (ESI+) m/z 430 (M+H)+; 1H NMR (DMSO-d6) δ 9.88 (s, 1H), 8.71 (d, 1H, J=7.2 Hz), 8.01–7.99 (m, 1H), 7.87 (d, 2H, J=8.6 Hz), 7.56 (d, 2H, J=8.2 Hz), 7.48 (dt, 1H, J=10.7, 2.2 Hz), 7.37 (dt, 1H, J=4, 6.7 Hz), 7.13 (dd, 1H, J=8.3, 2.7 Hz), 6.85 (td, 1H, J=8.3, 2.2 Hz), 5.85 (t, 1H, J=8.1 Hz), 1.05 (s, 9H); Anal. calcd for $C_{22}H_{21}ClFN_3O_3$: C, 61.47; H, 4.92; N, 9.78. Found: C, 61.31; H, 4.57; N, 9.99.

EXAMPLE 28

4-Chloro-N-(1-{[3,4-dioxo-2-(4-fluoroanilino)-1-cyclobuten-1-yl]amino}-2,2-dimethylpropyl)benzamide

EXAMPLE 28A

3-Ethoxy-4-(4-fluoro-phenylamino)-cyclobut-3-ene-1,2-dione

A solution of 4-fluoroaniline and 3,4-diethoxy-3-cyclobutene-1,2-dione in ethanol was processed as described in Example 1A to provide the title compound.
MS (DCI/NH3) m/z 236 (M+H)+.

EXAMPLE 28B

3-Amino-4-(3-fluoro-phenylamino)-cyclobut-3-ene-1,2-dione

A solution of the product from Example 28A and ammonia in methanol was processed as described in Example 1B to provide the title compound.
MS (DCI/NH3) m/z 207 (M+H)+.

EXAMPLE 28C

4-Chloro-N-(1-{[3,4-dioxo-2-(4-fluoroanilino)-1-cyclobuten-1-yl]amino}-2,2-dimethylpropyl benzamide A suspension of the product from Example 2A, the product from Example 28B, and $K_2CO_3$ was processed as described in Example 1D to provide the title compound.

mp 247–249° C.; MS (ESI+) m/z 430 (M+H)+; 1H NMR (DMSO-$d_6$) δ 9.78 (br s, 1H), 8.72 (b rd, 1H, J=6.8 Hz), 8.01–7.92 (m, 1H), 7.86 (d, 2H, J=8.6 Hz), 7.55 (d, 2H, J=8.4 Hz), 7.47–7.39 (m, 1H), 7.42 (dd, 1H, J=8.1, 4.8 Hz), 7.18 (t, 2H, J=8.8 Hz), 5.82 (t, 1H, J=8.0 Hz), 1.04 (s, 9H); Anal. calcd for $C_{22}H_{21}ClFN_3O_3$: C, 61.47, H, 4.92; N, 9.78. Found: C, 61.35; H, 4.99; N, 9.42.

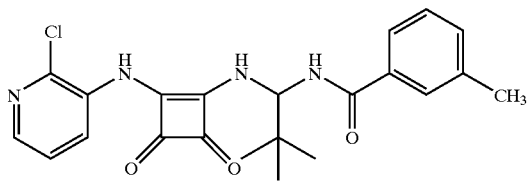

EXAMPLE 29

4-Chloro-N-[1-({2-[(2-chloro-3-pyridinyl)amino]-3,4-dioxo-1-cyclobuten-1-yl}amino)-2,2-dimethylpropyl]benzamide

EXAMPLE 29A 3-(2-Chloro-pyridin-3-ylamino)-4-ethoxy-cyclobut-3-ene-1,2-dione A solution of 2-chloro-3-aminopyridine and 3,4-diethoxy-3-cyclobutene-1,2-dione in ethanol was processed as described in Example 1A to provide the title compound.

MS (DCI/NH$_3$) m/z 253 (M+H)+.

EXAMPLE 29B

3-Amino-4-(2-chloro-pyridin-3-ylamino)-cyclobut-3-ene-1,2-dione

A solution of the product from Example 29A and ammonia in methanol was processed as described in Example 1B to provide the title compound.

MS (DCI/NH$_3$) m/z 224 (M+H)+.

EXAMPLE 29C

4-Chloro-N-[-1-({2-[(2-chloro-3-pyridinyl)amino]-3,4-dioxo-1-cyclobuten-1-yl}amino)-2,2-dimethylpropyl]benzamide A suspension of the product from Example 2A, the product from Example 29B, and $K_2CO_3$ was processed as described in Example 1D to provide the title compound.

mp 259–261° C.; MS (DCI/NH$_3$) m/z 464 (M+H)+, 1H NMR (DMSO-$d_6$) δ 9.46 (br s, 1H), 8.70 (d, 1H, J=8.1Hz), 8.48 (d, 1H, J=9.1 Hz), 8.10 (dd, 1H, J=4.6, 1.7 Hz), 8.00 (d, 1H, J=7.8 Hz), 7.85 (d, 2H, J=8.5 Hz), 7.55 (d, 2H, J=8.5 Hz), 7.42 (dd, 1H, J=8.1, 4.8 Hz), 5.88 (br t, 1H, J=8.3 Hz), 1.04 (s, 9H); Anal. calcd for $C_{21}H_{20}Cl_2N_4O_3$: C, 56.39; H, 4.51; N, 12.53. Found: C, 56.13; H, 4.99; N, 12.38.

EXAMPLE 30

N-[1-({2-[(5-Bromo-6-fluoro-3-pyridinyl)amino]-3,4-dioxo-1-cyclobuten-1-yl}amino)-2,2-dimethylpropyl]4-chlorobenzamide

EXAMPLE 30A 3-(5-Bromo-6-fluoro-pyridin-3-ylamino)-4-ethoxy-cyclobut-3-ene-1,2-dione A solution of 2-fluoro-3-bromo-5-aminopyridine and 3,4-diethoxy-3-cyclobutene-1,2-dione in ethanol was processed as described in Example 1A to provide the title compound.

MS (DCI/NH$_3$) m/z 315 (M+H)+.

EXAMPLE 30B

3-Amino-4-(5-bromo-6-fluoro-pyridin-3-ylamino)-cyclobut-3-ene-1,2-dione

A solution of the product from Example 30A and ammonia in methanol was processed as described in Example 1B to provide the title compound.

MS (DCI/NH$_3$) m/z 286 (M+H)+.

EXAMPLE 30C

N-[1-({2-[(5-Bromo-6fluoro-3-pyridinyl)amino]-3,4-dioxo-1-cyclobuten-1-yl}amino)-2,2-dimethylpropyl]4-chlorobenzamide A suspension of the product from Example 2A, the product from Example 30B, and $K_2CO_3$ was processed as described in Example 1D to provide the title compound.

mp 249–252° C.; MS (ESI+) m/z 509 (M+H)+; 1H NMR (DMSO-$d_6$) δ 10.00(br s, 1H), 8.72 (br d, 1H, J=7.0 Hz), 8.47 (br d, 1H, J=7.2 Hz), 8.10 (t, 1H, J=15 Hz), 8.04 (br s, 1H), 7.87 (d, 2H, J=8.5 Hz), 7.58 (d, 2H, J=8.5 Hz), 5.85 (br t, 1H, J=6.6 Hz), 1.05 (s, 9H); Anal. calcd for $C_{21}H_{19}BrClFN_4O_3$: C, 49.48; H, 3.76; N, 10.99. Found: C, 49.14; H, 3.83; N, 10.71.

EXAMPLE 31

4-Chloro-N-[1-({2-[(2-chloro-3-pyridinyl)amino]-3,4-dioxo-1-cyclobuten-1-yl}amino)-2,2-dimethyl-32-phenylpropyl]benzamide A suspension of the product from Example 18B, the product from Example 29B, and $K_2CO_3$ was processed as described in Example 1D to provide the title compound.

mp 236–237° C.; MS (DCI/NH$_3$) m/z 523 (M+H)+; 1H NMR (DMSO-$d_6$) δ 9.47 (br s, 1H), 8.71 (d, 1H, J=8.0 Hz), 8.48 (d, 1H, J=8.9 Hz), 8.10 (dd, 1H, J=4.7, 1.6 Hz), 8.02 (br d, 1H, J=8.3 Hz), 7.91–7.85 (m, 3H), 7.59–7.48 m, 2H), 7.42 (dd, 1H, J=7.8, 4.7 Hz), 7.32–7.16(m, 4H), 5.88 (br t, 1H, J=8.3 Hz), 2.72 (AB$_q$, 2H, $J_{AB}$=12.2 Hz, $\Delta v_{AB}$=28.5 Hz), 0.96 (s, 3H), 0.92 (s, 3H); Anal. calcd for $C_{27}H_{24}Cl_2N_4O_3$: C, 61.96; H, 4.62; N, 10.70. Found: C, 61.55; H, 4.66; N, 10.39.

EXAMPLE 32

N-[1-({2-[(2-Chloro-3-pyridinyl)amino]-3,4-dioxo-1-cyclobuten-1-yl}amino)-2,2-dimethylpropyl]-3-methylbenzamide A suspension of the product from Example 6A, the product from Example 29B, and $K_2CO_3$ was processed as described in Example 1D to provide the title compound.

mp 238–239° C.; MS (ESI+) m/z 427 (M+H)+; 1H NMR (DMSO-d6) δ 9.47 (s, 1H), 8.61 (d, 1H, J=8 Hz), 8.52 (d, 1H, J=9 Hz), 8.11 (dd, 1H, J=4,2 Hz), 8.03 (d, 1H, J=8 Hz), 7.67–7.61 (m, 2H), 7.44 (dd, 1H, J=8, 5 Hz), 7.39–7.35 (m, 2H), 5.92 (t, 1H, J=8 Hz), 2.37 (s, 3H), 1.07 (s, 9H); Anal. calcd for $C_{22}H_{23}ClN_4O_3$ 0.5$H_2O$: C, 61.04; H, 5.51; N, 12.94. Found: C, 60.87; H, 5.51; N, 12.90.

EXAMPLE 33

4-Chloro-N-(2,2-dimethyl-1-{[(3-pyridinylamino) sulfonyl]amino}propylbenzamide

EXAMPLE 33A

Tert-butyl 3-(3-Pyridinyl)diazathiane-1-carboxylate 2,2-dioxide tert-Butanol (2.0 mL, 21.1 mmol) was added to a solution of chlorosulfonyl- isocyanate (1.8 mL, 21.1 mmol) in $CH_2Cl_2$ (40 mL). The reaction mixture was stirred at ambient temperature for 0.5 hours and then treated with a solution of 3-aminopyridine (2.00 g, 21.1 mmol) and triethylamine (4.4 mL, 31.6 mmol) in $CH_2Cl_2$ (20 mL) via canula. The reaction mixture was stirred at ambient temperature for an additional 1.5 hours and then filtered through a 0.25 inch silica gel plug. The solvent was removed under reduced pressure and the residue was purified by flash chromatography on silica gel (elution with EtOAc) to provide 1.17 g of the title compound as a white solid.

MS (FSI+) m/z 274 (M+H)+.

EXAMPLE 33B

N-43-Pyridinyl)sulfamide

Trifluoroacetic acid (10 mL) was added to a solution of the product from Example 33A (1.17 g, 4.28 mmol) in $CH_2Cl_2$ (40 mL). The reaction mixture was stirred at ambient temperature for 2 hours and then the solvent was removed under reduced pressure. The crude reaction mixture was diluted with EtOAc (25 mL) and washed with saturated aqueous $NaHCO_3$ (50 mL). The aqueous layer was extracted with EtOAc (25 mL) and the organic phases were combined, dried over $Na_2SO_4$ and filtered. The filtrate was concentrated under reduced pressure and the residue was triturated from $Et_2O$/hexanes to provide 0.40 g of the title compound as a white powder.

MS (DCI/$NH_3$) m/z 174 (M+H)+.

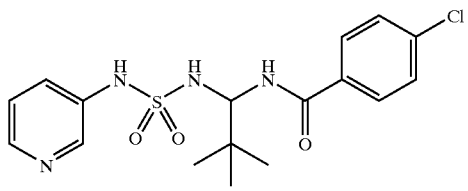

EXAMPLE 33C

4-Chloro-N-(2,2-dimethyl-1-{[(3-pyridinylamino) sulfonyl]amino}propyl)benzamide

A suspension of the product from Example 33B, the product from Example 2A, and $K_2CO_3$ was processed as described in Example 1D to provide the title compound.

mp 166–167° C.; MS (ESI+) m/z 397 (M+H)+; 1H NMR (DMSO-d6) δ 10.07 (s, 1H), 8.32 (d, 1H, J=2 Hz), 8.12, (d, 1H, J=9 Hz), 8.03 (dd, 1H, J=5, 1 Hz), 7.62 (d, 1H, J=9 Hz), 7.53 (d, 2H, J=9 Hz), 7.45 (ddd, 1H, J=8, 3, 2 Hz), 7.42 (d, 2H, J=8 Hz), 7.12 (dd, 1H, J=9, 5 Hz), 5.19 (t, 1H, J=9 Hz), 0.87 (s, 9H); Anal. calcd for $C_{17}H_{21}ClN_4O_3S$: C, 51.45; H, 5.33; N, 14.12. Found: C, 51.44; H, 5.56; N, 14.05.

EXAMPLE 34

N-(2,2-Dimethyl-1-{[(3-pyridinylamino)sulfonyl] amino}propyl)-4-iodobenzamide

A suspension of the product from Example 33B, the product from Example 3A, and $K_2CO_3$ was processed as described in Example 1D to provide the title compound.

mp 177–178° C.; MS (DCI/$NH_3$) m/z 489 (M+H)+; 1H NMR (DMSO-d6) δ 10.06 (s, 1H), 8.31 (d, 1H, J=2Hz), 8.10 (d, 1H J=9 Hz), 8.03 (dd, 1H, J=5, 2 Hz), 7.74 (d, 2H, J=8 Hz), 7.60 (d, 1H, J=9 Hz), 7.46 (ddd, 1H, J=8, 3, 2 Hz), 7.30 (d, 2H, J=8 Hz), 7.13 (dd, 1H, J=9, 5 Hz), 5.18 (t, 1H, J=9 Hz), 0.86 (s, 9H); Anal. calcd for $C_{17}H_{21}IN_4O_3S$: C, 41.81; H, 4.33; N, 11.47. Found: C, 42.00; H, 4.37; N, 11.26.

EXAMPLE 35

$N^1$-{1-[(4-Chlorobenzoyl)amino]-2,2-dimethylpropyl}-$N^2$-(3-pyridinyl)ethanediamide

EXAMPLE 35A

Ethyl Oxo(3-Pyridinylamino)acetate

To a solution 3-aminopyridine (3.00 g, 27.0 mmol) in methylene chloride (110 mL) at 23 ° C. was added triethylamine (7.53 mL, 54.0 mmol) and N,N-dimethylarninopyridine (330 mg, 2.70 mmol). The solution was cooled to 0° C. and chloroethyloxalate 4.42 g, 32.4 mmol) was added in a dropwise fashion. The reaction mixture was stirred at 0° C. for 2 hours and then quenched with water (30 mL) and partitioned. The organic portion was washed with 10% sodium bicarbonate solution (30 mL), dried over anhydrous sodium sulfate and concentrated under reduced pressure to provide 4.30 g of the title compound.

MS (ESI+) m/z 195 (M+H)+.

EXAMPLE 35B $N^1$-(3-Pyridinyl)ethanediamide

A solution of the product from Example 35A and ammonia in methanol was processed as described in Example 1B to provide the title compound.

MS (ESI–) m/z 164 (M–H)−.

EXAMPLE 35C $N^1$-{1-[(4-Chlorobenzoyl)amino]-2,2-dimethylpropyl}-$N^2$-(3-pyridinyl)ethanediamide A suspension of the product from Example 2A, the product from Example 35B, and $K_2CO_3$ was processed as described in Example 1D to provide the title compound.

mp 168–170° C.; MS (ESI+) m/z 389 (M+H)+; 1H NMR (DMSO-d6) δ 11.01 (s, 1H), 8.99 (d, 1H, J=2.3 Hz), 8.75 (d, 1H, J=9.2 Hz), 8.49 (d, 1H, J=8.8 Hz), 8.35 (dd, 1H, J=4.8, 1.4 Hz), 8.19 (br d, 1H, J=8.4 Hz), 7.88 (d, 2H, J=8.5 Hz), 7.60 (d, 2H, J=8.5 Hz), 7.41 (dd, 1H, J=8.5, 4.8 Hz), 5.82 (t, 1H, J=9.1 Hz), 0.94 (s, 9H); Anal. calcd for $C_{19}H_{21}ClN_4O_3$: C, 58.69; H, 5.44, N, 14.41. Found: C, 58.43; H, 5.41; N, 14.26.

EXAMPLE 36

N-(1-{[3,4-Dioxo-2-(3-pyridinylamino)-1-cyclobuten-1-yl]amino}-2,2-dimethylpropyl)-3-phenylpropanamide

EXAMPLE 36A

N-[1-(1H-1,2,3-Benzotriazol-1-yl)-2,2-dimethylpropyl]-3-phenylpropanamide

A suspension of 3-phenyl-propionamide, pivaldehyde, benzotriazole, and p-toluenesulfonic acid was processed as described in Example 1C to provide the title compound.

MS (DCI/NH$_3$) m/z 337 (M+H)$^+$.

EXAMPLE 36B

N-(1-{[3,4-Dioxo-2-(3-pyridinylamino)-1-cyclobuten-1-yl]amino}-2,2-dimethylpropyl)-3-phenylpropionamide A suspension of the product from Example 1B, the product from Example 36A, and K$_2$CO$_3$ was processed as described in Example 1D to provide the title compound.

mp 219–220° C.; MS (ESI+) m/z 407 (M+H)$^+$; $^1$H NMR (DMSO-d$_6$) δ 9.71 (s, 1H), 8.57 (d, 1H, J=3 Hz), 8.24 (dd, 1H, J=5, 1 Hz), 8.17(s, 1H), 7.95 (d, 1H, J=7 Hz), 7.89 (brs, 1H), 7.38 (dd, 1H, J=8, 5 Hz), 7.26–7.13 (m, 5H), 5.63 (br s, 1H), 2.83 (t, 2H, J=8 Hz), 2.61–2.43 (m, 2H), 0.94 (s, 9H), Anal. calcd for C$_{23}$H$_{26}$N$_4$O$_3$ 0.2H$_2$O: C, 67.36; H, 6.49; N, 13.66. Found: C, 67.22; H, 6.44; N, 13.95.

EXAMPLE 37

N-[1-({2-[(2-Chloro-3-pyridinyl)amino]-3,4-dioxo-1-cyclobuten-1-yl}amino)-2,2-dimethylpropyl]-3-(3-pyridinyl)propanamide

EXAMPLE 37A

Methyl 3-(3-Pyridinyl)propanoate

To a solution of 3-(3-pyridinyl)propanoic acid (2.50 g, 16.5 mmol) in CH$_2$Cl$_2$ (110 mL) and MeOH (1 mL) was added DMAP (0.010 g, 0.082 mmol) and diisopropylcarbodiimide (4.17 g, 33.1 mmol). The reaction was stirred for 2 hours at 23° C. then saturated aqueous NaHCO$_3$ (100 mL) was added. The mixture was extracted with CH$_2$Cl$_2$ (100 mL) and the combined extracts were dried over Na$_2$SO$_4$, filtered, and evaporated in vacuo. The residue was purified by flash chromatography on silica gel (elution with 60% EtOAc/hexanes) to provide 2.70 g (99%) of the desired product. MS (DCI/NH$_3$) m/z 166 (M+H)$^{30}$.

EXAMPLE 37B 3-(3-Pyridinyl)propanamide

A solution of the product from Example 37A (2.70 g, 16.3 mmol) in NH$_3$ (2.0 M in MeOH, 40 mL) was heated at 80° C. in a sealed vessel for 24 hours. The mixture was allowed to cool to 23° C. and the solvent was evaporated under reduced pressure. The crude product was recrystallized from EtOAc/hexanes to provide 1.71 g (69%) of the title compound.

MS (DCI/NH$_3$) m/z 151 (M+H)$^+$.

EXAMPLE 37C

N-[1-(1H-1,2,3-Benzotriazol-1-yl)-2,2-dimethylpropyl]-3-(3-pyridinyl)propanamide A suspension of the product from Example 37B, pivaldehyde, benzotriazole, and p-toluenesulfonic acid was processed as described in Example 1C to provide the desired product.

MS (DCI/NH$_3$) m/z 385 (M+H)$^+$.

EXAMPLE 37D

N-[1-({2-[(2-Chloro-3-pyridinyl)amino]-3,4-dioxo-1-cyclobuten-1-yl}amino)-2,2-dimethylpropyl]-3-(3-pyridinyl)propanamide A suspension of the product from Example 29B (0.199 g, 0.889 mmol), the product from Example 37C (0.300 g, 0.889 mmol), and K$_2$CO$_3$ (0.614 g, 4.45 mmol) in DMF (3 mL) was heated at 50° C. for 24 hours. The reaction mixture was allowed to cool to 23° C. and then applied to a silica gel column. Elution with 10% EtOH/EtOAc provided 14 mg (4%) of the title compound.

mp 179–180° C.; MS (ESI+) m/z 442 (M+H)$^+$, $^1$H NMR (DMSO-d$_6$) δ 9.31 (s, 1H), 8.44–8.38 (m, 3H), 8.18 (d, 1H, J=7 Hz), 8.10 (dd, 1H, J=5, 1 Hz), 8.06 (d, 1H, J=8 Hz), 7.61 (d, 1H, J=8 Hz), 7.44 (dd, 1H, J=8.5 Hz), 7.27 (dd, 1H, J=8, 5 Hz), 5.67 (t, 1H, J=8 Hz), 2.85 (t, 2H, J=7 Hz), 2.65–2.46 (m, 2H), 0.93 (s, 9H); Anal. calcd for C$_{22}$H$_{24}$ClN$_5$O$_3$ 0.8H$_2$O: C, 57.91; H, 5.65; N, 15.35. Found: C, 57.86; H, 5.51; N, 15.18.

EXAMPLE 38

N-(1-{[3,4-Dioxo-2-(3-pyridinylamino)-1-cyclobuten-1-yl]amino}-2,2-dimethylpropyl)-3-vinylbenzamide

EXAMPLE 38A

N-[1-(1H-1,2,3-Benzotriazol-1-yl)-2,2-dimethylpropyl]-3-vinylbenzamide

The product from Example 8A (0.500 g, 1.15 mmol), tributyl(vinyl)tin 0.410 g, 1.27 mmol), triphenylarsine 0.035 g, 0.115 mmol), and tris(dibenzylidineacetone)dipalladium (0) (0.053 g, 0.058 mmol) were combined in anhydrous NMP (4 mL) and stirred at 23° C. for 18 hours. The reaction mixture was diluted with EtOAc (50 mL) and filtered through a 0.25 inch frit of Celite and the frit was washed with additional EtOAc (25 mL). The filtrate was washed with 100 mL brine and the brine back extracted wit EtOAc (50 mL). The organic phases were combined, dried over Na$_2$SO$_4$, filtered, and absorbed onto silica gel. The crude material was purified by flash chromatography on silica gel (elution with EtOAc/CH$_2$Cl$_2$/hexanes, 5:47.5:47.5) to provide 223 mg (58%) the title compound.

MS (DCI/NH$_3$) rn/z 335 (M+H)$^+$.

EXAMPLE 38B

N-(1-{[3,4-Dioxo-2-(3-pyrdinylamino)-1-cyclobuten-1-yl]amino}-2,2-dimethylpropy])-3-vinylbenzamide A suspension of the product from Example 1B, the product from Example 38A, and K$_2$CO$_3$ was processed as described in Example 1D to provide the title compound.

mp 209–210° C.; MS (ESI+) m/z 405 (M+H)$^+$; $^1$H NMR (DMSO-d$_6$) δ 9.89 (s, 1H), 8.73 (d, 1H, J=6 Hz), 8.59 (d, 1H, J=2 Hz), 8.25 (dd, 1H, J=5, 1 Hz), 8.08 (brs, 1H), 7.94 (dd, 1H, J=1 Hz), 7.89 (s, 1H), 7.74 (d, 1H, J=8 Hz), 7.67 (d, 1H, J=8 Hz), 7.47 (t, 1H, J=8 Hz), 7.39 (dd, 1H, J=8, 5 Hz), 6.81 (dd, 1Hz, J$_{AB}$=18 Hz), 5.92 (d, J$_{AC}$=11 Hz, 5,92 (d, 1H, J$_{AB}$=18 Hz), 5.87 (s, 1H), 5.36 (d, 1H, J=11 Hz), 1.07 (s, 9H); Anal. calcd for C$_{23}$H$_{24}$N$_4$O$_3$ 0.1H$_2$O: C, 68.00; H, 6.00; N, 13.79. Found: C, 67.62; H, 5.67; N, 13.88.

EXAMPLE 39

N-(1-{[3,4-Dioxo-2-(3-pyridinylamino)-1-cyclobuten-1-yl]amino}-2,2-dimethylpropyl)[1,1'-biphenyl]-3-carboxamide

EXAMPLE 39A

N-[1-(1H-1,2,3-Benzotriazol-1-yl)-2,2-dimethylpropyl][1,1'-biphenyl]-3-carboxamide The product from Example 8A, trimethyl(phenyl)tin, triphenylarsine, and tris(dibenzylidineacetone)dipaladium (0) were processed as described in Example 38B to provide the title compound.

MS (DCI/NH$_3$) m/z 385 (M+H)$^+$.

EXAMPLE 39B

N-(1-{[3,4-Dioxo-2-(3-pyridinylamino)-1-cyclobuten-1-yl]amino}-2,2-dimethylpropyl)[1,1'-biphenyl]-3-carboxamide A suspension of the product from Example IB, the product from Example 39A, and K$_2$CO$_3$ was processed as described in Example 1D to provide the title compound.

mp 240–241° C.; MS (ESI+) rn/z 455 (M+H)$^+$; $^1$H NMR (DMSO-d$_6$) δ 9.89 (s, 1H), 8.82 (d, 1H, J=7 Hz), 8.59 (d, 1H, J=3 Hz), 8.25 (dd, 1H, J=5, 2 Hz), 8.10 (brs, 1H), 7.95 (ddd, 1H, J=8, 3, 1 Hz), 7.87–7.83 (m, 2H), 7.73 (dd, 2H, J=8, 1 Hz), 7.59 (t, 1H, J=8 Hz), 7.51 (t, 2H, J=7 Hz), 7.43–7.37 (m, 2H), 591 (br s, 1H), 1.08 (s, 9H); Anal. calcd for C$_{27}$H$_{26}$N$_4$O$_3$ 0.15H$_2$O: C, 70.93; H, 5.80; N, 12.25. Found: C, 70.90; H, 5.66; N, 12.25.

EXAMPLE 40

3-Acetyl-N-(1-{[3,4-dioxo-2-(3-pyridinylamino)-1-cyclobuten-1-yl]amino}-2,2-dimethylpropyl)benzamide

EXAMPLE 40A

3-Acetyl-N-[1H-1,2,3-benzotriazol-1-yl)-2,2-dimethylpropyl]benzamide

The product from Example 8A (0.500 g, 1.15 mmol), tributyl(1-ethoxyvinyl)tin (0.459 g, 1.27 mmol), triphenylarsine (0.035 g, 0.115 mmol), and tis(dibenzylidineacetone)dipalladium(0) (0.053 g, 0.058 mmol) were combined in anhydrous NMP (4 mL) and stirred at 23° C. for 18 hours. To this solution was added 2 N HCl (10 mL) and the reaction mixture was stirred for 30 minutes at 23° C. The mixture was extracted EtOAc (2×25 mL) and the combined organic phases were dried (Na$_2$SO$_4$), filtered, and absorbed onto silica gel. The crude material was purified by flash chromatography on silica gel (elution with 50% EtOAc/hexanes) to provide 207 mg (51%) of the title compound.

MS (ESI+) m/z 351 (M+H)$^+$.

EXAMPLE 40B

3-Acetyl-N-(1-{[3,4-dioxo-2-(3-pyridinylamino)-1-cyclobuten-1-yl]amino}-2,2-dimethylpropyl)benzamide A suspension of the product from Example 1B, Example 40A, and K$_2$CO$_3$ was processed as described in Example 1D to provide the title compound.

mp 218–219° C.; MS (ESI+) m/z 421 (M+H)$^+$; $^1$H NMR (DMSO-d$_6$) δ 10.28 (s, 1H), 8.89 (d, 1H, J=7 Hz), 8.62 (d, 1H, J=3 Hz), 8.35 (t, 1H, J=2 Hz), 8.34 (br s, 1H), 8.24 (dd, 1H, J=5, 1 Hz), 8.11 (ddt, 2H, J=16, 8, 2 Hz), 7.96 (dd, 1H, J=8, 2 Hz), 7.65 (t, 1H, J=8 Hz), 7.38 (dd, 1H, J=8, 5 Hz), 5.90 (d, 1H, J=6 Hz) 2.64 (s, 3H), 1.08 (s, 9H); Anal. calcd for C$_{23}$H$_{24}$N$_4$O$_4$: C, 63.26; H, 5.95; N, 12.83. Found: C, 63.04; H, 5.62; N 12.80.

EXAMPLE 41

N-(1-{[3,4-Dioxo-2-(3-pyridinylamino)-1-cyclobuten-1-yl]amino}-2,2-dimethypropyl)-2-pyridinecarboxamide

EXAMPLE 41A

N-[1-(1H-1,2,3-Benzotriazol-1-yl)-2,2-dimethylpropyl]-2-pyridinecarboxamide

A suspension of 2-pyridinecarboxamide, pivaldehyde, benzotriazole, and p-toluenesulfonic acid was processed as described in Example 1C to provide the desired product.

MS (DCI/NH$_3$) m/z 310 (M+H)$^+$.

EXAMPLE 41B

N-(1-{[3,4-Dioxo-2-(3-pyridinylamino)-1-cyclobuten-1-yl]amino}-2,2-dimethylprolyl)-2-pyridinecarboxamide A suspension of the product from Example 1B, the product from Example 41A, and K$_2$CO$_3$ was processed as described in Example 1D to provide the title compound.

MS (ESI+) m/z 380 (M+H)$^+$; $^1$NMR (DMSO-d$_6$) δ 10.26 (s, 1H), 8.89 (d, 1H, J=8 Hz), 8.71 (d, 1H, J=3 Hz), 8.65 (d, 1H, J=5 Hz), 8.37 (br s, 1H), 8.33 (d, 1H, J=5 Hz), 8.08 (dd, 1H, J=7, 1 Hz), 8.03–7.97 (m, 2H), 7.64–7.58 (m, 2H), 5.88 (t, 1H, J=7 Hz), 1.06 (s, 9H).

EXAMPLE 42

N-(1-{[3,4-Dioxo-2-(3-pyridinylamino)-1-cyclobuten-1-yl]amino }-2,2-dimethyllropyl)-4-fluoro-3-(trifluoromethyl)benzamide

EXAMPLE 42A

N-[1-(1H-1,2,3-Benzotriazol-1yl)-2,2-dimethylpropyl]-4- fluoro-3-(trifluoromethyl)benzamide A suspension of 4-fluoro-3-(trifluoromethyl)benzamide, pivaldehyde, benzotriazole, and p-toluenesulfonic acid was processed as in Example 1C to provide the title compound.

MS (ESI+) m/z 395 (M+H)$^+$.

EXAMPLE 42B

N-(1-{[3,4-Dioxo-2-(3-piridinylamino)-1-cyclobuten-1-yl]amino }-2,2-dimethylpropyl)-4-fluoro-3-(trifluoromethyl benzamide A suspension of the product from Example 1B, the product from Example 42A, and K$_2$CO$_3$ was processed as described in Example 1D to provide the title compound.

MS (DCI/NH$_3$) m/z 465 (M+H)$^+$; $^1$H NMR (DMSO-d$_6$) δ 9.86 (s, 1H), 8.90 (d, 1H, J=7.8 Hz), 8.59 (d, 1H, J=2.7 Hz), 8.30–8.16 (m, 3H), 8.12–8.00 (m, 1H), 7.95 (ddd, 1H, J=8.4, 2.7, 1.4 Hz), 7.66 (t, 1H, J=8.4 Hz), 7.39 (dd, 1H, J=8.3, 4.6 Hz), 5.89 (t, 1H, J=7.9 Hz), 1.67 (s, 9H).

EXAMPLE 43

N-(1-{[3,4-Dioxo-2-(3-pyridinylamino)-1-cyclobuten-1-yl]amino}-2,2-dimethylpropyl)-2-phenylacetamide Resin-bound benzotijazole, 2-phenylacetamide, pivaldehyde, p-toluenesulfonic acid, the product from Example 1B and $Cs_2CO_3$ were processed as described in Example 9 to provide the title compound.

MS (ESI+) m/z 393 (M+H)$^+$; $^1$H NMR (DMSO-d$_6$) δ 9.79 (s, 1H), 8.64 (s, 1H), 8.39 (br s, 1H), 8.29 (dd, 1H, J=4.8, 1.5 Hz), 8.02 (br d, 1H, J=7.7 Hz), 7.98 (br s, 1H), 7.50 (dd, 1H, J=8.4, 4.8 Hz), 7.32–7.24 (m, 4H), 7.23–7.19 (m, 1H), 5.61 (brs, 1H), 3.63–3.49 (m, 2H, Ph-CH$_2$, obscured), 0.98 (s, 9H).

EXAMPLE 44

N-(1-{[3,4-Dioxo-2-(3-pyridinylamino)-1-cyclobuten-1-yl]amino}-2,2-dimethylpropyl)-3-phenylpiop-2-enamide Resin-bound benzotriazole, 3-phenylacrylamide, pivaldehyde, p-toluenesulfonic acid, the product from Example 1B and $Cs_2CO_3$ were processed as described in Example 9 to provide the title compound.

MS (ESI+) m/z 405 (M+H)$^+$; $^1$H NMR (DMSO-d$_6$) δ 9.82 (s, 1H), 8.67 (d, 1H, J=2.6 Hz), 8.41 (br s, 1H), 8.30 (dd, 1H, J=5.1, 1.1 Hz), 8.04 (ddd, 1H, J=8.4, 2.6, 1.1 Hz), 8.01 (br s, 1H), 7.60–7.55 (m, 7.55–7.45 (m, 2H), 7.45–7.37 (m, 3H), 6.87 (d, 1H, J=15.7 Hz), 5.76 (br s, 1H), 1.04 (s, 9H).

EXAMPLE 45

4-Chloro-N-(2,2-dichloro-1-{[3,4-dioxo-2-(3-pyridinylamino)-1-cyclobuten-1-yl]amino}pentyl)benzamide

EXAMPLE 45A

N-[1-(1H-1,2,3-Benzotriazol-1-yl)-2,2-dichloropentyl]4-chlorobenzamide

A suspension of 4-chlorobenzamide, 2,2-dichloropentanal, benzotriazole, and p-toluenesulfonic acid was processed as in Example 1C to provide the title compound.

MS (ESI+) rn/z 411 (M+H)$^+$.

EXAMPLE 45B

4-Chloro-N-(2,2-dichloro-1-{[3,4-dioxo-2-(3-pyridinylamino) 1-cyclobuten-1-yl]amino}pentyl)benzamide A suspension of the product from Example 1B, the product from Example 45A, and $K_2CO_3$ was processed as described in Example 1D to provide the title compound.

mp 258–259° C., MS (DCI/NH$_3$) m/z 481 (M+H)$^+$; $^1$H NMR (DMSO-d$_6$) δ 10.21 (s, 1H), 9.37 (br d, 1H, J=8.0 Hz), 8.59–8.53 (m, 1H), 8.52–8.45 (m, 1H), 8.28 (brd, 1H, J=3.8 Hz), 7.93–7,88 (m, 3H), 7.63–7.58 (m, 2H), 7.41 (dd, 1H, J=8.2, 4.4 Hz), 6.69 (t, 1H, J=8.4 Hz), 2.32–2.23 (m, 2H), 1.77–1.68 (m, 2H), 3H, J=7.8 Hz), Anal. calcd for $C_{21}H_{19}Cl_3N_4O_3$: C, 52.35; H, 3.98; N, 11.63. Found: C, 52.45; H, 3.84; N, 11.53.

EXAMPLE 46

4-Chloro-N-(1-{[3,4-dioxo-2-(4-pyridinylamino)-1-cyclobuten-1-yl]amino}-2,2-dimethylpropyl)benzamide

EXAMPLE 46A

3-Ethoxy-4-(4-pyridinylamino)-3-cyclobutene-1,2-dione

A solution of 4-aminopyridine and 3,4-dietboxy-3-cyclobutene-1,2-dione in ethanol was processed as described in Example 1A to provide the title compound.

MS (DCI/NH$_3$) m/z 219 (M+H)$^+$.

EXAMPLE 46B

3-Amino4-(4-pyridinylamino)-3-cyclobuhtene-1,2-dione

A solution of the product from Example 46A and ammonia in methanol was processed as described in Example 1B to provide the title compound.

MS (DCI/NH$_3$) m/z 190 (M+H)$^+$.

EXAMPLE 46C

4-Chloro-N-(1-{[3,4-dioxo-2-(4-pyridinylamino)-1-cyclobuten-1-yl[amino]-2,2-dimethylpropyl)benzamide A suspension of the product from Example 46B, the product from Example 2A, and $K_2CO_3$ was processed as described in Example 1D to provide the title compound.

mp 244–246° C., MS (ESI+) m/z 413 (M+H)$^+$, $^1$H NMR (DMSO-d$_6$) δ 11.62 (brs, 1H), 8.79 (d, 1H, J=9.1 Hz), 8.72 (d, 1H, J=7.8 Hz), 8.60 (br d, 1H, J=6.4 Hz), 7.97–7.79 (m, 4H), 7.55 (d, 1H, J=8.4 Hz), 5.87 (t, 1H, J=8.1 Hz), 1.07 (s, 9H); Anal. calcd for $C_{21}H_{21}ClN_4O_3$: C, 61.09; H, 5.13; N, 13.57. Found: C, 60.95; H, 5.08; N, 13.51.

EXAMPLE 47

4-Chloro-N-(1-{[3,4-dioxo-2-(2-pyridinylamino)-1-cyclobuten-1-yl]amino}-2,2-dimethyltropyl)benzamide

EXAMPLE 47A

3-Ethoxy-4-(2-pyridinylamino)-3-cyclobutene-1,2-dione

A solution of 2-aminopyridine and 3,4-diethoxy-3-cyclobutene-1,2-dione in ethanol was processed as described in Example 1A to provide the title compound.

MS (DCI/NH$_3$) m/z 219 (M+H)$^+$.

EXAMPLE 47B

3-Amino-4-(2-pyridinylamino)-3-cyclobutene-1,2-dione

A solution of the product from Example 47A and ammonia in methanol was processed as described in Example 1B to provide the title compound.

MS (DCI/NH$_3$) m/z 190 (M+H)$^+$.

EXAMPLE 47C

4-Chloro-N-(1-{[3,4-dioxo-2-(2-pyridinylamino)-1-cyclobuten-1-yl]amino}-2,2-dimethylpropyl)benzamide A suspension of the product from Example 47B, the product from Example 2A, and $K_2CO_3$ was processed as described in Example 1D to provide the title compound.

mp 246–248° C.; MS (ESI+) m/z 413 (M+H)$^+$; $^1$HNMR (DMSO-d$_6$) δ 10.95 (brs, 1H), 9.82 (d, 1H, J=9.8 Hz), 8.88 (d, 1H, J=8.5 Hz), 8.31 (dd, 1H, J=5.1, 1.7 Hz), 7.86 (d, 2H, J=8.4 Hz), 7.85–7.77 (m, 2H), 7.57 (d, 1H, J=8.4 Hz), 7.23 (d, 1H, J=8.1 Hz), 7.08 (dd, 1H, J=6.8, 5.1 Hz), 6.06 (t, 1H, J=8.1 Hz), 1.03 (s, 9H), Anal. calcd for $C_{21}H_{21}ClN_4O_3$: C, 61.09; H, 5.13; N, 13.57. Found: C, 61.12; H, 5.24; N, 13.53.

EXAMPLE 48

N-(1-{[3,4-Dioxo-2-(3-pyridinylamino)-1-cyclobuten-1-yl]amino}-2,2-dimethylpropyl) benzamide

EXAMPLE 48A

N-[1-(1H-1,2,3-Benzotriazol-1-yl)-2,2-dimethylpropyl]benzamide

A suspension of benzamide, pivaldehyde, benzotriazole, and p-toluenesulfonic acid was processed as in Example 1C to provide the title compound.

MS (ESI+) m/z 309 (M+H)$^+$.

EXAMPLE 48B

N-(1-{[3,4-Dioxo-2-(3-pyridinylamino)-1-cyclobuten-1-yl]amino}-2,2-dimethylpropyl) benzamide A suspension of the product from Example 1B, the product from Example 48A, and $K_2CO_3$ was processed as described in Example 1D to provide the title compound.

mp 246–247° C.; MS (DCI/NH$_3$) m/z 379 (M+H)$^+$; $^1$H NMR (DMSO-d$_6$) δ 9.88 (s, 1H), 8.67 (br d, 1H, J=7.1 Hz), 8.57 (d, 1H, J=2.5 Hz), 8.23 (d, 1H, J=4.6 Hz), 8.04 (br s, 1H), 7.92 (br d, 1H, J=8.3 Hz), 7.83 (d, 2H, J=7.4 Hz), 7.53 (t, 1H, J=7.2 Hz), 7.47 (t, 2H, J=7.2 Hz), 7.36 (dd, 1H, J=8.3, 4.6 Hz), 5.87 (br s, 1H), 1.04 (s, 9H); Anal. calcd for $C_{21}H_{22}N_4O_3$·0.55 $H_2O$: C, 64.95; H, 6.00; N, 14.43. Found: C, 64.78; H, 5.69; N, 14.14.

EXAMPLE 49

(+)N-(1-{[3.4-Dioxo-2-(3-pyridinylamino)-1-cyclobuten-1-yl]amino}-2,2-dimethylpropyl)-3,5-difluorobenzamide The product from Example 16B was chromatographed over a Daicel Chiral Technologies Chiralpak AS chiral column (2.0 cm×25 cm) eluting with 10% ethanol/hexanes (flow rate=10 mL/minute) to provide the title compound as the dextrorotatory enantiomer.

$[α]_D^{23}$=+30° (c 0.013, DMSO); MS (ESI+) m/z 415 (M+H)$^+$; $^1$H NMR (DMSO-d$_6$) δ 9.87 (s, 1H), 8.78 (d, 1H, J=8.1 Hz), 8.57 (d, 1H, J=2.7 Hz), 8.25 (dd, 1H, J=4.4, 1.4 Hz), 8.02 (brs, 1H), 7.93 (ddd, 1H, J=8.1, 2.7, 1.4 Hz), 7.62–7.45 (m, 3H), 7.40 (dd, 1H, J=8.1, 4.4 Hz), 5.85 (t, 1H, J=8.1 Hz), 1.06 (s, 9H).

EXAMPLE 50

(−)N-(1-{[3,4-Dioxo-2-(3-pyridinylamino)-1-cyclobuten-1-yl]amino}-2,2-dimethylpropyl)-3,5-difluorobenzamide The product from Example 16B was chromatographed over a Daicel Chiral Technologies Chiralpak AS chiral column (2.0 cm×25 cm) eluting with 10% ethanol/hexanes (flow rate=10 mL/minute) to provide the title compound as the levorotatory enantiomer.

$[α]_D^{23}$=−26° (c 0.013, DMSO); MS (ESI+) m/z 415 (M+H)$^+$; $^1$H NMR (DMSO-d$_6$) δ 9.87 (s, 1H), 8.78 (d, 1H, J=8.1 Hz), 8.57 (d, 1H, J=2.7 Hz), 8.25 (dd, 1H, J=4.4, 1.4 Hz), 8.02 (br s, 1H), 7.93 (ddd, 1H, J=8.1, 2.7, 1.4 Hz), 7.62–7.45 (m, 3H), 7.40 (dd, 1H, J=8.1, 4.4 Hz), 5.85 (t, 1H, J=8.1 Hz), 1 06 (s, 9H).

EXAMPLE 51

N-(2,2-Dichloro-1-{[3,4dioxo-2-(3-pyridinylamino)-1-cyclobuten-1-yl]amino}propyl)-3,5-difluorobenzamide

EXAMPLE 51A

N-[1-(1H-1,2,3-Benzotriazol-1-yl-2,2-dichloropropyl]-3,5-difluorobenzamide 3,5-Difluorobenzamide, the product from Example 24A, benzotriazole, and p-toluenesulfonic acid were processed as described in Example 1C to provide the title compound.

MS (ESI+) m/z 385 (M+H)$^+$.

EXAMPLE 51B

N-(2,2-Dichloro-1- {[3 .4-dioxo-2-(3-pyridinylamino)-1-cyclobuten-1-yl]amino}propyl)-3,5-difluorobenzamide A suspension of the product from Example 1B, the product from Example 51A, and $K_2CO_3$ was processed as described in Example 1D to provide the title compound.

mp 231–232° C.; MS (ESI+) m/z 455 (M+H)$^+$; $^1$H NMR (DMSO-d$_6$) δ 10.22 (s, 1H), 9.50 (d, 1H, J=7.8 Hz), 8.58 (d, 1H, J=2.0 Hz), 8.46 (d, 1H, J=7.8 Hz), 8.28 (d, 1H, J=4.8 Hz), 7.91 (brd, 1H, J=7.8 Hz), 7.63–7.50 (, 3H), 7.41 (dd, 1H, J=8.5, 4.7 Hz), 6.64 (t, 1H, J=7.8 Hz), 2.24 (s, 31H); Anal. calcd for $C_{19}H_{14}Cl_2F_2N_4O_3$: C, 50.13; H, 3.10; N, 12.31. Found: C, 50.35; H, 3.14; N, 12.31.

EXAMPLE 52

4-Chloro-N-{1-[(3,4-dioxo-2-{[5-(trifluoromethyl) pyridin-3-yl]amino}-1-cyclobuten-1-yl) amino]-2,2-dimethylpropyl}benzamide

EXAMPLE 52A 5-(Trifluoromethyl)pyridin-3-ylamine

A suspension of 4-chloro-5-tifluoromethyl pyridine (4.86 g, 26.8 mmol), Ni(COD)$_2$ (0.368 g, 1.34 mmol), Pd(dppf)$_2$ CH$_2$Cl$_2$ (2.19 g, 2.68 mmol), 1,1′-bis(diphenylphosphino) ferrocene (1.00 g, 1.80 mmol), benzophenone imine (5.82 g, 32.1 mmol), and sodium tert-butoxide (3.60 g, 37.5 mmol) in toluene was heated at reflux for 16 hours. The reaction mixture was cooled and evaporated in vacuo. The crude material was purified by chromatography, eluting with EtOAc/hexanes (1:1). The chromatographed product was dissolved in THF (200 mL) and 2 N HCl (10 mL) was added and the mixture was stirred for 0.5 hours. The reaction mixture was partitioned between 0.5 M HCl and (2:1) hexanes/EtOAc. The aqueous layer was separated and made alkaline with 10% NaOH. The product aniline was extracted with CH$_2$Cl$_2$, dried over anhydrous Na$_2$SO$_4$ and concentrated in vacuo to provide 2.98 g (67 % yield) of white crystalline solid.

MS (DCI/NH$_3$) M/z 163 (M+H)$^+$.

EXAMPLE 52B

3-Ethoxy-4-(5-trifluoromethyl-3-pyridinylamino)-cyclobut-3-ene-1,2-dione

A solution of the product from Example 52A (2.98 g, 18.4 mmol) and 3,4,-diethoxy-3-cyclobutene-1,2-dione (3.13 g, 18.4 mmol) in EtOH (50 mL) was heated at reflux for 48 hours. The reaction mixture was filtered while still hot and the filtrate was absorbed onto silica gel. The crude material was purified by chromatography, eluting with EtOAc/hexanes (3:1) to provide 2.00 g (38% yield) of the desired compound as colorless crystals.

MS (DCI/NH$_3$) m/z 287 (M+H)$^+$.

EXAMPLE 52C

3-Amino4-(5-trifluoromethyl-3-pyridinylamino) cyclobut-3-ene-1,2-dione

The product from Example 52B (2.00 g, 6.99 mmol) was dissolved in 2.0 M NH$_3$ in MeOH and stirred in a sealed vessel for 5 hours. The reaction mixture was concentrated in vacuo to a volume of 15 mL and triturated with EtOAc. The product (1.59 g, 89% yield) was collected by filtration and used without further purification.

MS (DCI/NH$_3$) m/z 258 (M+H)$^+$.

EXAMPLE 52D

4-Chloro-N-{1-[(3,-dioxo-2-{[5-(trifluoromethyl) pyridin-3-yl]amino}-1-cyclobuten-1-yl)amino]-2,2-dimethylpropyl}benzamide A suspension of the product from Example 52C, the product from Example 2A, and K$_2$CO$_3$ was processed as described in Example 1D to provide the title compound.

mp 231–232° C.; MS (ESI+) m/z 481 (M+H)$^+$; $^1$H NMR (DMSO-d$_6$) δ 10.13 (s, 1H), 8.75 (d, 1H, J=2.4 Hz), 8.72 (br s, 1H), 8.59 (d, 1H, J=0.7 Hz), 8.34 (br s, 1H), 8.11 (br s, 1H), 7.87 (d, 2H, J=8.5 Hz), 7.57 (d, 2H, J=8.5 Hz), 5.86 (m, 1H), 1.06 (s, 9H); Anal. calcd for C$_{22}$H$_{20}$ClF$_3$N$_4$O$_3$: C, 54.95; H, 4.19; N, 11.65. Found: C, 54.58; H, 4.19; N, 11.99.

EXAMPLE 53

3,5-Dichloro-N-{1-[(3,4-dioxo-2-{[5-(trifluoromethyl)pyridin-3-yl]amino}-1-cyclobuten-1-yl)amino]-2,2-dimethylpropyl}benzamide A suspension of the product from Example 52C, the product from Example 12A, and K$_2$CO$_3$ was processed as described in Example 1D to provide the title compound.

mp 233–234° C.; MS (ESI+) m/z 515 (M+H)$^+$; $^1$H NMR (DMSO-d$_6$) δ 10.13 (s, 1H), 8.86 (d, 1H, J=6.9 Hz), 8.76 (d, 1H, J=2.4 Hz), 8.59 (s, 1H), 8.39 (s, 1H), 8.09 (br s, 1H), 7.85 (d, 2H, J=1.9 Hz), 7.82 (d, 1H, J=1.9 Hz), 5.86 (s, 1H), 1.07 (s, 1H); Anal. calcd for C$_{22}$H$_{19}$Cl$_2$F$_3$N$_4$O$_3$: C, 51.28; H, 3.72; N, 10.87. Found: C, 50.92; H, 3.62; N, 11.05.

EXAMPLE 54

4-Chloro-N-{1-[(3,4-dioxo-2-{[5-(trifluoromethyl) pyridin-3-yl]amino}-1-cyclobuten-1-yl)amino]-2,2-dimethyl-3-phenylpropyl}benzamide A suspension of the product from Example 52C, the product from Example 18B, and K$_2$CO$_3$ was processed as described in Example 1D to provide the title compound.

mp 194–195° C.; MS (ESI+) m/z 551 (M+H)$^+$; $^1$H NMR (DMSO-d$_6$) δ 10.14 (s, 1H), 8.84 (s, 1H), 8.77 (d, 1H, J=2.3 Hz), 8.60 (s, 1H), 8.41 (s, 1H), 8.21 (br s, 1H), 7.91 (d, 2H, J=8.5 Hz), 7.59 (d, 2H, J=8.7 Hz), 7.32–7.20 (m, 5H), 5.95 (br s, 1H), 2.75 (ABq, 2H, J$_{AB}$=12.8 Hz, Δν$_{AB}$=35.7 Hz), 0.98 (s, 3H), 0.95 (s, 3 H); Anal. calcd for C$_{28}$H$_{24}$ClF$_3$N$_4$O$_3$: C, 60.38; H, 4.34; N, 10.06. Found: C, 60.36; H, 4.46; N, 10.03.

EXAMPLE 55

N-(1-{[3,4-Dioxo-2-(3-pyridinylamino)-1-cyclobuten-1-yl]amino}-2,2-dimethyl-3-phenylpropyl)-3,5-difluorobenzamide

EXAMPLE 55A

N-[1-(1H-1,2,3-Benzotriazol-1-yl)-2,2-dimethyl-3-phenylpropyl]3.5-difluorobenzamide 3,5-Difluorobenzamide, the product from Example 18A, benzotriazole, and p-toluenesulfonic acid were processed as described in Example 18B to provide the title compound.

MS (DCI/NH$_3$) m/z 421 (M+H)$^+$.

EXAMPLE 55B

N-(1-{[3,4-Dioxo-2-(3-pyridinylamino)-1-cyclobuten-1-yl]amino}-2,2-dimethyl-3-phenylproly)-3.5-difluorobenzamide A suspension of the product from Example 1B, the product from Example 55A, and K$_2$CO$_3$ was processed as described in Example 1D to provide the title compound.

mp 223–224° C.; MS (ESI+) m/z 491 (M+H)$^+$; $^1$H NMR (DMSO-d$_6$) δ 9.88 (s, 1H), 8.89 (d, 1H, J=7.4 Hz), 8.59 (d, 1H, J=2.6 Hz), 8.26 (dd, 1H, J=4.5, 1.2 Hz), 8.12 (brs, 1H), 7.95 (ddd, 1H, J=8.5, 2.3, 1.2), 7.63–7.57 (m, 2H), 7.50 (tt, 1H, J=9.2, 2.4), 7.26 (ddd, 1H, J=8.5, 4.7, 0.7), 7.33–7.21 (m, 5H), 1H), 2.74 (ABq, 2H, J$_{AB}$=12.7 Hz, αν$_{AB}$=31.4 Hz), 0.97 (s, 3H), 0.95 (s, 3H); Anal. calcd for C$_{27}$H$_{24}$F$_2$N$_4$O$_3$: C, 66.11; H, 4.93, N, 11.42. Found: C, 65.87; H, 4.79; N, 11.40.

EXAMPLE 56

(+) 3-Chloro-N-(1-{[3.4-dioxo-2-(3-pyridinylamino)-1-cyclobuten-1-yl]amino}-2,2-dimethylpropyl)benzamide The product from Example 5B was chromatographed over a Daicel Chiral Technologies Chiralpak AS chiral column (2.0 cm×25 cm) eluting with 10% ethanol/hexanes (flow rate=10 mL/minute) to provide the title compound as the dextrorotatory enantiomer.

[α]$_D^{20}$=+40° (c 0.11, DMSO); MS (ESI+) m/z 413 (M+H)$^+$; $^1$H NMR (DMSO-d$_6$) δ 9.73 (br s, 1H), 9.40 (br d, 1H, J=8.4 Hz), 8.77 (d, 1H, J=2.5 Hz), 8.50(d, 1H, J=8.4 Hz), 8.26 (dd, 1H, J=5.5, 1.1 Hz), 7.93 (brs, 1H), 7.79 (brs, 1H), 7.83 (d, 1H, J=7.9 Hz), 7.61 (br d, 1H, J=8.6 Hz), 7.58 (t, 1H, J=8.2 Hz), 7.41 (dd, 1H, J=8.7, 4.8 Hz), 5.47 (t, 1H, J=8.5 Hz), 0.90 (s, 9H); Anal. calcd for C$_{21}$H$_{51}$ClN$_4$O$_3$: C, 61.09; H, 5.13; N, 13.57. Found: C, 61.26; H, 4.99; N, 13.49.

EXAMPLE 57

(−) 3-Chloro-N-(1-{[3,4-dioxo-2-(3-pyridinylamino)-1-cyclobuten-1-yl]amino}-2,2-dimethylpropyl)benzamide The product from Example 5B was chromatographed over a Daicel Chiral Technologies Chiralpak AS chiral column (2.0 cm×25 cm) eluting with 10% ethanol/hexanes (flow rate=10 mL/minute) to provide the title compound as the levorotatory enantiomer.

[α]$_D^{20}$=−43° (c 0.09, DMSO); MS (ESI+) m/z 413 (M+H)$^+$; $^1$H NMR (DMSO-d$_6$) δ 9.73 (br s, 1H), 9.40 (br d, 1H, J=8.4 Hz), 8.77 (d, 1H, J=2.5 Hz), 8.50 (d, 1H, J=8.4 Hz), 8.26 (dd, 1H, J=5.5, 1.1 Hz), 7.93 (brs, 1H), 7.79 (brs, 1H), 7.83 (d, 1H, J=7.9 Hz), 7.61 (br d, 1H, J=8.6 Hz), 7.58 (t, 1H, J=8.2 Hz), 7.41 (dd, 1H, J=8.7, 4.8 Hz), 5.47 (t, 1H, J=8.5 Hz), 0.90 (s, 9H); Anal. calcd for $C_{21}H_{51}ClN_4O_3$: C, 61.09; H, 5.13; N, 13.57. Found: C, 61.17; H, 5.00; N, 13.44.

EXAMPLE 58

3,5-Dichloro-N-(1-{[3,4-dioxo-2-(3-pyridinylamino)-1-cyclobuten-1-yl]amino}-2,2-dimethyl-3-phenylpropyl)benzamide

EXAMPLE 58A

N-[1-(1H-1,2,3-Benzotriazol-1-yl)-2,2-dimethyl-3-phenylpropyl]-3,5-dichlorobenzamide 3,5-Dichlorobenzamide, the product from Example 18A, benzotriazole, and p-toluenesulfonic acid were processed as described in Example 18B to provide the title compound.

MS (DCI/NH$_3$) m/z 453 (M+H)$^+$.

EXAMPLE 58B 3.5-Dichloro-N-(1-{[3,4-dioxo-2-(3-pyridinylamino)-1-cyclobuten-1-yl]amino}-2,2-dimethyl-3-phenylpropyl)benzamide A suspension of the product from Example 1B, the product from Example 58A, and K$_2$CO$_3$ was processed as described in Example 1D to provide the title compound.

mp 197–198° C.; MS (ESI+) m/z 523 (M+H)$^+$; $^1$H NMR (DMSO-d$_6$) δ 9.86 (s, 1H), 8.96 (d, 1H, J=7.6 Hz), 8.59 (d, 1H, J=2.8 Hz), 8.26 (dd, 1H, J=4.7, 1.4 Hz), 8.10 (brs, 1H), 7.94 (dd, 1H, J=8.3, 1.2 Hz), 7.87 (d, 2H, J=1.9 Hz), 7.85 (d, 1H, J=1.9 Hz), 7.39 (ddd, 1H, J=8.3, 4.8, 0.5 Hz), 7.32–7.20 (m, 5H), 5.93 (t, 1H, J=7.3 Hz), 5.48 (ABq, J$_{AB}$=13.0, αv$_{AB}$=29.7 Hz), 0.97 (s, 3H), 0.96 (s, 3H); Anal. calcd for C$_{27}$H$_{24}$Cl$_2$N$_4$O$_3$ 0.95 H$_2$O: C, 60.00; H, 4.83; N, 10.37. Found: C, 59.76; H, 4.59; N, 10.22.

EXAMPLE 59

3-Chloro-N-(1-{[3,4-dioxo-2-(3-pyridinylamino)-1-cyclobuten-1-yl]amino}-2,2-dimethyl-3-phenylpropyl)benzamide

EXAMPLE 59A

N-1-( 1H-1,2,3-Benzotriazol-1-yl)-2,2-dimethyl-3-phenylpropyl]-3-chlorobenzamide 3-Chlorobenzamide, the product from Example 18A, benzotriazole, and p-toluenesulfonic acid were processed as described in Example 18B to provide the title compound.

MS (DCI/NH$_3$) m/z 419 (M+H)$^+$.

EXAMPLE 59B 3-Chloro-N-(1-{[3,4-dioxo-2-(3-pyridinylamino-1-cyclobuten-1-yl]amino}-2,2-dimethyl-3-phenylpropyl)benzamide A suspension of the product from Example 1B, the product from Example 59A, and K$_2$CO$_3$ was processed as described in Example 1 D to provide the title compound.

mp 178–179° C.; MS (ESI+) m/z 489 (M+H)$^+$; $^1$H NMR (DMSO-d$_6$) δ 9.87 (s, 1H), 8.90 (d, 1H, J=3,7 Hz), 8.60 (d, 1H, J=1.6 Hz), 8.26 (d, 1H, J=4.2 Hz), 8.13 (brs, 1H), 7.95 (dd, 1H, J=8.3, 1.2 Hz), 7.90 (t, 1H, J=1.7 Hz), 7.83 dt, 1H, J=7.8, 1.2 Hz), 7.65 (ddd, 1H, J=8.0, 2.1, 1.2 Hz), 7.55 (t, 1H, J=8.1 Hz), 7.39 (dd, 1H, J=8.2, 4.7 Hz), 7.32–7.20 (m, 5H), 5.95 (s, 1H), 2.74 (ABq, J$_{AB}$=12.8, αv$_{AB}$=32.1 Hz), 0.97 (s, 3H), 0.95 (s, 3H); Anal. calcd for C$_{27}$H$_{25}$ClN$_4$O$_3$.0.5 H$_2$O: C, 65.12; H, 5.26; N, 11.25. Found: C, 65.19; H, 5.42; N, 11.26.

EXAMPLE 60

N-(1-{[3,4-Dioxo-2-(3-pyridinylamino)-1-cyclobuten-1-yl]amino}-2,2-dimethyl-3-phenylpropyl)-3-methylbenzamide

EXAMPLE 60A

N-[1(1H-1,2,3-Benzotriazol-1-yl)-2,2-dimethyl-3-phenylpropyl]-3-chlorobenzamide m-Toluamide, the product from Example 18A, benzotriazole, and p-toluenesulfonic acid were processed as described in Example 18B to provide the title compound.

MS (DCI/NH$_3$) m/z 399 M+H)$^+$.

EXAMPLE 60B

N-(1-{[3,4-Dioxo-2-(3-pyridinylamino)-1-cyclobuten-1-yl]amino}-2,2-dimethyl-3-phenylpropyl)-3-methylbenzamide A suspension of the product from Example 1B, the product from Example 60A, and K$_2$CO$_3$ was processed as described in Example 1D to provide the title compound.

mp 234–235° C.; MS (ESI+) m/z 469 (M+H)$^+$; $^1$H NMR (DMSO-d$_6$) δ 9.88 (s, 1H), 8.74 (br s, 1H), 8.60 (d, 1H, J=2.6 Hz), 8.26 (dd, 1H, J=4.7, 1.1 Hz), 8.14 (br s, 1H), 7.95 (dd, 1H, J=8.3, 1.0 Hz), 7.67 (m, 2H), 7.41–7.37 (m, 3H), 7.32–7.20 (m, 5H), 5.96 (br s, 1H), 5.48 (ABq, J$_{AB}$=12.8, ααv$_{AB}$=33.8 Hz), 238 (s, 3H), 0.97 (s, 3H), 0.95 (s, 3H); Anal. calcd for C$_{28}$H$_{28}$N$_4$O$_3$.0.1 H$_2$O: C, 69.12, H, 6.21; N, 11.51. Found: C, 69.21; H, 6.37; N, 11.48.

EXAMPLE 61

N-[1-({2[(2-Chloropyiridin-3-yl)amino]-3,4-dioxo-1-cyclobuten-1-yl}amino)-2,2-dimethyl-3-phenylpropyl]-3-methylbenzamide A suspension of the product from Example 29B, the product from Example 60A, and K$_2$CO$_3$ was processed as described in Example 1D to provide the title compound.

mp 234–235° C.; MS (ESI+) m/z 503 (M+H)$^+$; $^1$H NMR (DMSO-d$_6$) δ 9.47 (s, 1H), 8.73 (d, 1H, J=7.8 Hz), 8.62 (d, 1H, J=7.5 Hz), 8.12 (dd, 1H, J=4.8, 1.7 Hz), 8.05 (d, 1H, J=7.5 Hz), 7.70–7.65 (m, 2H), 7.45 (dd, 1H, J=8.3, 4.8 Hz), 7.40–7.38 (m, 2H), 7.32–7.28 (m, 2H), 7.25–7.21 (m, 3H), 6.01 (br s, 1H), 2.75 (ABq, J$_{AB}$=12.8, αv$_{AB}$=38.7 Hz), 2.39 (s, 3H), 0.99 (s, 3H), 0.95 (s, 3H); Anal. calcd for C$_{28}$H$_{27}$ClN$_4$O$_3$.0.2 H$_2$O: C, 66.39; H, 5.45; N, 11.06. Found: C, 66.57; H, 5.67; N, 10.82.

EXAMPLE 62

4-Chloro-N-[1-({2-[(6-chloropyridin-3-yl)amino]-3,4-dioxo-1-cyclobuten-1-yl}amino)-2,2-dimethylpropyl]benzamide

EXAMPLE 62A 4-(6-Chloro3-pyridinylamino)-3-ethoxy-cyclobut-3-ene-1,2-dione

5-Amino-2-chloropyridine (2.32 g, 18.0 mmol) in ethanol (50 mL) was added to a solution of 3,4-diethoxy-3- cyclobutene-1,2-dione 3.07 g, 18.0 mmol) in ethanol (200 mL) at 70° C. over a period of 6 hours. The mixture was then heated at 80° C. for an additional 18 hours, filtered, and the solvents removed in vacuo. The crude product was suspended in 10% EtOH/EtOAc (30 mL) and adsorbed onto silica gel (15 g). Purification by flash chromatography on silica gel (eluted with 5% EtOH/EtOAc) provided 1.98 g of the desired product as a pale yellow powder.

MS (DCI/NH$_3$) m/z 253 (M+H)$^+$.

EXAMPLE 62B

3-Amino 4-(6-chloro-3-pyridinylamino)-cyclobut-3-ene-1,2-dione

A solution of the product from Example 62A and ammonia in methanol was processed as described in Example 1B to provide the title compound.

MS (DCI/NH3) m/z 224 (M+H)$^+$.

EXAMPLE 62C

4-Chloro-N-[1-({2-[(6-chloropyridin-3-yl)amino]-3,4-dioxo-1-cyclobuten-1-yl}amino)-2,2-dimethylpropyl]benzamide A suspension of the product from Example 62B, the product from Example 2A, and K$_2$CO$_3$ was processed as described in Example 1D to provide the title compound.

mp 258–259° C.; MS (ESI+) m/z 447 (M+H)$^+$; $^1$H NMR (DMSO-d$_6$) δ 9.96 (brs, 1H), 8.74 (brd, 1H, J=9.1 Hz), 8.08–7.97(m, 1H), 7.92–7.84 (m, 3H), 7.77 (d, 1H, J=7.8 Hz), 7.61–7.48 (m, 3H), 5.85 (dd, 1H, J=9.2, 7.8 Hz), 1.04 (s, 9H); Anal. calcd for C$_{21}$H$_{20}$Cl$_2$N$_4$O$_3$: C, 56.39; H, 4.51; N, 12.53. Found: C, 56.43; H, 4.40; N, 12.46.

EXAMPLE 63

4-Chloro-N-[1-({2-[(2-fluoropyridin-3-yl)amino]-3,4-dioxo-1-cyclobuten-1-yl}amino)-2,2-dimethylpropyl]benzamide

EXAMPLE 63A

3-Amino-2-fluoropyridine

To a solution of 2-chloro-6-fluoro-5-nitropyridine (2.30 g, 13.0 mmol) in EtOH (50 mL) and sodium acetate dihydrate (1.69 g, 14.3 mmol) was added 10% Pd/C (230 mg). The suspension was hydrogenated (4 atm) at 23° C. for 5 hours then filtered through Celite. The filter cake was rinsed with EtOH and the filtrate concentrated to provide 1.34 g of the crude product as an off-yellow solid which was used without farther purification.

MS (DCI/NH$_3$) m/z 113 (M+H)$^+$.

EXAMPLE 63B 4-(2-Fluoropyridin-3-ylamino)-3-ethoxy-cyclobut-3-ene-1,2-dione

A solution of Example 63A and 3,4-diethoxy-3-cyclobutene-1,2-dione in ethanol was processed as described in Example 62A to provide the title compound.

MS (DCI/NH$_3$) m/z 237 (M+H)$^+$.

EXAMPLE 63C

3-Amino-4-(6-fluoro-3-pyridinylamino)-cyclobut-3-ene-1,2-dione

A solution of the product from Example 63B and ammonia in methanol was processed as described in Example 1B to provide the title compound.

MS (DCI/NH$_3$) m/z 208 (M+H)$^+$.

EXAMPLE 63D

4-Chloro-N-[1-({2-[(2-fluoropyridin-3-yl)amino]-3,4-dioxo- -cyclobuten-1-yl}amino)-2,2-dimeffiylpropyl]benzamide A suspension of the product from Example 63C, the product from Example 2A, and K$_2$CO$_3$ was processed as described in Example 1D to provide the title compound.

mp 231–234° C.; MS (ESI+) m/z 431 (M+H)$^+$; $^1$H NMR (DMSO-d$_6$) δ 9.47 (br s, 1H), 8.72 (d, 1H, J=7.8 Hz), 8.50 (d, 1H, J=8.8 Hz), 8.11 (dd, 1H, J=4.4, 1.4 Hz), 8.02 (d, 1H, J=7.8 Hz), 7.87 (d, 2H, J=8.5 Hz), 7.57 (d, 2H, J=8.5 Hz), 7.44 (dd, 1H, J=8.1, 4.4 Hz), 5.89 (t, 1H, J=8.5 Hz), 1.06 (s, 9H); Anal. calcd for C$_{21}$H$_{20}$ClFN$_4$O$_3$: C, 58.54; H, 4.68; N, 13.00. Found: C, 58.58; H, 4.70; N, 13.18.

EXAMPLE 64

3-Chloro-N-(1-{[3,4-dioxo-2-(3 pyridinylamino)-1-cyclobuten-1-yl]amino}-3,3-dimethylbutyl) benzamide

EXAMPLE 64A

N-(1-Benzotriazol-1-yl-3,3-dimethyl-butyl)-3-chloro-benzamide

A suspension of 3-chlorobenzamide, 3,3-dimethyl-butyraldehyde, and benzotriazole were processed as described in Example 1C to provide the desired product MS (DCI/NH$_3$) m/z 357 (M+H)$^+$.

EXAMPLE 64B

3-Chloro-N-(1-{[3,4-dioxo-2-(3-pyridinylamino)-1-cyclobuten-1yl]amino}-3,3-dimethylbutyl) benzamide A suspension of the product from Example 1B, the product from Example 64A, and K$_2$CO$_3$ was processed as described in Example 1D to provide the title compound.

mp 238–239° C.; MS (ESI+) m/z 427 (M+H)$^+$; $^1$H NMR (DMSO-d$_6$) δ 9.89 (s, 1H), 9.25 (s, 1H), 8.57 (d, 1H, J=2.6 Hz), 8.34 (br s, 1H) 8.27 (dd, 1H, J=4.5, 1.2 Hz), 7.95–7.91 (m, 2H), 7.85 (d, 1H, J=7.8 Hz), 7.64 (ddd, 1H J=8.0, 2.1, 0.9 Hz), 7.54 (t, 1H, J=7.8 Hz), 7.37 (ddd, 1H, J=8.3, 4.7,0.5 Hz), 5.99–5.87 (m, 1H), 2.04 (dd, 1H, J=14.2, 6.4 Hz), 1.86 (dd, 1H, J=14.4, 6.3 Hz), 0.98 (s, 9H); Anal. calcd for C$_{22}$H$_{23}$ClN$_4$O$_3$: C, 61.90; H, 5.43; N, 13.12. Found: C, 62.00; H, 5.39; N, 12.89.

EXAMPLE 65

N-(1-{[3,4-Dioxo-2-(3-pyridinylamino)-1-cyclobuten-1-yl]amino}-2,2-dimethylpropyl) thiophene-2-carboxamide

EXAMPLE 65A

N-(1-(1H-1,2,3-Benzotriazol-1-yl)-2,2-dimethylpropyl)thiophene-2-carboxamide

A suspension of thiophene-2-carboxamide, pivaldehyde, benzotriazole, and p-toluenesulfonic acid was processed as in Example 1C to provide the title compound.

MS (ESI+) m/z 315 (M+H)$^+$.

EXAMPLE 65B

N-(1-{[3,4-Dioxo-2-(3-pyridinylamino)-1-cyclobuten-1-yl]amino}-2,2-dimethylpropyl)thiophene-2-carboxamide A suspension of the product from Example 1B, the product from Example 65A, and $K_2CO_3$ was processed as described in Example 1D to provide the title compound.

MS (ESI+) m/z 385 (M+H)$^+$; $^1$H NMR(DMSO-d$_6$) δ 10.19 (s, 1H), 8.75 (brs, 1H), 8.57 (br d, 1H, J=5.2 Hz), 8.36 (d, 1H, J=4.7 Hz), 8.24 (br s, 1H), 8.11 (br d, 1H, J=8.1 Hz), 7.94 (d, 1H, J=3.4 Hz), 7.94 (d, 1H, J=5.0 Hz), 7.62 (dd, 1H, J=8.4, 5.0 Hz), 7.18 (dd, 1H, J=5.0, 3.7 Hz), 5.81 (t, 1H J=7.5 Hz), 1.05 (s, 9H).

EXAMPLE 66

3-Bromo-N-(1-{[3,4-dioxo-2-(3-pyridinylamino)-1-cyclobuten-1-y]amino}-2,2-dimethylpropyl)benzamide

EXAMPLE 66A

N-(1-(1H-1,2,3-benzotriazol-1-yl)-2,2-dimethylpropyl)-3-bromobenzamide

A suspension of 3-bromobenzamide, pivaldehyde, benzotriazole, and p-toluenesulfonic acid was processed as described in Example 1C to provide the title compound.

MS (DCI/NH$_3$) m/z 387 (M+H)$^+$.

EXAMPLE 66B

3-Bromo-N-(1-{[3,4-dioxo-2-(3-pyridinylamino)-1-cyclobuten-1-yl]amino}-2,2-dimethylpropyl)benzamide A suspension of the product from Example 1B, the product from Example 66A, and $K_2CO_3$ was processed as described in Example 1D to provide the title compound.

mp 244–245° C.; MS (ESI+) m/z 459 (M+H)$^+$; $^1$H NMR (DMSO-d$_6$) δ 9.86 (br s, 1H), 8.79 (d, 1H, J=7.8 Hz), 8.57 (d, 1H, J=3.1 Hz), 8.11 (dd, 1H, J=4.4, 1.4 Hz), 8.09–8.00 (m, 1H), 7.99 (t, 1H, J=1.7 Hz), 7.93 (ddd, 1H, J=8.2, 2.6, 1.0 Hz), 7.83 (dt, 2H, J=7.8, 1.4 Hz), 7.76 (ddd, 1H, J=8.2, 2.2, 1.0 Hz), 7.46 (t, 1H, J=7.8 Hz), 7.38 (dd, 1H, J=8.5, 4.8 Hz), 5.86 (t, 1H, J=8.5 Hz), 1.06 (s,9H); Anal. calcd for $C_{21}H_{21}BrN_4O_3$: C, 55.15; H, 4.63; N, 12.25. Found: C, 54.94; H, 4.45; N, 12.31.

EXAMPLE 67

3-Bromo-N-[1-({2-[(2-chloropyridin-3-yl) amino]-3,4-dioxo-1-cyclobuten-1-yl }amino)-2,2-dimethylpropyl]benzamide A suspension of the product from Example 29B, the product from Example 66A, and $K_2CO_3$ was processed as described in Example 1D to provide the title compound.

mp 257–259° C.; MS (ESI+) m/z 493 (M+H)$^+$; $^1$H NMR (DMSO-d$_6$) δ 9.46 (br s, 1H), 8.78 (d, 1H, J=7.8 Hz), 8.48 (d, 1H, J=8.5 Hz), 8.11 (dd, 1H, J=4.4, 1.4 Hz), 8.05–8.02 (m, 1H), 8.00 (t, 1H, J=1.7 Hz), 7.84 (dt, 1H, J=7.8, 1.4 Hz), 7.76 (ddd, 1H, J=8.1, 2.0, 1.0 Hz), 7.46 (t, 1H, J=8.1 Hz), 7.44 (dd, 1H, J=8.1, 3.4 Hz), 5.89 (t, 1H, J=8.1 Hz), 1.07 (s, 9H); Anal. calcd for $C_{21}H_{20}BrClN_4O_3$.0.1 $H_2O$: C,51.10; H, 4.12; N, 11.35. Found: C, 50.78 H, 3.78; N, 11.11.

EXAMPLE 68

N-(1-{[3,4-Dioxo-2-(3-pyridinylamino)-1-cyclobuten-1-yl]amino}-2,2-dimethylpropyl)-9-oxo-9H-fluorene-4-carboxamide

EXAMPLE 68A

9-Oxo-9H-fluorene-4-carboxamide

9-Oxo-9H-fluorene-4-carbonyl chloride (5.00 g, 20.6 mmoL) in 200 mL of THF was cooled to 0° C. and 100 mL of a solution of $H_2O$/$NH_4OH$ (2:1) was added dropwise over 10 minutes. The reaction mixture was warmed to 23° C. and stirred for 45 minutes then concentrated in vacuo to a volume of approximately 100 mL. The mixture was filtered and the filter cake was washed with 100 mL of $H_2O$ and 25 mL EtOAc/Et$_2$O (1:1). The product was dried in vacuo and used without further purification.

MS (DCI/NH$_3$) m/z 224 (M+H)$^+$.

EXAMPLE 68B

N-[1-(1H-1,2,3-Benzotriazol-1-yl)-2,2-dimethylpropyl]-9-oxo-9H-fluorene-4-carboxamide A suspension of the product from Example 68A, pivaldehyde, benzotriazole, and p-toluenesulfonic acid was processed as in Example 1C to provide the title compound.

MS (ESI+) m/z 411 (M+H)$^+$.

EXAMPLE 68C

N-(1-{[3,4-Dioxo-2-(3-pyridinylamino)-1-cyclobuten-1-yl]amino}-2,2-dimethylpropyl)-9-oxo-9H-fluorene-4-carboxamide A suspension of the product from Example 1B, the product from Example 68B, and $K_2CO_3$ was processed as described in Example 1D to provide the title compound.

mp 201–202° C.; MS (ESI+) m/z 481 (M+H)$^+$; $^1$H NMR (DMSO-d$_6$) δ 9.89 (s, 1H), 9.23 (d, 1H, J=8.0 Hz), 8.61 (d, 1H, J=2.6 Hz), 8.27 (dd, 1H, J=4.7, 1.2 Hz), 8.09 (br s, 1H), 7.99 (ddd, 1H, J=8.2, 2.6, 1.1 Hz), 7.72 (dd, 1H, J=7.3, 1.2 Hz), 7.66–7.63 (m, 1H), 7.62 (d, 1H, J=7.1 Hz), 7.56 (dd, 1H, 7.5, 1.2 Hz), 7.49 (d, 1H, J=7.3 Hz), 7.46–7.36 (m, 3H), 6.02 (t, 1H, J=8.7 Hz), 1.09 (s, 9H); Anal. calcd for $C_{28}H_{24}N_4O_4$.1.05 $H_2O$: C, 67.34; H, 5.27, N, 11,22. Found: C, 67.68; H, 5.41;N, 10.85.

EXAMPLE 69

Methyl 3-{[(1-{[3,4-Dioxo-2-(3-pyridinylamino)-1-cyclobuten-1-yl]amino}-2,2-dimethylpropyl)amino]carbonyl}benzoate

EXAMPLE 69A

Methyl 3-(Aminocarbonyl)benzoate 3-(Methoxycarbonyl)benzoic acid (1.0 g, 5.55 mmol) and SOCl$_2$ (0.81 g, 11.1 mmol) were dissolved in 20 mL of toluene. A catalytic amount of DMF (3 drops) was added and the reaction mixture was heated at 92° C. for 2.5 hours. The mixture was cooled to 23° C. and the solvent removed in vacuo. The crude material was dissolved in 25 mL THF and 3 mL NH$_4$OH was added. The reaction was stirred for 10 minutes then diluted with 50 mL of EtOAc and washed with 10 mL of 2 N HCl. The aqueous layer was extracted with 25 mL of EtOAc and the combined extracts were washed with NaHCO$_3$, dried over Na$_2$SO$_4$, and filtered through a ¼" silica gel frit. The filtrate was concentrated in vacuo and the crude material was recrystallized from EtOAc/hexanes to provide the desired product (0.817 g, 82% yield).

MS (DCI/NH$_3$) m/z 180 (M+H)$^+$.

EXAMPLE 69B

Methyl 3-({[1-(1H-1,2,3-Benzotriazol-1-yl)-2,2-dimethylpropyl]amino}carbonyl)benzoate A suspension of the product from Example 69A, pivaldehyde, benzotriazole, and p-toluenesulfonic acid was processed as in Example 1C to provide the title compound.

MS (ESI+) m/z 367 (M+H)$^+$.

EXAMPLE 69C

Methyl 3-{[(1-{[3,4-Dioxo-2-(3-pyridinylamino)-1-cyclobuten-1-yl]amino}-2,2-dimethylpropyl)amino[carbonyl}benzoate A suspension of the product from Example 1B, the product from Example 69B, and $K_2CO_3$ was processed as described in Example 1D to provide the title compound.

mp 228–229° C.; MS (ESI+) m/z 437 (M+H)$^+$; $^1$H NMR (DMSO-d$_6$) δ 9.89 (s, 1H), 8.90 (d, 1H, J=7.6 Hz), 8.58 (d, 1H, J=2.4 Hz), 8.39 (t, 1H, J=1.8 Hz), 8.25 (dd, 1H, J=4.7, 1.4 Hz), 8.14–8.09 (m, 2H), 8.05 (br s, 1H), 7.94 (ddd, 1H, J=8.5, 2.8, 1.4 Hz), 7.66 (t, 1H, J=8.0 Hz), 7.39 (dd, 1H, J=8.5, 4.7 Hz), 5.90 (br s, 1H), 3.90 (s, 3H), 1.07 (s, 9H); Anal. calcd for $C_{23}H_{24}N_4O_5$: C, 63.29; H. 5.54; N. 12.84. Found: C, 62.92; H, 5.61; N, 13.04.

EXAMPLE 70

(+)N-(1-{[3,4-Dioxo-2-(3-pyridinylamino)-1-cyclobuten-1-yl]amino}-2,2-dimethylpropyl)-3-methylbenzamide The product from Example 6B was chromatographed over a Daicel Chiral Technologies Chiralpak AS chiral column (2.0 cm×25 cm) eluting with 15% ethanol/hexanes (flow rate=15 mL/minute) to provide the title compound as the dextrorotatory enantiomer.

$[\alpha]_D^{23}$=+98° (c 0.25, EtOH); HRMS (FAB) calcd for $C_{22}H_{25}N_4O_3$ (M+H)$^+$393.1927, found 393.1917, $^1$H NMR (DMSO-d$_6$) δ 9.93 (br s, 1H), 8.64 (br d, 1H, J=7.1 Hz), 8.57 (d, 1H, J=2.7 Hz), 8.25 (dd, 1H, J=4.7, 1.4 Hz), 8.08 (brs, 1H), 7.93 (br d, 1H, J=7.9 Hz), 7.66–7.60 (m, 2H), 7.41–7.34 (m, 3H), 5.87 (brt, 1H, J=6.8 Hz), 2.37 (s, 3H), 1.05 (s, 9H).

EXAMPLE 71

(−)-N-(1-{[3,4-Dioxo-2-(3-pyridinylamino)-1-cyclobuten-1-yl]amino}-2,2-dimethylpropyl)-3-methylbenzamide The product from Example 6B was chromatographed over a Daicel Chiral Technologies Chiralpak AS chiral column (2.0 cm×25 cm) eluting with 15% ethanol/hexanes (flow rate=15 mL/minute) to provide the title compound as the levorotatory enantiomer.

$[\alpha]_D^{23}$=−96° (c 0.30, EtOH); HRMS (FAB) calcd for $C_{22}H_{25}N_4O_3$ (M+H)$^+$ 393.1927, found 393.1933; $^1$H NMR (DMSO-d$_6$) δ 9.93 (br s, 1H), 8.64 (br d, 1H, J=7.1Hz), 8.57 (d, 1H, J=2.7 Hz), 8.25 (dd, 1H, J=4.7, 1.4 Hz), 8.08 (br s, 1H), 7.93 (br d, 1H, J=7.9 Hz), 7.66–7.60 (m, 2H), 7.41–7.34 (m, 3H), 5.87 (brt, 1H, J=6.8 Hz), 2.37 (s, 3H), 1.05 (s, 9H).

EXAMPLE 72

(+) N-(1-{[3,4-Dioxo-2-(3-pyridinylamino)-1-cyclobuten-1-yl]amino}-2,2-dimethyl-3-phenylpropyl)-3-methylbenzamide The product from Example 60B was chromatographed over a Daicel Chiral Technologies Chiralpak AS chiral column (2.0 cm×25 cm) eluting with 15% ethanol/hexanes (flow rate=15 mL/minute) to provide the title compound as the dextrorotatory enantiomer.

$[\alpha]_D^{23}$=+105° (c 0.36, EtOH); HRMS (FAB) calcd for $C_{28}H_{29}N_4O_3$ (M+H)$^+$ 469.2240, found 469.2243; $^1$H NMR (DMSO-d$_6$) δ 9.88 (s, 1H), 8.74 (br s, 1H), 8.60 (d, 1H, J=2.6 Hz), 8.26 (dd, 1H, J=4.7, 1.1 Hz), 8.14 (br s, 1H), 7.95 (dd, 1H, J=8.3, 1.0 Hz), 7.67 (m, 2H), 7.41–7.37 (m, 3H), 7.32–7.20 (m, 5H), 5.96 (brs, 1H), 5.48 (ABq, J$_{AB}$=12.8, αv$_{AB}$=33.8 Hz), 2.38 (s,3H), 0.97 (s,3H), 0.95 (s,3H).

EXAMPLE 73

(−) N-(1-{[3,4-Dioxo-2-(3-pyridinylamino)-1-cyclobuten-1-yl]amino}-2,2-dimethyl-3-phenylpropyl)-3-methylbenzamide The product from Example 60B was chromatographed over a Daicel Chiral Technologies Chiralpak AS chiral column (2.0 cm×25 cm) eluting with 15% ethanol/hexanes (flow rate=15 mL/minute) to provide the title compound as the levorotatory enantiomer.

$[\alpha]_D^{23}$=−96° (c 0.34, EtOH); HRMS (FAB) calcd for $C_{28}H_{29}N_4O_3$ (M+H)$^+$ 469.2240, found 469.2252; $^1$H NMR (DMSO-d$_6$) δ 9.88 (s, 1H), 8.74 (br s, 1H), 8.60 (d, 1H, J=2.6Hz), 8.26 (dd, 1H, J=4.7, 1.1 Hz), 8.14 (br s, 1H), 7.95 (dd, 1H, J=8.3, 1.0 Hz), 7.67 (m, 2H), 7.41–7.37 (m, 3H), 7.32–7.20 (m, 5H), 5.96 (brs, 1H), 5.48 (ABq, J$_{AB}$=12.8, αv$_{AB}$=33.8 Hz), 2.38 (s, 3H), 0.97 (s, 3H), 0.95 (s, 3H).

EXAMPLE 74

(+) N-[1-({2-[(2-chloropyridin-3-yl)amino]-3,4-dioxo-1-cyclobuten-1-yl}amino)-2,2-dimethylpropyl]-3-methylbenzamide The product from Example 32 was chromatographed over a Daicel Chiral Technologies Chiralpak AS chiral column (2.0 cm×25 cm) eluting with 15% ethanol/hexanes (flow rate=15 mL/minute) to provide the title compound as the dextrorotatory enantiomer. $[\alpha]_D^{23}$=+77° (c 0.22, EtOH); HRMS (FAB) calcd for $C_{27}H_{25}F_2N_4O_3$ (M+H)$^+$ 491.1895, found 491.1893; $^1$H NMR (DMSO-d$_6$) δ 9.88 (s, 1H), 8.89 (d, 1H, J=7.6 Hz), 8.59 (d, 1H, J=2.4 Hz), 8.26 (dd, 1H, J=4.7, 1.0 Hz), 8.12 (brs, 1H), 7.95 (ddd, 1H, J=8.0, 2.5, 1.0 Hz), 7.63–7.57 (m, 2H), 7.50 (dt, 1H, J=9.0, 2.4 Hz), 7.39 (dd, 1H, J=9.0, 4.7 Hz), 7.33–7.27 (m, 2H), 7.26–7.19 (m, 3H), 5.94 (br s, 1H), 2.74 (ABq, J$_{AB}$=12.8, αv$_{AB}$=31.2 Hz), 0.97 (s, 3H), 0.95 (s, 3H).

EXAMPLE 75

(−) N-[1-({2-[(2-chloropyridin-3-yl)amino]-3,4-dioxo-1-cyclobuten-1-yl}amino)-2,2-dimethylpropyl]-3-methylbenzamide The product from Example 32 was chromatographed over a Daicel Chiral Technologies Chiralpak AS chiral column (2.0 cm×25 cm) eluting with 15% ethanol/hexanes (flow rate=15 mL/minute) to provide the title compound as the levorotatory enantiomer.

$[\alpha]_D^{23}$=−136°(c 0.27, EtOH); HRMS (FAB) calcd for $C_{22}H_{24}ClN_4O_3$ (M+H)$^+$ 427.1537, found 427.1529; $^1$H NMR (DMSO$_6$) δ 9.47 (s, 1H), 8.61 (d, 1H, J=8.0 Hz), 8.52 (d, 1H, J=8.8 Hz), 8.11 (dd, 1H, J=4.5, 1.6 Hz), 8.03 (d, 1H, J=7.8 Hz), 7.67–7.61 (m,2H), 7.44 (dd, J=8.3, 4.7 Hz), 7.39–7.35 (m, 2H), 5.92 (t, 1H, J=8.0 Hz), 2.37 (s, 3H), 1.07 (s, 9H).

EXAMPLE 76

(+) N-(1-{[3,4-Dioxo-2-(3-pyridinylamino)-1-cyclobuten-1-yl]amino}-2,2-dimethyl-3-phenylpropyl)-3,5-difluorobenzamide The product from Example 55B was chromatographed over a Daicel Chiral Technologies Chiralpak AS chiral column (2.0 cm×25 cm) eluting with 15% ethanolnhexanes (flow rate=15 mL/minute) to provide the title compound as the dextrorotatory enantiomer.

$[\alpha]_D^{23}$=+77° (c 0.22, EtOH); HRMS (FAB) calcd for $C_{27}H_{25}F_2N_4O_3$ (M+H)+ 491.1895, found 491.1893; $^1$H NMR (DMSO-$d_6$) δ 9.88 (s, 1H), 8.89 (d, 1H, J=7.6 Hz), 8.59 (d, 1H, J=2.4 Hz), 8.26 (dd, 1H, J=4.7, 1.0 Hz), 8.12 (br s, 1H), 7.95 (ddd, 1H, J=8.0, 2.5, 1.0 Hz), 7.63–7.57 (m, 2H), 7.50 (dt, 1H, J=9.0, 2.4 Hz), 7.39 (dd, 1H, J=9.0,4.7 Hz), 7.33–7.27 (m, 2H), 7.26–7.19 (m, 3H), 5.94 (brs, 1H), 2.74 (ABq, $J_{AB}$=12.8, $\alpha v_{AB}$=31.2 Hz),0.97 (s, 3H), 0.95 (s, 3H).

EXAMPLE 77

N-(1-{[3,4-Dioxo-2-(3-peridinylamino)-1-cyclobuten-1-yl]amino}-2,2-dimethylpropyl)-3-(2-furyl)benzamide

Example 77A

N-[1-(1H-1,2,3-Benzotriazol-1-yl)-2,2-dimethylpropyl]-3-(2-furyl)benzamide

A solution of the product from Example 8A (0.50 g, 1.15 mmol), 2-(tributylstannyl)furan (0.45 g, 1.27 mmol), triphenylarsinine (0.035 g, 0.115 mmol), and tris(dibenzylideneacetone)dipalladium(0) (0.053 g, 0.058 mmol) in 6.0 mL NMP was stirred at 23° C. for 16 hours. The mixture was diluted with 50 mL $H_2O$ and extracted twice with 50 mL of EtOAc. The combined extracts were dried over $Na_2SO_4$, and absorbed onto silica gel. The crude product was purified by flash chromatography (eluting with EtOAc/hexanes (1:4)) to provide 0.34 g of the desired compound. MS (DCI/NH$_3$) m/z 375 (M+H)+.

EXAMPLE 77B

N-(1-{[3,4-Dioxo-2-(3-pyridinylamino)-1-cyclobuten-1-yl]amino}-2,2-dimethylpropyl)-3-(2-furyl)benzamide A suspension of the product from Example 1B, the product from Example 77A, and $K_2CO_3$ was processed as described in Example 1D to provide the title compound.

mp 251–252° C.; MS (ESI+) m/z 445 (M+H)+; $^1$H NMR (DMSO-$d_6$) δ 9.89 (s, 1H), 8.80 (d, 1H, J=7.4 Hz), 8.59 (d, 1H, J=2.8 Hz), 8.25 (dd, 1H, J=4.6, 1.2 Hz), 8.11 (s, 1H), 8.09 (br s, 1H), 7.95 (ddd, 1H, J=8.3, 2.5, 1,2 Hz., 7.88(dt, 1H, J=8.0, 1.2 Hz), 7.80 (d, 1H, J=1.5 Hz), 7.75 (d, 1H, J=8.0 Hz), 7.55 (t, 1H, J=8.0 Hz), 7.39 (dd, 1H, J=8.3, 4.6 Hz), 7.04 (d, 1H, J=3.4 Hz), 6.63 (dd, 1H, J=3.4, 1.8 Hz), 5.90 (t, 1H, J=8.0 Hz), 1.8 (s, 9H); Anal. calcd for $C_{25}H_{24}N_4O_4$ 0.25 $H_2O$: C, 66.88; H, 5.50; N. 12.48. Found: C, 66.74; H, 5.55; N, 12.69.

EXAMPLE 78

N-[1-({2-(2-Chloropyridin-3-yl)amino]-3,4-dioxo-1-cyclobuten-1-yl}amino)-2,2-dimethylpropyl]-3-fluorobenzamide A suspension of the product from Example 29B, the product from Example 7A, and $K_2CO_3$ was processed as described in Example 1D to provide the title compound.

mp 228–229° C.; MS (ESI+) m/z 431 (M+H)+; $^1$H NMR (DMSO-$d_6$) δ 9.47 (s, 1H), 8.72 (d, 1H, J=7.7 Hz), 8.51 (d, 1H, J=8.3 Hz), 8.12 (dd, 1H, J=4.6, 1.5 Hz), 8.03 (d, 1H, J=7.4 Hz), 7.71 (dt, 1H, J=8.0, 1.2 Hz), 7.66 (ddd, 1H, J=9.8, 2.5, 1.5 Hz), 7.55 (td, 1H, J=8.0, 5.8 Hz), 7.45 (dd, 1H, J=8.0, 4.6 Hz), 7.44–7.39 (m, 1H), 5.91 (t, 1H, J=8.0 Hz), 1.07 (s, 9H); Anal. calcd for $C_{21}H_{20}ClFN_4O_4$: C, 58.54, H, 4.68; N, 13.00. Found: C, 58.35; H, 4.90; N, 12.98.

EXAMPLE 79

3,5-Dichloro-N-[1-({2-[(2-chloropyridin-3-yl)amino]-3,4-dioxocyclobut-1-en-1-yl}amino)-2,2-dimethylpropyl]benzamide A suspension of the product from Example 29B, the product from Example 12A, and $K_2CO_3$ was processed as described in Example 1D to provide the title compound.

mp 233–234° C.; MS (ESI+) m/z 482 (M+H)+; $^1$H NMR (DMSO-$d_6$) δ 9.45 (s, 1H), 8.86 (d, 1H, J=7.7 Hz), 8.47 (d, 1H, J=8.9 Hz), 8.12 (dd, 1H, J=4.6, 1.8 Hz), 8.03 (d, 1H, J=8.0 Hz), 7.86 (d, 2H, J=2.2 Hz), 7.82 (t, 1H, J=1.8Hz), 7.45 (dd, 1H, J=8.3, 4.6 Hz), 5.90 (t, 1H, J=8.0 Hz), 1.08 (s, 9H); Anal. calcd for $C_{21}H_{19}Cl_3N_4O_4$: C, 52.35; H, 3.98; N, 11.63. Found: C, 52.32; H, 4.04, N, 12.00.

EXAMPLE 80

4-Chloro-N-[1-({2-[(2-methoxypyridin-3-yl)amino]-3,4-dioxo-1-cyclobuten-1-yl amino)-2,2-dimethylpropyl]benzamide

EXAMPLE 80A

3-Ethoxy-4[(2-methoxypyridin-3yl)amino]cyclobut-3-ene-1,2dione

A solution of 3-amino-2-methoxypyridine and 3,4-diethoxy-3-cyclobutene-1,2-dione in ethanol was processed as described in Example 62A to provide the title compound. MS (DCI/NH$_3$) m/z 249 (M+H)+.

EXAMPLE 80B

3-Amino-4-[(2-methoxypyridin-3-yl)amino] cyclobut-3-ene-1,2-dione

A solution of the product from Example 80A and ammonia in methanol was processed as described in Example 1B to provide the title compound.

MS (DCI/NH$_3$) m/z 220 (M+H)+.

EXAMPLE 80C

4-Chloro-N-[1-({2-[(2-methoxypyridin-3-yl)amino]-3,4-dioxo-1-cyclobuten-1-yl}amino)-2,2-dimethylpropyl]benzamide A suspension of the product from Example 80B, the product from Example 2A, and $K_2CO_3$ was processed as described in Example 1D to provide the title compound.

mp239–241° C.; MS (ESI+) m/z 443 (M+H)+; $^1$H NMR (DMSO-$d_6$) δ 9.47 (brs, 1H), 8.70 (d, 1H, J=8.1 Hz), 8.49 (d, 1H, J=8.8 Hz), 8.07 (d, 1H, J=7.8 Hz), 7.90–7.82 (m, 3H), 7.56 (d, 2H, J=8.5 Hz), 7.01 (dd, 1H, J=7.8, 5.1 Hz), 5.87 (t, 1H, J=8.1 Hz), 3.99 (s, 3H), 1.05 (s, 9H); Anal. calcd for $C_{22}H_{23}ClN_4O_4$: C, 59.66, H, 5.23; N, 12.65. Found: C, 59.51; H, 5.13; N, 12.49.

EXAMPLE 81

N-[1-({2-[(2-Methoxypyridin-3-yl)amino]3,4-dioxo-1-cyclobuten-1-yl}amino)-2,2-dimethylpropyl]-3-methylbenzamide A suspension of the product from Example 80B, the product from Example 6A, and $K_2CO_3$ was processed as described in Example 1D to provide the title compound.

mp 224–226° C.; MS (ESI+) m/z 423 (M+H)⁺; ¹H NMR (DMSO-d₆) δ 9.50 (br s, 1H), 8.61 (d, 1H, J=8.1 Hz), 8.52 (d, 1H, J=8.8 Hz), 8.07 (d, 1H, J=7.8 Hz), 7.83 (dd, 1H, J=4.8, 1.4 Hz), 7.66–7.59 (m,2H),7.39–7.33 (m, 2H), 7.00 (dd, 1H, J=7.8,4.8 Hz), 5.89 (t, 1H, J=8.1 Hz), 3.99 (s, 3H),2.37 (s, 3(s, 9H); Anal. calcd for $C_{22}H_{26}N_4O_4$: C, 65.39, H, 6.20, N, 13.28. Found: C, 65.45; H, 6.11; N, 13.28.

EXAMPLE 82

3,5-Difluoro-N-[1-({2-[(2-methoxypyridin-3-yl) amino]-3,4-dioxo-1-cyclobuten-1-yl}amino)-2,2-dimethylpropyl]benzamide A suspension of the product from Example 80B, the product from Example 16A, and $K_2CO_3$ was processed as described in Example 1D to provide the title compound.

mp 221–223° C.; MS (ESI+) m/z 445 (M+H)⁺; ¹H NMR (DMSO-d₆) δ 9.48 (br s, 1H),8.76 (d, 1H, J=7.8 Hz), 8.47 (d, 1H, J=8.8 Hz), 8.06 (dd, 1H, J=7.8, 1.4 Hz), 7.84 (dd, 1H, J=4.8, 1.4 Hz), 7.61–7.53 (m, 2H), 7.49 (tt, 1H, J=9.2, 2.4 Hz), 7.01 (dd, 1H, J=7.8, 5.1 Hz), 5.87 (t, 1H, J=8.1 Hz), 3.99 (s, 3H), 1.06 (s, 9H); Anal. calcd for $C_{22}H_{22}F_2N_4O_4$: C, 59.45, H, 4.99; N, 12.61. Found: C, 59.33; H, 12.66.

EXAMPLE 83

N-[1-({2-[(2-Methoxypyridin-3-yl)amino]-3,4-dioxo-1-cyclobuten-1-yl}amino)-2,2-dimethyl-3-phenylpropyl]-3-methylbenzamide A suspension of the product from Example 80B, the product from Example 60A, and $K_2CO_3$ was processed as described in Example 1D to provide the title compound.

mp 233–235° C.; MS (ESI+) m/z 499 (M+H)⁺; ¹H NMR (DMSO-d₆) δ 9.49 (br s, 1H),8.73 (d, 1H, J=8.1 Hz), 8.61 (d, 1H, J=8.8 Hz), 8.08 (d, 1H, J=7.5 Hz), 7.84 (dd, 1H, J=5.1,1.7 Hz), 7.69–7.63 (m, 2H), 7.41–7.36 (m, 2H), 7.34–7.18 (m, 5H), 7.01 (dd, 1H, J=7.8, 5.1 Hz), 5.97 (t, 1H, J=8.1 Hz), 4.00 (s, 3, H), 2.73 (Abq, 2H, $J_{AB}$=12.5 Hz, $\Delta v_{AB}$=26.8 Hz), 2.38 (s, 3H), 0.96 (s, 3H), 0.93 (s, 3H); Anal. calcd for $C_{29}H_{30}N_4O_4$: C, 69.86; H, 6.06; N, 11.24. Found: C, 69.73; H, 5.95; N, 11.18.

EXAMPLE 84

3-Chloro-N-[1-({2-[(2-methoxypridin-3-yl)amino]-3,4-dioxo-1-cyclobuten-1-yl}amino)-2,2-dimethylpropyl]benzamide A suspension of the product from Example 80B, the product from Example 5A, and $K_2CO_3$ was processed as described in Example 1D to provide the title compound.

mp 208–210° C.; MS (ESI+) m/z 443 (M+H)⁺; ¹H NMR (DMSO-d₆) δ 9.50 (br s, 1H), 8.77 (d, 1H, J=7.8 Hz), 8.53 (d, 1H, J=8.1 Hz), 8.06 (d, 1H, J=7.4 Hz), 7.87 (t, 1H, J=1.8 Hz), 7.84 (dd, 1H, J=5.1, 1.7 Hz), 7.80 (br d, 1H, J=7.8 Hz), 7.63 (br d, 1H, J=8.2 Hz), 7.52 (t, 1H, J=7.8 Hz), 7.00 (dd, 1H, J=7.8, 5.1 Hz), 5.88 (t, 1H, J=8.1 Hz), 3.99 (s, 3H), 1.05 (s, 9H); Anal. calcd for $C_{22}H_{23}ClN_4O_4$: C, 59.66, H, 5.23; N, 12.65. Found: C, 59.49; H, 5.04, N, 12.62.

EXAMPLE 85

N-[1-({2-[(2-Chloropyridin-3-yl)amino]-3,4-dioxo-1-cyclobuten-1-yl} amino)-2,2-dimethyl-3-phenylpropyl]benzamide

EXAMPLE 85A

N-(1-Benzotriazol-1-yl-2,2-dimethyl-3-phenylropyl)-benzamide

A suspension of benzaamide, the product from Example 18A, and benzotriazole were processed as described in Example 18B to provide the desired product.

MS (DCI/NH₃) m/z 385 (M+H)⁺.

EXAMPLE 85B

N-[1-({2-f(2-chloropiydin-3-yl)amino]-3,4-dioxo-1-cyclobuten-1-yl} amino)-2,2-dimethyl-3-phenylpropyl]benzamide A suspension of the product from Example 29B, the product from Example 85A, and $K_2CO_3$ was processed as described in Example 1D to provide the title compound.

mp 225–226° C.; MS (ESI+) m/z 489 (M+H)⁺; ¹H NMR (DMSO-d₆) δ 9.18 (s, 1H), 8.49 (d, 1H, J=6.8 Hz), 8.33 (d, 1H, J=6.8 Hz), 7.82 (dd, 1H, J=4.6, 1.5 Hz), 7.75 (d, 1H, J=7.7 Hz), 7.62–7.57 (m, 2H), 7.32–7.26 (m, 1H), 7.24–7.19 (m, 2H), 7.15 (dd, 1H, J=8.3, 4.6 Hz), 7.03–6.97 (m,2H), 6.96–6.90 (m, 3H), 5.72 (br s, 1H), 2.46 (ABq, $J_{AB}$=12.9, $\alpha v_{AB}$=37.8 Hz), 0.70 (s, 3H), 0.65 (s,3H); Anal. calcd for $C_{27}H_{25}ClN_4O_4$: C, 66.32; H, 5.15; N, 11.46. Found: C, 66.14; H, 5.03; N, 11.33.

EXAMPLE 86

N-(1-{3,4-Dioxo-2-(3-pyridinylamino)-1-cyclobuten-1-yl]amino}-2,2-dimethyl-3-phenylpropyl)benzamide A suspension of the product from Example 1B, the product from Example 85A, and $K_2CO_3$ was processed as described in Example 1D to provide the title compound.

mp 237–238° C.; MS (ESI+) m/z 455 (M+H)⁺; ¹H NMR (DMSO-d₆) δ 9.91 (s, 1H), 8.80 (s, 1H), 8.60 (d, 1H, J=2.8 Hz), 8.26 (dd, 1H, J=4.6, 1.2 Hz), 8.16(brs, 1H),7.98–7.92 (m, 1H), 7.90–7.86(m,2H), 7.61–7.55 (m, 1H), 7.54–7.48 (rn, 2H), 7.39 (dd, 1H, J=8.3, 4.9 Hz), 7.33–7.27 (m, 2H), 7.25–7.19 (m, 3H), 5.96 (brs, 1H), 2.75 (ABq, $J_{AB}$=12.9, $\Delta v_{AB}$=32.8 Hz), 0.97 (s, 3H), 0.95 (s, 3H); Anal. calcd for $C_{27}H_{26}N_4O_4 \cdot 0.85 H_2O$: C, 69.02; H, 5.94; N, 11.92. Found: C, 68.73; H, 5.91; N, 12.30.

EXAMPLE 87

N-[1-({2-[(2-chloropyridin-3-yl)amino]-3,4-dioxo-1-cyclobuten-1-yl}amino)-2,2-dimethylpropy1]-3-phenylpropanamide A suspension of the product from Example 29B, the product from Example 36A, and $K_2CO_3$ was processed as described in Example 1D to provide the title compound.

mp 160–161° C.; MS (ESI+) m/z 441 (M+H)⁺; ¹H NMR (DMSO-d₆) δ 9.32 (s, 1H), 8.42 (d, 1H, J=9.2 Hz), 8.17 (d, 1H, J=7.4 Hz), 8.10(dd, 1H, J=4.6, 1.5 Hz), 8.07 (d, 1H, J=7.7 Hz), 7.45 (dd, 1H, J=8.0, 4.6 Hz), 7.28–7.13 (m, 5H), 5.69 (t, 1H, J=8.0 Hz), 2.83 (t, 2H, J=7.7 Hz), 2.63–2.43 (m, 2H), 0.95 (s, 9H);

Anal. calcd for $C_{23}H_{25}ClN_4O_3$: C, 62.65; H, 5.71; N, 12.71. Found: C, 62.37; H, 5.63; N, 12.66.

EXAMPLE 88

N-(1-{[3,4-Dioxo-2-(3-pyridinylamino)-1-cyclobuten-1-yl]amino}-2,2-dimethylpropyl)-2-phenoxyacetamide

EXAMPLE 88A 2-(Phenoxy)acetamide

To a solution of phenoxyacetyl chloride (6.18 g, 36.2 mmol) in 175 mL of THF was added 75 mL of $NH_4OH$ over 15 minutes. The reaction was stirred for 16 hours at 23° C. then concentrated under reduced pressure. The crude product was dissolved in 200 mL of EtOAc and washed with 100 mL of 2 N HCL, 100 mL NaHCO$_3$, and 100 mL of brine. The organic phase was dried over Na$_2$SO$_4$ and concentrated. The product was purified by recrystallization from EtOAc/hexanes to provide 4.05 g (74% yield) of the desired product as a white powder.

MS (DCI/NH$_3$) m/z 152 (M+H)$^+$.

EXAMPLE 88B

N-[1-(1H-1,2,3-Benzotriazol-1-yl)-2,2-dimethylpropyl]-2-phenoxyacetamide

A suspension of the product from Example 88A, pivaldehyde, and benzotriazole were processed as described in Example 18B to provide the desired product.

MS (DCI/NH$_3$) m/z 339 (M+H)$^+$.

EXAMPLE 88C

N-(1-{[3,4-Dioxo-2-(3-pyridinylamino)-1-cyclobuten-1-yl]amino}-2,2-dimethylpropyl)-2-phenoxyacetamide A suspension of the product from Example 1B, the product from Example 88B, and K$_2$CO$_3$ was processed as described in Example 1D to provide the title compound.

mp 227–228° C.; MS (ESI+) m/z 409 (M+H)$^+$; $^1$H NMR (DMSO4) δ 9.79 (s, 114), 8.57 (d, 1H, J=2.8 Hz), 8.45 (d, 1H, J=8.0 Hz), 8.25 (dd, 1H, J=4.6, 1.2 Hz), 8.02 (br s, 1H), 7.93 (d, 1H, J=8.0 Hz), 7.38 (dd, 1H, J=8.3, 4.6 Hz), 7.29 (t, 2H, J=8.0 Hz), 6.98–6.91 (m, 3H), 5.68 (br s, 1H), 4.61 (ABq, J$_{AB}$=14.7, αv$_{AB}$=21.8 Hz), 0.97 (s, 9H); Anal. calcd for C$_{22}$H$_{24}$N$_4$O$_4$·0.2 H$_2$O: C, 64.13; H, 5.97; N, 13.60. Found: C, 63.91; H, 5.89; N, 13.89.

EXAMPLE 89

N-[1-({2-Chloropyridin-3-yl)amino]-3,4-dioxo-1-cyclobuten-1-yl} amino)-2,2-dimethylpropyl]-2-phenoxyacetamide A suspension of the product from Example 29B, the product from Example 88B, and K$_2$CO$_3$ was processed as described in Example 1D to provide the title compound.

mp 220–221° C.; MS (ESI+) m/z 443 (M+H)$^+$; $^1$H NMR (DMSO-d$_6$) δ 9.37 (s, 1H), 8.50 (d, 1H, J=8.6 Hz), 8.44 (d, 1H, J=8.3 Hz), 8.11 (dd, 1H, J4.6, 1.5 Hz), 8.03 (d, 1H, J-7.4 Hz), 7.44 (dd, 1H, J=8.3, 4.6 Hz), 7.29 (t, 2H, J=8.0 Hz), 6.98–6.91 (m, 3H), 5.72 (t, 1H, J=8.0 Hz), 4.62 (ABq, J$_{AB}$-14.7, αv$_{AB}$=22.1 Hz), 0.98 (s, 9H); Anal. calcd for C$_{22}$H$_{23}$ClN$_4$O$_4$: C, 59.66; H, 5.23; N, 12.65. Found: C, 59.55; H, 5.18; N, 12.68.

EXAMPLE 90

N-(1-{[3,4-Dioxo-2-(3-pyridinylamino)-1-cyclobuten-1-yl]amino}-2,2-dimethylpropyl)-2-methyl-2-phenylpropanamide

EXAMPLE 90A

2-Methyl-2-phenylpropanamide

To a solution of 2-methyl-2-phenylpropionic acid in 100 mL of CH$_2$Cl$_2$ was added 0.50 mL of DMF and oxalyl chloride (3.40 g, 26.8 mmol). The mixture was stirred at 23° C. for 4 hours then the solvent was removed under reduced pressure. The crude material was dissolved in 50 mL of THF and 30 mL of NH$_4$OH was added. The mixture was stirred at 23° C. for 1 hour then and the mixture was concentrated under reduced pressure. The crude product was dissolved in 150 mL of EtOAc and washed with 100 mL of 2 N HCl, 100 mL NaHCO$_3$, and 100 mL of brine. The organic phase was dried over Na$_2$SO$_4$ and concentrated. The product was purified by recrystallization from EtOAc/hexanes to provide 3.50 g (88% yield) of the desired product as a white powder.

MS (DCI/NH$_3$) m/z 164 (M+H)$^+$.

EXAMPLE 90B

N-[1-(1H-1,2,3-Benzotriazol-1-yl)-2,2-dimethylpropyl]-2-methyl-2-phenylpropanamide A suspension of the product from Example 90A, pivaldehyde, and benzotniazole were processed as described in Example 18B to provide the desired product.

MS (DCI/NH$_3$) m/z 351 (M+H)$^+$.

EXAMPLE 90C

N-(1-{[3,4-Dioxo-2-(3-pyridinylamino)-1-cyclobuten-1-yl]amino}-2,2-dimethylpropyl)-2-methyl-2-phenylpropanamide A suspension of the product from Example 1B, the product from Example 90B, and K$_2$CO$_3$ was processed as described in Example 1D to provide the title compound.

mp 247–248° C.; MS (ESI+) m/z 421 (M+H)$^+$; $^1$H NMR (DMSO-d$_6$) δ 9.86 (s, 1H), 8.57 (d, 1H, J=2.6 Hz), 8.26 (d, 1H, J=4.6, 1.2 Hz), 7.97 (brs, 1H), 7.93 (d, 1H, J=8.0 Hz), 7.39 (d, 1H, J=8.3, 4.6 Hz), 7.39–7.28 (m, 5H), 7.26–7.19 (m, 1H), 5.58 (t, 1H, J=8.0 Hz), 1.49 (s, 3H), 1.48 (s, 3H), 0.85 (s, 9H); Anal. calcd for C$_{24}$H$_{28}$N$_4$O$_3$: C, 68.55; H, 6.71; N, 13.32. Found: C, 68.34; H, 6.75; N, 13.35.

EXAMPLE 91

3-Chloro-N-(1-{[3,4-dioxo-2-(pyrazin-2-ylamino)-1-cyclobuten-1-yl]amino}-2,2-dimethylpropyl)benzamide

EXAMPLE 91A

3-Ethoxy-4-(2-pyrazinylamino)-3-cyclobutene-1,2-dione

A solution of aminopyrazine and 3,4-diethoxy-3-cyclobutene-1,2-dione in ethanol was processed as described in Example 1A to provide the title compound. MS (DCI/NH$_3$) m/z 220 (M+H)$^+$.

EXAMPLE 91B

3-Amino-4-(2-pyrazinylamino)-3-cyclobutene-1,2-dione

A solution of the product from Example 91A and ammonia in methanol was processed as described in Example 1B to provide the title compound.

MS (DCI/NH$_3$) m/z 191 (M+H)$^+$.

EXAMPLE 91C

3-Chloro-N-(1-{[3,4-dioxo-2-(pyrazin-2-ylamino)-1-cyclobuten-1-yl]amino}-2,2-dimethylpropyl)benzamide A suspension of the product from Example 91B, the product from Example 5A, and K$_2$CO$_3$ was processed as described in Example 1D to provide the title compound.

mp 245–247° C.; MS (ESI+) m/z 414 (M+H)$^+$; $^1$H NMR (DMSO-d$_6$) δ 11.28 (br s, 1H), 8.88 (d, 1H, J=8.5 Hz), 8.83 (d, 1H, J=10.2 Hz), 8.61 (d, 1H, J=1.4 Hz), 8.31–8.27 (m, 2H), 7.85 (t, 1H, J=1.7 Hz), 7.79 (dt, 1H, J=7.5, 1.4 Hz), 7.63 (ddd, 1H, J=8.1, 2.2, 1.4 Hz), 7.53 (t, 1H, J=7.8 Hz), 6.05 (dd, 1H, J=9.0, 8.1 Hz), 1.03 (s, 9H); Anal. calcd for C$_{20}$H$_{20}$ClN$_5$O$_4$: C, 58.04; H, 4.87; N, 16.92. Found: C, 57.67; H, 4.85; N, 16.89.

EXAMPLE 92

N-[1-({2-[(2-Chloropyridin-3-yl)amino]-3,4-dioxo-1-cylobuten-1-yl}amino)-3,3-dimethylbutyl] benzamide

EXAMPLE 92A

N-[1-(1H-1,2,3-benzotriazol-1-yl)-3,3-dimethylbutyl]benzamide

A suspension of benzamide, 3,3-dimethyl-butyraldehyde, and benzotriazole were processed as described in Example 18B to provide the desired product.

MS (DCI/NH$_3$) m/z 323 (M+H)$^+$.

EXAMPLE 92B

N-[1-({2-[(2-Chloropyridin-3-yl)amino]-3,4-dioxo-1-cyclobuten-1-yl}amino)-3,3-dimethylbutyl] benzamide A suspension of the product from Example 29B, the product from Example 92A, K$_2$CO$_3$, and DMSO as the solvent was processed as described in Example 1D to provide the title compound.

mp 259–260.° C.; MS (ESI+) m/z 427 (M+H)$^+$; $^1$H NMR (DMSO-d$_6$) δ 9.47 (s, 1H), 9.07 (br s, 1H), 8.87 (br s, 1H), 8.08 (dd, 1H, J=4.6, 1.5 Hz), 8.03 (d, 1H, J=8.0 Hz), 7.87 (d, 1H, J=7.1 Hz), 7.58–7.52 (m, 1H), 7.51–7.45 (m, 2H), 7.41 (dd, 1H, J=8.0, 4.6 Hz), 5.97 (br s, 1H), 2.07 (dd, 1H, J=14.1, 6.8 Hz), 1.83 (dd, 1H, J=14.1, 5.8 Hz), 0.97 (s, 9H); Anal. calcd for C$_{22}$H$_{23}$ClN$_4$O$_3$.75 C$_4$H$_8$O$_2$: C, 60.91; H, 5.93; N, 11.36. Found: C, 60.82; H, 5.76; N, 11.77.

EXAMPLE 93

3-Chloro-N-[1-({2-[(6-chloropyridin-3-yl)amino}-3,4-dioxo-1-cyclobuten-1-yl}amino)-2,2-dimethypropyl]benzamide A suspension of the product from Example 62B, the product from Example 5A, and K$_2$CO$_3$ was processed as described in Example 1D to provide the title compound.

mp 241–242° C.; MS (ESI+) m/z 481 (M+H)$^+$; $^1$H NMR (DMSO-d$_6$) δ 9.95 (s, 1H), 8.77 (d, 1H, J=7.7 Hz), 8.38 (d, 1H, J=2.9 Hz), 8.04 (br s, 1H), 7.99 (dd, 1H, J=8.8, 2.9 Hz), 7.87 (t, 1H, J=1.8 Hz), 7.80 (dt, 1H, J=7.7, 1.5 Hz), 7.63 (ddd, 1H, J=8.1, 2.2, 1.1 Hz), 7.56–7.47 (m, 2H), 5.86 (t, 1H, J=8.4 Hz), 1.06 (s, 9H);

Anal. calcd for C$_{22}$H$_{20}$Cl$_2$N$_4$O$_3$: C, 56.39; H, 4.51; N, 12.53. Found: C, 56.11; H, 4.53; N, 12.33.

EXAMPLE 94

3-Chloro-N-{1-[(3,4-dioxo-2-{[6-(trifluoromethyl) pyridin-3-yl]amino}-1-cyclobuten-1-yl)amino]-2,2-dimethylpropyl}benzamide

EXAMPLE 94A 3,4-Dichlorocyclobut-3-ene-1,2-dione

To a solution of squaric acid (5.00 g, 43.8 mmol) in 60 mL of CH$_2$Cl$_2$ and 5 drops of DMF was added oxalyl chloride (12.2 g, 96.4 mmol), dropwise. The reaction was stirred at 23° C. for 10 minutes then heated at reflux for 16 hours. The mixture was cooled to 23° C. and the solvent removed under reduced pressure. The crude product was distilled at 80° C. (1 mm Hg) to provide the product (5.92 g, 89% yield) as a bright yellow solid upon cooling which was used immediately to avoid decomposition.

EXAMPLE 94B

3-Chloro-4-methoxycyclobut-3-ene-1,2-dione

To a solution of the product from Example 94A (5.92 g, 39.2 mmol) in 100 mL of THF was added MeOH (1.26 g, 39.2 mmol). The mixture was heated at reflux for 2 hours then allowed to cool to ambient temperature. The solvent was removed under reduced pressure and the crude product was dissolved in 100 mL of EtOAc/hexanes (1:1). The mixture was filtered through a ½" silica gel frit and the frit was washed with an additional 50 mL of EtOAc/hexanes (1:1). The solvent was removed in vacuo to provide a pale yellow oil which solidified on standing. The product (4.56 g, 80% crude yield) was used without further purification.

EXAMPLE 94C

3-Methoxy-4-{[6-(trifluoromethyl)pyridin-3-yl]amino}-3-cyclobutene-1,2-dione

Example 94B (1.51 g, 10.3 mmol) was dissolved in 3 mL of DMF and NaHCO$_3$ (0.865 g, 10.3 mmol) was added. A solution of 6-(trifluoromethyl)pyridin-3-ylamine (1.67 g, 10.3 mmol) in 12 mL of CH$_2$Cl$_2$ was added dropwise and the mixture was stirred at ambient temperature for 16 hours. The mixture was diluted with 75 mL of EtOAc and filtered through a pad of Celite. The filtrate was washed with 50 mL of H$_2$O and the aqueous layer was extracted twice with 50 mL of EtOAc. The combined organic extracts were washed with 50 mL of brine, dried over Na$_2$SO$_4$ and concentrated under reduced pressure. The crude material was purified by flash chromatography eluting with EtOAC/hexanes (3:2) to provide the desired product (0.281 g, 10% yield) as a pale yellow powder.

MS (DCI/NH$_3$) m/z 273 (M+H)$^+$.

EXAMPLE 94D

3-Amino-4-{[6-(trifluoromethyl)pyridin-3-yl]amino}-3-cyclobutene-1,2-dione

EXAMPLE 94C (0.281 g, 1.03 mmol) was dissolved in 20 mL 2.0 M NH$_3$ in MeOH and the mixture was stirred in a sealed vessel for 16 hours. The solvent was removed under reduced pressure and the crude material was triturated with Et$_2$O to provide the desired product (0.230 g, 87% yield) as a pale yellow powder.

MS (ESI+) m/z 258 (M+H)$^+$.

EXAMPLE 94E

3-Chloro-N-{1-[(3,4-dioxo-2-{[6-(trifluoromethyl) pyridin-3-yl]amino}-1-cyclobuten-1-yl)amino]-2,2-dimethylpropyl}benzamide A suspension of the product from Example 94D, the product from Example 5A, and K$_2$CO$_3$ was processed as described in Example 1D to provide the title compound.

mp 226–227° C.; MS (ESI+) m/z 481 (M+H)$^+$; $^1$H NMR (DMSO-d$_6$) δ 10.16 (s, 1H), 8.78 (d, 1H, J=7.0 Hz), 8.68 (d,

1H, J=2.2 Hz), 8.21–8.06 (m, 2H), 7.92–7.85 (m, 2H), 7.80 (d, 1H, J=7.7 Hz), 7.64 (ddd, 1H, J=8.1, 1.8, Hz), 7.53 (t, 1H, J=7.8 Hz), 5.88 (brs, 1H), 1.07 (s, 9H); Anal. calcd for $C_{22}H_{20}F_3N_4O_3$: C, 54.95; H, 4. 19;N, 11.65. Found: C, 54.80; H, 4.17; N, 11.52.

EXAMPLE 95

3-Chloro-N-[1-({2-[(2-chloropyridin-3-yl)amino]-3, 4-dioxo-1-cyclobuten-1-yl}amino)-2,2-dimethylpropyl]benzamide A suspension of the product from Example 29B, the product from Example 5A, and $K_2CO_3$ was processed as described in Example 1D to provide the title compound.

mp 213–214° C.; MS (ESI+) m/z 448 (M+H)$^+$; $^1$H NMR (DMSO-d$_6$) δ 9.46 (s, 1H), 8.77 (d, 1H, J=8.1 Hz), 8.50 (d, 1H, J=8.8 Hz), 8.12 (dd, 1H, J=4.4, 1.5 Hz), 8.03 (dd, 1H, J=8.1, 1.5 Hz), 788 (t, 1H, J=1.7 Hz), 7.81 (dt, 1H, J=7.7, 1.5 Hz), 7.63 (ddd, 1H, J=8.1, 1.8, 1.8 Hz), 7.57–7.48 (m, 1H), 7.44 (dd, 1H, J=8.1, 4.8 Hz), 5.91 (t, 1H, J=8.1 Hz), 1.07 (s, 9H); Anal. calcd for $C_{21}H_{20}Cl_2N_4O_3 \cdot 0.65 H_2O$: C, 54.95, N, 4.68; N, 12.21. Found: C, H, 4.40; N, 11.92.

EXAMPLE 96

N-(1-{[3,4-Dioxo-2-(3-pyridinylamino)-1-cyclobuten-1-yl]amino}-2,2-dimethyl-3-phenylpropyl)isonicotinamide

EXAMPLE 96A

N-[1-(1H-1,2,3-benzotriazol-1-yl)-2,2-dimethyl-3-phenylpropyl]isonicotinamide

The product from Example 18A, isonicotinamide, benzotriazole, and p-toluenesulfonic acid in toluene were processed as described in Example 18B to provide the title compound.

MS (ESI+) m/z 386 (M+H)$^+$.

EXAMPLE 96B

N-(1-{[3,4-Dioxo-2-(3-pyridinylamino)-1-cyclobuten-1-yl]amino}-2,2-dimethyl-3-phenylpropyl)isonicotinamide A suspension of the product from Example 1B, the product from Example 96A, and $K_2CO_3$ was processed as described in Example 1D to provide the title compound.

mp 251–254° C.; MS (ESI+) m/z 456 (M+H)$^+$; $^1$H NMR (DMSO-d$_6$) δ 9.92 (br s, 1H), 9.07 (br d, 1H, J=8.1Hz), 8.79–8.75 (m, 2H), 8.58 (d, 1H, J-2.7 Hz), 8.27 (dd, 1H, J=4.7, 1.2 Hz), 8.19–8.11 (m, 1H), 7.95 (br d, 1H, J=7. 1 Hz), 7.78–7.75 (m, 2H), 7.40 (dd, 1H, J=8.5, 4.8 Hz), 7.34–7.19 (m, 5H), 5.95 (t, 1H, J=7.8 Hz), 2.73 (ABq, 2H, $J_{AB}$=12.9 Hz, $αv_{AB}$=25.1 Hz), 0.96 (s, 3H), 0.94 (s, 3H), Anal. calcd for $C_{26}H_{25}N_5O_3$: C, 68.56; H, 5.53; N, 15.37. Found: C, 68.37; H, 5.31; N, 15.20.

EXAMPLE 97

N-(1-{[3,4-Dioxo-2-(3-pyridinylamino)-1-cyclobuten-1-yl]amino}-2,2-dimethyl-3-phenylpropyl)-3-phenylpropanamide

EXAMPLE 97A

N-[1-(1H-1,2,3-Benzotriazol-1-yl)-2,2-dimethyl-3-phenylpropyl]-3-phenylpropionamide A suspension of 3-(phenyl)propionamide, the product from Example 18A, benzotriazole, and p-toluenesulfonic acid was processed as described in Example 1C to provide the title compound.

MS (DCI/NH$_3$) m/z 413 (M+H)$^+$.

EXAMPLE 97B

N-(1-{[3,4-Dioxo-2-(3-pyridinylamino)-1-cyclobuten-1-yl]amino}-2,2-dimethyl-3-phenylpropyl)-3-phenylpropanamide A suspension of the product from Example 1B, the product from Example 97A, and $K_2CO_3$ was processed as described in Example 1D to provide the title compound.

mp 221–223° C.; MS (ESI+) m/z 483 (M+H)$^+$; $^1$H NMR (DMSO-d$_6$) δ 9.73 (s, 1H), 8.57 (d, 1H, J=2.4 Hz), 8.34 (br s, 1H), 8.24 (dd, 1H, J=4.8, 1.4 Hz), 8.06–7.90 (m, 2H), 7.39 (dd, 1H, J=8.1, 4.8 Hz), 7.33–7.09 (m, 10H), 5.70 (br s, 1H), 2.91–2.81 (m, 2H), 2.69–2.54 (m, 4H), 0.85 (s, 3H), 0.81 (s, 3H); Anal. calcd for $C_{29}H_{30}N_4O_3$: C, 72.18; H, 6.27; N, 11.61. Found: C, 71.86; H, 6.02; N, 11.41.

EXAMPLE 98

N-(1-{[3,4-Dioxo-2-3-pyridinylamino)-1-cyclobuten-1-yl]amino}-2,2-dimethyl-3-phenylpropyl)-2-methyl-2-phenylpropanamide

EXAMPLE 98A

N-[1-(1H-1,2,3-Benzotriazol-1-yl)-2,2-dimethyl-3-phenylpropyl]-2-methyl-2-phenylpropanamide A suspension of the product from Example 90A, the product from Example 18A, benzotriazole, and p-toluenesulfonic acid was processed as described in Example 1C to provide the title compound.

MS (DCI/NH$_3$) m/z 427 (M+H)$^+$.

EXAMPLE 98B

N-(1-{[3,4-Dioxo-2-(3-pyridinylamino)-1-cyclobuten-1-yl]amino}-2,2-dimethyl-3-phenylpropyl)-2-methyl-2-phenylpropanamide A suspension of the product from Example 1B, the product from Example 98A, and $K_2CO_3$ was processed as described in Example 92B to provide the title compound.

mp 228–231° C.; MS (ESI+) m/z 497 (M+H)$^+$; $^1$H NMR (DMSO-d$_6$) δ 9.90 (s, 1H), 8.58 (d, 1H, J=2.7 Hz), 8.26 (dd, 1H, J=4.7, 1.4 Hz), 8.05 (br s, 1H), 7.94 (d, 1H, J=7.7 Hz), 7.51 (br s, 1H), 7.40 (dd, 1H, J=8.5,4.8 z), 7.37–7.16 (m, 7H), 7.10–7.03 (m, 3H), 5.67 (br s, 1H), 2.51–2.44 (m, 2H, PhCH$_2$ obscured), 1.50 (s, 6H), 0.74 (s, 3H), 0.72 (s, 3H); Anal. calcd for $C_{30}H_{32}N_4O_3$: C, 72.56; H, 6.49; N, 11.28. Found: C, 72.72; H, 6.40; N, 11.26.

EXAMPLE 99

N-(1-{[3,4-Dioxo-2-(3-pyridinylamino)-1-cyclobuten-1-yl]amino}-2,2-dimethyl-3-phenylpropyl)-2-phenoxyacetamide

EXAMPLE 99A

N-[1-(1H-1,2,3-Benzotriazol-1-yl)-2,2-dimethyl-3-phenylpropyl]-2-phenoxyacetamide A suspension of the product from Example 88A, the product from Example 18A, benzotriazole, and p-toluenesulfonic acid was processed as described in Example 1C to provide the title compound.

MS (DCI/NH$_3$) m/z 415 (M+H)$^+$.

EXAMPLE 99B

N-(1-{[3,4-Dioxo-2-(3-pyridinylamino)-1-cyclobuten-1-yl]amino}-2,2-dimethyl-3-phenylpropyl)-2-phenoxyacetamide A suspension of the product from Example 1B, the product from Example 99A, and K$_2$CO$_3$ was processed as described in Example 1D to provide the title compound.

mp 249–250° C.; MS (ESI+) m/z 485 (M+H)$^+$; $^1$H NMR (DMSO-d$_6$) δ 9.80 (s, 1H), 8.62 (d, 1H, J=7.5 Hz), 8.57 (d, 1H, J=2.4 Hz), 8.25 (dd, 1H, J=4.7, 1.4 Hz), 8.10 (br s, 1H), 7.93 (d, 1H, J=8.2 Hz), 7.39 (dd, 1H, J=8.5, 4.7 Hz), 7.34–7.18 (m, 5H), 7.17–7.11 (m, 2H), 6.99–6.91 (m, 3H), 5.74 (br s, 1H), 4.66 (ABq, 2H, J$_{AB}$=14.6 Hz, Δv$_{AB}$=20.7 Hz), 2.61 (d, 2H, J=4.4 Hz), 0.87 (s, 3H), 0.84 (s, 3H); Anal. calcd for C$_{28}$H$_{28}$N$_4$O$_4$: C, 69.41; H, 5.82; N, 11.56. Found: C, 69.51; H, 5.76; N, 11.44.

EXAMPLE 100

N-(1-{[3,4-Dioxo-2-(3-pyridinylamino)-1-cyclobuten-1-yl]amino}-2,2-dimethyl-3-phenylpropyl)nicotinamide

EXAMPLE 100A

N-[1-(1H-1,2,3-Benzotriazol-1-yl)-2,2-dimethyl-3-phenylpropyl]nicotinamide

The product from Example 18A, nicotinamide, benzotriazole, and p-toluenesulfonic acid in xylene were processed as described in Example 18B to provide the title compound.

MS (ESI+) m/z 386 (M+H)$^+$.

EXAMPLE 100B

N-(1-{[3,4-Dioxo-2-(3-pyridinylamino)-1-cyclobuten-1-yl]amino}-2,2-dimethyl-3-phenylpropyl)nicotinamide A suspension of the product from Example 1B, the product from Example 100A, and K$_2$CO$_3$ was processed as described in Example 1D to provide the title compound.

mp 253–254° C.; MS (ESI+) m/z 456 (M+H)$^+$; $^1$H NMR (DMSO-d$_6$) δ 9.87 (s, 1H), 9.03 (d, 1H, J=2.1 Hz), 8.98 (br d, 1H, J=7.5 Hz), 8.75 (dd, 1H, J=4.8, 1.7 Hz), 8.59 (d, 1H, J=2.8 Hz), 8.25 (dd, 1H, J=4.7, 1.4 Hz), 8.21 (dt, 1H, J=7.8, 1.7 Hz), 8.20–8.13 (m, 1H), 7.95 (br d, 1H, J=8.4 Hz), 7.55 (ddd, 1H, J=8.1, 4.7, 0.7 Hz), 7.39 (dd, 1H, J=8.4, 4.7 Hz), 7.34–7.26 (m, 2H), 7.26–7.18 (m, 3H), 5.96 (t, 1H, J=7.5 Hz), 2.75 (ABq, 2H, J$_{AB}$=12.9 Hz, Δv$_{AB}$=25.8 Hz), 0.97 (s, 3H), 0.92 (s, 3H); Anal. calcd for C$_{26}$H$_{25}$N$_5$O$_3$: C, 68.56; H, 5.53; N, 15.37. Found: C, 68.42; H, 5.52; N, 15.40.

EXAMPLE 101

N-(1-{[3,4-Dioxo-2-(3-pyridinylamino)-1-cyclobuten-1-yl]amino}-2,2-dimethylpropyl)nicotinamide

EXAMPLE 101A

N-[1-(1H-1,2,3-Benzotriazol-1-yl)-2,2-dimethylpropyl]nicotinamide

Nicotinamide, benzotriazole, pivaldehyde and p-toluenesulfonic acid in xylene were processed as described in Example 18B to provide the title compound.

MS (ESI+) m/z 310 (M+H)$^+$.

EXAMPLE 101B

N-(1-{[3,4-Dioxo-2-(3-pyridinylamino)-1-cyclobuten-1-yl]amino}-2,2-dimethyl-3-phenylpropyl)nicotinamide A suspension of the product from Example 1B, the product from Example 101A, and K$_2$CO$_3$ was processed as described in Example 1D to provide the title compound.

mp 233–234° C.; MS (ESI+) m/z 380 (M+H)$^+$; $^1$H NMR (DMSO-d$_6$) δ 9.86 (br s, 1H), 8.98 (d, 1H, J=2.4 Hz), 8.87 (br d, 1H, J=7.8 Hz), 8.73 (dd, 1H, J=4.7, 1.4 Hz), 8.57 (d, 1H, J=2.4 Hz), 8.25 (dd, 1H, J=4.7, 1.4 Hz), 8.17 (dt, 1H, J=8.1, 2.0 Hz), 8.11–8.04 (m, 1H), 7.94 (ddd, 1H, J=9.2, 2.7, 1.0 Hz), 7.53 (dd, 1H, J=8.1, 4.7 Hz), 7.39 (dd, 1H, J=8.1, 4.7 Hz), 5.88 (t, 1H, J=7.8 Hz), 1.07 (s, 9H); Anal. calcd for C$_{20}$H$_{21}$N$_5$O$_3$: C, 63.61; H, 5.58; N, 18.43. Found: C, 63.61; H, 5.67; N, 18.43.

EXAMPLE 102

N-(1-{[3,4-Dioxo-2-(3-pyridinylamino)-1-cyclobuten-1-yl]amino)-2,2-dimethylpropyl)isonicotinamide

EXAMPLE 102A

N-[1-(1H-1,2,3-Benzotriazol-1-yl)-2,2-dimethylpropyl]isonicotinamide

Isonicotinamide, pivaldehyde, benzotriazole, and p-toluenesulfonic acid in xylene were processed as described in Example 18B to provide the title compound.

MS (ESI+) m/z 310 (M+H)$^+$.

EXAMPLE 102B

N-(1-{[3,4-Dioxo-2-(3-pyridinylamino)-1-cyclobuten-1-yl]amino}-2,2-dimethyl-3-phenylpropyl)nicotinamide A suspension of the product from Example 1B, the product from Example 102A, and K$_2$CO$_3$ was processed as described in Example 1D to provide the title compound.

mp 220–222° C.; MS (ESI+) m/z 380 (M+H)$^+$; $^1$H NMR (DMSO-d$_6$) δ 9.88 (br s, 1H), 8.95 (d, 1H, J=7.5 Hz), 8.76–8.71 (m, 2H), 8.57 (d, 1H, J=2.7 Hz), 8.25 (dd, 1H, J=4.7, 1.4 Hz), 8.05 (br s, 1H), 7.93 (ddd, 1H, J=8.1, 2.7, 1.4 Hz), 7.74–7.71 (m, 2H), 7.39 (dd, 1H, J=8.5, 4.7 Hz), 5.86 (t, 1H, J=7.5 Hz), 1.06 (s, 9H); Anal. calcd for C$_{20}$H$_{21}$N$_5$O$_3$: C, 63.61; H, 5.58; N, 18.46. Found: C, 63.31; H, 5.67; N, 18.47.

EXAMPLE 103

N-(1-{[3,4-Dioxo-2-(3-pyridinylamino)-1-cyclobuten-1-yl]amino}-2,2-dimethylpropyl)-2-furamide

EXAMPLE 103A

N-[1-(1H-1,2,3-Benzotriazol-1-yl)-2,2-dimethylpropyl]-2-furamide

Furan-2-carboxamide, pivaldehyde, benzotriazole, and p-toluenesulfonic acid in xylene were processed as described in Example 18B to provide the title compound.

MS (ESI+) m/z 299 (M+H)$^+$.

EXAMPLE 103B

N-(1-{[3,4-Dioxo-2-(3-pyridinylamino)-1-cyclobuten-1-yl]amino}-2,2-dimethyl-3-phenylpropyl)nicotinamide A suspension of the product from Example 1B, the product from Example 103A, and $K_2CO_3$ was processed as described in Example 1D to provide the title compound.

mp 204–205° C.; MS (ESI+) m/z 369 (M+H)$^+$; $^1$H NMR (DMSO-d$_6$) δ 9.95 (br s, 1H), 8.61 (br d, 1H, J=8.1 Hz), 8.57 (d, 1H, J=2.7 Hz), 8.25 (dd, 1H, J=4.7, 1.4 Hz), 8.18–8.08 (m, 1H), 7.98–7.91 (m, 2H), 7.82 (dd, 1H, J=5.1, 1.4 Hz), 7.38 (dd, 1H, J=8.1, 4.7 Hz), 7.18 (dd, 1H, J=5.1, 3.7 Hz), 5.80 (t, 1H, J=8.5 Hz), 1.05 (s, 9H); Anal. calcd for $C_{19}H_{20}N_4O_4$: C, 61.95; H, 5.47; N, 15.21. Found: C, 61.72; H, 5.33; N, 15.24.

EXAMPLE 104

N-(1-{[3,4-Dioxo-2-(3-pyridinylamino)-1-cyclobuten-1-yl]amino}-2,2-dimethyl-3-pyridin-4-ylpropyl)-3-methylbenzamide

EXAMPLE 104A 2,2-Dimethyl-3-pyridin-4-ylpropanal 4-(Bromomethyl)pyridine hydrobromide (5.00 g, 19.8 mmol) was suspended in ethyl acetate (40 mL) and water (20 mL) and washed with 10% aq. $NaHCO_3$ solution (35 mL) to generated the free base. The layers were partitioned and the organic portion was concentrated and redissolved in benzene (30 mL). To this solution was added tetrabutylammonium iodide (112 mg, 0.303 mmol) and isobutyraldehyde (1.10 g, 15.2 mmol). The solution of aledyde and bromide was then added via addition funnel in dropwise fashion over a period of 30 minutes to a stirred suspension of powdered NaOH (608 mg, 15.2 mmol) in benzene (90 mL) at 60° C. The reaction was stirred at 60° C. for 5 hours then cooled to ambient temperature. EtOAc (40 mL) was added and the reaction mixture was washed with water (40 mL), satd. aq. sodium bisulfite solution (2×25 mL), then brine (30 mL). The organic portion was dried ($Na_2SO_4$) and concentrated. Purification of the resulting oily residue by flash chromatography (gradient elution: hexanes then 7% EtOH/hexanes) provided the title compound (608 mg, 3.73 mmol) as a off-yellow waxy solid.

MS (DCI/NH$_3$) m/z 164 (M+H)$^+$.

EXAMPLE 104B

N-[1-(1H-1,2,3-Benzotriazol-1yl)-2,2-dimethyl-3-(pyridin-4-yl)propyl]-3-methylbenzamide The product from Example 104A, m-toluamide, benzotriazole, and p-toluenesulfonic acid were processed as described in Example 1C to provide the title compound.

MS (DCI/NH$_3$) m/z 400 (M+H)$^+$.

EXAMPLE 104C

N-(1-{[3,4-Dioxo-2-(3-pyridinylamino)-1-cyclobuten-1-yl]amino}-2,2-dimethyl-3-pyridin-4-ylpropyl)-3-methylbenzamide A suspension of the product from Example 1B, the product from Example 104B, and $K_2CO_3$ was processed as described in Example 1D to provide the title compound.

mp 219–221° C.; MS (ESI+) m/z 470 (M+H)$^+$; $^1$H NMR (DMSO-d$_6$) δ 8.81 (br s, 1H), 8.59 (br d, 1H, J=2.4 Hz), 8.50–8.43 (m, 2H), 8.24 (dd, 1H, J=4.7, 1.4 Hz), 7.98–7.86 (m, 2H), 7.71–7.62 (m, 3H), 7.44(dd, 1H, J=6.4, 3.1 Hz), 7.41–7.23 (m, 4H), 5.99–5.92 (m, 1H), 2.84 (ABq, 2H, $J_{AB}$=11.2, $\Delta v_{AB}$=22.0 Hz), 2.41 (s, 3H), 0.99 (s, 3H), 0.91 (s, 3H); Anal. calcd for $C_{27}H_{27}N_5O_3$: C, 69.07; H, 5.80; N, 14.92. Found: C, 68.90; H, 5.88, N, 14.77.

EXAMPLE 105

(−) 3-Chloro-N-(1-{[3,4-dioxo-2-(3-pyridinylamino)-1-cyclobuten-1-yl]amino}-2,2-dimethyl-3-phenylpropyl)benzamide The product from Example 59B was chromatographed over a Daicel Chiral Technologies Chiralpak AS chiral column (2.0 cm×25 cm) eluting with 10% ethanol/hexanes (flow rate=10 mL/minute) to provide the title compound as the levorotatory enantiomer.

$[\alpha]_D^{20}$=−80° (c 0.20, DMSO); mp 178–179° C.; MS (ESI+) m/z 489 (M+H)$^+$; $^1$H NMR (DMSO-d$_6$) δ 9.87 (s, 1H), 8.90 (d, 1H, J=3.7 Hz), 8.60 (d, 1H, J=1.6 Hz), 8.26 (d, 1H, J=4.2 Hz), 8.13 (br s, 1H), 7.95 (dd, 1H, J=8.3, 1.2 Hz), 7.90 (t, 1H, J=1.7 Hz), 7.83 dt, 1H, J=7.8, 1.2 Hz), 7.65 (ddd, 1H, J=8.0, 2.1, 1.2 Hz), 7.55 (t, 1H, J=8.1 Hz), 7.39 (dd, 1H, J=8.2, 4.7 Hz), 7.32–7.20 (m, 5H), 5.95 (s, 1H), 2.74 (ABq, $J_{AB}$=12.8, $\Delta v_{AB}$=32.1 Hz), 0.97 (s, 3H), 0.95 (s, 3H).

EXAMPLE 106

(+) 3-Chloro-N-(1-{[3,4-dioxo-2-(3-pyridinylamino)-1-cyclobuten-1-yl]amino}-2,2-dimethyl-3-phenylpropyl)benzamide The product from Example 59B was chromatographed over a Daicel Chiral Technologies Chiralpak AS chiral column (2.0 cm×25 cm) eluting with 10% ethanol/hexanes (flow rate=10 mL/minute) to provide the title compound as the dextrorotatory enantiomer.

$[\alpha]_D^{20}$=+78° (c 0.24, DMSO); mp 178–179° C.; MS (ESI+) m/z 489 (M+H)$^+$; $^1$H NMR (DMSO-d$_6$) δ 9.87 (s, 1H), 8.90 (d, 1H, J=3.7 Hz), 8.60 (d, 1H, J=1.6 Hz), 8.26 (d, 1H, J=4.2 Hz), 8.13 (br s, 1H), 7.95 (dd, 1H, J=8.3, 1.2 Hz), 7.90 (t, 1H, J=1.7 Hz), 7.83 dt, 1H, J=7.8, 1.2 Hz), 7.65 (ddd, 1H, J=8.0, 2.1, 1.2 Hz), 7.55 (t, 1H, J=8.1 Hz), 7.39 (dd, 1H, J=8.2, 4.7 Hz), 7.32–7.20 (m, 5H), 5.95 (s, 1H), 2.74 (ABq, $J_{AB}$=12.8, $\Delta v_{AB}$=32.1 Hz), 0.97 (s, 3H), 0.95 (s, 3H); Anal. calcd for $C_{27}H_{25}ClN_4O_3$. 0.5 $H_2O$: C, 65.12; H, 5.26; N, 11.25. Found: C, 65.19; H, 5.42; N, 11.26.

EXAMPLE 107

4-Chloro-N-({[3,4-dioxo-2-(3-pyridinylamino)-1-cyclobuten-1-yl]amino}methyl)benzamide

EXAMPLE 107A

N-(1H-1,2,3-Benzotriazol-1-ylmethyl)-4-chlorobenzamide

4-Chlorobenzamide, paraformaldehyde, benzotriazole, and p-toluenesulfonic acid were processed as described in Example 18B to provide the title compound.

MS (DCI/NH$_3$) m/z 287 (M+H)$^+$.

EXAMPLE 107B

4-Chloro-N-({[3,4-dioxo-2-(3-pyridinylamino)-1-cyclobuten-1-yl]amino}methyl)benzamide A suspension of the product from Example 1B, the product from Example 107A, and $K_2CO_3$ was processed as described in Example 1B to provide the title compound.

mp 174–176° C.; MS (ESI+) m/z 357 (M+H)+; $^1$H NMR (DMSO-d$_6$) δ 9.99 (br t, 1H, J=6.1 Hz), 8.04 (br d, 2H, J=8.4 Hz), 7.91 (d, 2H, J=8.8 Hz), 7.63–7.52 (m, 4H), 7.43 (d, 1H, J=8.1 Hz), 7.40 (d, 1H, J=8.1 Hz), 6.21 (app d, 2H, J=6.4 Hz); Anal. calcd for C$_{17}$H$_{13}$N$_4$O$_3$: C, 57.23; H, 3.67; N, 15.70. Found: C, 56.85; H, 3.65; N, 16.10.

EXAMPLE 108

(+) 3,5-Dichloro-N-[(1S)-1-({2-[(2-chloropyridin-3-yl)amino]-3,4-dioxocyclobut-1-en-1-yl}amino)-2,2-dimethylpropyl]benzamide The product from Example 79 was chromatographed over a Regis Technologies Whelk-O1 chiral column (2.0 cm×25 cm) using gradient elution (10% methanol-CH$_2$Cl$_2$ (2:1)/hexanes to 30% methanol-CH$_2$Cl$_2$ (2:1)/hexanes, flow rate=10 mL/minute) to provide the title compound.

[α]$_D^{20}$=+45° (c 0.15, DMSO); mp 233–234° C.; MS (ESI+) m/z 482 (M+H)+; HRMS (FAB) calcd for C$_{21}$H$_{20}$Cl$_3$N$_4$O$_3$ (M+H)+ 481.0601; found 481.0581; $^1$H NMR (DMSO-d$_6$) δ 9.45 (s, 1H), 8.86 (d, 1H, J=7.7 Hz), 8.47 (d, 1H, J=8.9 Hz), 8.12 (dd, 1H, J=4.6, 1.8 Hz), 8.03 (d, 1H, J=8.0 Hz), 7.86 (d, 2H, J=2.2 Hz), 7.82 (t, 1H, J=1.8 Hz), 7.45 (dd, 1H, J=8.3, 4.6 Hz), 5.90 (t, 1H, J=8.0 Hz), 1.08 (s, 9H); Anal. calcd for C$_{21}$H$_{19}$Cl$_3$N$_4$O$_3$: C, 52.35; H, 3.98; N, 11.63. Found: C, 52.38; H, 3.84; N, 11.82.

EXAMPLE 109

(−) 3,5-Dichloro-N-[(1R)-1-({2-[(2-chloropyridin-3-yl)amino]-3,4-dioxocyclobut-1-yl}amino)-2,2-dimethylpropyl]benzamide The product from Example 79 was chromatographed over a Regis Technologies Whelk-O1 chiral column (2.0 cm×25 cm) using gradient elution (10% methanol-CH$_2$Cl$_2$ (2:1)/hexanes to 30% methanol-CH$_2$Cl$_2$ (2:1)/hexanes, flow rate=10 mL/minute) to provide the title compound. The absolute stereochemistry was determined by x-ray diffraction.

[α]$_D^{20}$=−46° (c 0.15, DMSO); mp 233–234° C.; Crystal data: Single crystals suitable for x-ray diffraction were grown by slow evaporation from hexanes:CH$_2$Cl$_2$:methanol, crystal dimensions 0.40×0.40×0.10 mm, orthorhombic, P2$_1$2$_1$2$_1$ (#19), a=8.344(1) Å, b=11.832(2) Å, c=24.993(3) Å, V=2467.3(5) Å$^3$, Z=4, D$_{calc}$=1.383 g/cm$^3$. Crystallographic data were collected using Mo K α radiation (λ=0.71069 Å); Refinement of the structure using full matrix least squares refinement was based on 4011 observed reflections (I>3.00σ(I)) and 298 variable parameters, R=0.069, R$_w$=0.088;

MS (ESI+) mn/z 482 (M+H)+; $^1$H NMR (DMSO-d$_6$) δ 9.45 (s, 1H), 8.86 (d, 1H, J=7.7 Hz), 8.47 (d, 1H, J=8.9 Hz), 8.12 (dd, 1H, J=4.6, 1.8 Hz), 8.03 (d, 1H, J=8.0 Hz), 7.86 (d, 2H, J=2.2 Hz), 7.82 (t, 1H, J=1.8 Hz), 7.45 (dd, 1H, J=8.3, 4.6 Hz), 5.90 (t, 1H, J=8.0 Hz), 1.08 (s, 9H).

EXAMPLE 110

(+) N-(1-{[3,4-Dioxo-2-(2-chloro3-pyridinylamino)-1-cyclobuten-1-yl]amino}-2,2-dimethylpropyl)-3,5-difluorobenzamide

EXAMPLE 110A

N-(1-{[3,4-Dioxo-2-(2-chloro3-pyridinylamino)-1-cyclobuten-1-yl]amino}-2,2-dimethylpropyl)-3,5-difluorobenzamide A suspension of the product from Example 29B, the product from Example 16A, and K$_2$CO$_3$ was processed as described in Example 1D to provide the title compound.

mp 215–217° C.; MS (ESI+) m/z 449 (M+H)+; $^1$H NMR (DMSO-d$_6$) δ 9.47 (s, 1H), 8.77 (d, 1H, J=8.1 Hz), 8.48 (d, 1H, J=8.8 Hz), 8.11 (dd, 1H, J=4.8, 1.7 Hz), 8.02 (dd, 1H, J=8.1, 1.4 Hz), 7.62–7.42 (m, 4H), 5.89 (t, 1H, J=8.1 Hz), 1.08 (s, 9H).

EXAMPLE 110B (+) N-(1-{[3,4-Dioxo-2-(2-chloro3-pyridinylamino)-1-cyclobuten-1-yl]amino}-2,2-dimethylpropyl)-3,5-difluorobenzamide The product from Example 110A was chromatographed over a Regis Technologies Whelk-O1 chiral column (2.0 cm×25 cm) using gradient elution (10% methanol-CH$_2$Cl$_2$ (2:1)/hexanes to 30% methanol-CH$_2$Cl$_2$ (2:1)/hexanes, flow rate=10 mL/minute) to provide the title compound as the dextrororotatory enantiomer.

[α]$_D^{20}$=+73° (c 0.13, DMSO); mp 215–216° C.; MS (ESI+) m/z 449 (M+H)+; $^1$H NMR (DMSO-d$_6$) δ 9.47 (s, 1H), 8.77 (d, 1H, J=8.1 Hz), 8.48 (d, 1H, J=8.8 Hz), 8.11 (dd, 1H, J=4.8, 1.7 Hz), 8.02 (dd, 1H, J=8.1, 1.4 Hz), 7.62–7.42 (m, 4H), 5.89 (t, 1H, J=8.1 Hz), 1.08 (s, 9H); Anal. calcd for C$_{21}$H$_{19}$FCl$_2$N$_4$O$_3$: C, 56.19; H, 4.27; N, 12.48. Found: C, 56.00; H, 4.23; N, 12.29.

EXAMPLE 111

(−) N-(1-{[3,4-Dioxo-2-(2-chloro-3-pyridinylamino)-1-cyclobuten-1-yl]amino}-2,2-dimethylpropyl)-3,5-difluorobenzamide The product from Example 110A was chromatographed over a Regis Technologies Whelk-O1 chiral column (2.0 cm×25 cm) using gradient elution (10% methanol-CH$_2$Cl$_2$ (2:1)/hexanes to 30% methanol-CH$_2$Cl$_2$ (2:1)/hexanes, flow rate=10 mL/minute) to provide the title compound as the levororotatory enantiomer.

[α]$_D^{20}$=69° (c 0.20, DMSO); mp 215–217° C.; MS (ESI+) m/z 449 (M+H)+; $^1$H NMR (DMSO-d$_6$) δ 9.47 (s, 1H), 8.77 (d, 1H, J=8.1 Hz), 8.48 (d, 1H, J=8.8 Hz), 8.11 (dd, 1H, J=4.8, 1.7 Hz), 8.02 (dd, 1H, J=8.1, 1.4 Hz), 7.62–7.42 (m, 4H), 5.89 (t, 1H, J=8.1 Hz), 1.08 (s, 9H); Anal. calcd for C$_{21}$H$_{19}$FCl$_2$N$_4$O$_3$: C, 56.19; H, 4.27; N, 12.48. Found: C, 55.93; H, 4.48; N, 12.20.

Determination of Potassium Channel Opening Activity Membrane Hyperpolarization Assays Compounds were evaluated for potassium channel opening activity using primary cultured guinea-pig urinary bladder (GPB) cells.

For the preparation of urinary bladder smooth muscle cells, urinary bladders were removed from male guinea-pigs (Hartley, Charles River, Wilmington, Mass.) weighing 300–400 g and placed in ice-cold Ca$^{2+}$-free Krebs solution (composition, mM: KCl, 2.7, KH$_2$PO$_4$, 1.5; NaCl, 75, Na$_2$HPO$_4$, 9.6; Na$_2$HPO$_4$. 7H$_2$O, 8; MgSO$_4$, 2; glucose, 5; HEPES, 10; pH 7.4). Cells were isolated by enzymatic dissociation as previously described with minor modifications (Klockner and Isenberg, Pflugers Arch. (1985), 405, 329–339), hereby incorporated by reference. The bladder was cut into small sections and incubated in 5 mL of the Kreb's solution containing 1 mg/mL collagenase (Sigma, St. Louis, Mo.) and 0.2 mg/mL pronase (Calbiochem, La Jolla, Calif.) with continuous stirring in a cell incubator for 30 minutes. The mixture was then centrifuged at 1300×g for 5 minutes, and the pellet resuspended in Dulbecco's PBS (GIBCO, Gaithersburg, Md.) and recentrifuged to remove residual enzyme. The cell pellet was resuspended in 5 mL growth media (composition: Dulbecco's modified Eagle's medium supplemented with 10% fetal bovine serum, 100 units/mL penicillin, 100 units/mL streptomycin and 0.25 mg/mL amphotericin B) and further dissociated by pipetting the suspension through a flame-polished Pasteur pipette and passing it through a polypropylene mesh membrane (Spectrum, Houston, Tex.). The cell density was adjusted to 100,000 cells/mL by resuspension in growth media Cells were plated in clear-bottomed black 96-well plates (Packard) for membrane potential studies at a density of 20,000 cells/well and maintained in a cell incubator with 90% air: 10% $CO_2$ until confluent. Cells were confirmed to be of smooth muscle type by cytoskeletal staining using a monoclonal mouse anti human-α-smooth muscle actin (Biomeda, Foster City, Calif.).

Functional activity at potassium channels was measured by evaluating changes in membrane potential using the bis-oxonol dye $DiBAC(4)_3$ (Molecular Probes) in a 96-well cell-based kinetic assay system, Fluorescent Imaging Plate Reader (FLIPR) (K. S. Schroeder et al., J. Biomed. Screen., v. 1 pp. 75–81 (1996)), hereby incorporated by reference. $DiBAC(4)_3$ is an anionic potentiometric probe which partitions between cells and extracellular solution in a membrane potential-dependent manner. With increasing membrane potential (for example, $K^+$ depolarization), the probe further partitions into the cell; this is measured as an increase in fluorescence due to dye interaction with intracellular lipids and proteins. Conversely, decreasing membrane potential (hyperpolarization by potassium channel openers) evokes a decrease in fluorescence.

Confluent guinea-pig urinary bladder cells cultured in black clear-bottomed 96-well plates were rinsed twice with 200 mL assay buffer (composition, mM: HEPES, 20; NaCl, 120; KCl, 2; $CaCl_2$, 2, $MgCl_2$, 1, glucose, 5; pH 7.4 at 25° C.) containing 5 µM $DiBAC(4)_3$ and incubated with 180 mL of the buffer in a cell incubator for 30 minutes at 37° C. to ensure dye distribution across the membrane. After recording the baseline fluorescence for 5 minutes, the reference or test compounds, prepared at 10 times the concentration in the assay buffer, were added directly to the wells. Changes in fluorescence were monitored for an additional 25 minutes. Hyperpolarization responses were corrected for any background noise and were normalized to the response observed with 10 µM of the reference compound P1075 (assigned as 100%), a potent opener of smooth muscle $K_{ATP}$ channels (Quast et al., Mol. Phanmacol., v. 43 pp. 474–481 (1993)).

Routinely, five concentrations of P1075 or test compounds (log or half-log dilutions) were evaluated and the maximal steady-state hyperpolarization values (expressed as % relative to P1075) plotted as a function of concentration. The $EC_{50}$ (concentration that elicites 50% of the maximal response for the test sample) values were calculated by non-linear regression analysis using a four parameter sigmoidal equation. The maximal response of each compound (expressed as % relative to P1075) is reported. Stock solutions of compounds were prepared in 100% DMSO and further dilutions were carried out in the assay buffer and added to a 96-well plate.

TABLE 1

Membrane Hyperpolarization (MHP) in Guinea-Pig Bladder (GPB) Cells

| Example # | Maximal Response (%P1075) | MHP GPB $EC_{50}$ (µM) |
|---|---|---|
| 1 | 91 | 0.15 |
| 2 | 108 | 0.16 |
| 17 | 96 | 0.18 |
| 18 | 97 | 0.51 |
| 19 | <20 | >10 |
| 20 | 98 | 0.58 |
| 60 | 83 | 0.093 |

In Vitro Functional Models

Compound were evaluated for functional potassium channel opening activity using tissue strips obtained from Landrace pig bladders.

Landrace pig bladders were obtained from female Landrace pigs of 9–30 kg. Landrace pig were euthanized with an intraperitoneal injection of pentobarbital solution, Somlethal ®, J. A. Webster Inc. Sterling Mass. The entire bladder was removed and immediately placed into Krebs Ringer bicarbonate solution (composition, mM: NaCl, 120; $NaHCO_3$, 20; dextrose, 11; KCl, 4.7; $CaCl_2$, 2.5; $MgSO_4$, 1.5; $KH_2PO_4$, 1.2; $K_2EDTA$, 0.01, equilibrated with 5% $CO_2$/ 95% $O_2$ pH 7.4 at 37° C.). Propranolol (0.004 mM) was included in all of the assays to block β-adrenoceptors. The trigonal and dome portions were discarded. Strips 3–5 mm wide and 20 mm long were prepared from the remaining tissue cut in a circular fashion. The mucosal layer was removed. One end was fixed to a stationary glass rod and the other to a Grass FT03 transducer at a basal preload of 1.0 gram. Two parallel platinum electrodes were included in the stationary glass rod to provide field stimulation of 0.05 Hz, 0.5 milli-seconds at 20 volts. This low frequency stimulation produced a stable twitch response of 100–500 centigrams. Tissues were allowed to equilibrate for at least 60 minutes and primed with 80 mM KCl. A control concentration response curve (cumulative) was generated for each tissue using the potassium channel opener P1075 as the control agonist. P1075 completely eliminated the stimulated twitch in a dose dependent fashion over a concentration range of $10^{-9}$ to $10^{-5}$ M dissolved in DMSO using ½ log increments. After a 60 minute rinsing period, a concentration response curve (cumulative) was generated for the test agonist in the same fashion as that used for control agonist P1075. The maximal efficacy of each compound (expressed as % relative to P1075) is reported. The amount of agent necessary to cause 50% of the agent's maximal response ($ED_{50}$) was calculated using "ALLFIT" (DeLean et al., Am. J. Physiol., 235, E97 (1980)), hereby incorporated by reference. Agonist potencies were also expressed as an index relative to P1075. The index was calculated by dividing the $ED_{50}$ for P1075 by the $ED_{50}$ for the test agonist in a given tissue. Each tissue was used for only one test agonist, and the indices obtained from each tissue were averaged to provide an average index of potency. These data are shown in Table 2.

TABLE 2

Functional Potassium Channel Opening Activity in Isolated Bladder Strips

Landrace Pig Bladder

| Example # | Efficacy (%P1075) | $ED_{50}$ ($\mu M$) | Index |
|---|---|---|---|
| 1 | 54 | 19 | 0.008 |
| 2 | 79 | 6.9 | 0.047 |
| 3 | 73 | 2.2 | 0.062 |
| 5 | 98 | 0.38 | 0.059 |
| 6 | 100 | 1.0 | 0.067 |
| 7 | 89 | 8.4 | 0.025 |
| 8 | 84 | 2.8 | 0.047 |
| 12 | 78 | 2.6 | 0.12 |
| 13 | 75 | 0.37 | 0.57 |
| 16 | 94 | 3.8 | 0.046 |
| 17 | 92 | 5.8 | 0.028 |
| 18 | 62 | 17 | 0.055 |
| 21 | 68 | 4.0 | 0.092 |
| 26 | 64 | 0.42 | 0.64 |
| 29 | 81 | 3.0 | 0.028 |
| 31 | 76 | 2.9 | 0.039 |
| 32 | 99 | 1.3 | 0.076 |
| 36 | 99 | 0.97 | 0.063 |
| 49 | 100 | 1.2 | 0.071 |
| 50 | 79 | 6.8 | 0.14 |
| 51 | 96 | 1.4 | 0.080 |
| 55 | 75 | 2.3 | 0.053 |
| 56 | 94 | 2.2 | 0.028 |
| 57 | 81 | 4.0 | 0.015 |
| 59 | 57 | 1.7 | 0.062 |
| 60 | 88 | 0.68 | 0.87 |
| 61 | 64 | 0.47 | 0.50 |
| 64 | 76 | 4.2 | 0.025 |
| 66 | 74 | 4.2 | 0.040 |
| 67 | 72 | 2.5 | 0.029 |
| 78 | 98 | 0.84 | 0.18 |
| 79 | 60 | 4.6 | 0.024 |
| 86 | 85 | 0.64 | 0.24 |
| 87 | 96 | 1.9 | 0.039 |
| 108 | 89 | 4.2 | 0.033 |

As shown by the data in Tables 1 and 2, the compounds of this invention reduce stimulated contractions of the bladder by opening potassium channels and therefore can have utility in the treatment of diseases prevented by or ameliorated with potassium channel openers.

The term "pharmaceutically acceptable carrier," as used herein, means a non-toxic, inert solid, semi-solid or liquid filler, diluent, encapsulating material or formulation auxiliary or any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The present invention provides pharmaceutical compositions which comprise compounds of the present invention formulated together with one or more non-toxic pharmaceutically acceptable carriers. The pharmaceutical compositions can be formulated for oral administration in solid or liquid form, for parenteral injection or for rectal administration.

Further included within the scope of the present invention are pharmaceutical compositions comprising one or more of the compounds of formula I–IV prepared and formulated in combination with one or more non-toxic pharmaceutically acceptable compositions. The pharmaceutical compositions can be formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous, intraarticular injection and infusion.

Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It can also be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the present invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

The active compounds can also be in micro-encapsulated form, if appropriate, with one or more excipients as noted above. The solid dosage forms of tablets, dragees, capsules, pills, and granules can be prepared with coatings and shells such as enteric coatings, release controlling coatings and other coatings well known in the pharmaceutical formulating art In such solid dosage forms the active compound can be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of such composition that they release the active ingredient(s) only, or preferentially, in a certain part of the intestinal tract in a delayed manner. Examples of embedding compositions which can be used include polymeric substances and waxes.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate, e) solution retarding agents such as paraffin); f) absorption accelerators such as quaternaly ammonium compounds, g) wetting agents such as cetyl alcohol and glycerol monostearate;) absorbents such as kaolin and bentonite clay; and i) lubricants such as talc, calcium stearate, magnesium stearate, solid polyethylene glycols, sodium lauryl sulfate, and mixtures thereof In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions which can be used include polymeric substances and waxes.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, excipients, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

The term "pharmaceutically acceptable salt," as used herein, refers to salts that are well known in the art. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include nitrate, bisulfate, borate, formate, butyrate, valerate, 3-phenylpropionate, camphorate, adipate, benzoate, oleate, palmitate, stearate, laurate, lactate, fumarate, ascorbate, aspartate, nicotinate, p-toluenesulfonate, camphorsulfonate, methanesulfonate, 2-hydroxyethanesulfonate, gluconate, glucoheptonate, lactobionate, glycerophosphate, pectinate, lauryl sulfate, and the like, metal salts such as sodium, potassium, magnesium or calcium salts or amino salts such as ammonium, triethylamine salts, and the like, all of which may be prepared according to conventional methods.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

The present invention contemplates compounds of formula I–IV formed by synthetic means or formed by in vivo biotransformation.

The compounds of the invention, including but not limited to those specified in the examples, possess potassium channel opening activity in mammals (especially humans). As potassium channel openers, the compounds of the present invention may be useful for the treatment and prevention of diseases such as asthma, epilepsy, male sexual dysfunction, female sexual dysfunction, pain, bladder overactivity, stroke, diseases associated with decreased skeletal blood flow such as Raynaud's phenomenon and intermittent claudication, eating disorders, functional bowel disorders, neurodegeneration, benign prostatic hyperplasia (BPH), dysmenorrhea, premature labor, alopecia, cardioprotection, coronary artery disease, angina and ischemia.

The ability of the compounds of the present invention, including but not limited to those specified in the examples, to treat bladder overactivity, sensations of incontinence urgency, urinary incontinence, pollakiuria, bladder instability, nocturia, bladder hyerreflexia, and enuresis may be demonstrated by (Resnick, The Lancet (1995) 346, 94–99; Hampel, Urology (1997) 50 (Suppl 6A), 4–14; Bosch, BJU International (1999) 83 (Suppl 2), 7–9; Andersson, Urology (1997) 50 (Suppl 6A), 74–84; Lawson, Pharmacol. Ther., (1996) 70, 39–63; Nurse., Br. J. Urol., (1991) 68, 27–31; Howe, J. Pharmacol. Exp. Ther., (1995) 274, 884–890; Gopalakrishnan, Drug Development Research, (1993) 28, 95–127).

The ability of the compounds of the present invention, including but not limited to those specified in the examples, to treat male sexual dysfunction such as male erectile dysfunction, impotence and premature ejaculation may be demonstrated by (Anderson, Pharmacological Reviews (1993) 45, 253; Lee, Int. J. Impot Res. (1999) 11(4), 179–188; Andersson, Pharmacological Reviews (1993) 45, 253; Lawson, Pharmacol. Ther., (1996) 70, 39–63, Vick, J. Urol. (2000) 163: 202).

The ability of the compounds of the present invention, including but not limited to those specified in the examples, to treat female sexual dysfunction such as clitoral erectile insufficiency, vaginismus and vaginal engorgement may be demonstrated by (Kim et al., J. Urol. (2000) 163 (4): 240; Goldstein and Berman., Int. J. Impotence Res. (1998) 10:S84–S90).

The ability of the compounds of the present invention, including but not limited to those specified in the examples, to treat benign prostatic hyperplasia (BPH) may be demonstrated by (Pandita, The J. of Urology (1999) 162, 943; Andersson, Prostate (1997) 30: 202–215).

The ability of the compounds of the present invention, including but not limited to those specified in the examples, to treat premature labor and dysmenorrhea may be demonstrated by (Sanborn, Semin. Perinatol. (1995) 19, 31–40; Morrison, Am. J. Obstet. Gynecol. (1993) 169(5), 1277–85; Kostrzewska, Acta Obstet. Gynecol. Scand. (1996) 75(10), 886–91; Lawson, Pharmacol. Ther., (1996) 70, 39–63).

The ability of the compounds of the present invention, including but not limited to those specified in the examples, to treat functional bowel disorders such as irritable bowel syndrome may be demonstrated by (Lawson, Pharmacol. Ther., (1996) 70, 39–63).

The ability of the compounds of the present invention, including but not limited to those specified in the examples, to treat asthma and airways hyperreactivity may be demonstrated by (Lawson, Pharmacol. Ther., (1996) 70, 39–63, Buchheit, Pulmonary Pharmacology & Therapeutics (1999) 12, 103; Gopalakrishnan, Drug Development Research, (1993) 28, 95–127).

The ability of the compounds of the present invention, including but not limited to those specified in the examples, to treat various pain states including but not limited to migraine and dyspareunia may be demonstrated by (Rodrigues, Br. J. Pharmacol. (2000) 129(1), 110–4; Vergoni, Life Sci. (1992) 50(16), PL135–8; Asano, Anesth. Analg. (2000) 90(5), 1146–51; Lawson, Pharmacol. Ther., (1996) 70, 39–63; Gopalakrishnan, Drug Development Research, (1993) 28, 95–127; Gehlert, Prog. Neuro-Psychopharmacol. & Biol. Psychiat., (1994) 18, 1093–1102).

The ability of the compounds of the present invention, including but not limited to those specified in the examples, to treat epilepsy may be demonstrated by (Lawson, Pharmacol. Ther., (1996) 70, 39–63; Gopalakrishnan, Drug Development Research, (1993) 28, 95–127; Gehlert, Prog. Neuro-Psychopharmacol & Biol. Psychiat., (1994) 18, 1093–1102).

The ability of the compounds of the present invention, including but not limited to those specified in the examples, to treat neurodegenerative conditions and diseases such as cerebral ischemia, stroke, Alzheimer's disease and Parkinson's disease may be demonstrated by (Lawson, Pharmacol. Ther., (1996) 70, 39–63; Gopalakrishnan, Drug Development Research, (1993) 28, 95–127; Gehlert, Prog. Neuro-Psychopharmacol. & Biol. Psychiat., (1994) 18, 1093–1102; Freedman, The Neuroscientist (1996) 2, 145).

The ability of the compounds of the present invention, including but not limited to those specified in the examples, to treat diseases or conditions associated with decreased skeletal muscle blood flow such as Raynaud's syndrome and intermittent claudicatiori may be demonstrated by (Lawson, Pharmacol. Ther., (1996) 70, 39–63; Gopalakrishnan, Drug Development Research, (1993) 28, 95–127; Dompeling Vasa. Supplementum (1992) 3434; WO9932495).

The ability of the compounds of the present invention, including but not limited to those specified in the examples, to treat eating disorders such as obesity may be demonstrated by (Spanswick, Nature, (1997) 390, 521–25; Freedman, The Neuroscientist (1996) 2, 145).

The ability of the compounds of the present invention, including but not limited to those specified in the examples, to treat alopecia may be demonstrated by (Lawson, Pharmacol. Ther., (1996) 70, 39–63; Gopalakrishnan, Drug Development Research, (1993) 28, 95–127).

The ability of the compounds of the present invention, including but not limited to those specified in the examples, to treat myocardial injury during ischemia and reperfusion may be demonstrated by (Garlid, Circ Res (1997) 81(6), 1072–82; Lawson, Pharmacol. Ther., (1996) 70, 39–63; Grover, J. Mol. Cell Cardiol. (2000) 32, 677).

The ability of the compounds of the present invention, including but not limited to those specified in the examples, to treat coronary artery disease may be demonstrated by (Lawson, Pharmacol. Ther., (1996) 70, 39–63, Gopalakrishnan, Drug Development Research, (1993) 28, 95–127).

Aqueous liquid compositions of the present invention are particularly useful for the treatment and prevention of asthma, epilepsy, hypertension, Raynaud's syndrome, male sexual dysfunction, female sexual dysfunction, migraine, pain, eating disorders, urinary incontinence, functional bowel disorders, neurodegeneration and stroke.

When used in the above or other treatments, a therapeutically effective amount of one of the compounds of the present invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder, activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.003 to about 50 mg/kg/day. For purposes of oral administration, more preferable doses can be in the range of from about 0.01 to about 25 mg/kg/day. If desired, the effective daily dose can be divided into multiple doses for purposes of administration; consequently, single dose compositions may contain such amounts or submultiples thereof to make up the daily dose.

What is claimed is:

1. A compound of formula (I)

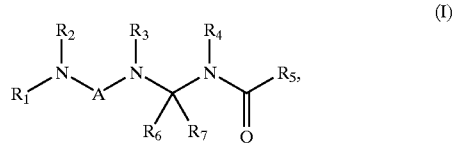

or a pharmaceutically acceptable salt thereof wherein
A is selected from the group consisting of

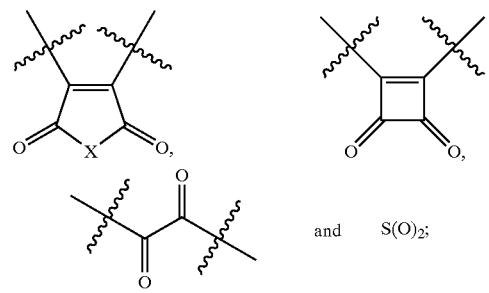

X is selected from the group consisting of $CH_2$, O and N(Z);

Z is selected from the group consisting of hydrogen and alkyl;

$R_1$ is selected from the group consisting of aryl, arylalkyl, heterocycle and heterocyclealkyl;

$R_2$, $R_3$ and $R_4$ are independently selected from the group consisting of hydrogen and alkyl;

R₅ is selected from the group consisting of aryl, arylalkenyl, arylalkyl, aryloxyalkyl, heterocycle and heterocyclealkyl;

R₆ is selected from the group consisting of hydrogen, alkenyl, alkenyloxyalkyl, alkenyloxy(alkenyloxy) alkyl, alkoxyalkyl, alkoxycarbonyl, alkoxycarbonylalkyl, alkoxycarbonyl(halo)alkyl, alkoxy(halo)alkyl, alkyl, alkylcarbonyl, alkylcarbonylalkyl, alkylcarbonyl(halo)alkyl, alkylcarbonyloxyalkyl, alkylsulfinylalkyl, alkylsulfonylalkyl, alkylthioalkyl, alkynyl, aryl, arylalkoxyalkyl, arylalkoxycarbonyl, arylalkoxycarbonylalkyl, arylalkyl, arylcarbonyl, arylcarbonylalkyl, arylcarbonyloxyalkyl, aryl(halo)alkyl, aryloxyalkyl, aryloxycarbonyl, aryloxycaibonylalkyl, arylalkylthioalkyl, arylsulfonylalkyl, carboxy, carboxyalkyl, carboxy(halo)alkyl, cyanoalkyl, cyano(halo)alkyl, cycloalkenyl, cycloalkenylalkyl, cycloalkyl, cycloalkylalkoxyalkyl, cycloalkylalkyl, cycloalkylcarbonyl, cycloalkyloxyalkyl, cycloalkylalkylthioalkyl, formyl, haloalkenyl, haloalkyl, haloalkylcaibonyl, haloalkynyl, heterocycle, heterocyclealkoxyalkyl, heterocyclealkyl, heterocyclecaibonyl, heterocycleoxyalkyl, heterocyclealkylthioalkyl, hydroxyalkyl, mercaptoalkyl, sulfamylalkyl, sulfamyl(halo)alkyl, (NR₉R₁₀)alkyl, (NR₉R₁₀)carbonyl and (NR₉R₁₀)carbonylalkyl;

R₇ is selected from the group consisting of hydrogen, haloalkyl, and lower alkyl; or R₆ and R₇ taken together with the carbon atom to which they are attached, together form a 5 or 6 membered carbocyclic ring wherein the 5 or 6 membered carbocyclic ring is optionally substituted with 1 or 2 substituents independently selected from the group consisting of alkenyl, alkoxy, alkyl, alkynyl, halogen, haloalkoxy, and haloalkyl;

R₉ and R₁₀ are independently selected from the group consisting of hydrogen, alkoxysulfonyl, alkyl, alkylcarbonyl, alkylsulfonyl, aryl, arylalkyl, arylcarbonyl, arylsulfonyl and formyl.

2. A compound according to claim 1 wherein A is selected from the group consisting of

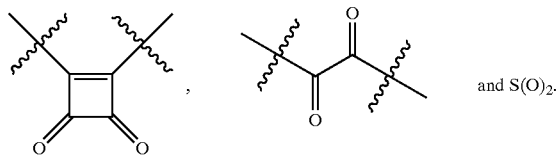

and S(O)₂.

3. A compound according to claim 1 of formula (II)

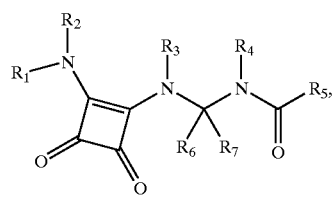

(II)

or a pharmaceutically acceptable salt thereof.

4. A compound according to claim 3 wherein
R₁ is heterocycle; and

R₅ is aryl.

5. A compound according to claim 3 wherein
R₁ is heterocycle wherein said heterocycle is selected from the group consisting of optionally substituted pyridinyl and optionally substituted pyrazinyl, and
R₅ is aryl wherein said aryl is optionally substituted phenyl.

6. A compound according to claim 3 wherein
R₁ is heterocycle wherein said heterocycle is selected from the group consisting of optionally substituted pyridinyl and optionally substituted pyrazinyl;
R₂ is hydrogen;
R₃ is hydrogen;
R₄ is hydrogen;
R₅ is aryl wherein said aryl is optionally substituted phenyl;
R₆ is selected from the group consisting of hydrogen and alkyl; and
R₇ is hydrogen.

7. A compound according to claim 6 selected from the group consisting of

N-(1-{[3,4-dioxo-2-(3-pyridinylamino)-1-cyclobuten-1-yl]amino}-2,2-dimethylpropyl)-4-methylbenzamide;

4-chloro-N-(1-{[3,4-dioxo-2-(3-pyridinylamino)-1-cyclobuten-1-yl]amino}-2,2-dimethylpropyl)benzamide;

N-(1-{[3,4-dioxo-2-(3-pyridinylamino)-1-cyclobuten-1-yl]amino}-2,2-dimethylpropyl)-4-iodobenzamide;

N-(1-{[3,4-dioxo-2-(3-pyridinylamino)-1-cyclobuten-1-yl]amino}-2,2-dimethylpropyl)-4-(2-furyl)benzamide;

3-chloro-N-(1-{[3,4-dioxo-2-(3-pyridinylamino)-1-cyclobuten-1-yl]amino}-2,2-dimethylpropyl)benzamide;

N-(1-{[3,4-dioxo-2-(3-pyridinylamino)-1-cyclobuten-1-yl]amino}-2,2-dimethylpropyl)-3-methylbenzamide;

N-(1-{[3,4-dioxo-2-(3-pyridinylamino)-1-cyclobuten-1-yl]amino}-2,2-dimethylpropyl)-3-fluorobenzamide;

N-(1-{[3,4-dioxo-2-(3-pyridinylamino)-1-cyclobuten-1-yl]amino}-2,2-dimethylpropyl)-3-iodobenzamide;

N-(1-{[3,4-dioxo-2-(3-pyridinylamino)-1-cyclobuten-1-yl]amino}-2,2-dimethylpropyl)-3,4-dimethylbenzamide;

N-(1-{[3,4-dioxo-2-(3-pyridinylamino)-1-cyclobuten-1-yl]amino}-2,2-dimethylpropyl)-3,4-dimethoxybenzamide, 3,5-dichloro-N-(1-{[3,4-dioxo-2-(3-pyridinylamino)-1-cyclobuten-1-yl]amino}-2,2-dimethylpropyl)benzamide;

N-(1-{[3,4-dioxo-2-(3-pyridinylamino)-1-cyclobuten-1-yl]amino}-2,2-dimethylpropyl)-3,5-dimethoxybenzamide;

(−) N-(1-{[3,4-dioxo-2-(3-pyridinylamino)-1-cyclobuten-1-yl]amino}-2,2-dimethylpropyl)-3,5-dimethoxybenzamide (+) N-(1-{[3,4-dioxo-2-(3-pyridinylamino)-1-cyclobuten-1-yl]amino}-2,2-dimethylpropyl)-3,5-dimethoxybenzamide;

N-(1-{[3,4-dioxo-2-(3-pyridinylamino)-1-cyclobuten-1-yl]amino}-2,2-dimethylpropyl)-3,5-difluorobenzamide;

4-chloro-N-(1-{[3,4-dioxo-2-(3-pyridinylamino)-1-cyclobuten-1-yl]amino}-2-ethylbutyl)benzamide;

4-chloro-N-[1-({2-[(2-chloro-3-pyridinyl)amino]-3,4-dioxo-1-cyclobuten-1-yl}amino)-2,2-dimethylpropyl]benzamide;

N-[1-({2-[(5-bromo-6-fluoro-3-pyridinyl)amino]-3,4-dioxo-1-cyclobuten-1-yl}amino)-2,2-dimethylpropyl]-4-chlorobenzamide;

N-[1-({2-[(2-chloro-3-pyridinyl)amino]-3,4-dioxo-1-cyclobuten-1-yl}amino)-2,2-dimethylpropyl]-3-methylbenzamide;

N-(1-{[3,4-dioxo-2-(3-pyridinylamino)-1-cyclobuten-1-yl]amino}-2,2-dimethylpropyl)-3-vinylbenzamide;

N-(1-{[3,4-dioxo-2-(3-pyridinylamino)-1-cyclobuten-1-yl]amino}-2,2-dimethylpropyl)[1,1'-biphenyl]-3-carboxamide;

3-acetyl-N-(1-{[3,4-dioxo-2-(3-pyridinylamino)-1-cyclobuten-1-yl]amino}-2,2-dimethylpropyl)benzamide;

N-(1-{[3,4-dioxo-2-(3-pyridinylamino)-1-cyclobuten-1-yl]amino}-2,2-dimethylpropyl)-4-fluoro-3-(trifluoromethyl)benzamide;

4-chloro-N-(1-{[3,4-dioxo-2-(4-pyridinylamino)-1-cyclobuten-1-yl]amino}-2,2-dimethylpropyl)benzamide;

4-chloro-N-(1-{[3,4-dioxo-2-(2-pyridinylamino)-1-cyclobuten-1-yl]amino}-2,2-dimethylpropyl)benzamide;

N-(1-{[3,4-dioxo-2-(3-pyridinylamino)-1-cyclobuten-1-yl]amino}-2,2-dimethylpropyl)benzamide;

(+) N-(1-{[3,4-dioxo-2-(3-pyridinylamino)-1-cyclobuten-1-yl]amino}-2,2-dimethylpropyl)-3,5-difluorobenzamide;

(−) N-(1-{[3,4-dioxo-2-(3-pyridinylamino)-1-cyclobuten-1-yl]amino}-2,2-dimethylpropyl)-3,5-difluorobenzamide;

4-chloro-N-{1-[(3,4-dioxo-2-{[5-(trifluoromethyl)pyridin-3-yl]amino}-1-cyclobuten-1-yl)amino]-2,2-dimethylpropyl}benzamide;

3,5-dichloro-N-{1-[(3,4-dioxo-2-{[5-(trifluoromethyl)pyridin-3-yl]amino}cyclobuten-1-yl)amino]-2,2-dimethylpropyl}benzamide;

(+) 3-chloro-N-(1-{[3,4-dioxo-2-(3-pyridinylamino)-1-cyclobuten-1-yl]amino}-2,2-dimethylpropyl)benzamide;

(−) 3-chloro-N-(1-{[3,4-dioxo-2-(3-pyridinylamino)-1-cyclobuten-1-yl]amino}-2,2-dimethylpropyl)benzamide;

4-chloro-N-[1-({2-[(6-chloropyridin-3-yl)amino]-3,4-dioxo-1-cyclobuten-1-yl}amino)-2,2-dimethylpropyl]benzamide;

4-chloro-N-[1-({2-[(2-fluoropyridin-3-yl)amino]-3,4-dioxo-1-cyclobuten-1-yl}amino)-2,2-dimethylpropyl]benzamide;

3-chloro-N-(1-{[3,4-dioxo-2-(3-pyridinylamino)-1-cyclobuten-1-yl]amino}-3,3-dimethylbutyl)benzamide;

3-bromo-N-(1-{[3,4-dioxo-2-(3-pyridinylamino)-1-cyclobuten-1-yl]amino}-2,2-dimethylpropyl)benzamide;

3-bromo-N-[1-({2-[(2-chloropyridin-3-yl)amino]-3,4-dioxo-1-cyclobuten-1-yl}amino)-2,2-dimethylpropyl]benzamide;

methyl 3-{[(1-{[3,4-dioxo-2-(3-pyridinylamino)-1-cyclobuten-1-yl]amino}-2,2-dimethylpropyl)amino]carbonyl}benzoate, (+) N-(1-{[3,4-dioxo-2-(3-pyridinylamino)-1-cyclobuten-1-yl]amino}-2,2-dimethylpropyl)-3-methylbenzamide;

(−) N-(1-{[3,4-dioxo-2-(3-pyridinylamino)-1-cyclobuten-1-yl]amino}-2,2-dimethylpropyl)-3-methylbenzamide;

(+) N-[1-({2-[(2-chloropyridin-3-yl)amino]-3,4-dioxo-1-cyclobuten-1-yl}amino)-2,2-dimethylpropyl]-3-methylbenzamide;

(−) N-[1-({2-[(2-chloropyridin-3-yl)amino]-3,4-dioxo-1-cyclobuten-1-yl}amino)-2,2-dimethylpropyl]-3-methylbenzamide;

N-(1-{[3,4-dioxo-2-(3-pyridinylamino)-1-cyclobuten-1-yl]amino}-2,2-dimethylpropyl)-3-(2-furyl)benzamide;

N-[1-({2-[(2-chloropyridin-3-yl)amino]-3,4-dioxo-1-cyclobuten-1-yl}amino)-2,2-dimethylpropyl]-3-fluorobenzamide;

3,5-dichloro-N-[1-({2-[(2-chloropyridin-3-yl)amino]-3,4-dioxocyclobut-1-en-1-yl}amino)-2,2-dimethylpropyl]benzamide;

4-chloro-N-[1-({2-[(2-methoxypyridin-3-yl)amino]-3,4-dioxo-1-cyclobuten-1-yl}amino)-2,2-dimethylpropyl]benzamide;

N-[1-({2-[(2-methoxypyridin-3-yl) amino]-3,4-dioxo-1-cyclobuten-1-yl}amino)-2,2-dimethylpropyl]-3-methylbenzamide;

3,5-difluoro-N-[1-({2-[(2-methoxypyridin-3-yl)amino]-3,4-dioxo-1-cyclobuten-1-yl}amino)-2,2-dimethylpropyl]benzamide;

3-chloro-N-[1-({2-[(2-methoxypyridin-3-yl)amino]-3,4-dioxo-1-cyclobuten-1-yl}amino)-2,2-dimethylpropyl]benzamide;

3-chloro-N-(1-{[3,4-dioxo-2-(pyrazin-2-ylamino)-1-cyclobuten-1-yl]amino}-2,2-dimethylpropyl)benzamide;

N-[1-({2-[(2-chloropyridin-3-yl)amino]-3,4-dioxo-1-cyclobuten-1-yl)}amino)-3,3-dimethylbutyl]benzamide;

3-chloro-N-[1-({2-[(6-chloropyridin-3-yl)amino]-3,4-dioxo-1-cyclobuten-1-yl}amino)-2,2-dimethylpropyl]benzamide;

3-chloro-N-{1-[(3,4-dioxo-2-{[6-(trifluoromethyl)pyridin-3-yl]amino}-1-cyclobuten-1-yl)amino]-2,2-dimethylpropyl}benzamide;

3-chloro-N-[1-({2-[(2-chloropyridin-3-yl)amino]-3,4-dioxo-1-cyclobuten-1-yl}amino)-2,2-dimethylpropyl]benzamide;

4-chloro-N-({[3,4-dioxo-2-(3-pyridinylamino)-1-cyclobuten-1-yl]amino}methyl)benzamide;

(−) 3,5-dichloro-N-[(1R)-1-({2-[(2-chloropyridin-3-yl}amino]-3,4-dioxocyclobut-1-en-1-yl}amino)-2,2-dimethylpropyl]benzamide;

(+) N-(1-{[3,4-dioxo-2-(2-chloro3-pyridinylamino)-1-cyclobuten-1-yl]amino}-2,2-dimethylpropyl)-3,5-difluorobenzamide; and (−) N-(1-{[3,4-dioxo-2-(2-chloro3-pyridinylamino)-1-cyclobuten-1-yl]amino}-2,2-dimethylpropyl)-3,5-difluorobenzamide.

8. A compound according to claim 6 that is (+) 3,5-dichloro-N-[(1S)-1-({2-[(2-chloropyridin-3-yl)amino]-3,4-dioxocyclobut-1-en-1-yl}amino)-2,2-dimethylpropyl]benzamide.

9. A compound according to claim 3 wherein $R_1$ is heterocycle wherein said heterocycle is optionally substituted pyridinyl;

R$_2$ is hydrogen;
R$_3$ is hydrogen;
R$_4$ is hydrogen;
R$_5$ is aryl wherein said aryl is optionally substituted phenyl;
R$_6$ is selected from the group consisting of arylalkyl and heterocyclealkyl wherein the aryl portion of said arylalkyl is optionally substituted phenyl and the heterocycle portion of said heterocyclealkyl is optionally substituted pyridinyl; and
R$_7$ is hydrogen.

10. A compound according to claim 9 selected from the group consisting of 4-chloro-N-(1-{[3,4-dioxo-2-(3-pyridinylamino)-1-cyclobuten-1-yl]amino}-2,2-dimethyl-3-phenylpropyl)benzamide;

4-chloro-N-[1-({2-[(2-chloro-3-pyridinyl)amino]-3,4-dioxo-1-cyclobuten-1-yl}amino)-2,2-dimethyl-3-phenylpropyl]benzamide;

4-chloro-N-{1-[(3,4-dioxo-2-{[5-(trifluoromethyl)pyridin-3-yl]amino}-1-cyclobuten-1-yl)amino]-2,2-dimethyl-3-phenylpropyl}benzamide;

N-(1-{[3,4-dioxo-2-(3-pyridinylamino)-1-cyclobuten-1-yl]amino}-2,2-dimethyl-3-phenylpropyl)-3,5-difluorobenzamide;

3,5-dichloro-N-(1-{[3,4-dioxo-2-(3-pyridinylamino)-1-cyclobuten-1-yl]amino}-2,2-dimethyl-3-phenylpropyl)benzamide;

3-chloro-N-(1-{[3,4-dioxo-2-(3-pyridinylamino)1-cyclobuten-1-yl]amino}-2,2-dimethyl-3-phenylpropyl)benzamide;

N-(1-{[3,4-dioxo-2-(3-pyridinylamino)-1-cyclobuten-1-yl]amino}-2,2-dimethyl-3-phenylpropyl)-3-methylbenzamide;

N-[1-({2-[(2-chloropyridin-3-yl)amino]-3,4-dioxo-1-cyclobuten-1-yl}amino)-2,2-dimethyl-3-phenylpropyl]-3-methylbenzamide;

(+) N-(1-{[3,4-dioxo-2-(3-pyridinylamino)-1-cyclobuten-1-yl]amino}-2,2-dimethyl-3-phenylpropyl)-3-methylbenzamide;

(−) N-(1-{[3,4-dioxo-2-(3-pyridinylamino)-1-cyclobuten-1-yl]amino}-2,2-dimethyl-3-phenylpropyl)-3-methylbenzamide;

(+) N-(1-{[3,4-dioxo-2-(3-pyridinylamino)-1-cyclobuten-1-yl]amino}-2,2-dimethyl-3-phenylpropyl)-3,5-difluorobenzamide;

N-[1-({2-[(2-methoxypyridin-3-yl)amino]-3,4-dioxo-1-cyclobuten-1-yl}amino)-2,2-dimethyl-3-phenylpropyl]-3-methylbenzamide;

N-[1-({2-[(2-chloropyridin-3-yl)amino]-3,4-dioxo-1-cyclobuten-1-yl}amino)-2,2-dimethyl-3-phenylpropyl]benzamide;

N-(1-{[3,4-dioxo-2-(3-pyridinylamino)-1-cyclobuten-1-yl]amino}-2,2-dimethyl-3-phenylpropyl)benzamide;

N-(1-{[3,4-dioxo-2-(3-pyridinylamino)-1-cyclobuten-1-yl]amino}-2,2-dimethyl-3-pyridin4-ylpropyl)3-methylbenzamide;

(−) 3-chloro-N-(1-{[3,4-dioxo-2-(3-pyridinylamino)-1-cyclobuten-1-yl]amino}-2,2-dimethyl-3-phenylpropyl)benzamide; and (+) 3-chloro-N-(1-{[3,4-dioxo-2-(3-pyridinylamino)-1-cyclobuten-1-yl]amino}-2,2-dimethyl-3-phenylpropyl)benzamide.

11. A compound according to claim 3 wherein
R$_1$ is heterocycle wherein said heterocycle is optionally substituted pyridinyl;
R$_2$ is hydrogen;
R$_3$ is hydrogen;
R$_4$ is hydrogen;
R$_5$ is aryl wherein said aryl is optionally substituted phenyl;
R$_6$ is haloalkyl; and
R$_7$ is hydrogen.

12. A compound according to claim 11 selected from the group consisting of 4-chloro-N-(2,2-dichloro-1-{[3,4-dioxo-2-(3-pyridinylamino)-1-cyclobuten-1-yl]amino}propyl)benzamide;

3-chloro-N-(2,2-dichloro-1-{[3,4-dioxo-2-(3-pyridinylamino)-1-cyclobuten-1-yl]amino}propyl)benzamide;

3-chloro-N-(1-{[3,4-dioxo-2-(3-pyridinylamino)-1-cyclobuten-1-yl]amino}-2,2,3,3,3-pentafluoropropyl)benzamide;

4-chloro-N-(2,2-dichloro-1-{[3,4-dioxo-2-(3-pyridinylamino)-1-cyclobuten-1-yl]amino}pentyl)benzamide; and N-(2,2-dichloro-1-{[3,4-dioxo-2-(3-pyridinylamino)-1-cyclobuten-1-yl]amino}propyl)-3,5-difluorobenzamide.

13. A compound according to claim 3 wherein
R$_1$ is heterocycle wherein said heterocycle is optionally substituted pyridinyl;
R$_2$ is hydrogen;
R$_3$ is hydrogen;
R$_4$ is hydrogen;
R$_5$ is aryl wherein said aryl is optionally substituted phenyl;
R$_6$ is selected from the group consisting of alkenyl, alkenyloxy(alkenyloxy)alkyl, cyanoalkyl and cycloalkylalkyl; and
R$_7$ is hydrogen.

14. A compound according to claim 13 selected from the group consisting of 4-chloro-N-(1-{[3,4-dioxo-2-(3-pyridinylamino)-1-cyclobuten-1-yl]amino}-2,2-dimethyl-4-pentenyl)benzamide;

4-chloro-N-(4-cyano-1-{[3,4-dioxo-2-(3-pyridinylamino)-1-cyclobuten-1-yl]amino}-2,2-diethylbutyl)benzamide;

N-(2,2-bis[(allyloxy)methyl]-1-{[3,4-dioxo-2-(3-pyridinylamino)-1-cyclobuten-1-yl]amino}butyl)-4-chlorobenzamide;

4-chloro-N-(2-cyclohexyl-1-{[3,4-dioxo-2-(3-pyridinylamino)-1-cyclobuten-1-yl]amino}-2-methylpropyl)benzamide; and N-(2-(1-adamantyl)-1-{[3,4-dioxo-2-(3-pyridinylamino)-1-cyclobuten-1-yl]amino}ethyl)-4-chlorobenzamide.

15. A compound according to claim 3 wherein
R$_1$ is heterocycle wherein heterocycle is optionally substituted pyridinyl; and
R$_5$ is aryl wherein aryl is selected from the group consisting of optionally substituted naphthyl and optionally substituted fluorenyl.

16. A compound according to claim 3 wherein

R₁ is heterocycle wherein heterocycle is optionally substituted pyridinyl;
R₂ is hydrogen;
R₃ is hydrogen;
R₄ is hydrogen;
R₅ is aryl wherein aryl is selected from the group consisting of optionally substituted naphthyl and optionally substituted fluorenyl;
R₆ is selected from the group consisting of alkenyl, alkenyloxy(alkenyloxy)alkyl, arylalkyl wherein the aryl portion of said arylalkyl is optionally substituted phenyl, cyanoalkyl, cycloalkylalkyl and haloalkyl, and
R₇ is hydrogen.

17. A compound according to claim 3 wherein
R₁ is heterocycle wherein heterocycle is optionally substituted pyridinyl;
R₂ is hydrogen;
R₃ is hydrogen;
R₄ is hydrogen;
R₅ is aryl wherein aryl is selected from the group consisting of optionally substituted naphthyl and optionally substituted fluorenyl;
R₆ is alkyl; and
R₇ is hydrogen.

18. A compound according to claim 17 selected from the group consisting of
N-(1-{[3,4-dioxo-2-(3-pyridinylamino)-1-cyclobuten-1-yl]amino}-2,2-dimethylpropyl)-1-naphthamide; and
N-(1-{[3,4-dioxo-2-(3-pyridinylamino)-1-cyclobuten-1-yl]amino}-2,2-dimethylpropyl)-9-oxo-9H-fluorene-4-carboxamide.

19. A compound according to claim 3 wherein
R₁ is aryl; and
R₅ is aryl.

20. A compound according to claim 3 wherein
R₁ is aryl wherein said aryl is optionally substituted phenyl; and
R₅ is aryl wherein said aryl is optionally substituted phenyl.

21. A compound according to claim 3 wherein
R₁ is aryl wherein said aryl is optionally substituted phenyl;
R₂ is hydrogen;
R₃ is hydrogen;
R₄ is hydrogen;
R₅ is aryl wherein said aryl is optionally substituted phenyl;
R₆ is selected from the group consisting of alkenyl, alkenyloxy(alkenyloxy)alkyl, alkyl, arylalkyl wherein the aryl portion of said arylalkyl is optionally substituted phenyl, cyanoalkyl, cycloalkylalkyl and haloalkyl; and
R₇ is hydrogen.

22. A compound according to claim 3 wherein
R₁ is aryl wherein said aryl is optionally substituted phenyl;
R₂ is hydrogen;
R₃ is hydrogen;
R₄ is hydrogen;
R₅ is aryl wherein said aryl is optionally substituted phenyl;
R₆ is alkyl; and
R₇ is hydrogen.

23. A compound according to claim 22 selected from the group consisting of
4-chloro-N-(1-{[2-(3-fluoroanilino)-3,4-dioxo-1-cyclobuten-1-yl]amino}-2,2-dimethylpropyl)benzamide; and
4-chloro-N-(1-{[2-(4-fluoroanilino)-3,4-dioxo-1-cyclobuten-1-yl]amino}-2,2-dimethylpropyl)benzamide.

24. A compound according to claim 3 wherein
R₁ is heterocycle; and
R₅ is arylalkyl.

25. A compound according to claim 3 wherein
R₁ is heterocycle wherein said heterocycle is optionally substituted pyridinyl;
R₅ is selected from the group consisting of arylalkyl, arylalkenyl and aryloxyalkyl wherein the aryl portion of said arylalkyl is optionally substituted phenyl, the aryl portion of said arylalkenyl is optionally substituted phenyl and the aryl portion of said aryloxyalkyl is optionally substituted phenyl.

26. A compound according to claim 3 wherein
R₁ is heterocycle wherein said heterocycle is optionally substituted pyridinyl;
R₂ is hydrogen;
R₃ is hydrogen;
R₄ is hydrogen;
R₅ is selected from the group consisting of arylalkyl, arylalkenyl and aryloxyalkyl wherein the aryl portion of said arylalkyl is optionally substituted phenyl, the aryl portion of said arylalkenyl is optionally substituted phenyl and the aryl portion of said aryloxyalkyl is optionally substituted phenyl;
R₆ is selected from the group consisting of alkenyl, alkenyloxy(alkenyloxy)alkyl, arylalkyl wherein the aryl portion of said arylalkyl is optionally substituted phenyl, cyanoalkyl, cycloalkylalkyl and haloalkyl; and
R₇ is hydrogen.

27. A compound according to claim 3 wherein
R₁ is heterocycle wherein said heterocycle is optionally substituted pyridinyl;
R₂ is hydrogen;
R₃ is hydrogen;
R₄ is hydrogen;
R₅ is selected from the group consisting of arylalkyl, arylalkenyl and aryloxyalkyl wherein the aryl portion of said arylalkyl is optionally substituted phenyl, the aryl portion of said arylalkenyl is optionally substituted phenyl and the aryl portion of said aryloxyalkyl is optionally substituted phenyl;
R₆ is selected from the group consisting of alkyl and arylalkyl wherein the aryl portion of said arylalkyl is optionally substituted phenyl; and
R₇ is hydrogen.

28. A compound according to claim 27 selected from the group consisting of
(1-{[3,4-dioxo-2-(3-pyridinylamino)-1-cyclobuten-1-yl]amino}-2,2-dimethylpropyl)-3-phenylpropanamide;
N-(1-{[3,4-dioxo-2-(3-pyridinylamino)-1-cyclobuten-1-yl]amino}-2,2-dimethylpropyl)-2-phenylacetamide;
N-(1-{[3,4-dioxo-2-(3-pyridinylamino)-1-cyclobuten-1-yl]amino}-2,2-dimethylpropyl)-3-phenylprop-2-enamide;

N-[1-({2-[(2-chloropyridin-3-yl)amino]-3,4-dioxo-1-cyclobuten-1-yl}amino)-2,2-dimethylpropyl]-3-phenylpropanamide;

N-(1-{[3,4-dioxo-2-(3-pyridinylamino)-1-cyclobuten-1-yl]amino}-2,2-dimethylpropyl)-2-phenoxyacetamide;

N-[1-({2-[(2-chloropyridin-3-yl)amino]-3,4-dioxo-1-cyclobuten-1-yl}amino)-2,2-dimethylpropyl]-2-phenoxyacetamide;

N-(1-{[3,4-dioxo-2-(3-pyridinylamino)-1-cyclobuten-1-yl]amino}-2,2-dimethylpropyl)-2-methyl-2-phenylpropanamide;

N-(1-{[3,4-dioxo-2-(3-pyridinylamino)-1-cyclobuten-1-yl]amino}-2,2-dimethyl-3-phenylpropyl)-3-phenylpropanamide;

N-(1-{[3,4-dioxo-2-(3-pyridinylamino)-1-cyclobuten-1-yl]amino}-2,2-dimethyl-3-phenylpropyl)-2-methyl-2-phenylpropanamide; and N-(1-{[3,4-dioxo-2-(3-pyridinylamino)-1-cyclobuten-1-yl]amino}-2,2-dimethyl-3-phenylpropyl)-2-phenoxyacetamide.

29. A compound according to claim 3 wherein
$R_1$ is heterocycle; and
$R_5$ is heterocyclealkyl.

30. A compound according to claim 3 wherein
$R_1$ is heterocycle wherein said heterocycle is optionally substituted pyridinyl;
$R_5$ is heterocyclealkyl wherein the heterocycle portion of said heterocyclealkyl is optionally substituted pyridinyl.

31. A compound according to claim 3 wherein
$R_1$ is heterocycle wherein said heterocycle is optionally substituted pyridinyl;
$R_2$ is hydrogen;
$R_3$ is hydrogen;
$R_4$ is hydrogen;
$R_5$ is heterocyclealkyl wherein the heterocycle portion of said heterocyclealkyl is optionally substituted pyridinyl;
$R_6$ is selected from the group consisting of alkenyl, alkenyloxy(alkenyloxy)alkyl, arylalkyl wherein the aryl portion of said arylalkyl is optionally substituted phenyl, cyanoalkyl, cycloalkylalkyl and haloalkyl; and
$R_7$ is hydrogen.

32. A compound according to claim 3 wherein
$R_1$ is heterocycle wherein said heterocycle is optionally substituted pyridinyl;
$R_2$ is hydrogen;
$R_3$ is hydrogen;
$R_4$ is hydrogen;
$R_5$ is heterocyclealkyl wherein the heterocycle portion of said heterocyclealkyl is optionally substituted pyridinyl;
$R_6$ is alkyl; and
$R_7$ is hydrogen.

33. A compound according to claim 32 that is N-[1-({2-[(2-chloro-3-pyridinyl)amino]-3,4dioxo-1-cyclobuten-1-yl}amino)-2,2-dimethylpropyl]-3-(3-pyridinyl)propanamide.

34. A compound according to claim 3 wherein
$R_1$ is heterocycle; and
$R_5$ is heterocycle.

35. A compound according to claim 3 wherein
$R_1$ is heterocycle wherein said heterocycle is optionally substituted pyridinyl;
$R_5$ is heterocycle wherein said heterocycle is selected from the group consisting of optionally substituted pyridinyl, optionally substituted thienyl and optionally substituted furyl.

36. A compound according to claim 3 wherein
$R_1$ is heterocycle wherein said heterocycle is optionally substituted pyridinyl;
$R_2$ is hydrogen;
$R_3$ is hydrogen;
$R_4$ is hydrogen;
$R_5$ is heterocycle wherein said heterocycle is selected from the group consisting of optionally substituted pyridinyl, optionally substituted thienyl and optionally substituted furyl;
$R_6$ is selected from the group consisting of alkenyl, alkenyloxy(alkenyloxy)alkyl, arylalkyl wherein the aryl portion of said arylalkyl is optionally substituted phenyl, cyanoalkyl, cycloalkylalkyl and haloalkyl; and
$R_7$ is hydrogen.

37. A compound according to claim 3 wherein
$R_1$ is heterocycle wherein said heterocycle is optionally substituted pyridinyl;
$R_2$ is hydrogen;
$R_3$ is hydrogen;
$R_4$ is hydrogen;
$R_5$ is heterocycle wherein said heterocycle is selected from the group consisting of optionally substituted pyridinyl, optionally substituted thienyl and optionally substituted furyl;
$R_6$ is selected from the group consisting of alkyl and arylalkyl wherein the aryl portion of said arylalkyl is optionally substituted phenyl; and
$R_7$ is hydrogen.

38. A compound according to claim 37 selected from the group consisting of

N-(1-{[3,4-dioxo-2-(3-pyridinylamino)-1-cyclobuten-1-yl]amino}-2,2-dimethylpropyl)-2-pyridinecarboxamide;

N-(1-{[3,4-dioxo-2-(3-pyridinylamino)-1-cyclobuten-1-yl]amino}-2,2-dimethylpropyl)thiophene-2-carboxamide;

N-(1-{[3,4-dioxo-2-(3-pyridinylamino)-1-cyclobuten-1-yl]amino}-2,2-dimethyl-3-phenylpropyl)isonicotinamide;

N-(1-{[3,4-dioxo-2-(3-pyridinylamino)-1-cyclobuten-1-yl]amino}-2,2-dimethyl-3-phenylpropyl)nicotinamide;

N-(1-{[3,4-dioxo-2-(3-pyridinylamino)-1-cyclobuten-1-yl]amino}-2,2-dimethylpropyl)nicotinamide;

N-(1-{(3,4-dioxo-2-(3-pyridinylamino)-1-cyclobuten-1-yl]amino}-2,2-dimethylpropyl)isonicotinamide; and N-(1-{[3,4-dioxo-2-(3-pyridinylamino)-1-cyclobuten-1-yl]amino}-2,2-dimethylpropyl)-2-furamide.

39. A compound according to claim 1 of formula (III)

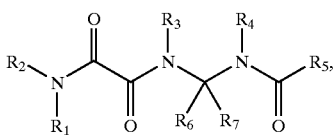

(III)

or a pharmaceutically acceptable salt therof.

40. A compound according to claim 39 wherein
$R_1$ is heterocycle; and
$R_5$ is aryl.

41. A compound according to claim 39 wherein
$R_1$ is heterocycle wherein said heterocycle is optionally substituted pyridinyl; and
$R_5$ is aryl wherein said aryl is optionally substituted phenyl.

42. A compound according to claim 39 wherein
$R_1$ is heterocycle wherein said heterocycle is optionally substituted pyridinyl;
$R_2$ is hydrogen;
$R_3$ is hydrogen;
$R_4$ is hydrogen;
$R_5$ is aryl wherein said aryl is optionally substituted phenyl;
$R_6$ is selected from the group consisting of alkenyl, alkenyloxy(alkenyloxy)alkyl, arylalkyl wherein the aryl portion of said arylalkyl is optionally substituted phenyl, cyanoalkyl, cycloalkylalkyl and haloalkyl; and
$R_7$ is hydrogen.

43. A compound according to claim 39 wherein
$R_1$ is heterocycle wherein said heterocycle is optionally substituted pyridinyl;
$R_2$ is hydrogen;
$R_3$ is hydrogen;
$R_4$ is hydrogen;
$R_5$ is aryl wherein said aryl is optionally substituted phenyl;
$R_6$ is alkyl; and
$R_7$ is hydrogen.

44. A compound according to claim 43 that is $N^1$-{1-[(4-chlorobenzoyl)amino]-2,2-dimethylpropyl}-$N^2$-(3-pyridinyl)ethanediamide.

45. A compound according to claim 1 of formula (IV)

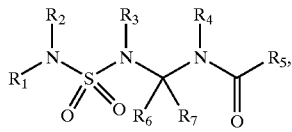

(IV)

or a pharmaceutically acceptable salt therof.

46. A compound according to claim 45 wherein
$R_1$ is heterocycle; and
$R_5$ is aryl.

47. A compound according to claim 45 wherein
$R_1$ is heterocycle wherein said heterocycle is optionally substituted pyridinyl; and
$R_5$ is aryl wherein said aryl is optionally substituted phenyl.

48. A compound according to claim 45 wherein
$R_1$ is heterocycle wherein said heterocycle is optionally substituted pyridinyl;
$R_2$ is hydrogen;
$R_3$ is hydrogen;
$R_4$ is hydrogen;
$R_5$ is aryl wherein said aryl is optionally substituted phenyl;
$R_6$ is selected from the group consisting of alkenyl, alkenyloxy(alkenyloxy)alkyl, arylalkyl wherein the aryl portion of said arylalkyl is optionally substituted phenyl, cyanoalkyl, cycloalkylalkyl and haloalkyl; and
$R_7$ is hydrogen.

49. A compound according to claim 45 wherein
$R_1$ is heterocycle wherein said heterocycle is optionally substituted pyridinyl;
$R_2$ is hydrogen;
$R_3$ is hydrogen;
$R_4$ is hydrogen;
$R_5$ is aryl wherein said aryl is optionally substituted phenyl;
$R_6$ is alkyl; and
$R_7$ is hydrogen.

50. A compound-according to claim 49 selected from the group consisting of
4-chloro-N-(2,2-dimethyl-1-{[(3-pyridinylamino)sulfonyl]amino}propyl)benzamide; and
N-(2,2-dimethyl-1-{[(3-pyridinylamino)sulfonyl]amino}propyl)4-iodobenzamide.

51. A pharmaceutical composition comprising a therapeutically effective amount of a compound of claim 1 in combination with a pharmaceutically acceptable carrier.

52. A method of treating a disorder in a host mammal in need of such treatment comprising administering to the mammal a therapeutically effective amount of a compound of formula (I).

53. The method of claim 52 wherein the disorder is selected from the group consisting of asthma, epilepsy, Raynaud's syndrome, intermittent claudication, migraine, pain, pollakiuria, bladder instability, nocturia, bladder hyperreflexia, enuresis, alopecia, cardioprotection, ischemia, eating disorders, functional bowel disorders, and neurodegeneration.

54. The method of claim 52 wherein the disorder is bladder overactivity.

55. The method of claim 52 wherein the disorder is benign prostatic hyperplasia.

56. The method of claim 52 wherein the disorder is dysmenorrhea.

57. The method of claim 52 wherein the disorder is premature labor.

58. The method of claim 52 wherein the disorder is urinary incontinence.

59. The method of claim 52 wherein the disorder is selected from the group consisting of male erectile dysfunction and premature ejaculation.

60. The method of claim 52 wherein the disorder is female sexual dysfunction.

61. A process for the preparation of a compound of formula (V)

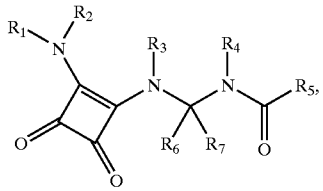

(V)

wherein

R$_1$ is selected from the group consisting of aryl, arylalkyl, heterocycle and heterocyclealkyl;

R$_2$, R$_3$ and R$_4$ are independently selected from the group consisting of hydrogen and alkyl;

R$_5$ is selected from the group consisting of aryl, arylalkyl, heterocycle and heterocyclealkyl;

R$_6$ is selected from the group consisting of hydrogen, alkenyl, alkenyloxyalkyl, alkenyloxy(alkenyloxy) alkyl, alkoxyalkyl, alkoxycarbonyl, alkoxycarbonylalkyl, alkoxycarbonyl(halo)alkyl, alkoxy(halo)alkyl, alkyl, alkylcarbonyl, alkylcarbonylalkyl, alkylcarbonyl(halo)alkyl, alkylcarbonyloxyalkyl, alkylsulfinylalkyl, alkylsulfonylalkyl, alkylthioalkyl, alkynyl, amido, amidoalkyl, aryl, arylalkoxyalkyl, arylalkoxycarbonyl, arylalkoxycarbonylalkyl, arylalkyl, arylcarbonyl, arylcarbonylalkyl, arylcarbonyloxyalkyl, aryl(halo) alkyl, aryloxyalkyl, aryloxycarbonyl, aryloxycarbonylalkyl, arylalkylthioalkyl, arylsulfonylalkyl, carboxy, carboxyalkyl, carboxy (halo)alkyl, cyanoalkyl, cyano(halo)alkyl, cycloalkenyl, cycloalkenylalkyl, cycloalkyl, cycloalkylalkoxyalkyl, cycloalkylalkyl, cycloalkylcarbonyl, cycloalkyloxyalkyl, cycloalkylalkylthioalkyl, formyl, haloalkenyl, haloalkyl, haloalkylcarbonyl, haloalkynyl, heterocycle, heterocyclealkoxyalkyl, heterocyclealkyl, heterocyclecaibonyl, heterocycleoxyalkyl, heterocyclealkylthioalkyl, hydroxyalkyl, mercaptoalkyl, sulfamylalkyl, sulfamyl(halo)alkyl and (NR$_9$R$_{10}$)alkyl; and R$_9$ and R$_{10}$ are independently selected from the group consisting of hydrogen, alkyl, alkylcarbonyl, aryl, arylalkyl, arylcarbonyl, formyl, and S(O)$_2$R$_{11}$ wherein R$_{11}$ is selected from the group consisting of alkoxy, alkyl, aryl and arylalkyl;

the process comprising:

(a) reacting an aldehyde of formula (VI)

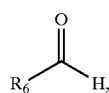

(VI)

an amide of formula (VII)

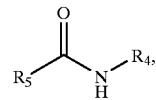

(VII)

1H-benzotriazole-polystyrene resin and an acid in a first solvent at about 50° C. to about 80° C., wherein R$_4$, R$_5$ and R$_6$ are as defined above;

(b) reacting the product of step (a), a base and a compound of formula (VIII)

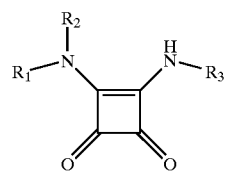

(VIII)

in a second solvent wherein R$_1$, R$_2$ and R$_3$ are as defined above to provide a compound of formula (V).

62. The process according to claim 61 wherein the acid is selected from the group consisting of para-toluenesulfonic acid monohydrate and acetic acid.

63. The process according to claim 61 wherein the first solvent is selected from the group consisting of 1,4-dioxane, 2-methoxyethanol, tetrahydrofuran, trimethyl orthoformate, and mixtures thereof.

64. The process according to claim 61 wherein the first solvent is selected from the group consisting of tetrahydrofuran:2-methoxyethanol in about a (1:1) ratio, tetrahydrofuran:trimethyl orthoformate in about a (1:1) ratio and 1,4-dioxane:trimethyl orthoformate in about a (1:0.3) to (1:3) ratio.

65. The process according to claim 61 wherein step (a) is conducted for a period of about 12 hours to about 48 hours.

66. The process according to claim 61 wherein the base is selected from the group consisting of cesium carbonate, potassium carbonate and sodium carbonate.

67. The process according to claim 61 wherein the second solvent is selected from the group consisting of dimethylacetamide, N,N-dimethylformamide, dimethylsulfoxide and mixtures thereof.

68. The process according to claim 61 wherein step (b) is conducted at about 15° C. to about 50° C.

69. The process according to claim 61 wherein step (b) is conducted for a period of about 24 hours to about 168 hours.

70. The process according to claim 61 wherein the acid is para-toluenesulfonic acid monohydrate; the first solvent is tetrahydrofuran:2-methoxyethanol in about a (1:1) ratio; and step (a) is conducted for a period of about 12 hours to about 48 hours.

71. The process according to claim 70 wherein the base is cesium carbonate; the second solvent is dimethylacetamide; step (b) is conducted at about 18° C. to about 23° C.; and step (b) is conducted for a period of about 48 hours to about 168 hours.

* * * * *